US011453680B2

(12) United States Patent
Linge et al.

(10) Patent No.: US 11,453,680 B2
(45) Date of Patent: Sep. 27, 2022

(54) BISBENZOFURAN-FUSED INDENO[1,2-B]FLUORENE DERIVATIVES AND RELATED COMPOUNDS AS MATERIALS FOR ORGANIC ELECTROLUMINESCENT DEVICES (OLED)

(71) Applicant: Merck Patent GmbH, Darmstadt (DE)

(72) Inventors: Rouven Linge, Darmstadt (DE); Lara-Isabel Rodriguez, Darmstadt (DE); Sebastian Meyer, Aschaffenberg (DE); Holger Heil, Frankfurt am Main (DE)

(73) Assignee: MERCK PATENT GMBH, Darmstadt (DE)

( * ) Notice: Subject to any disclaimer, the term of this patent is extended or adjusted under 35 U.S.C. 154(b) by 628 days.

(21) Appl. No.: 16/463,507

(22) PCT Filed: Nov. 22, 2017

(86) PCT No.: PCT/EP2017/079992

§ 371 (c)(1),
(2) Date: May 23, 2019

(87) PCT Pub. No.: WO2018/095940

PCT Pub. Date: May 31, 2018

(65) Prior Publication Data

US 2019/0375757 A1 Dec. 12, 2019

(30) Foreign Application Priority Data

Nov. 25, 2016 (EP) .................................... 16200702

(51) Int. Cl.

| | |
|---|---|
| ***C07D 493/22*** | (2006.01) |
| ***C07D 307/91*** | (2006.01) |
| ***C07D 493/04*** | (2006.01) |
| ***H01L 51/00*** | (2006.01) |
| ***H01L 51/50*** | (2006.01) |
| ***C09K 11/06*** | (2006.01) |
| ***C07F 7/08*** | (2006.01) |

(52) U.S. Cl.
CPC ......... *C07D 493/22* (2013.01); *C07D 307/91* (2013.01); *C07D 493/04* (2013.01); *C07F 7/0816* (2013.01); *C09K 11/06* (2013.01); *H01L 51/0058* (2013.01); *H01L 51/0073* (2013.01); *H01L 51/0074* (2013.01); *H01L 51/5012* (2013.01)

(58) Field of Classification Search
CPC ................ C07D 307/91; C07D 493/04; C07D 493/22; C07F 7/0816; C09K 11/06; H01L 27/32; H01L 51/0058; H01L 51/0073; H01L 51/0074; H01L 51/5012
See application file for complete search history.

(56) References Cited

U.S. PATENT DOCUMENTS

| | | | | |
|---|---|---|---|---|
| 4,539,507 | A | 9/1985 | VanSlyke et al. | |
| 11,158,816 | B2 * | 10/2021 | Heil | H01L 51/0059 |
| 2008/0145708 | A1 | 6/2008 | Heil et al. | |
| 2009/0184313 | A1 | 7/2009 | Buesing et al. | |
| 2009/0261717 | A1 | 10/2009 | Buesing et al. | |
| 2012/0138918 | A1 | 6/2012 | Naraoka et al. | |
| 2013/0048955 | A1 | 2/2013 | Lee et al. | |
| 2016/0204355 | A1 | 7/2016 | Kim et al. | |
| 2016/0254456 | A1 | 9/2016 | Heil et al. | |
| 2018/0248129 | A1 | 8/2018 | Heil et al. | |
| 2018/0277761 | A1 | 9/2018 | Hayashi et al. | |

FOREIGN PATENT DOCUMENTS

| | | | |
|---|---|---|---|
| CN | 102030619 | A | 4/2011 |
| CN | 104245690 | A | 12/2014 |
| CN | 105061463 | A | 11/2015 |
| CN | 107573357 | A | 1/2018 |
| CN | 107573357 | B * | 10/2019 |
| EP | 2487991 | A1 | 8/2012 |
| EP | 3050887 | A1 | 8/2016 |
| JP | 2007019294 | A | 1/2007 |
| JP | 2012-528088 | A | 11/2012 |
| JP | 2013-043889 | A | 3/2013 |
| JP | 2014-231507 | A | 12/2014 |
| JP | 2020-510615 | A | 4/2020 |
| KR | 10-2012-0081539 | A | 7/2012 |
| KR | 20180106234 | A * | 10/2018 |
| WO | 2006108497 | A1 | 10/2006 |
| WO | 2007140847 | A1 | 12/2007 |
| WO | 2008006449 | A1 | 1/2008 |
| WO | 2009/148015 | A1 | 12/2009 |
| WO | 2011/043083 | A1 | 4/2011 |
| WO | 2012/141273 | A1 | 10/2012 |
| WO | 2014111269 | A2 | 7/2014 |
| WO | 2014/199943 | A1 | 12/2014 |

(Continued)

OTHER PUBLICATIONS

Machine translation for WO 2017/028460 A1 (publication date Feb. 2017). (Year: 2017).*
Jin Woo Choi et al., "Solution-processed bulk heterojunction organic solar cells with high polarity small molecule sensitizer", Solar Energy Materials & Solar Cells, 2011, pp. 2069-2076, vol. 95, No. 8.
Kazuki Niimi et al., "Dianthra[2,3-b:2'3'-f]thieno[3,2-b]thiophene (DATT): Synthesis, Characterization, and FET Characteristics of New Π-Extended Heteroarene with Eight Fused Aromatic Rings", Journal of The American Chemical Society, 2011, pp. 8732-8739, vol. 133, No. 22.
Changsheng Wang et al., "Synthesis, Characterization, and OFET and OLED Properties of Π-Extended Ladder-Type Heteroacenes Based on Indolodibenzothiophene", Bulletin of the Chemical Society of Japan, 2012, pp. 136-143, vol. 85, No. 1.
International Search Report dated Jan. 26, 2018 in International Patent Application No. PCT/EP2017/079992.

(Continued)

*Primary Examiner* — Dawn L Garrett
(74) *Attorney, Agent, or Firm* — Faegre Drinker Biddle & Reath LLP

(57) ABSTRACT

The present invention relates to Bisbenzofuran-fused indeno [1,2-b]fluorene derivatives and related compounds as materials for organic electroluminescent devices (OLEDs).

20 Claims, No Drawings

(56) References Cited

FOREIGN PATENT DOCUMENTS

| | | | | |
|---|---|---|---|---|
| WO | 2015174682 | A1 | | 11/2015 |
| WO | 2016079944 | A1 | | 5/2016 |
| WO | WO 2017/028460 | A1 | * | 2/2017 |
| WO | 2017036574 | A1 | | 3/2017 |

OTHER PUBLICATIONS

Baryshnikov et al., "Nine-ring angular fused biscarbazoloanthracene displaying a solid state based excimer emission suitable for OLED application", Journal of Materials Chemistry C: Materials for Optical and Electronic Devices, vol. 4, No. 24, 2016, pp. 5795-5805.

Goldfinger et al., "Directed Electrophilic Cyclizations: Efficient Methodology for the Synthesis of Fused Polycyclic Aromatics", Journal of the American Chemical Society, vol. 119, No. 20, 1997, pp. 4578-4593.

International Preliminary Reporton Patentability received for PCT Patent Application No. PCT/EP2017/079992, dated Jun. 6, 2019, 8 pages.

International Search Report and Written Opinion received for PCT Patent Application No. PCT/EP2017/079992, dated Feb. 5, 2018,12 pages.

Ku et al., "Time-Dependent Density Functional Theory Study on Benzothiadiazole-Based Low-Band-Gap Fused-Ring Copolymers for Organic Solar Cell Applications", Journal of Physical Chemistry C, vol. 115, No. 43, 2011, pp. 21508-21516.

Nakanishi et al., "Oligonaphthofurans: Fan-Shaped and Three-Dimensional Pie-Compounds", Journal of the American Chemical Society, vol. 136, No. 19, 2014, pp. 7101-7109.

Registry(STN)[online], Publication date: May 19, 2014 or earlier, Search date: Sep. 20, 2021, CAS No. 191798-18-2, 1426233-88-6, 1426233-89-7, 1426233-90-0, 1293279-04-5, 920503-08-8, 1426233-91-1, 1426233-92-2, 1606998-82-6, 1606998-83-7.

* cited by examiner

BISBENZOFURAN-FUSED INDENO[1,2-B]FLUORENE DERIVATIVES AND RELATED COMPOUNDS AS MATERIALS FOR ORGANIC ELECTROLUMINESCENT DEVICES (OLED)

RELATED APPLICATIONS

This application is a national stage entry, filed pursuant to 35 U.S.C. § 371, of PCT/EP2017/079992, filed Nov. 22, 2017, which claims the benefit of European Patent Application No. 16200702.5, filed Nov. 25, 2016, which is incorporated herein by reference in its entirety.

The present invention relates to a compound of the formula (1), to the use of the compound in an electronic device, and to an electronic device comprising a compound of the formula (1). The present invention furthermore relates to a process for the preparation of a compound of the formula (1) and to a formulation comprising one or more compounds of the formula (1).

The development of functional compounds for use in electronic devices is currently the subject of intensive research. The aim is, in particular, the development of compounds with which improved properties of electronic devices in one or more relevant points can be achieved, such as, for example, power efficiency and lifetime of the device as well as colour coordinates of the emitted light.

In accordance with the present invention, the term electronic device is taken to mean, inter alia, organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the last-mentioned electronic devices called OLEDs. The general structure and the functional principle of OLEDs are known to the person skilled in the art and are described, for example, in U.S. Pat. No. 4,539,507.

Further improvements are still necessary with respect to the performance data of OLEDs, in particular with a view to broad commercial use, for example in display devices or as light sources. Of particular importance in this connection are the lifetime, the efficiency and the operating voltage of the OLEDs and as well as the colour values achieved. In particular, in case of blue-emitting OLEDs, there is potential for improvement with respect to the lifetime and efficiency of the devices.

An important starting point for achieving the said improvements is the choice of the emitter compound and of the host compound employed in the electronic device.

Blue-fluorescent emitters known from the prior art are a multiplicity of compounds, in particular arylamines containing one or more condensed aryl groups and/or indenofluorene groups. Examples thereof are benzoindenofluorenamines, for example in accordance with WO 2008/006449, and dibenzoindenofluorenamines, for example in accordance with WO 2007/140847. Benzoindenofluorene derivatives and dibenzoindenofluorene derivatives may also be employed as matrix materials in OLEDs and in other electronic devices.

Furthermore, indenofluorene derivatives may be employed as hole-transport materials in OLEDs and in other electronic devices, for examples in accordance with WO 2006/108497.

Thus, compounds based on indenofluorene derivatives, benzoindenofluorene derivatives and dibenzoindenofluorene derivatives have been successfully used as materials in OLEDs over the past years.

However, further improvements with regard to this type of compounds are still necessary with respect to the lifetime, the efficiency and the colour values achieved in the case of blue-emitting OLEDs. More particularly, there is a need for deep-blue fluorescent emitters for OLEDs, which exhibit very good colour properties in terms of colour-depth and narrow emission band and at the same time still exhibit good properties in terms lifetime, efficiency and operating voltage of the OLEDs. Furthermore, there is also a need for compounds that are suitable for solution processing, especially in the case of blue-emitting OLEDs.

The present invention is thus based on the technical object of providing compounds which are suitable for use in electronic devices, such as OLEDs, which can be employed as blue emitters, as matrix materials and/or as hole-transport materials and which are suitable for vacuum processing and/or for solution processing.

In investigations on novel compounds for use in electronic devices, it has now been found, unexpectedly, that compounds of formula (1) as defined below are eminently suitable for use in electronic devices. In particular, they achieve one or more, preferably all, of the above-mentioned technical objects of provision of OLEDs having deep-blue colour coordinates of the emitted light, provision of OLEDs having a long lifetime and provision of compounds having good solubility in organic solvents.

The invention thus relates to compounds of formula (1), formula (1)

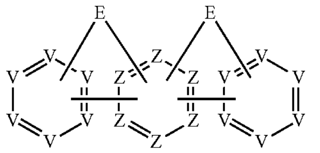

where the following applies to the symbols and indices used:

Z is CR or N, and Z is C when Z is bonded to a group V or to a group E;

V is $CR^1$, N, or V is C when V is bonded to a group Z or to a group E; and at least two adjacent groups V, in each 6-membered ring comprising some groups V in formula (1), stand for a group of the formula (V-1), formula (V-1)

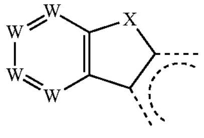

where the dashed bond indicate the bonding to the structure of formula (1);

E is identically or differently on each occurrence, selected from $—BR^0—$, $—C(R^0)_2—$, $—C(R^0)_2—C(R^0)_2—$, $—C(R^0)_2—O—$, $—C(R^0)_2—S—$, $—R^0C{=}CR^0—$, $—R^0C{=}N—$, $—Si(R^0)_2—$, $—Si(R^0)_2—Si(R^0)_2—$, $Ge(R^0)_2$, $—C({=}O)—$, $—C({=}NR^0)—$, $—C({=}C(R^0)_2)—$, $—O—$, $—S—$, $—Se—$, $—S({=}O)—$, $—SO_2—$, $—N(R^0)—$, $—P(R^0)—$ and $—P(({=}O)R^0)—$, preferably $—C(R^0)_2—$, $—C(R^0)_2—C(R^0)_2—$, $—R^0C═CR^0—$, $—Si(R^0)_2—$ and $—Si(R^0)_2—Si(R^0)_2—$, more preferably $—C(R^0)_2—$ and $—Si(R^0)_2—$; and two groups E may be in a cis- or trans-position relative to each other;

X is identically or differently on each occurrence, selected from —O—, —S—, —S(═O)—, $—SO_2—$, $—N(R^0)—$, $—BR^0—$, $Si(R^0)_2$, $—P(R^0)—$ and $—P((═O)R^0)—$;

W is CR or N;

R, $R^0$ stand on each occurrence, identically or differently, for H, D, F, Cl, Br, I, CHO, CN, $N(Ar)_2$, C(═O)Ar, $P(═O)(Ar)_2$, S(═O)Ar, $S(═O)_2Ar$, $NO_2$, $Si(R^2)_3$, $B(OR^2)_2$, $OSO_2R^2$, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals $R^2$, where in each case one or more non-adjacent $CH_2$ groups may be replaced by $R^2C═CR^2$, C≡C, $Si(R^2)_2$, $Ge(R^2)_2$, $Sn(R^2)_2$, C═O, C═S, C═Se, $P(═O)(R^2)$, SO, $SO_2$, O, S or $CONR^2$ and where one or more H atoms may be replaced by D, F, CI, Br, I, CN or $NO_2$, an aromatic or heteroaromatic ring systems having 5 to 60 aromatic ring atoms, which may in each case be substituted by one or more radicals $R^2$, or an aryloxy groups having 5 to 60 aromatic ring atoms, which may be substituted by one or more radicals $R^2$, where two adjacent substituents R and/or two adjacent substituents $R^0$ may form a mono- or polycyclic, aliphatic ring system or aromatic ring system, which may be substituted by one or more radicals $R^2$;

$R^1$ stands on each occurrence, identically or differently, for H, D, F, Cl, Br, I, CHO, CN, C(═O)Ar, $P(═O)(Ar)_2$, S(═O)Ar, $S(═O)_2Ar$, $NO_2$, $Si(R^2)_3$, $B(OR^2)_2$, $OSO_2R^2$, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals $R^2$, where in each case one or more non-adjacent $CH_2$ groups may be replaced by $R^2C═CR^2$, CC, $Si(R^2)_2$, $Ge(R^2)_2$, $Sn(R^2)_2$, C═O, C═S, C═Se, $P(═O)(R^2)$, SO, $SO_2$, O, S or $CONR^2$ and where one or more H atoms may be replaced by D, F, Cl, Br, I, CN or $NO_2$, an aromatic or heteroaromatic ring systems having 5 to 60 aromatic ring atoms, which may in each case be substituted by one or more radicals $R^2$, or an aryloxy groups having 5 to 60 aromatic ring atoms, which may be substituted by one or more radicals $R^2$, where two adjacent substituents $R^1$ may form a mono- or polycyclic, aliphatic ring system or aromatic ring system, which may be substituted by one or more radicals $R^2$;

$R^2$ stands on each occurrence, identically or differently, for H, D, F, Cl, Br, I, CHO, CN, $N(Ar)_2$, C(═O)Ar, $P(═O)(Ar)_2$, S(═O)Ar, $S(═O)_2Ar$, $NO_2$, $Si(R^3)_3$, $B(OR^3)_2$, $OSO_2R^3$, a straight-chain alkyl, alkoxy or thioalkyl groups having 1 to 40 C atoms or branched or cyclic alkyl, alkoxy or thioalkyl groups having 3 to 40 C atoms, each of which may be substituted by one or more radicals $R^3$, where in each case one or more non-adjacent $CH_2$ groups may be replaced by $R^3C═CR^3$, C≡C, $Si(R^3)_2$, $Ge(R^3)_2$, $Sn(R^3)_2$, C═O, C═S, C═Se, $P(═O)(R^3)$, SO, $SO_2$, O, S or $CONR^3$ and where one or more H atoms may be replaced by D, F, CI, Br, I, CN or $NO_2$, an aromatic or heteroaromatic ring systems having 5 to 60 aromatic ring atoms, which may in each case be substituted by one or more radicals $R^3$, or an aryloxy group having 5 to 60 aromatic ring atoms, which may be substituted by one or more radicals $R^3$, where two adjacent substituents $R^2$ may form a mono- or polycyclic, aliphatic ring system or aromatic ring system, which may be substituted by one or more radicals $R^3$;

$R^3$ stands on each occurrence, identically or differently, for H, D, F, Cl, Br, I, CN, a straight-chain alkyl, alkoxy or thioalkyl groups having 1 to 20 C atoms or branched or cyclic alkyl, alkoxy or thioalkyl groups having 3 to 20 C atoms, where in each case one or more non-adjacent $CH_2$ groups may be replaced by SO, $SO_2$, O, S and where one or more H atoms may be replaced by D, F, Cl, Br or I, or an aromatic or heteroaromatic ring system having 5 to 24 C atoms;

Ar is an aromatic or heteroaromatic ring system having 5 to 60 aromatic ring atoms, which may in each case also be substituted by one or more radicals $R^3$.

Concerning formula (1), the bonding between a group E and the adjacent 6-membered rings comprising V or Z can occur at each free position of these 6-membered-rings. Thus, it is to be understood that the groups E can be in cis- or in trans-position relative to each other, as mentioned in the definition of the group E above.

Adjacent substituents in the sense of the present invention are substituents which are bonded to atoms which are linked directly to one another or which are bonded to the same atom.

Furthermore, the following definitions of chemical groups apply for the purposes of the present application:

An aryl group in the sense of this invention contains 6 to 60 aromatic ring atoms, preferably 6 to 40 aromatic ring atoms, more preferably 6 to 20 aromatic ring atoms; a heteroaryl group in the sense of this invention contains 5 to 60 aromatic ring atoms, preferably 5 to 40 aromatic ring atoms, more preferably 5 to 20 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system, preferably 6 to 40 C atoms, more preferably 6 to 20 C atoms. A heteroaromatic ring system in the sense of this invention contains 5 to 60 aromatic ring atoms, preferably 5 to 40 aromatic ring atoms, more preferably 5 to 20 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. This is illustrated by the following schemes:

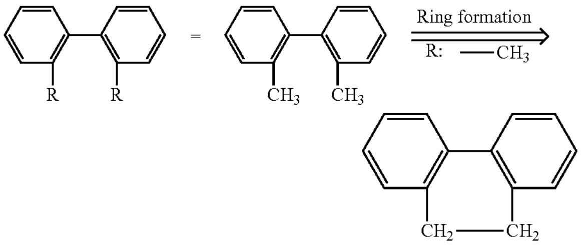

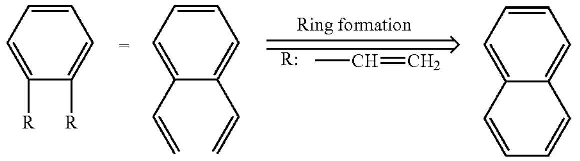

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

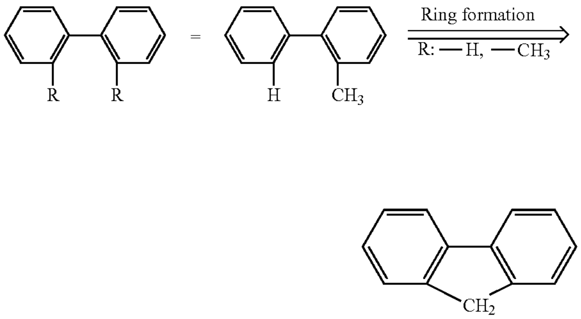

In accordance with a preferred embodiment, the bonds between the 6-membered rings comprising V and the 6-membered ring comprising Z in formula (1) are in para positions.

As mentioned above, at least two adjacent groups V, in each 6-membered ring comprising some groups V in formula (1), stand for a group of the formula (V-1). It is preferred that exactly two adjacent groups V, in each 6-membered ring comprising some groups V in formula (1), stand for a group of the formula (V-1)

In accordance with a preferred embodiment, compounds of formula (1) are selected from compounds of formulae (1-1) to (1-18), formula (1-1)

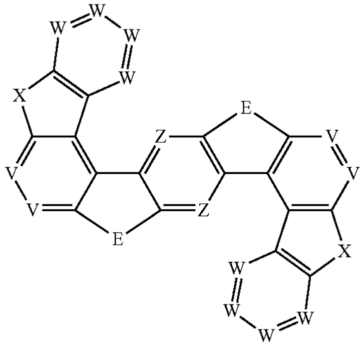

formula (1-2)

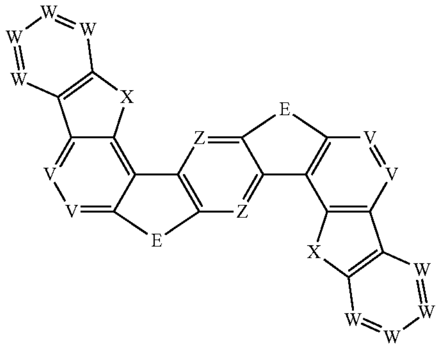

-continued formula (1-3)

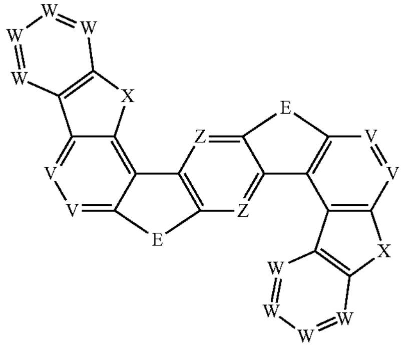

formula (1-4)

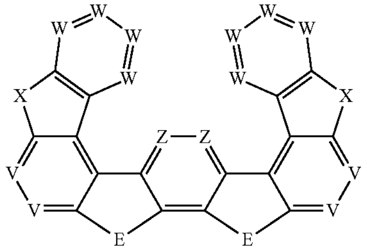

formula (1-5)

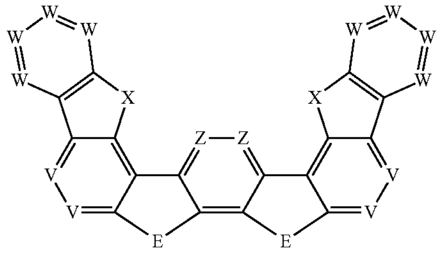

formula (1-6)

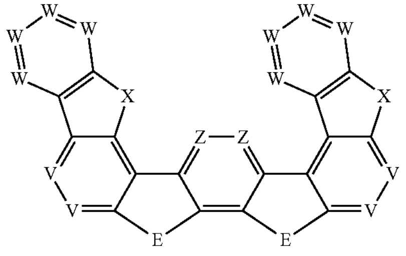

formula (1-7)

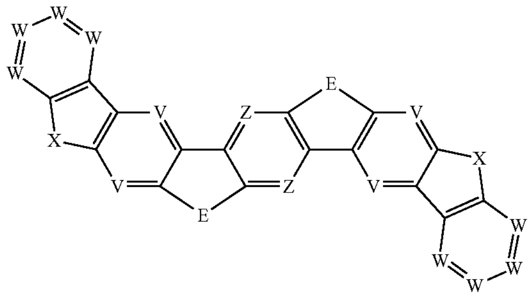

formula (1-8)

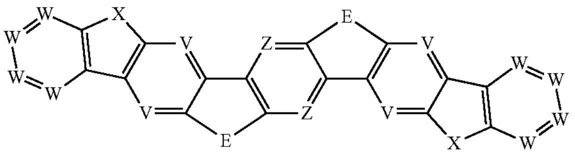

-continued formula (1-9)

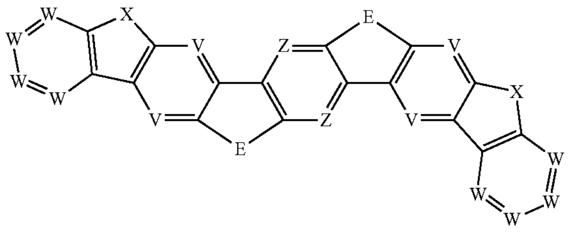

formula (1-10)

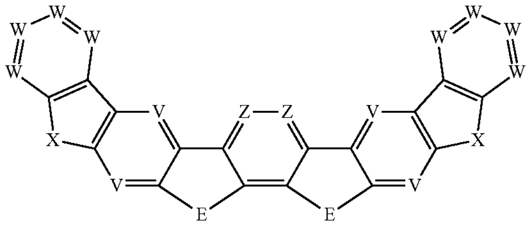

formula (1-11)

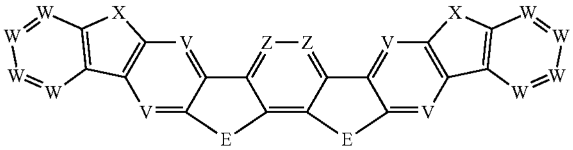

formula (1-12)

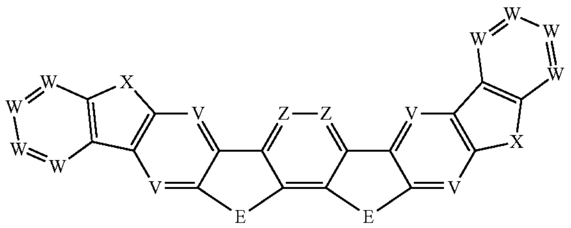

formula (1-13)

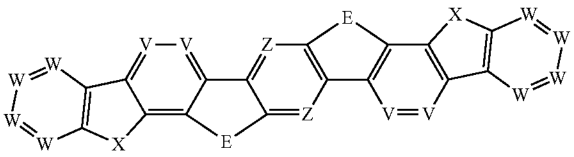

formula (1-14)

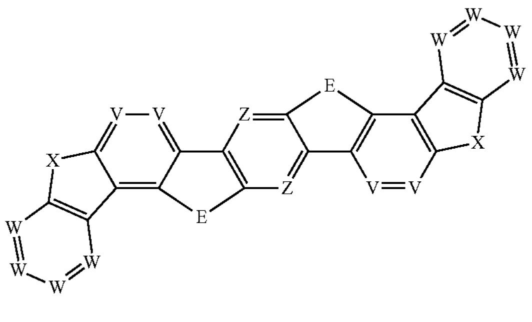

-continued formula (1-15)

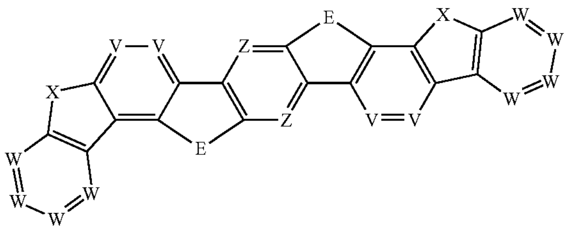

formula (1-16)

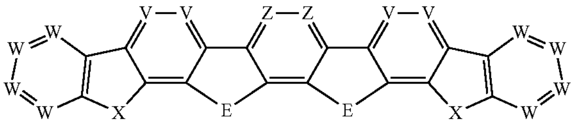

formula (1-17)

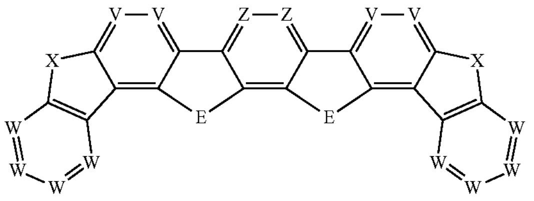

formula (1-18)

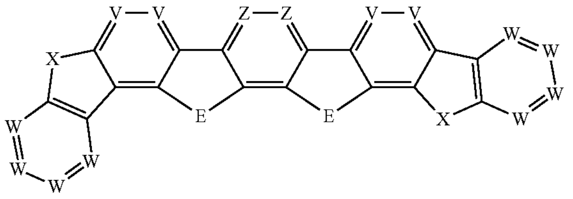

where the symbols E, X, V, W and Z have the same meaning as above.

In formulae (1-1) to (1-18), It is preferred that at least one group V, in each 6-membered ring comprising groups V, stands for a group $CR^1$, where $R^1$ is an aromatic or heteroaromatic ring system having 5 to 60 aromatic ring atoms, which may in each case be substituted by one or more radicals $R^2$.

Among formulae (1-1) to (1-18), formulae (1-1) to (1-6) are preferred, formulae (1-1) to (1-3) are very preferred.

In accordance with a very preferred embodiment, compounds of formula (1) are selected from compounds of formulae (1-1a) to (1-6a), formula (1-1a)

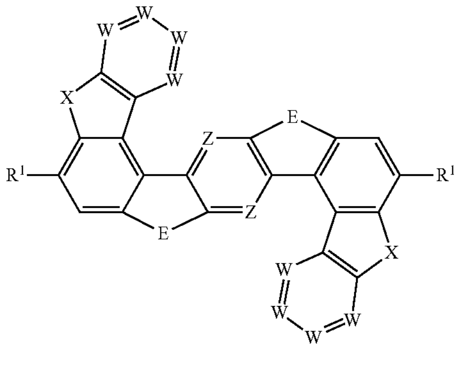

-continued formula (1-2a)

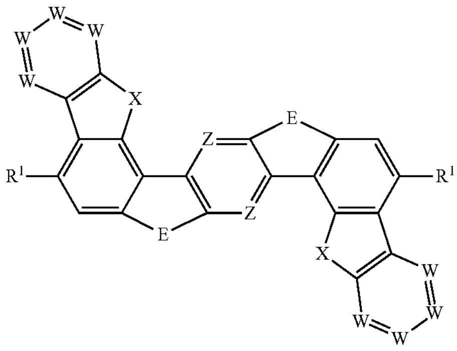

formula (1-3a)

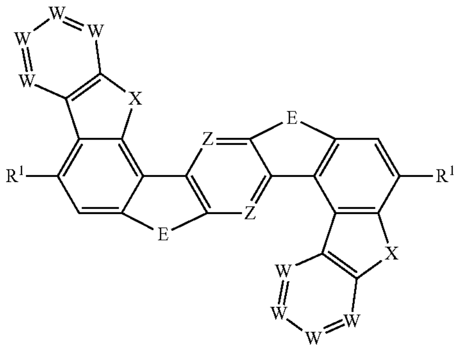

formula (1-4a)

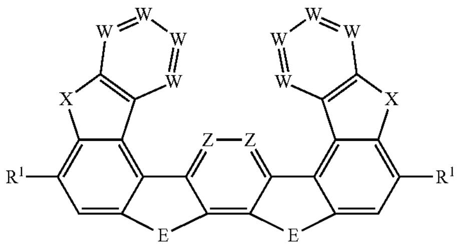

formula (1-5a)

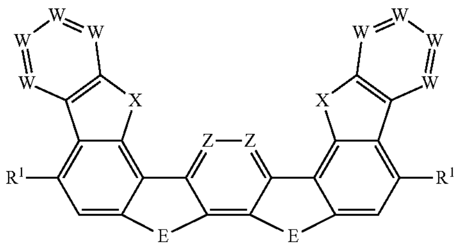

formula (1-6a)

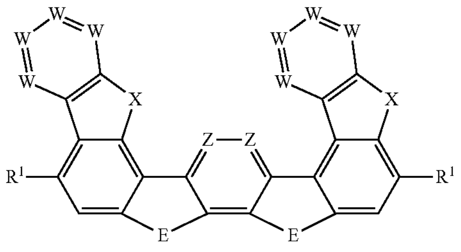

where the symbols X, E, Z, V, W, $R^1$ have the same meaning as above.

Furthermore, it is preferred that in formulae (1-1a) to (1-6a), the group $R^1$ stands for an aromatic or heteroaromatic ring system having 5 to 60 aromatic ring atoms, which may in each case be substituted by one or more radicals $R^2$.

Among formulae (1-1a) to (1-6a), formulae (1-1a) to (1-3a) are preferred.

In accordance with a particularly preferred embodiment, compounds of formula (1) are selected from compounds of formulae (1-1 b) to (1-6c), formula (1-1b)

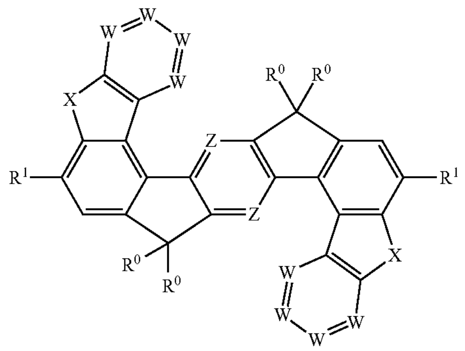

formula (1-2b)

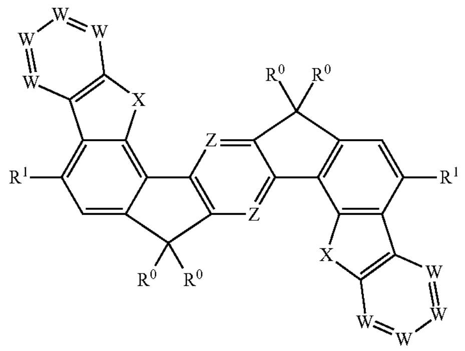

formula (1-3b)

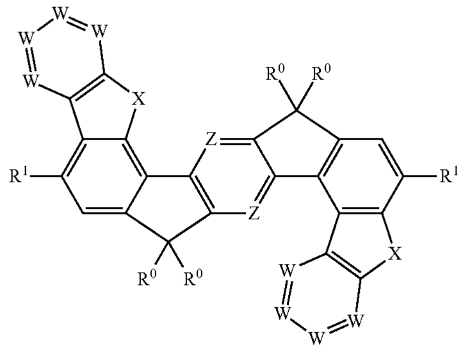

-continued
formula (1-4b)
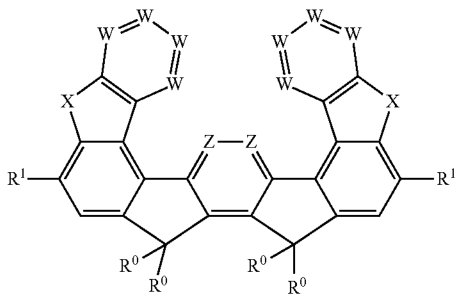
formula (1-5b)
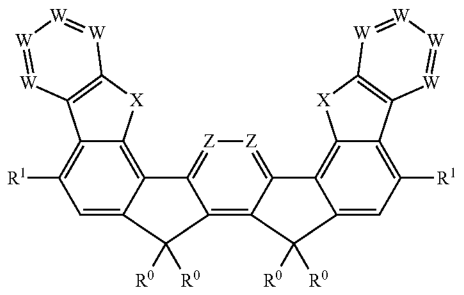
formula (1-6b)
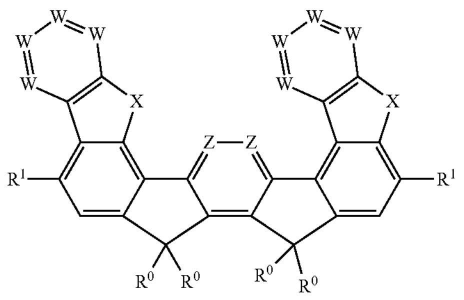
formula (1-1c)
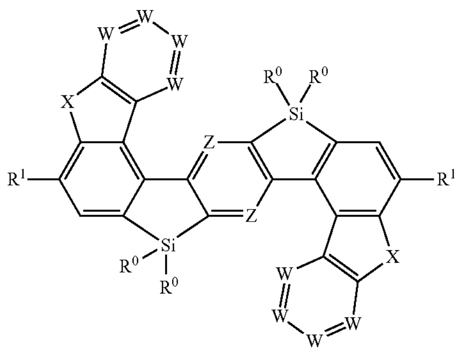
-continued
formula (1-2c)
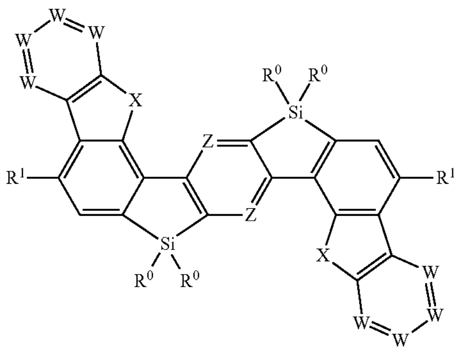
formula (1-3c)
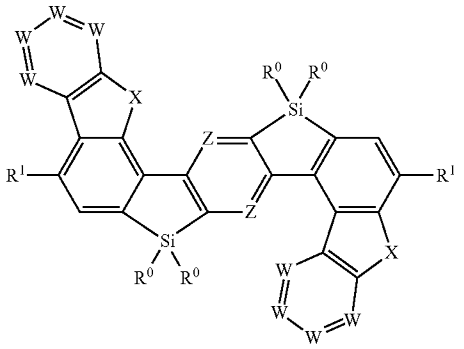
formula (1-4c)
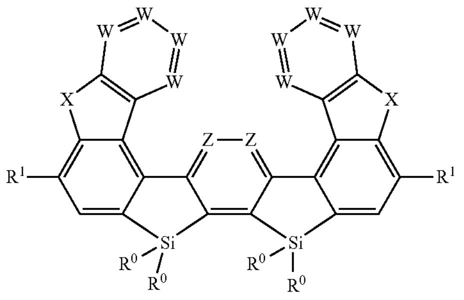
formula (1-5c)
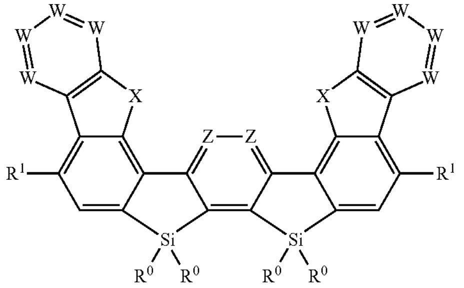

-continued formula (1-6c)

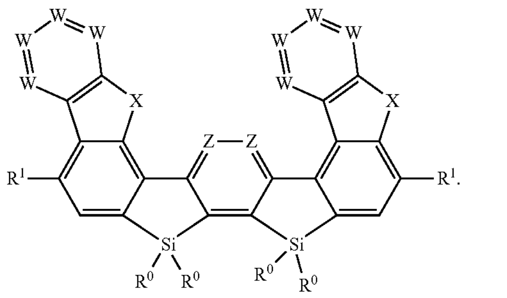

where the symbols X, Z, V, W, $R^1$ and $R^0$ have the same meaning as above

Furthermore, it is preferred that in formulae (1-1 b) to (1-6c), the group $R^1$ stands for an aromatic or heteroaromatic ring system having 5 to 60 aromatic ring atoms, which may in each case be substituted by one or more radicals $R^2$.

Among formulae (1-1b) to (1-6c), formulae (1-1b) to (1-3b) and (1-1c) to (1-3c) are preferred.

In accordance with a very particularly preferred embodiment, compounds of formula (1) are selected from compounds of formulae (1-1d) to (1-6e), formula (1-1d)

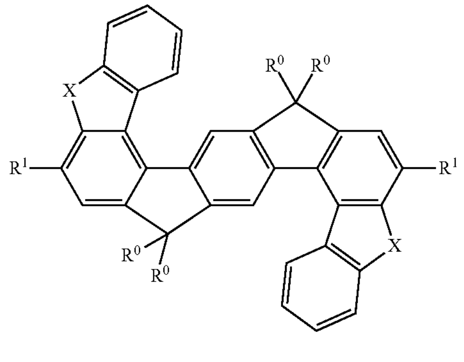

formula (1-2d)

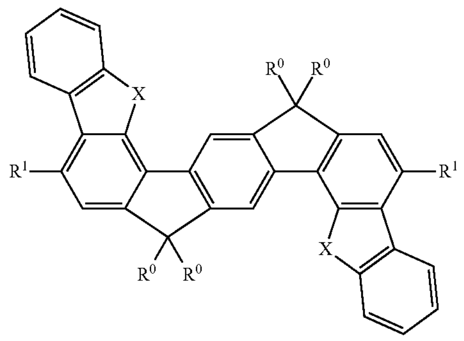

-continued formula (1-3d)

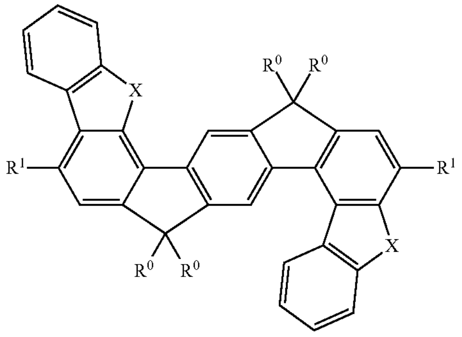

formula (1-4d)

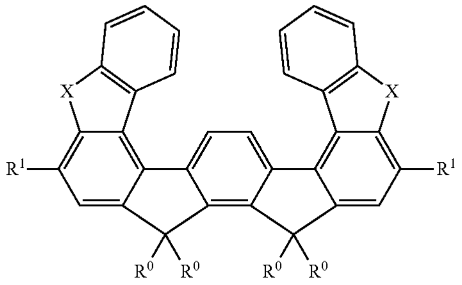

formula (1-5d)

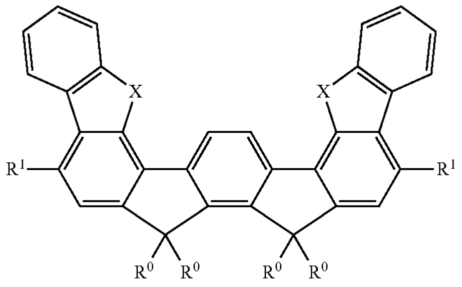

formula (1-6d)

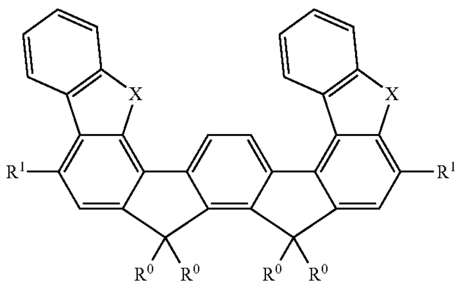

formula (1-1e)

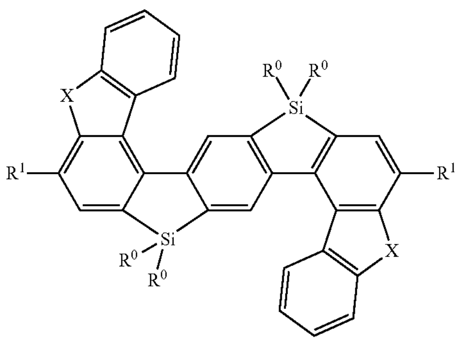

-continued formula (1-2e)

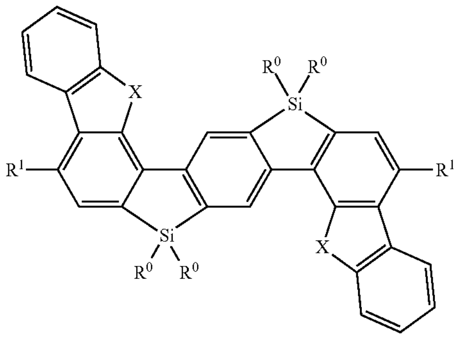

formula (1-3e)

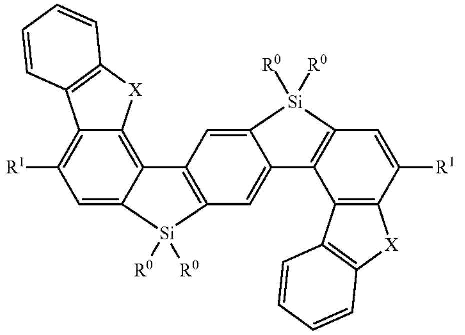

formula (1-4e)

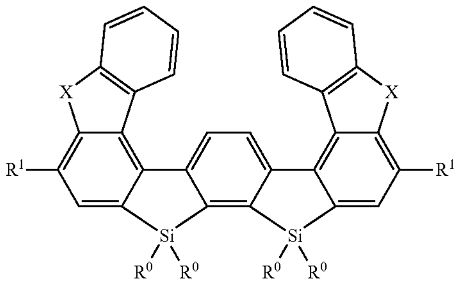

formula (1-5e)

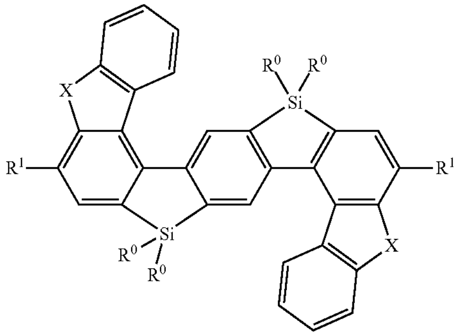

-continued formula (1-6e)

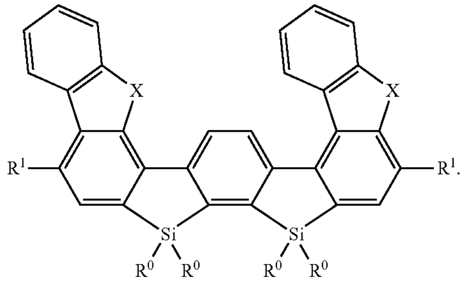

where the symbols X, E, $R^1$ and $R^0$ have the same meaning as in above.

Furthermore, it is preferred that in formulae (1-1d) to (1-6e), the group $R^1$ stands for an aromatic or heteroaromatic ring system having 5 to 60 aromatic ring atoms, which may in each case be substituted by one or more radicals $R^2$.

Among formulae (1-1d) to (1-6e), formulae (1-1d) to (1-3d) and (1-1e) to (1-3e) are preferred.

When the group $R^1$ stands for an aromatic or heteroaromatic ring system, it is preferably selected from the groups of the following formula ($R^1$-1), $$- - -[Ar^3]_n - Ar^4 \qquad (R^1\text{-}1)$$

Where the dashed bond indicates the bonding to the structure;

$Ar^3$, $Ar^4$ are selected on each occurrence, identically or differently, from benzene, naphthalene, anthracene, phenanthrene, biphenyl, terphenyl, fluorene, benzofluorene, spirobifluorene, cis- or trans-indenofluorene, cis- or trans-benzindenofluorene, furan, benzofuran, dibenzofuran, thiophene, benzothiophene, dibenzothiophene, pyrrole, indole, carbazole, indolocarbazole, indenocarbazole, pyridine, quinoline, pyrazole, indazole, imidazole, benzimidazole, pyridazine, benzopyridazine, pyrimidine, benzopyrimidine, pyrazine, quinoxaline, 1,3,5-triazine, 1,2,4-triazine and 1,2,3-triazine, which may in each case be substituted by one or more radicals $R^2$; and n is an integer from 0 to 20, more preferably from 0 to 10, particularly preferably from 0 to 5.

When n is 0, it has to be understood that the group $Ar^3$ is absent and the group $Ar^4$ is directly bonded to the structural unit.

As an example, formula (1-1a) corresponds:

to the following formula (1-1a-1), when $R^1$ stands for a group of formula ($R^1$-1), where n is equal to 0;

to the following formula (1-1a-2), when $R^1$ stands for a group of formula ($R^1$-1), where n is equal to 1;

to the following formula (1-1a-3), when $R^1$ stands for a group of formula ($R^1$-1), where n is equal to 2, formula (1-1a-1)

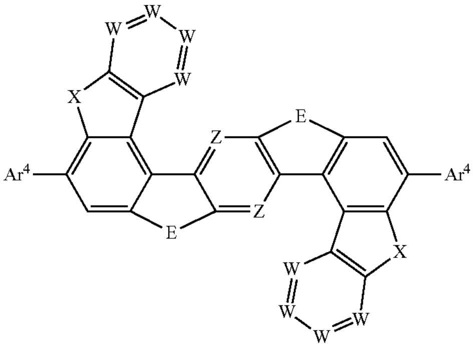

formula (1-1a-2)

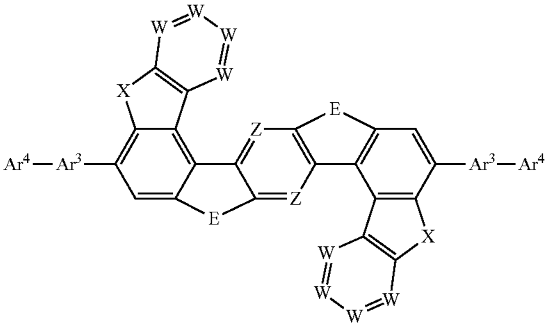

formula (1-1a-3)

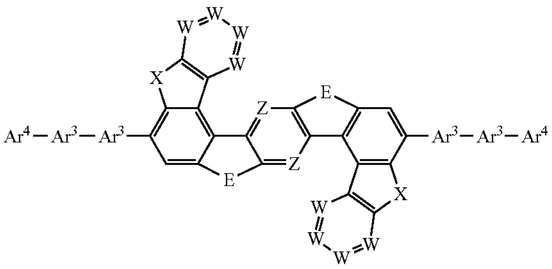

The groups $Ar^3$ and $Ar^4$ are preferably selected on each occurrence, identically or differently, from benzene, naphthalene, anthracene, phenanthrene, biphenyl, terphenyl, fluorene, benzofluorene, spirobifluorene, cis- or trans-indenofluorene, cis- or trans-benzindenofluorene, furan, benzofuran, dibenzofuran, thiophene, benzothiophene, dibenzothiophene, pyrrole, indole, carbazole, indolocarbazole and indenocarbazole, which may in each case be substituted by one or more radicals $R^2$.

In accordance with a preferred embodiment, $Ar^3$ is, when present, selected from one of the formulae (Ar3-1) to (Ar3-25), (Ar3-1)

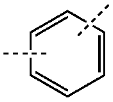

-continued (Ar3-2)

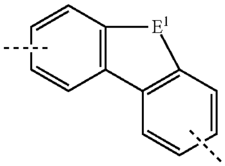

(Ar3-3)

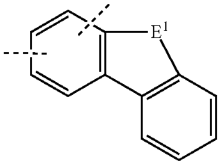

(Ar3-4)

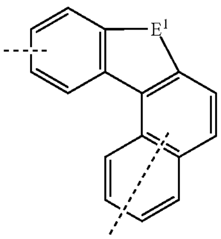

(Ar3-5)

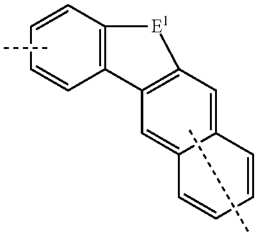

(Ar3-6)

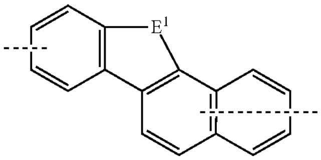

(Ar3-7)

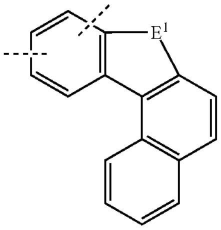

(Ar3-8)

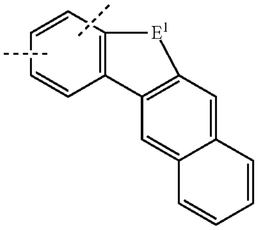

-continued
(Ar3-9)
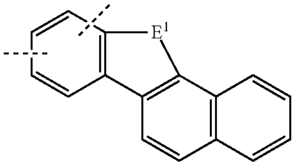
(Ar3-10)
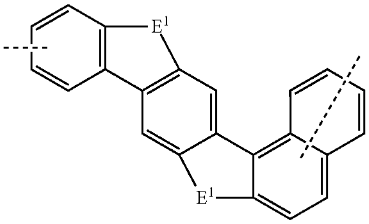
(Ar3-11)
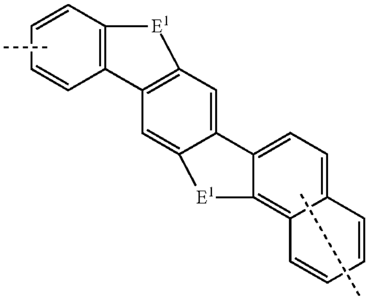
(Ar3-12)
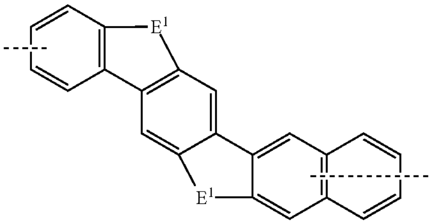
(Ar3-13)
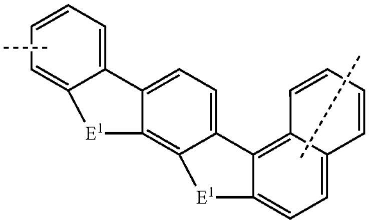
(Ar3-14)
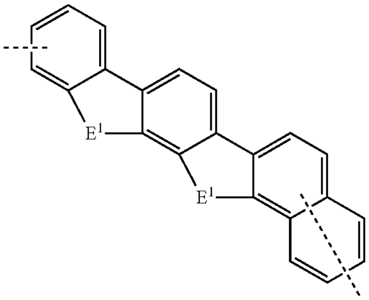
-continued
(Ar3-15)
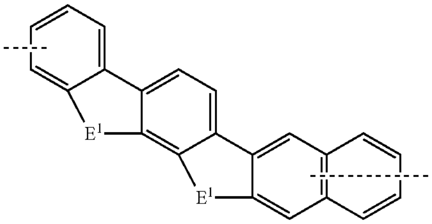
(Ar3-16)
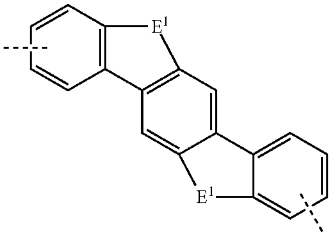
(Ar3-17)
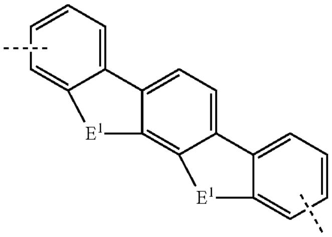
(Ar3-18)
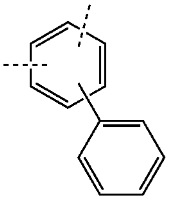
(Ar3-19)
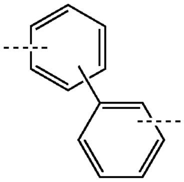
(Ar3-20)
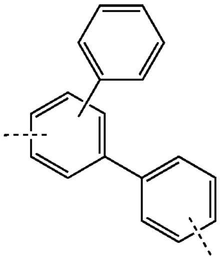
(Ar3-21)
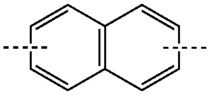
(Ar3-22)
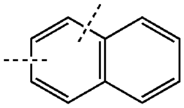

-continued (Ar3-23)

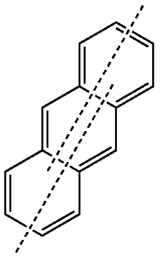

(Ar3-24)

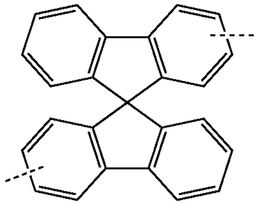

(Ar3-25)

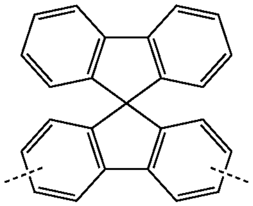

where the dashed bonds indicate the bonding to the structural unit of formula (1) and to a group $Ar^3$ or $Ar^4$, and where the groups of formulae (Ar3-1) to (Ar3-25) may be substituted at each free position by a group $R^2$, which has the same meaning as above, and where $E^1$, in formulae (Ar3-2) to (Ar3-17), is selected from $—B(R^0—)$, $—C(R^0)_2—$, $—C(R^0)_2—C(R^0)_2^-$, $—Si(R^0)_2—$, $—C(=O)—$, $—C(=NR^0)—$, $—C=(C(R^0))_2^-$, $—O—$, $—S—$, $—S(=O)—$, $—SO_2—$, $—N(R^0)—$, $—P(R^0)—$ and $—P((=O)R^0)—$, where the substituent $R^0$ has the same meaning as above.

Preferably, $E^1$ is selected from $—C(R^0)_2—$, $—C(R^0)_2—C(R^0)_2—$, $—O—$, $—S—$ and $—N(R^0)—$, where the substituent $R^0$ has the same meaning as above. Very preferably, $E^1$ stands for $—C(R^0)_2—$.

Among formulae (Ar3-1) to (Ar3-25), formulae (Ar3-1), (Ar3-2), (Ar3-4), (Ar3-10), (Ar3-13), (Ar3-16), (Ar3-19) and (Ar3-22) are preferred. Formulae (Ar3-1), (Ar3-2), (Ar3-4) and (Ar3-19) are particularly preferred.

In accordance with a very preferred embodiment, $Ar^3$ is selected from one of the formulae (Ar3-1-1) to (Ar3-25-3), (Ar3-1-1)

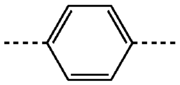

(Ar3-1-2)

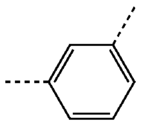

-continued (Ar3-2-1)

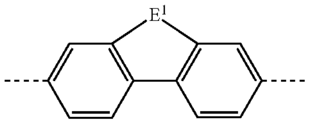

(Ar3-2-2)

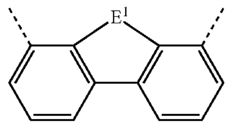

(Ar3-2-3)

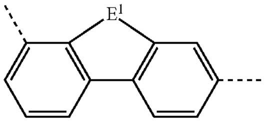

(Ar3-3-1)

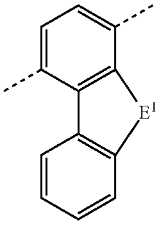

(Ar3-3-2)

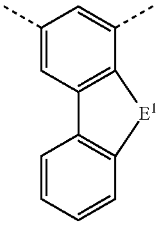

(Ar3-4-1)

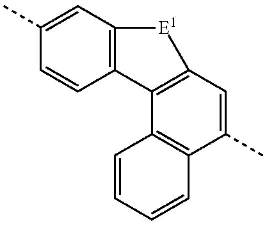

(Ar3-5-1)

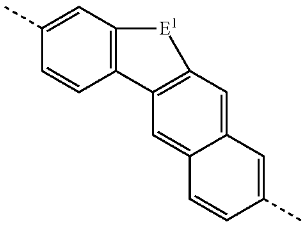

(Ar3-6-1)

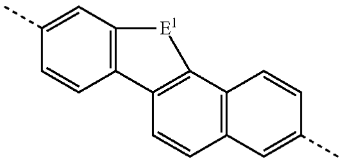

-continued
(Ar3-7-1)
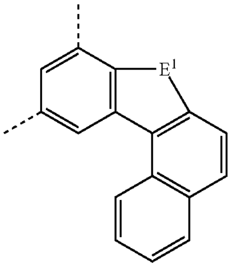
(Ar3-8-1)
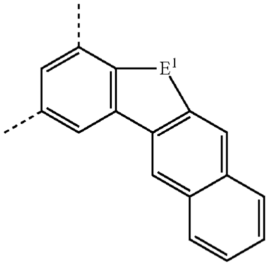
(Ar3-9-1)
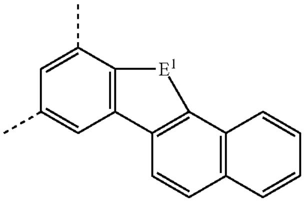
(Ar3-10-1)
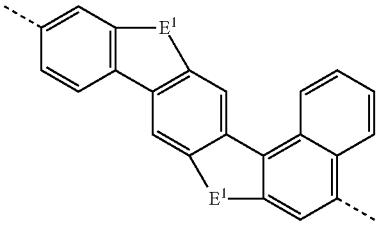
(Ar3-11-1)
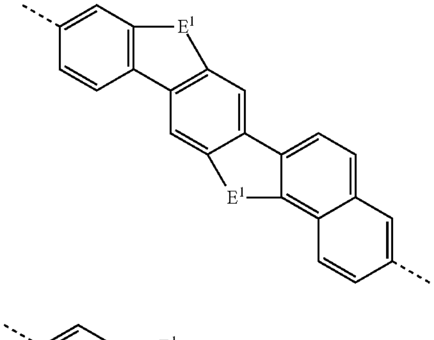
(Ar3-12-1)
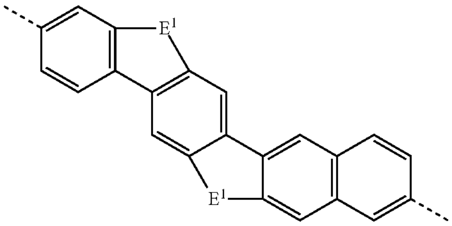
-continued
(Ar3-13-1)
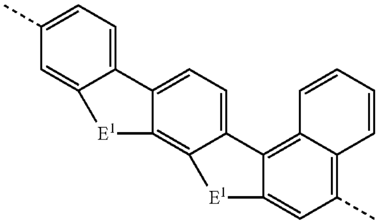
(Ar3-14-1)
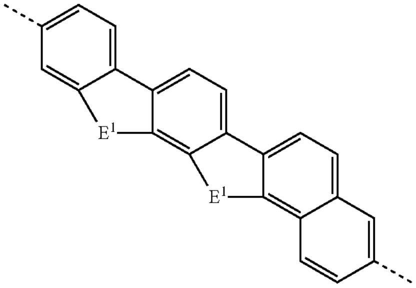
(Ar3-15-1)
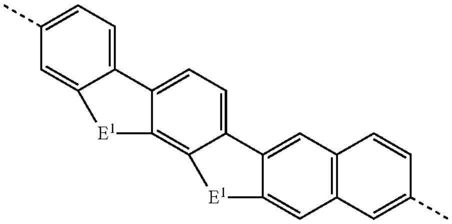
(Ar3-16-1)
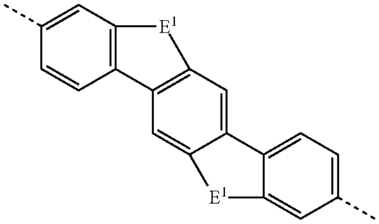
(Ar3-17-1)
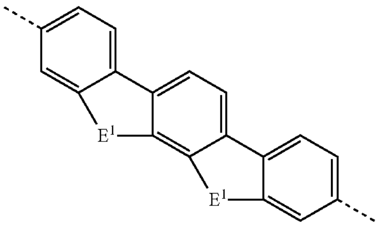
(Ar3-18-1)
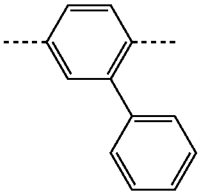

-continued
(Ar3-18-2)
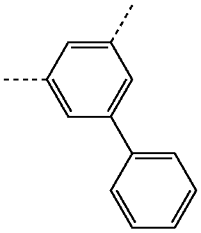
(Ar3-19-1)
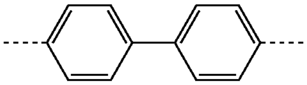
(Ar3-19-2)
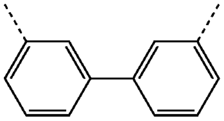
(Ar3-19-3)
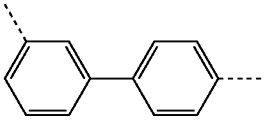
(Ar3-20-1)
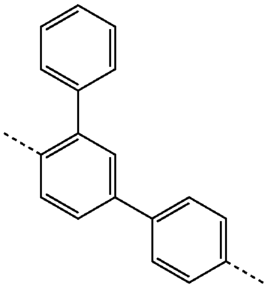
(Ar3-20-2)
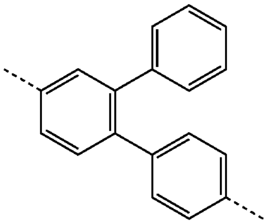
(Ar3-21-1)
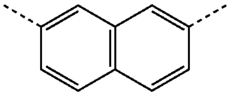
(Ar3-21-2)
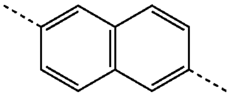
(Ar3-22-1)
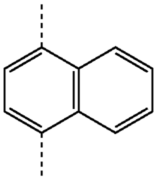
-continued
(Ar3-22-2)
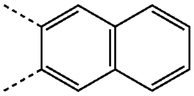
(Ar3-23-1)
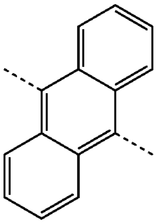
(Ar3-23-2)
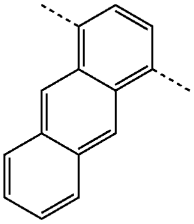
(Ar3-23-3)
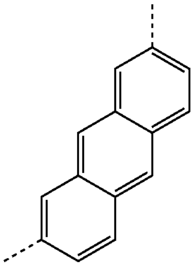
(Ar3-24-1)
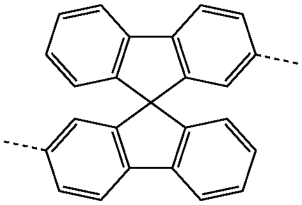
(Ar3-24-2)
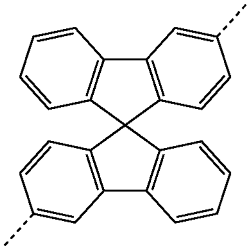
(Ar3-25-1)
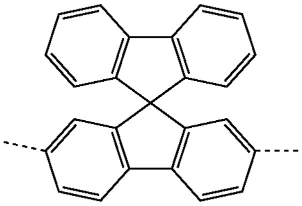

-continued (Ar3-25-2)

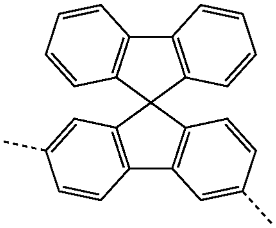

(Ar3-25-3)

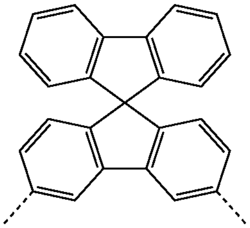

where the dashed bonds indicate the bonding to the structural unit of formula (1) and to a group $Ar^3$ or $Ar^4$, and where the groups of formulae (Ar3-1-1) to (Ar3-25-3) may be substituted at each free position by a group $R^2$, which has the same meaning as above, and where $E^1$ has the same meaning as above.

Among formulae (Ar3-1-1) to (Ar3-25-3), formulae (Ar3-1-1), (Ar3-2-1), (Ar3-4-1), (Ar3-10-1), (Ar3-13-1), (Ar3-16-1), (Ar3-19-1) and (Ar3-22-1) are preferred. Formulae (Ar3-1-1), (Ar3-2-1) and (Ar3-4-1) and (Ar3-19-1) are particularly preferred.

In accordance with a preferred embodiment, $Ar^4$ is selected from one of the formulae (Ar4-1) to (Ar4-27), (Ar4-1)

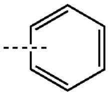

(Ar4-2)

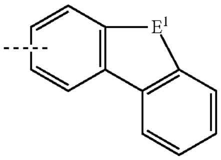

(Ar4-3)

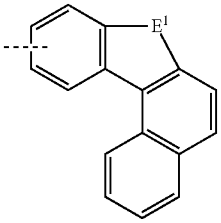

(Ar4-4)

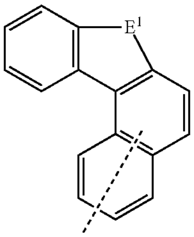

-continued (Ar4-5)

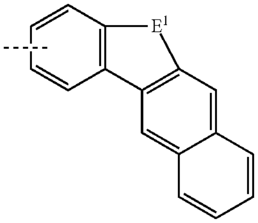

(Ar4-6)

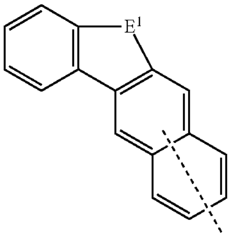

(Ar4-7)

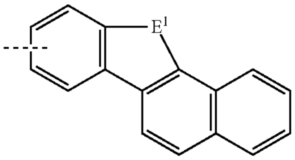

(Ar4-8)

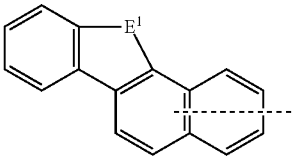

(Ar4-9)

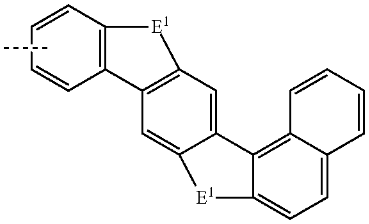

(Ar4-10)

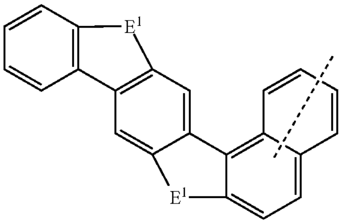

(Ar4-11)

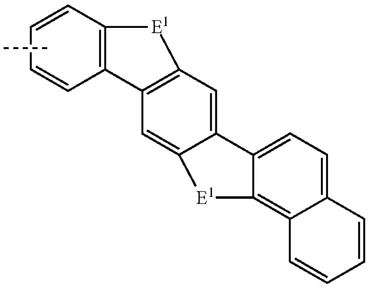

-continued
(Ar4-12)
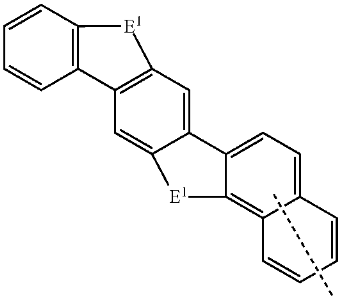
(Ar4-13)
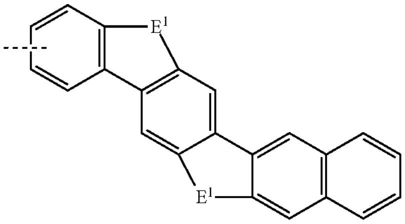
(Ar4-14)
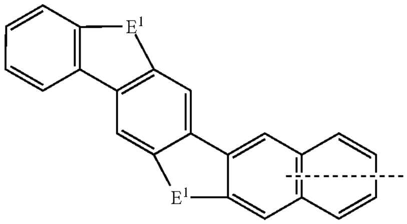
(Ar4-15)
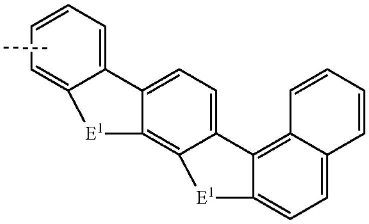
(Ar4-16)
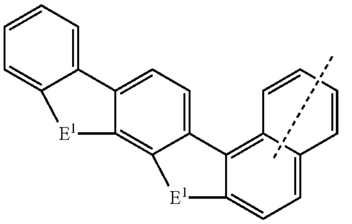
(Ar4-17)
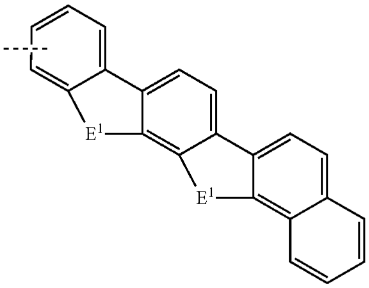
-continued
(Ar4-18)
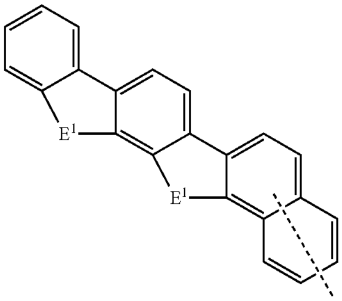
(Ar4-19)
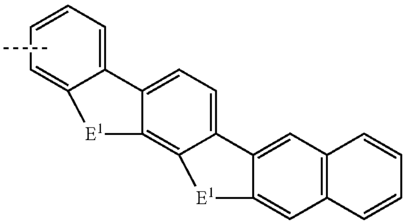
(Ar4-20)
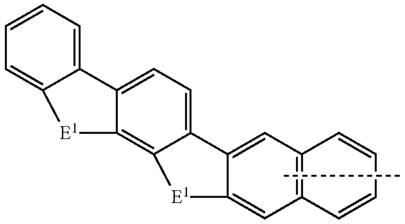
(Ar4-21)
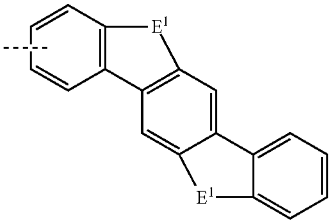
(Ar4-22)
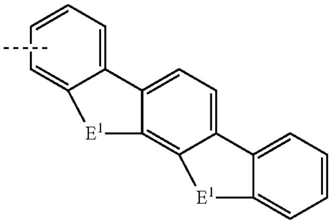
(Ar4-23)
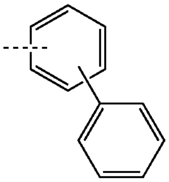

-continued (Ar4-24)

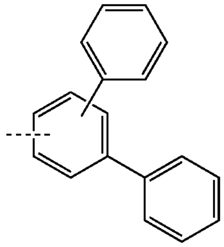

(Ar4-25)

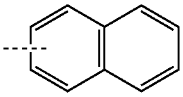

(Ar4-26)

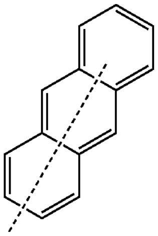

(Ar4-27)

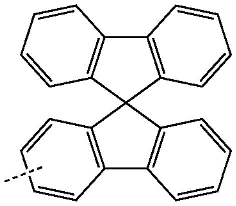

where the dashed bond indicates the bonding to the structural unit of formula (1) or $Ar^3$, where $E^1$ has the same meaning as above, and where the groups of formulae (Ar4-1) to (Ar4-27) may be substituted at each free position by a group $R^2$, which has the same meaning as above.

Among formulae (Ar4-1) to (Ar4-27), formulae (Ar4-1), (Ar4-2), (Ar4-3), (Ar4-9), (Ar4-15), (Ar4-23), and (Ar4-25) are preferred. Formulae (Ar4-1), (Ar4-2) and (Ar4-3) are particularly preferred.

In accordance with a very preferred embodiment, $Ar^4$ is selected from one of the formulae (Ar4-1-1) to (Ar4-27-3), (Ar4-1-1)

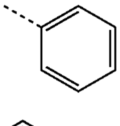

(Ar4-2-1)

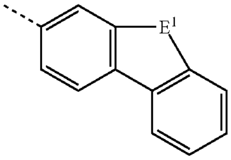

-continued (Ar4-2-2)

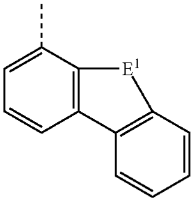

(Ar4-2-3)

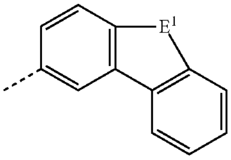

(Ar4-3-1)

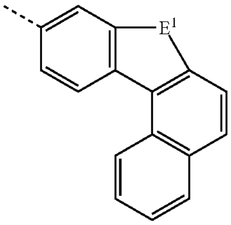

(Ar4-3-2)

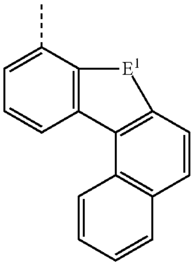

(Ar4-3-3)

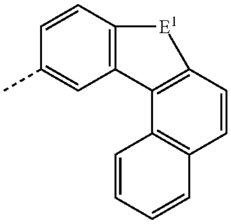

(Ar4-4-1)

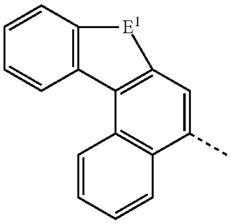

(Ar4-5-1)

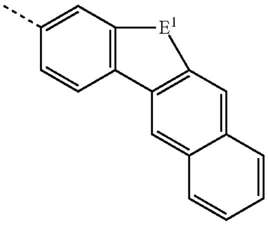

-continued
(Ar4-6-1)
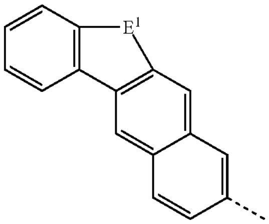
(Ar4-7-1)
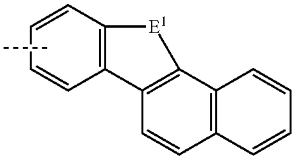
(Ar4-8-1)
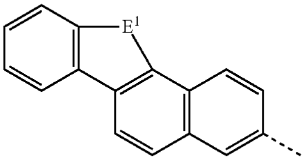
(Ar4-9-1)
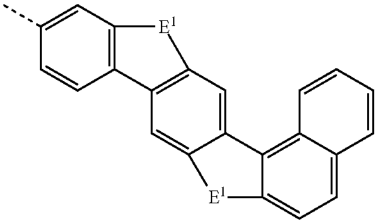
(Ar4-10-1)
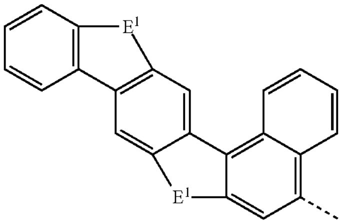
(Ar4-11-1)
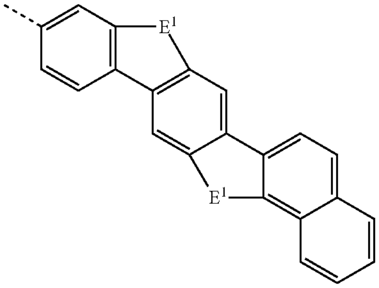
(Ar4-12-1)
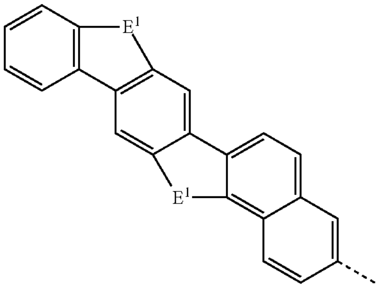
-continued
(Ar4-13-1)
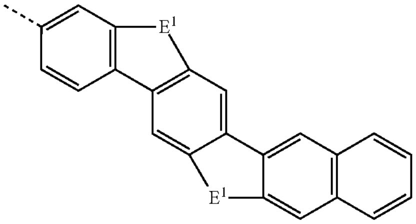
(Ar4-14-1)
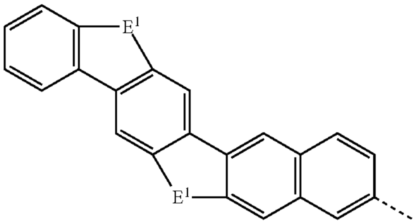
(Ar4-15-1)
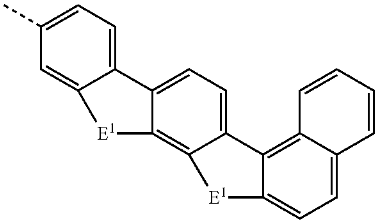
(Ar4-16-1)
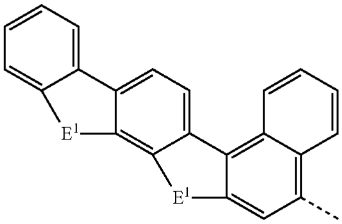
(Ar4-17-1)
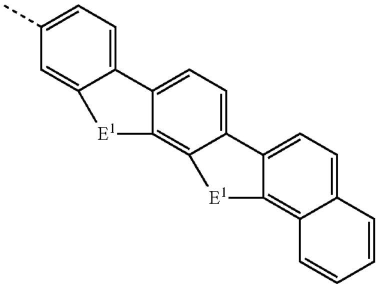
(Ar4-18-1)
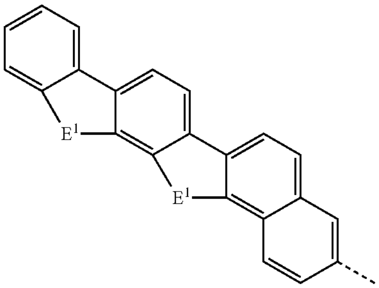

-continued
(Ar4-19-1)
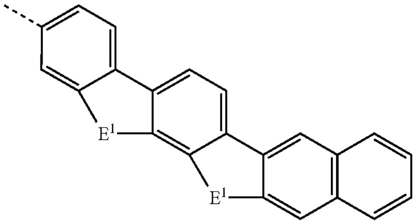
(Ar4-20-1)
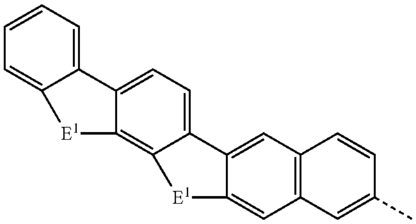
(Ar4-21-1)
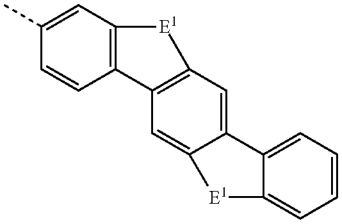
(Ar4-22-1)
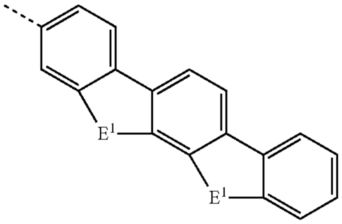
(Ar4-23-1)
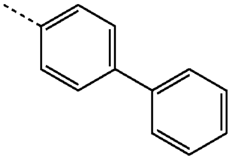
(Ar4-23-2)
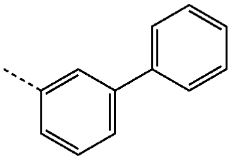
(Ar4-24-1)
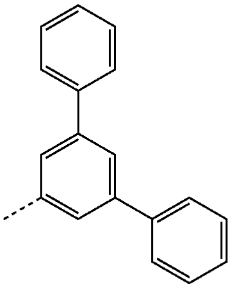
-continued
(Ar4-24-2)
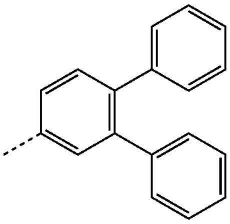
(Ar4-24-3)
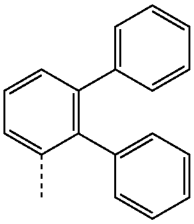
(Ar4-25-1)
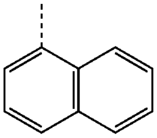
(Ar4-25-2)
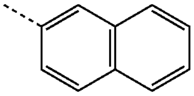
(Ar4-26-1)
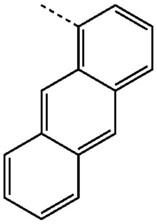
(Ar4-26-2)
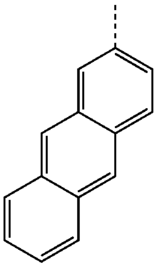
(Ar4-26-3)
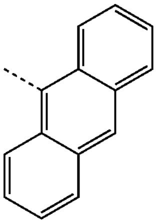

-continued (Ar4-27-1)

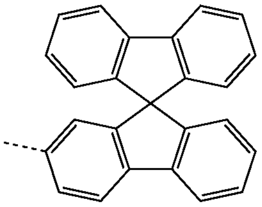

(Ar4-27-2)

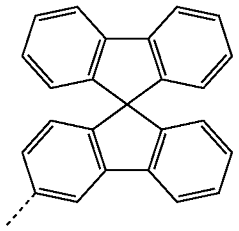

(Ar4-27-3)

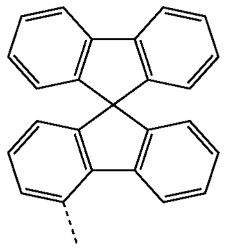

where the dashed bond indicates the bonding to $Ar^3$, where $E^1$ has the same meaning as above, and where the groups of formulae (Ar4-1-1) to (Ar4-27-3) may be substituted at each free position by a group $R^2$, which has the same meaning as above.

Among formulae (Ar4-1-1) to (Ar4-27-3), formulae (Ar4-1-1), (Ar4-2-1), (Ar4-3-1), (Ar4-9-1), (Ar4-15-1), (Ar4-23-1) and (Ar4-25-1) are preferred. Formulae (Ar4-1-1), (Ar4-2-1) and (Ar4-3-1) are particularly preferred.

Preferably, the group X is on each occurrence, identically or differently, selected from O and S. More preferably, X stands on each occurrence for 0.

Preferably, $R^0$ stands on each occurrence, identically or differently, for H, D, F, CN, a straight-chain alkyl groups having 1 to 10 C atoms or a branched or cyclic alkyl groups having 3 to 10 C atoms, each of which may be substituted by one or more radicals $R^2$, where in each case one or more H atoms may be replaced by F, or an aryl or heteroaryl groups having 5 to 25 aromatic ring atoms, which may in each case be substituted by one or more radicals $R^2$, where two adjacent substituents $R^0$ may form a mono- or polycyclic, aliphatic ring system or aromatic ring system, which may be substituted by one or more radicals $R^2$.

When two adjacent substituents $R^0$ form a mono- or polycyclic, aliphatic ring system or aromatic ring system, following rings are preferably formed:

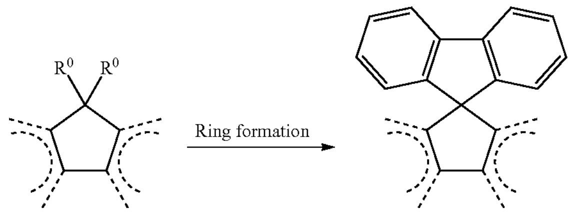

-continued

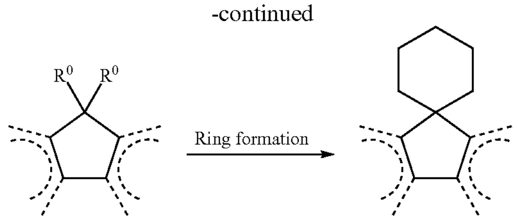

where the dashed bonds indicate the 6-membered rings adjacent to the 5-membered ring comprising the bridge $—C(R^0)_2—$.

In accordance with another preferred embodiment, $R^0$ stands on each occurrence, identically or differently, for H, D, F, CN, a straight-chain alkyl groups having 1 to 10 C atoms or a branched or cyclic alkyl groups having 3 to 10 C atoms, each of which may be substituted by one or more radicals $R^2$, where in each case one or more H atoms may be replaced by F.

In accordance with a preferred embodiment, the compounds of formula (1), (1-1) to (1-18), (1-1a) to (1-6a), (1-1 b) to (1-6b) and (1-1c) to (1-6c) contain at least one group R, $R^0$, $R^1$ or $R^2$, which stands for a straight-chain alkyl group having 2 to 10 C atoms or a branched or cyclic alkyl group having 3 to 10 C atoms.

In accordance with a preferred embodiment, R, $R^1$ stand on each occurrence, identically or differently, for H, D, F, Cl, Br, I, CN, a straight-chain alkyl or alkoxy groups having 1 to 20, preferably 1 to 10 C atoms, or branched or a cyclic alkyl or alkoxy groups having 3 to 20, preferably 3 to 10 C atoms, each of which may be substituted by one or more radicals $R^2$, where in each case one or more non-adjacent $CH_2$ groups may be replaced by $R^2C{=}CR^2$, O or S and where one or more H atoms may be replaced by D or F, an aromatic or heteroaromatic ring systems having 5 to 30, preferably 5 to 20 aromatic ring atoms, which may in each case be substituted by one or more radicals $R^2$, where two adjacent substituents R may form a mono- or polycyclic, aliphatic ring system or aromatic ring system, which may be substituted by one or more radicals $R^2$;

More preferably, $R^1$ is selected on each occurrence, identically or differently, from the group consisting of H, D, F, CN, $Si(R^2)_3$, or an aromatic or heteroaromatic ring system having 5 to 60 aromatic ring atoms, which may in each case be substituted by one or more radicals $R^2$.

In accordance with a preferred embodiment, $R^2$ stands on each occurrence, identically or differently, for H, D, F, Cl, Br, I, CN, $N(Ar)_2$, a straight-chain alkyl or alkoxy groups having 1 to 20, preferably 1 to 10 C atoms, or branched or a cyclic alkyl or alkoxy groups having 3 to 20, preferably 3 to 10 C atoms, each of which may be substituted by one or more radicals $R^3$, where in each case one or more non-adjacent $CH_2$ groups may be replaced by $R^2C{=}CR^2$, O or S and where one or more H atoms may be replaced by D or F, an aromatic or heteroaromatic ring systems having 5 to 30, preferably 5 to 20 aromatic ring atoms, which may in each case be substituted by one or more radicals $R^3$, where two adjacent substituents $R^2$ may form a mono- or polycyclic, aliphatic ring system or aromatic ring system, which may be substituted by one or more radicals $R^3$;

In accordance with a preferred embodiment, Ar is an aromatic or heteroaromatic ring system having 5 to 18 aromatic ring atoms, which may in each case also be substituted by one or more radicals $R^3$.

The following compounds are examples of compounds of the formula (1):
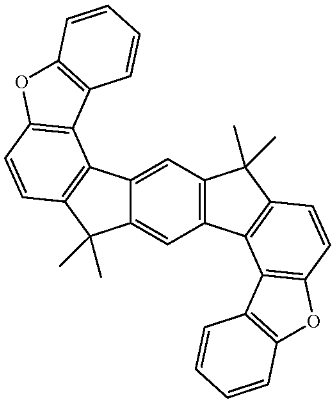
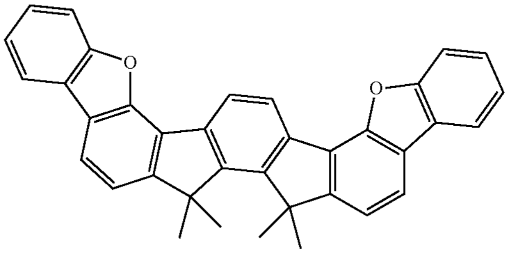
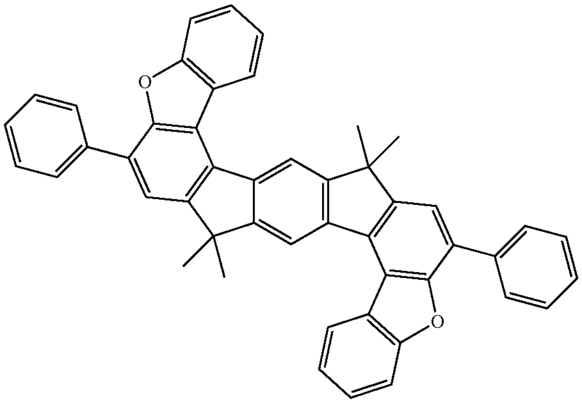
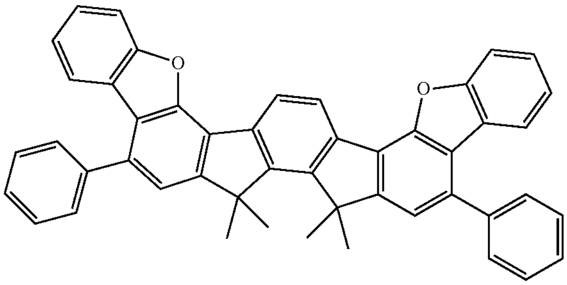
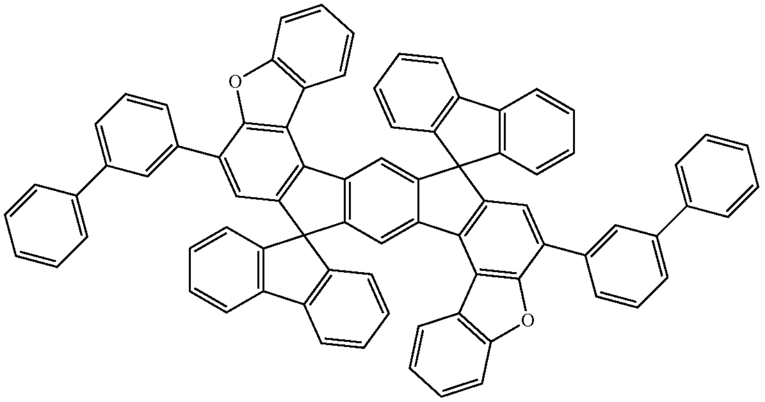
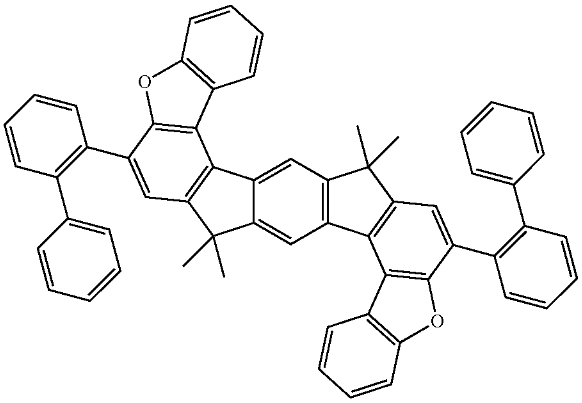
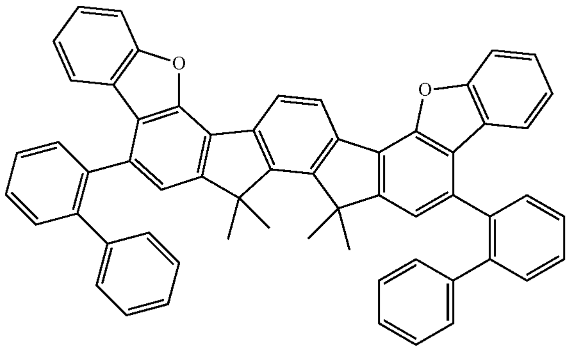

-continued
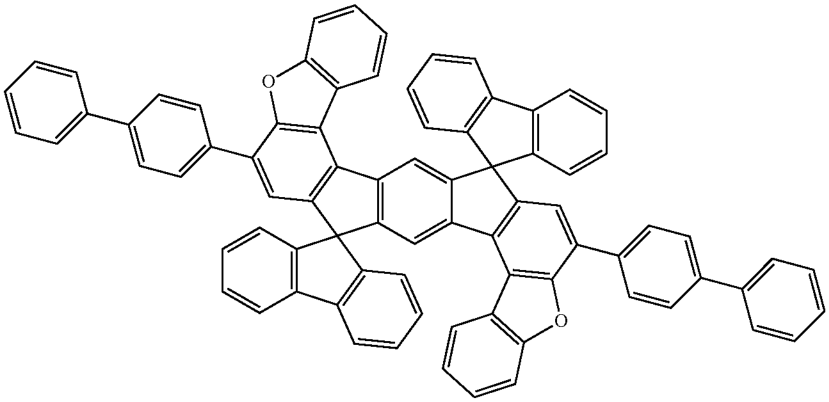
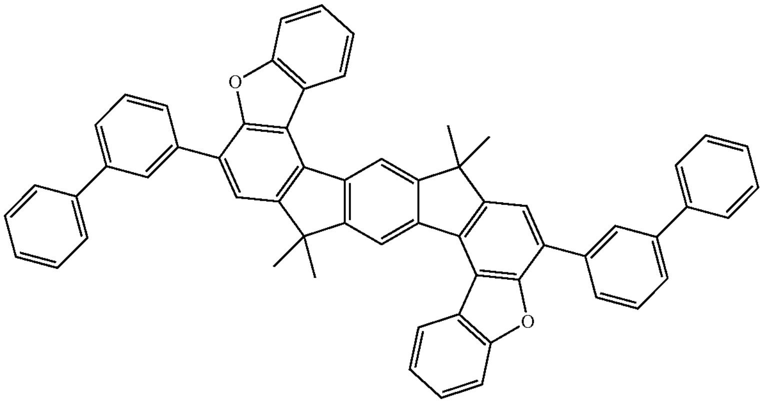
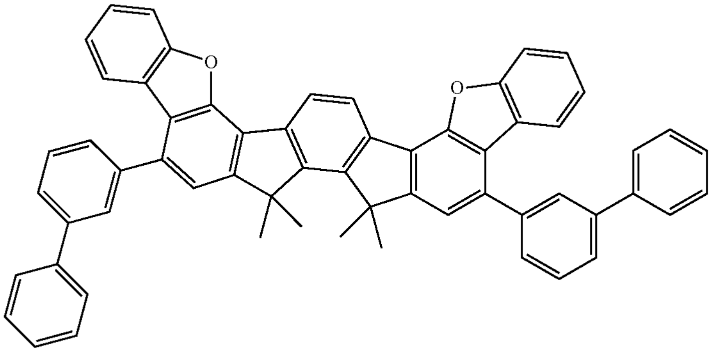
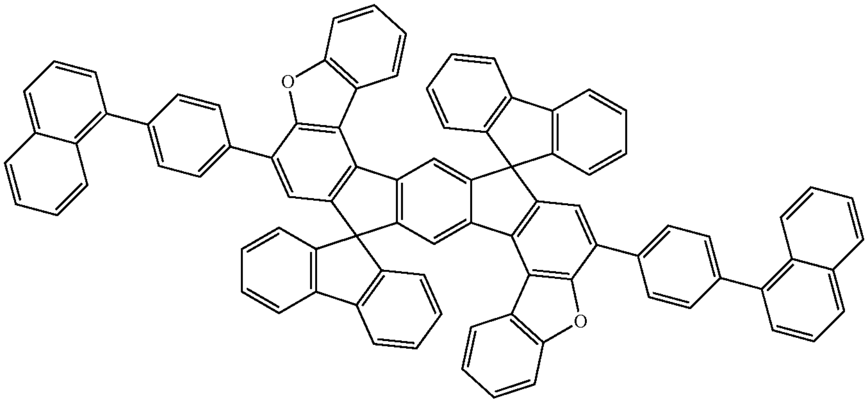

-continued
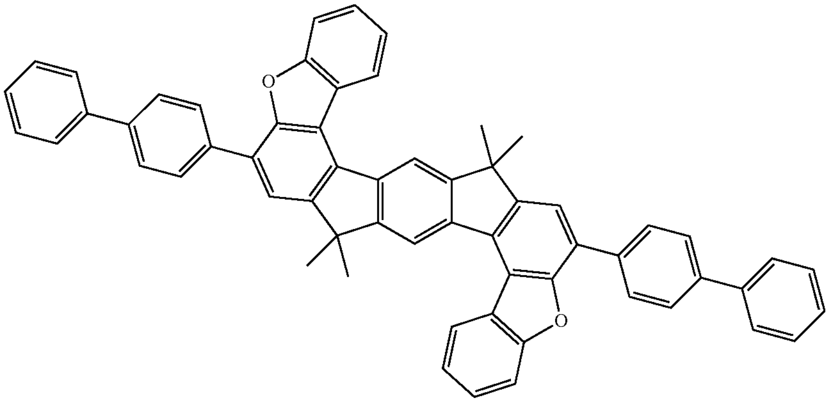
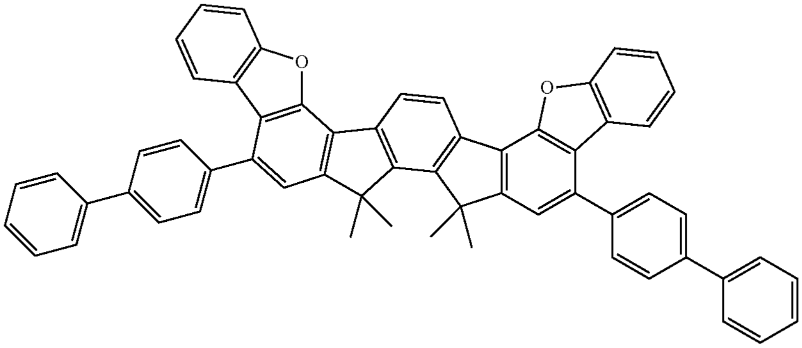
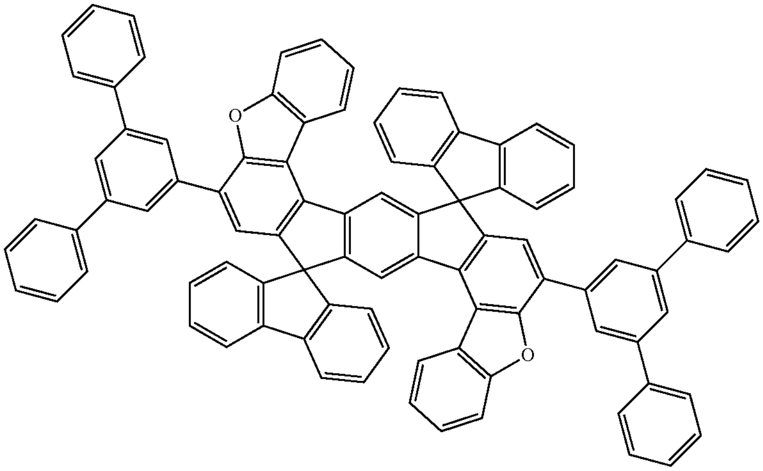
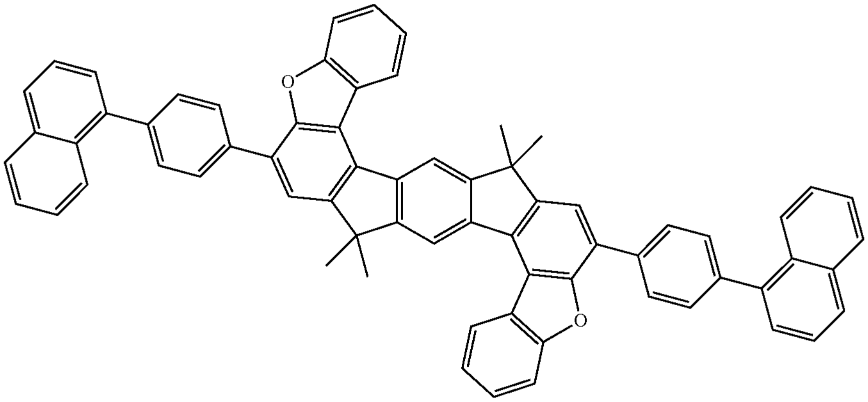

-continued
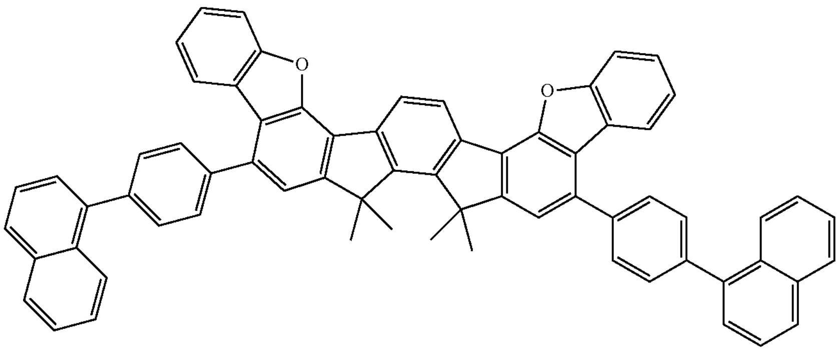
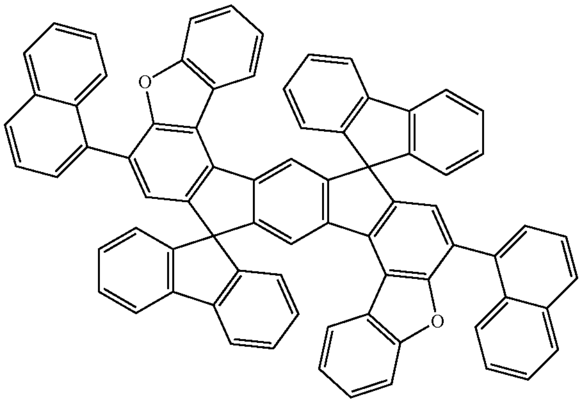
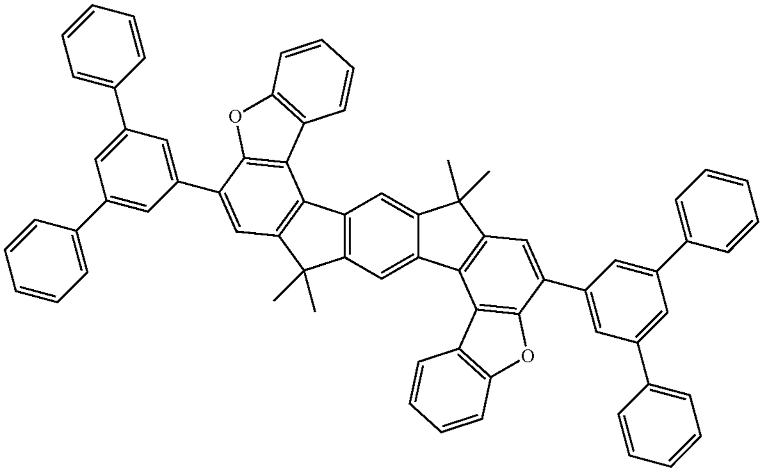
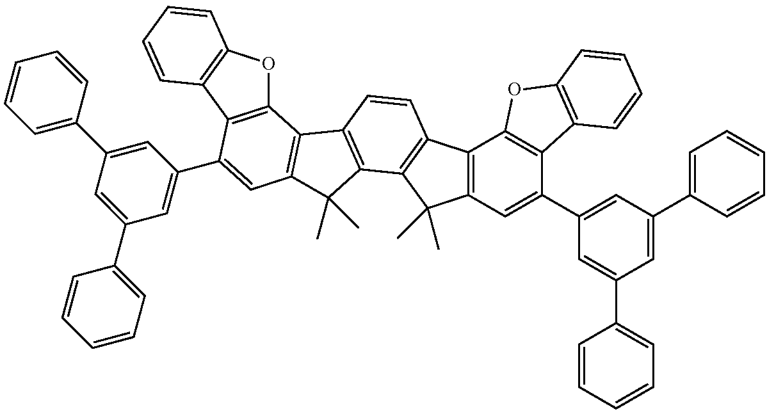

-continued
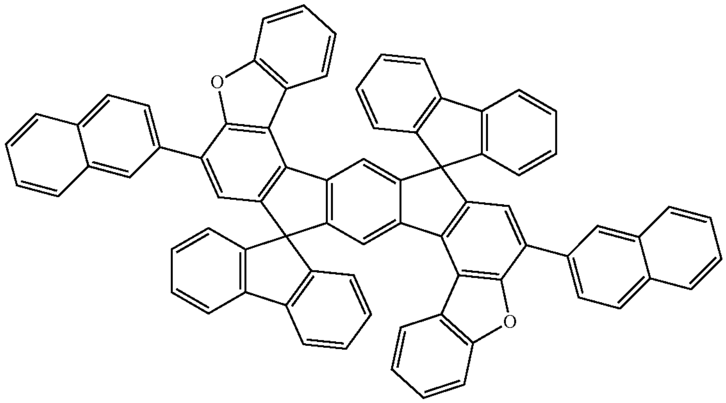
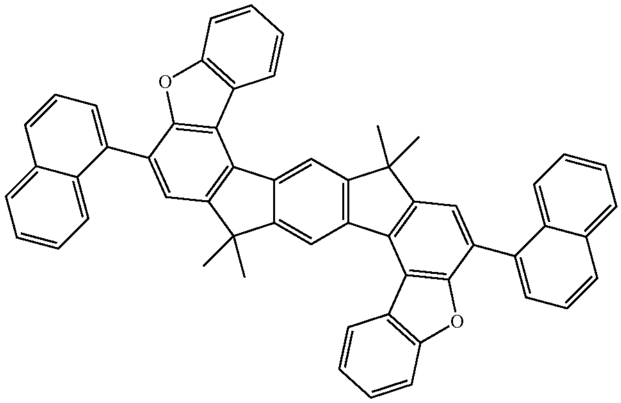
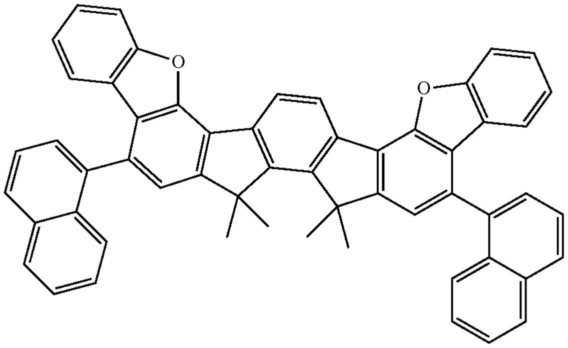
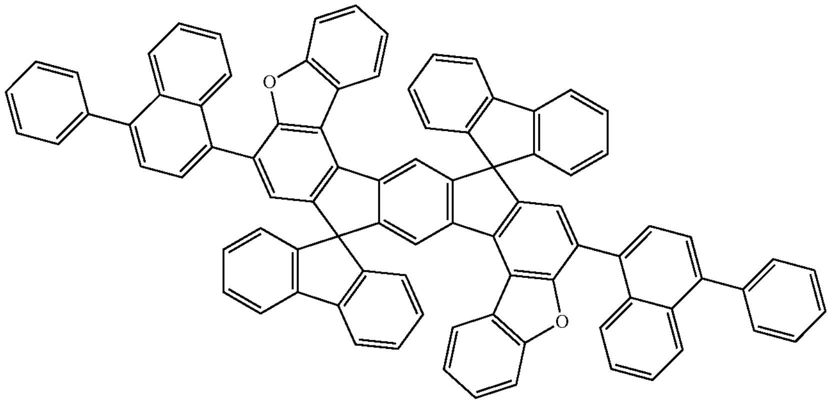
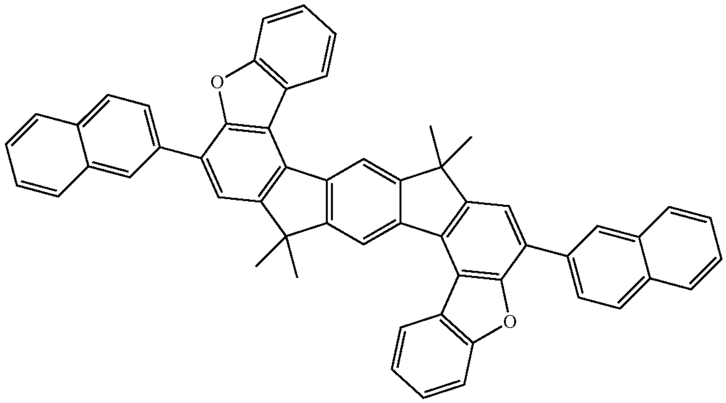

-continued
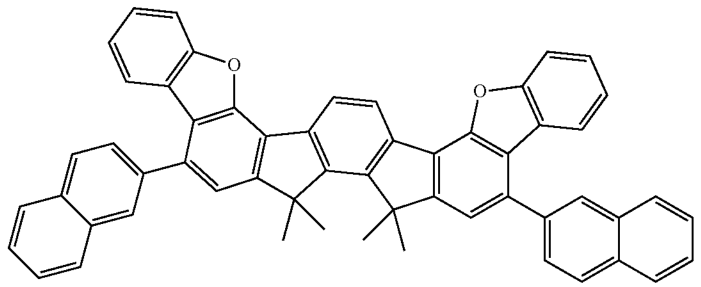
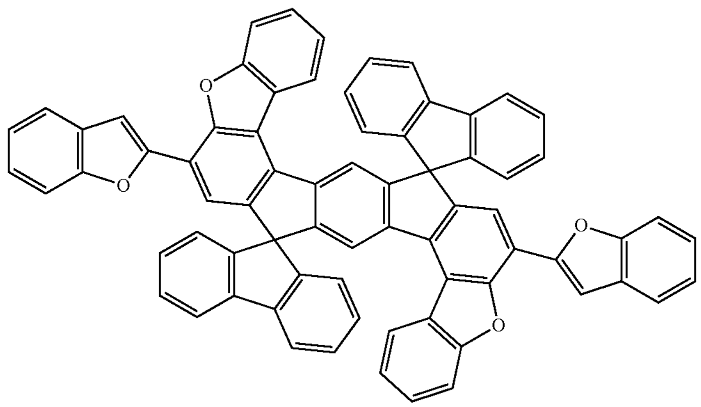
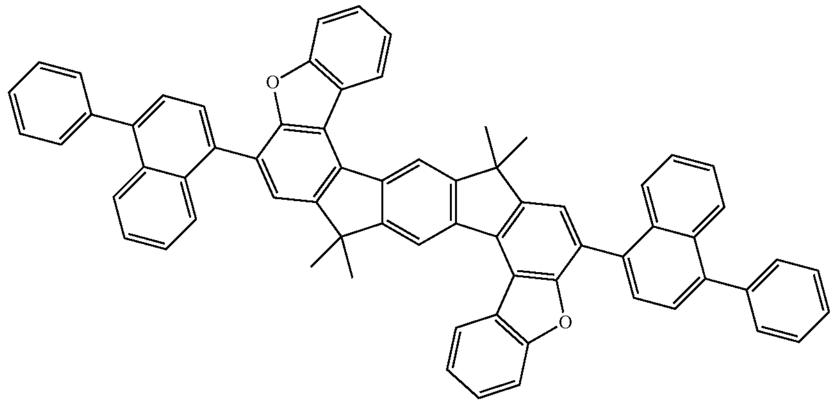
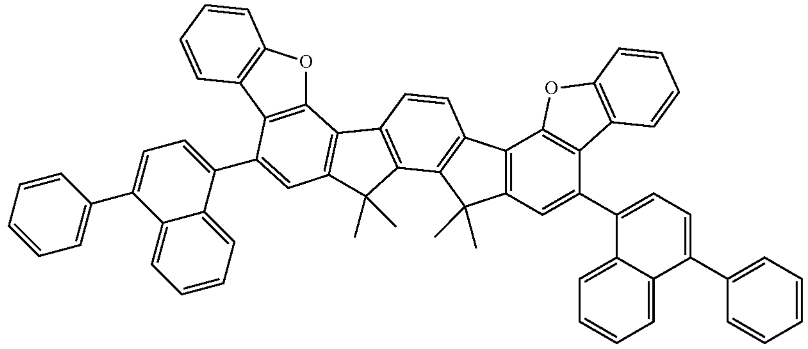

-continued
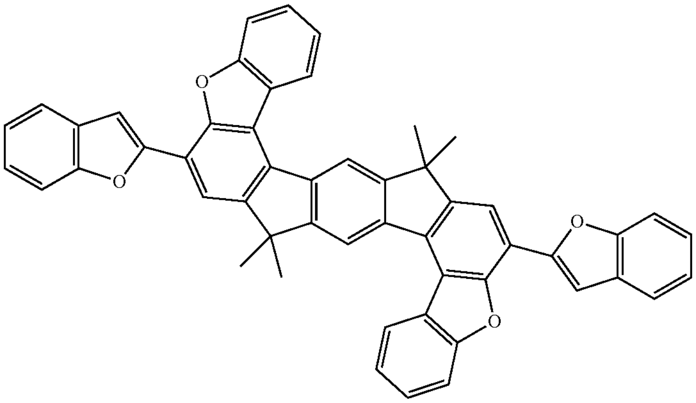
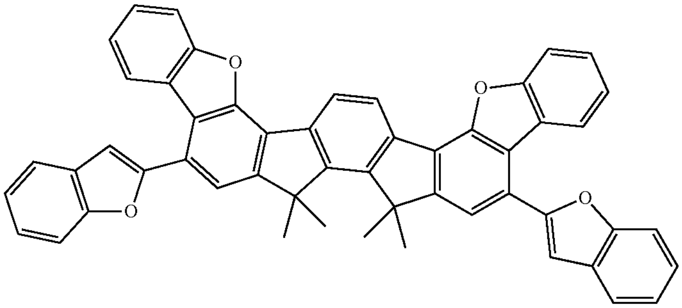
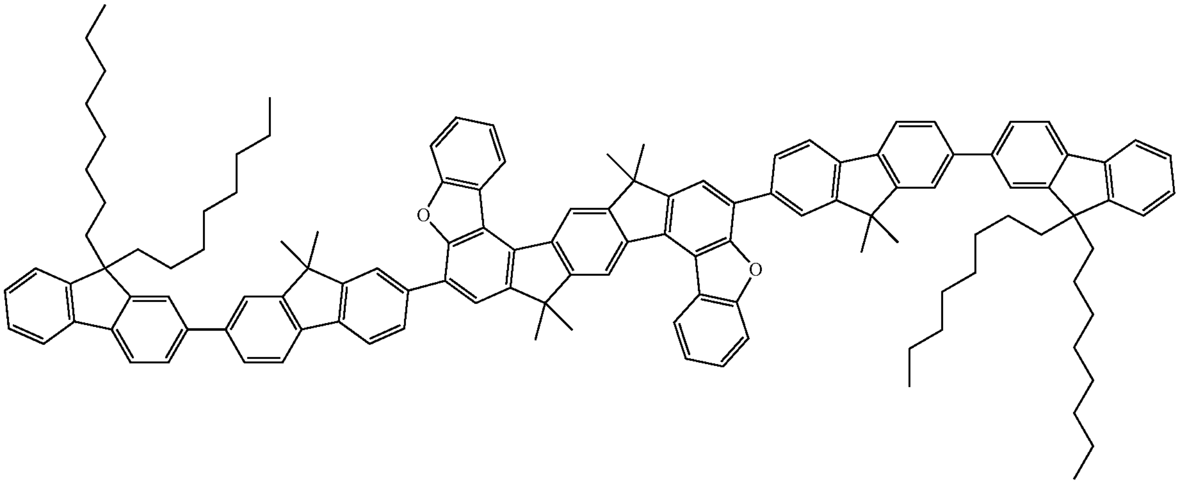
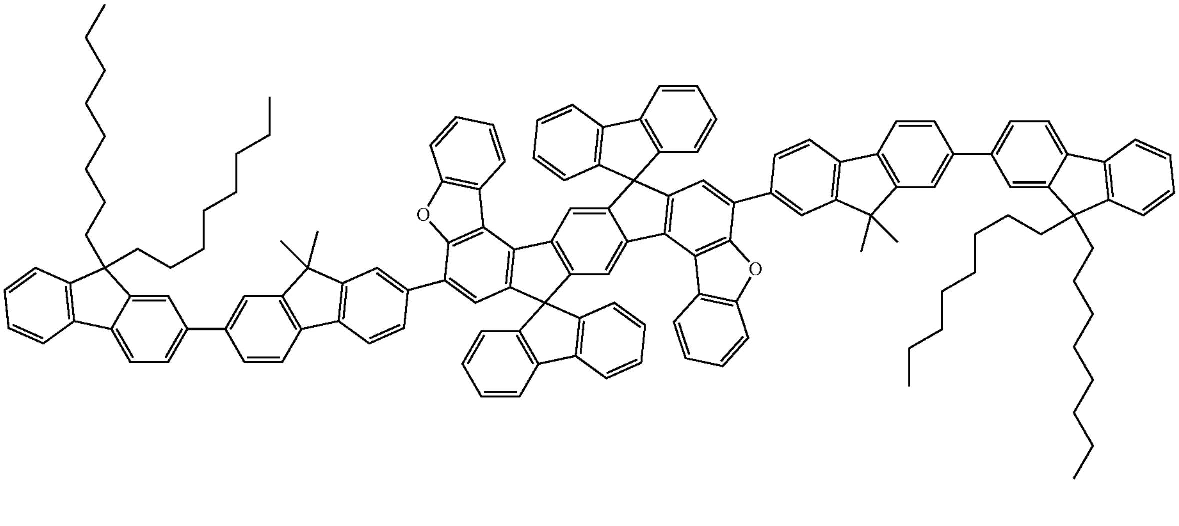

-continued
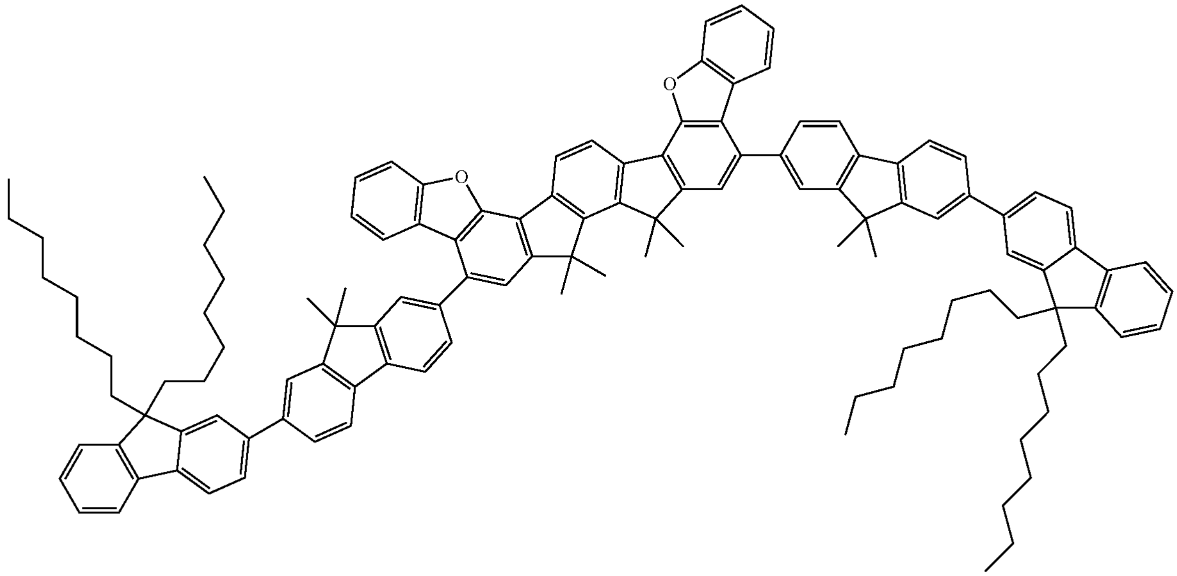
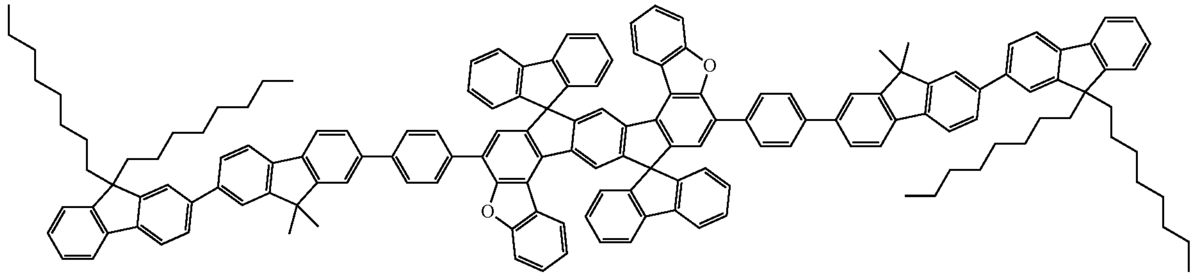
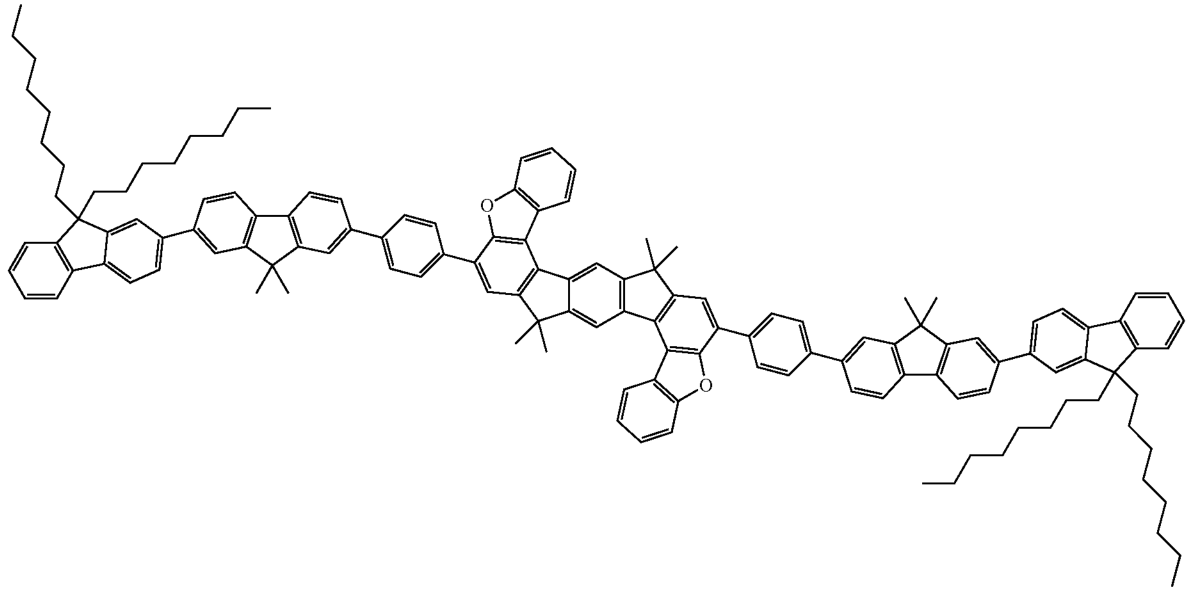

-continued
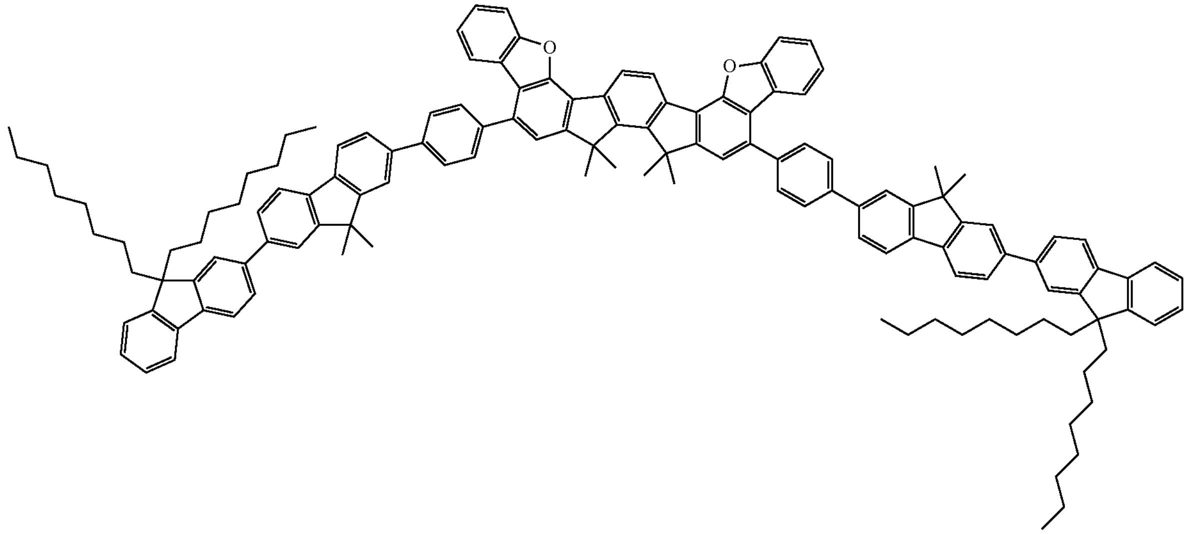
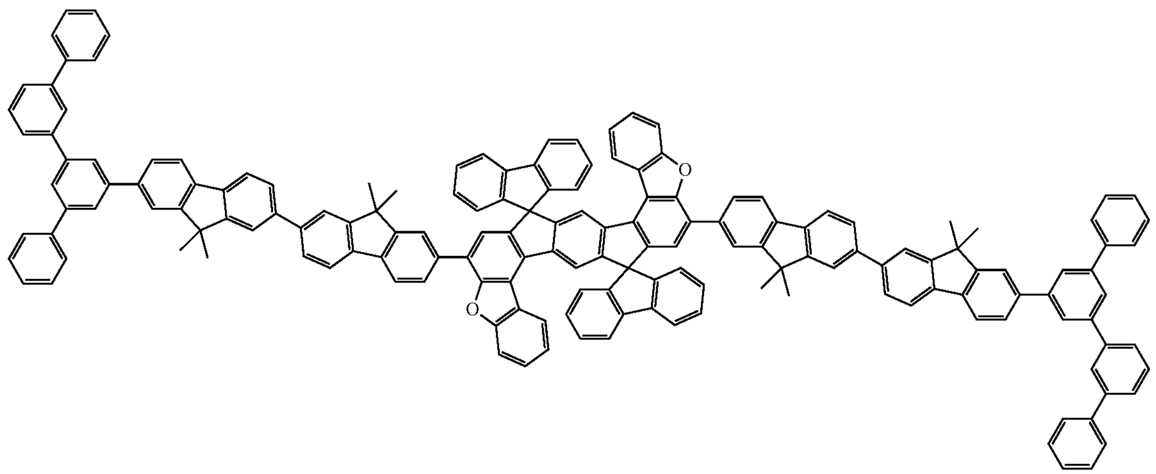
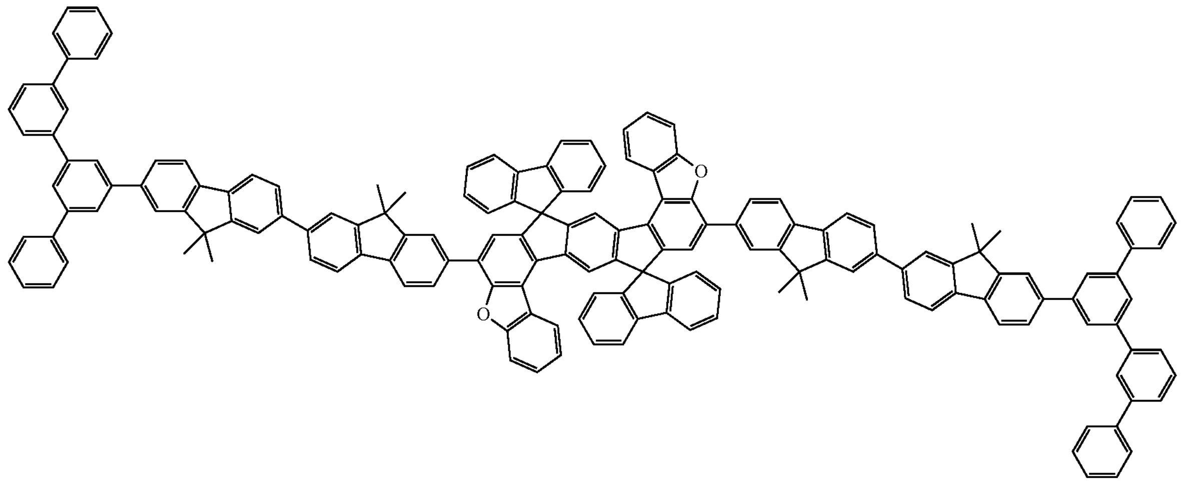

-continued
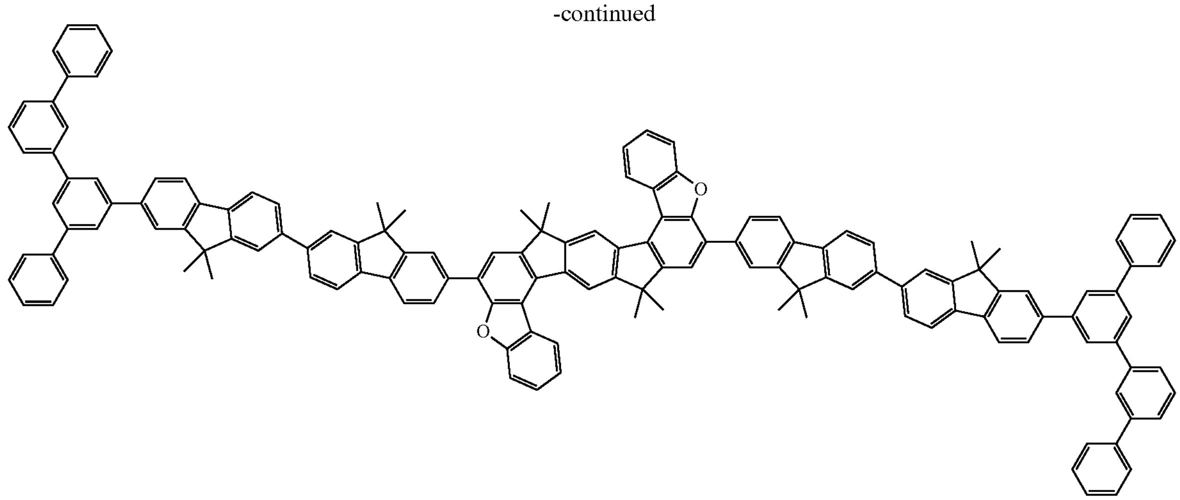
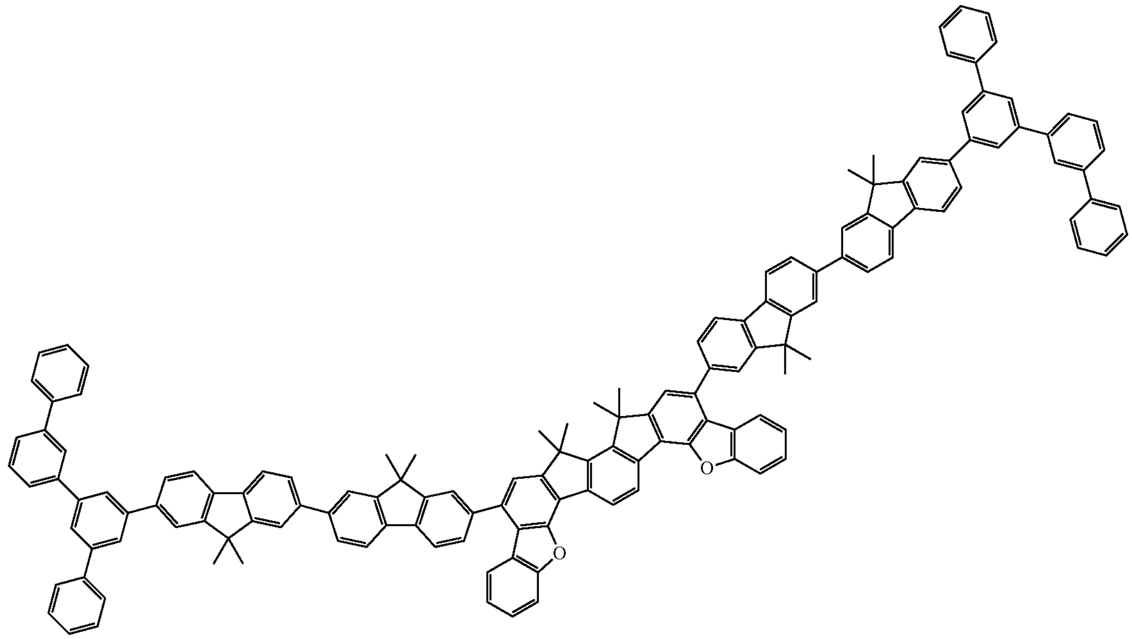
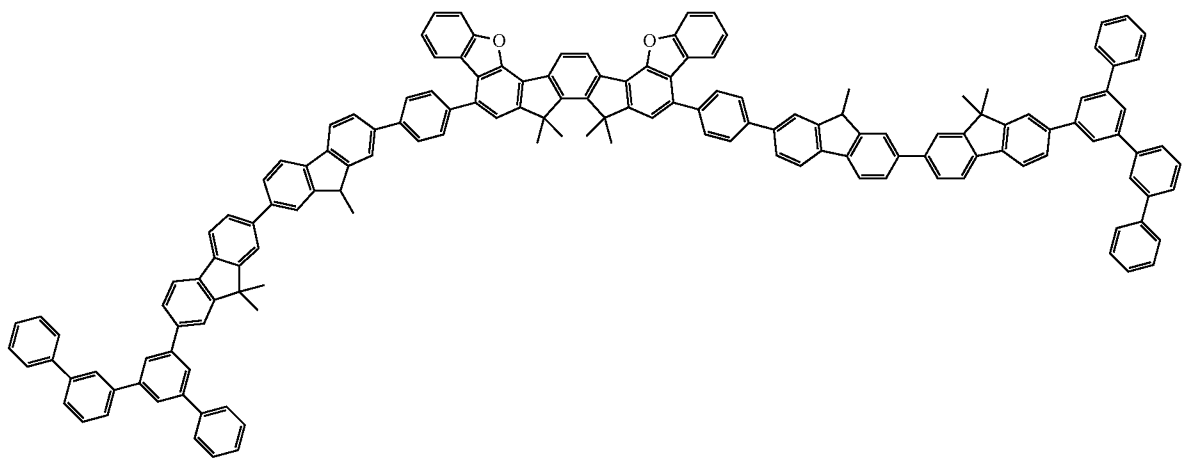

-continued
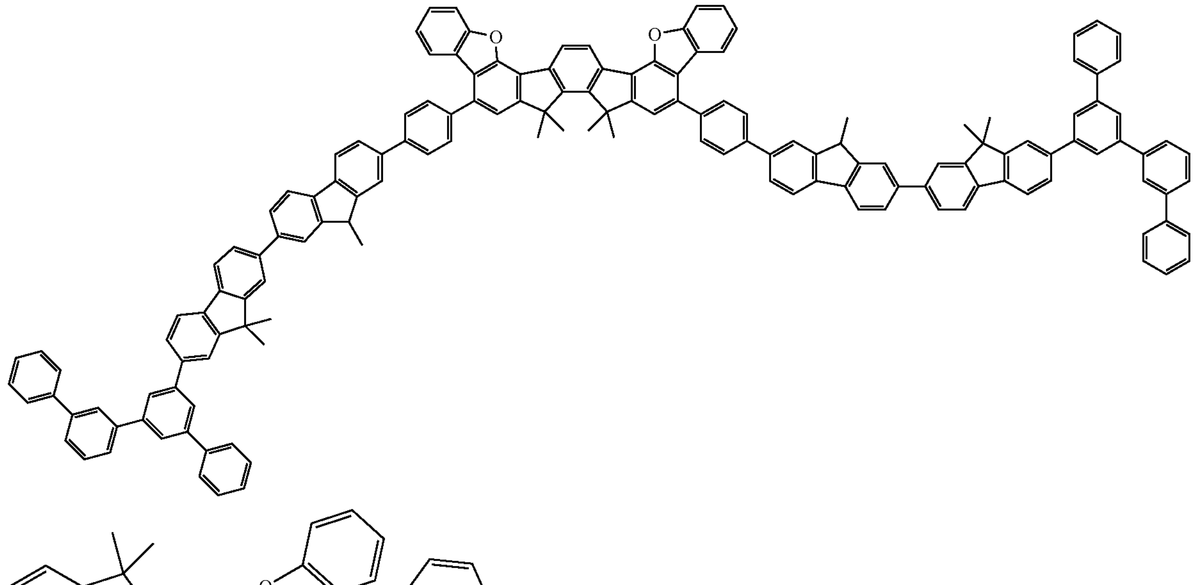
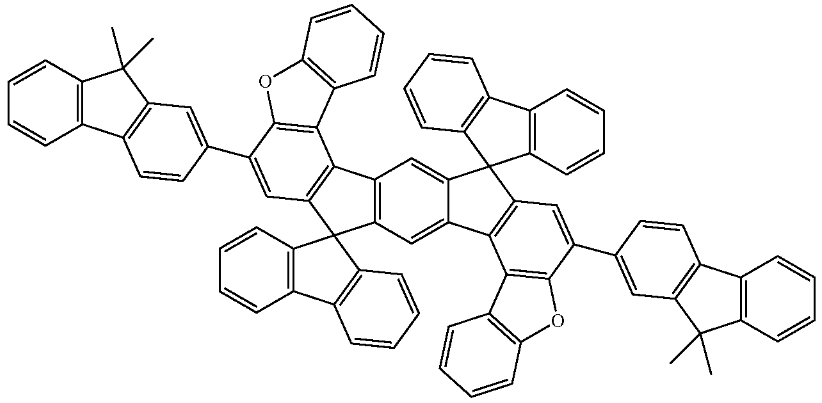
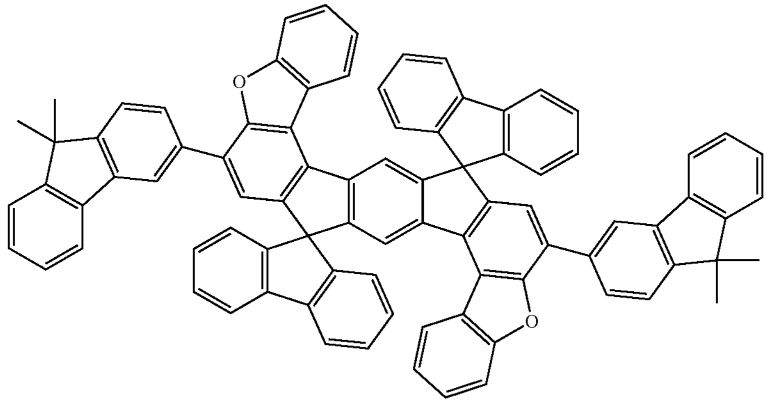
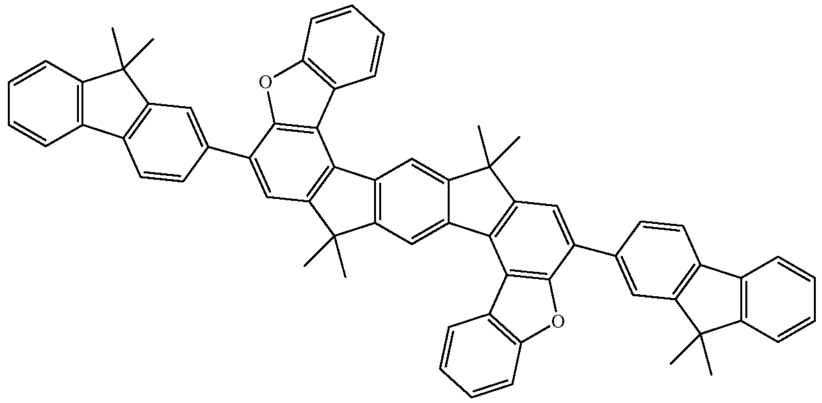

-continued
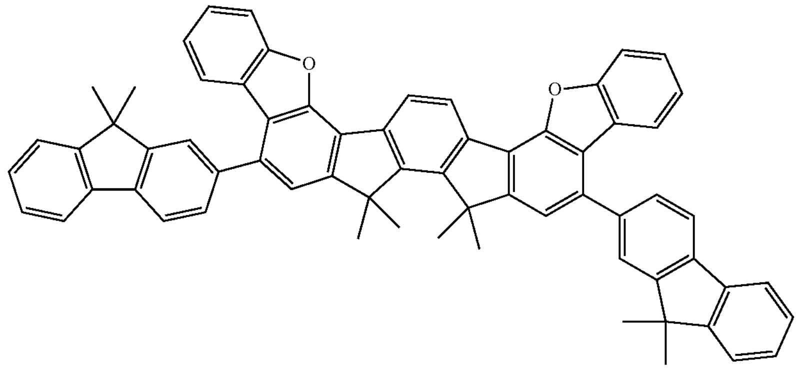
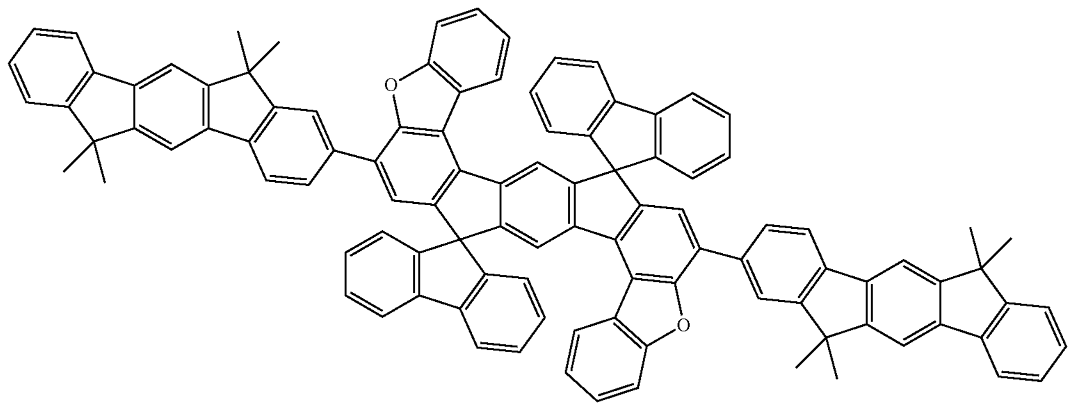
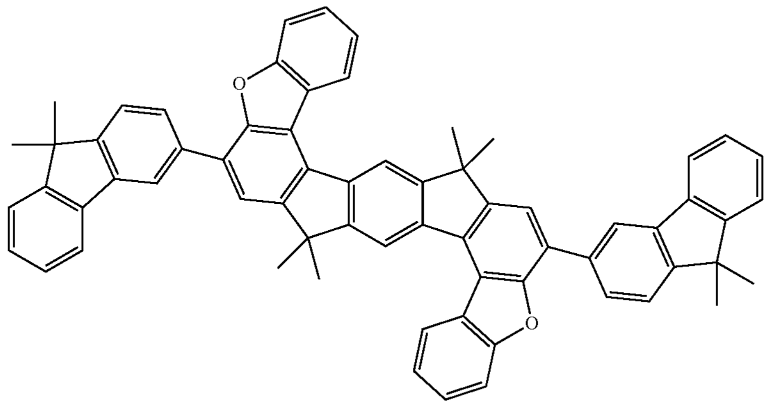
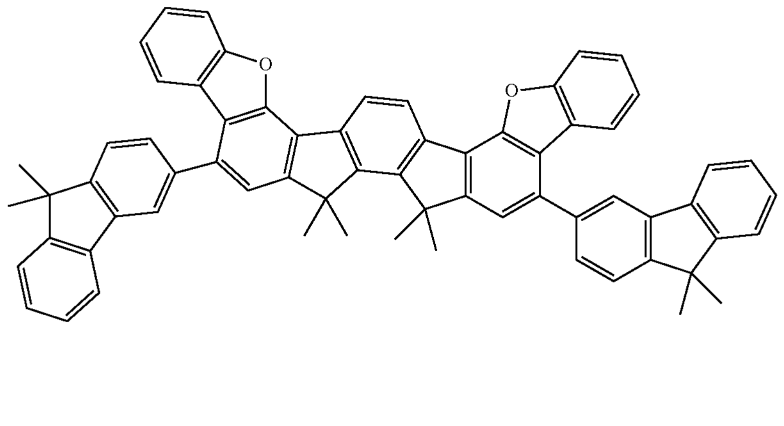

-continued
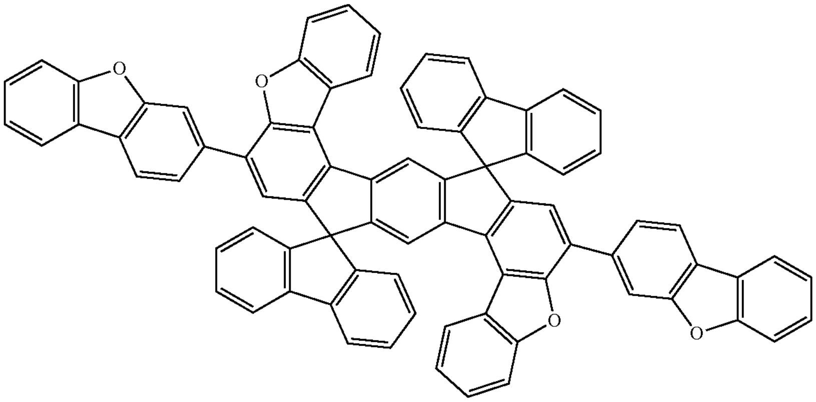
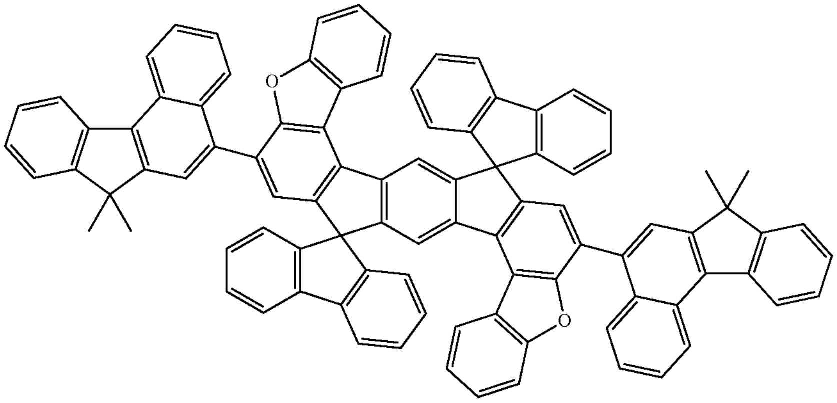
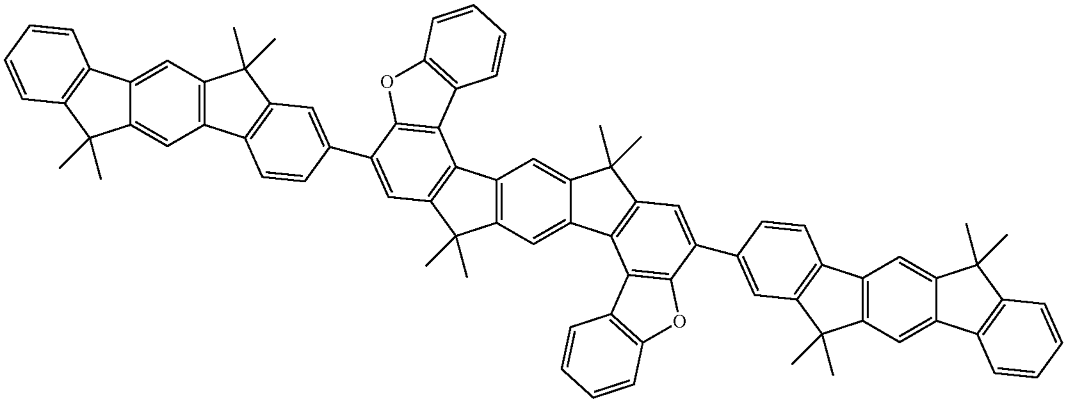
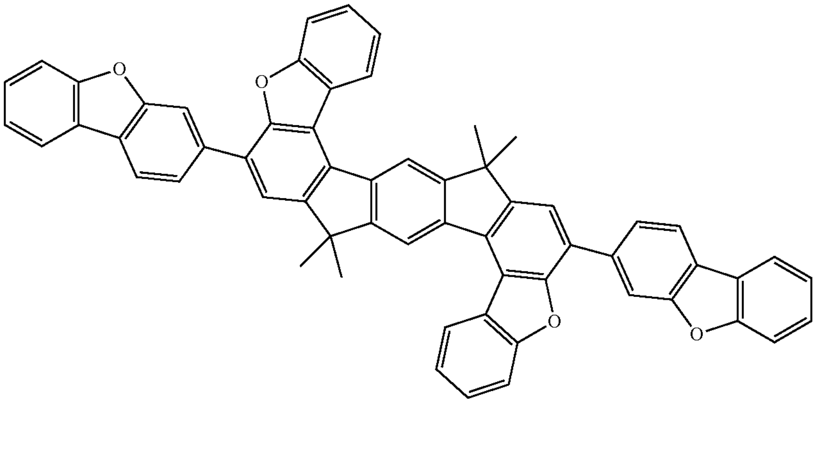

-continued
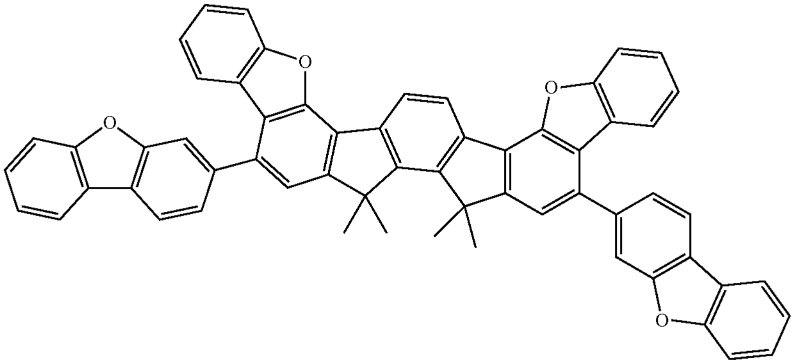
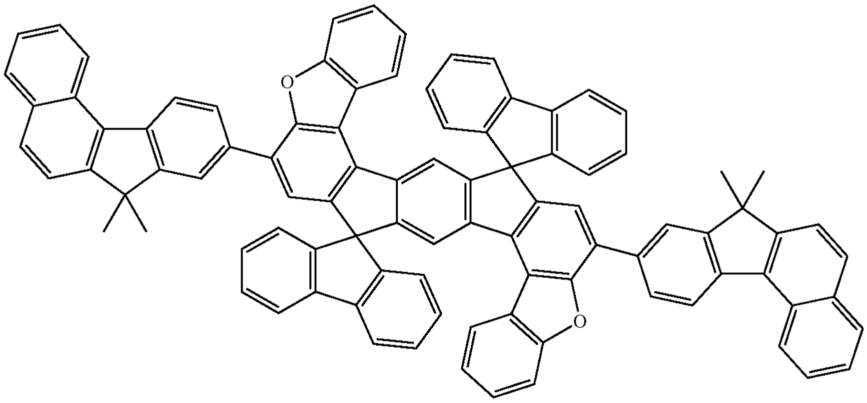
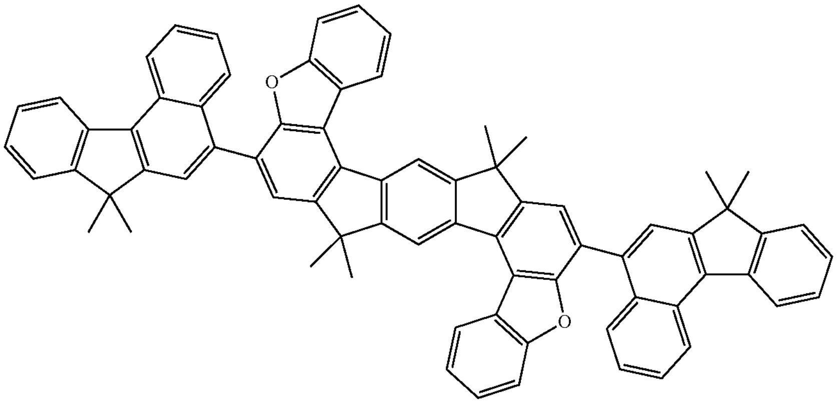
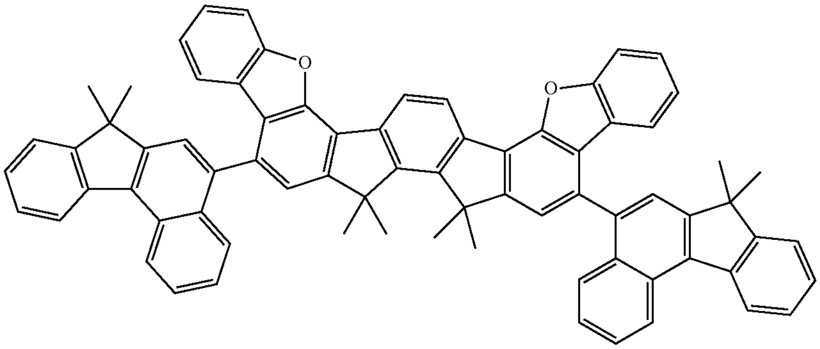

-continued
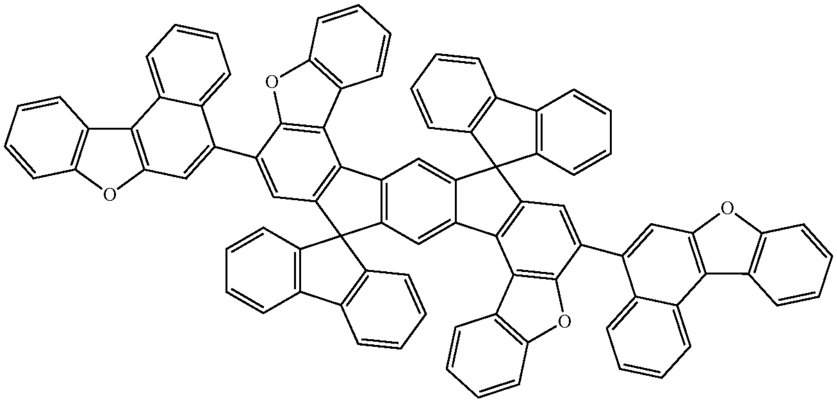
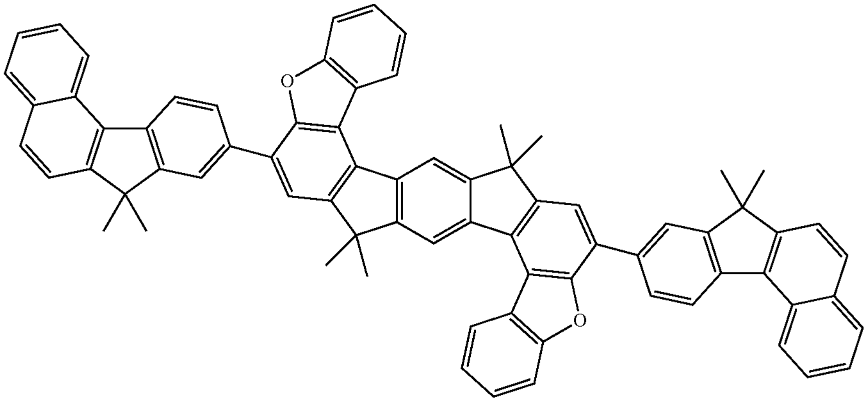
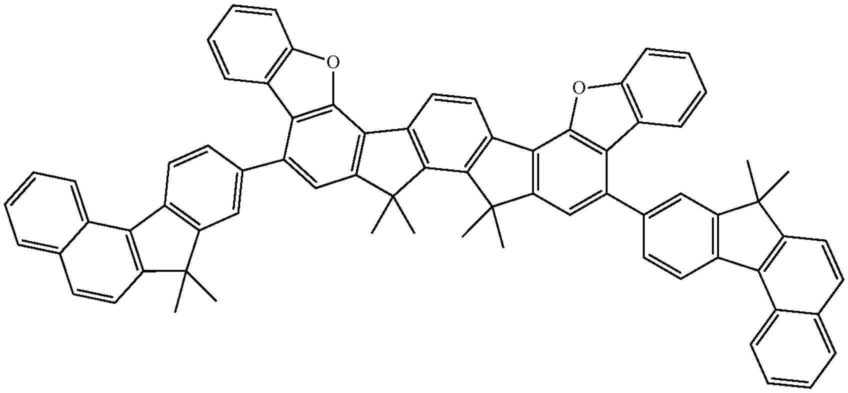
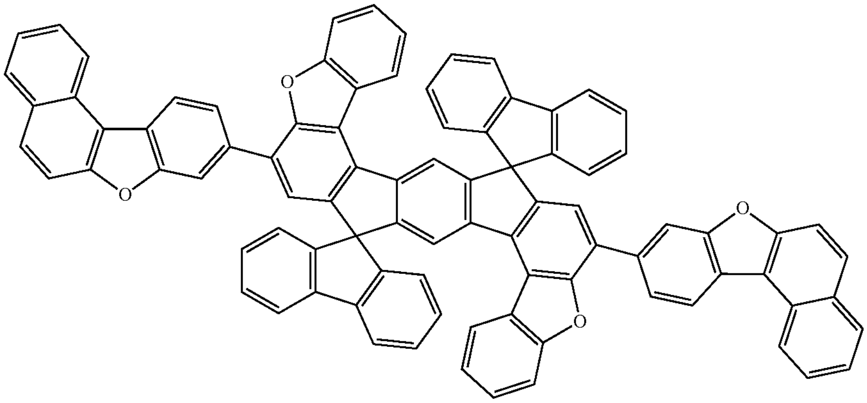

-continued
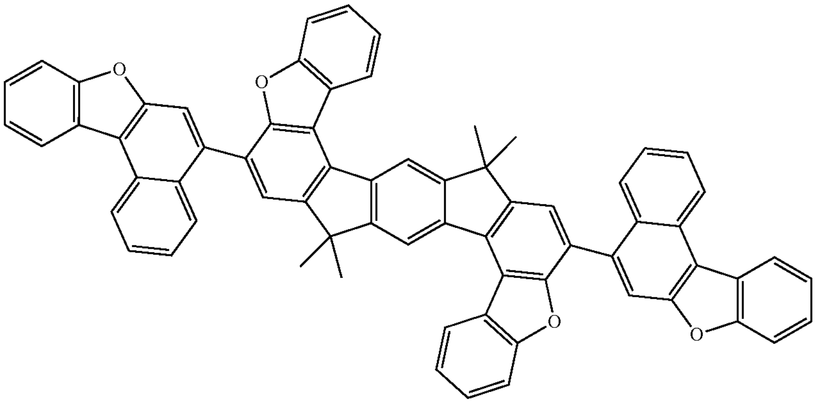
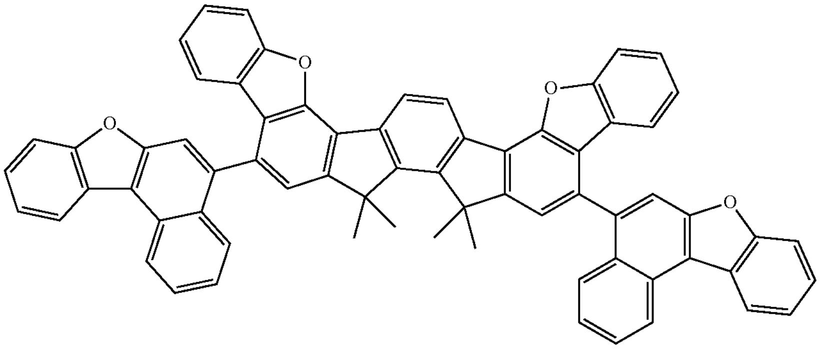
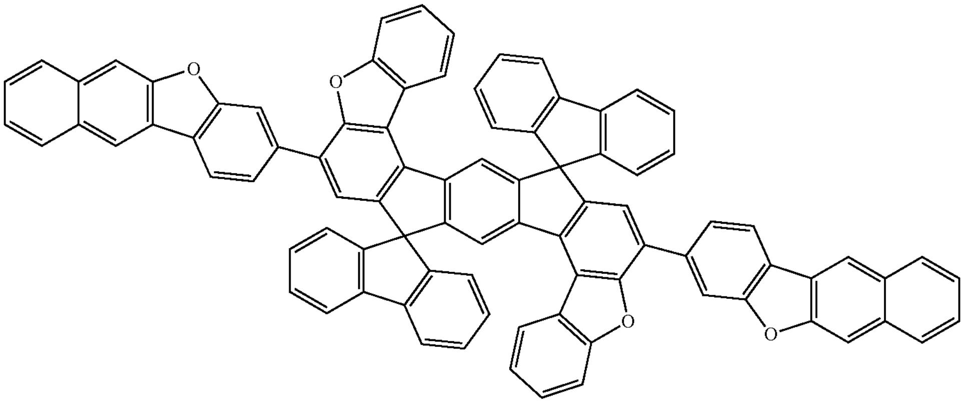
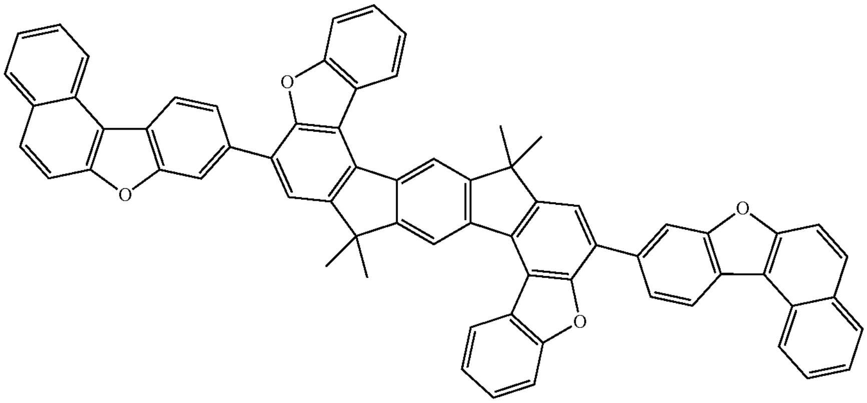

-continued
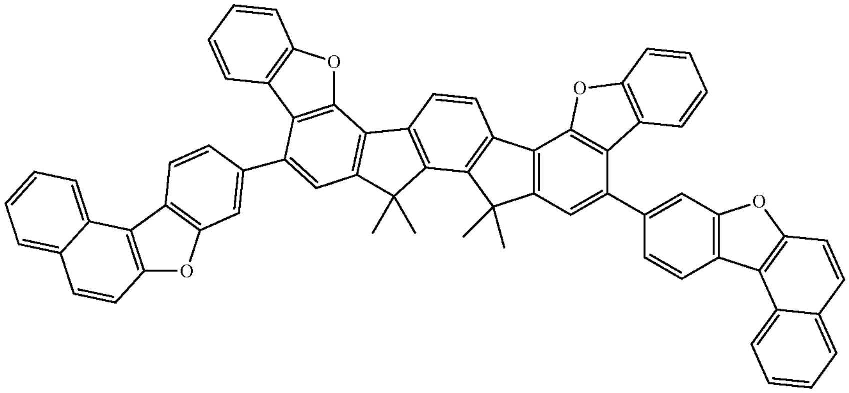
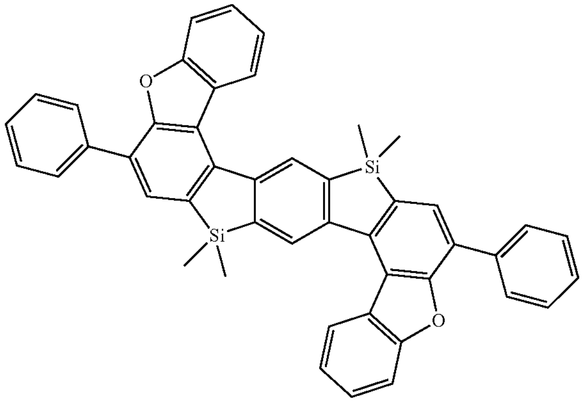
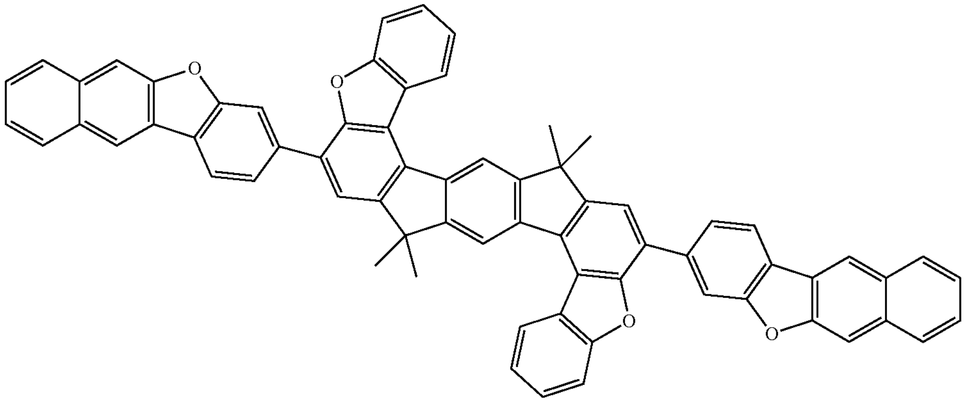
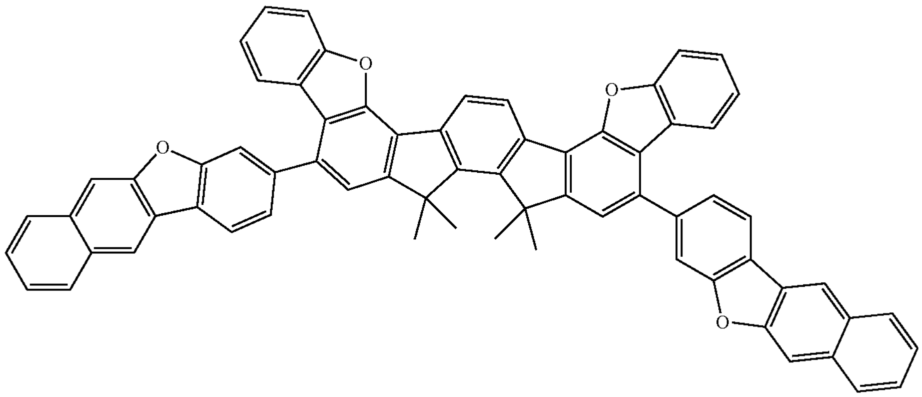

-continued
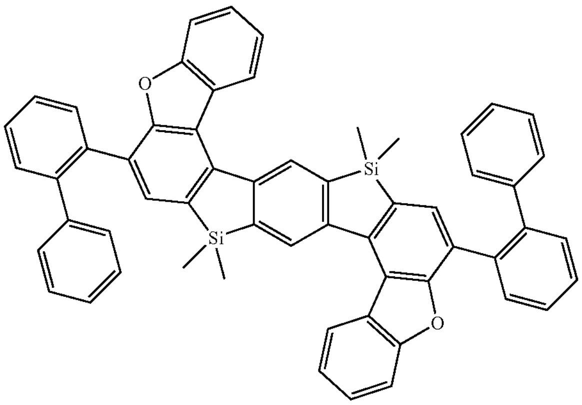
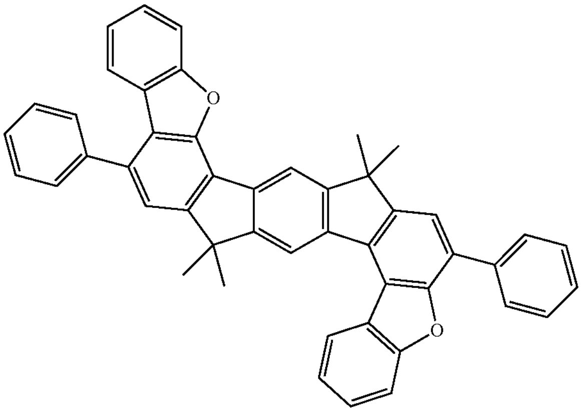
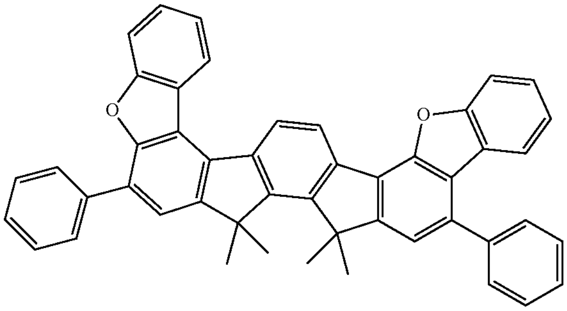
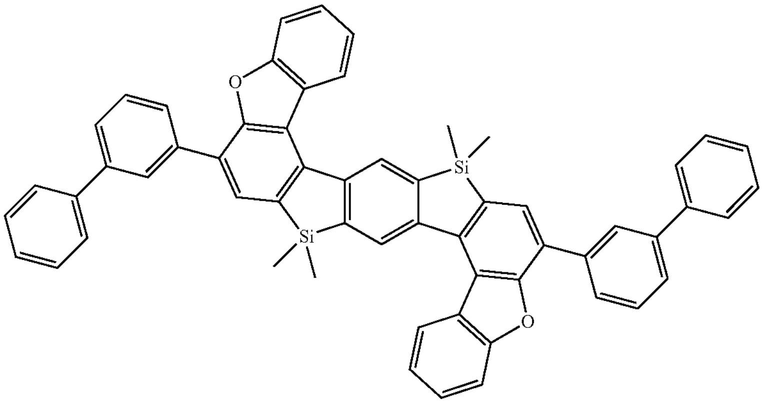
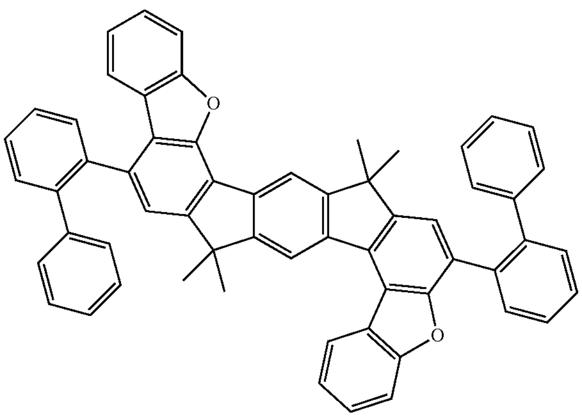
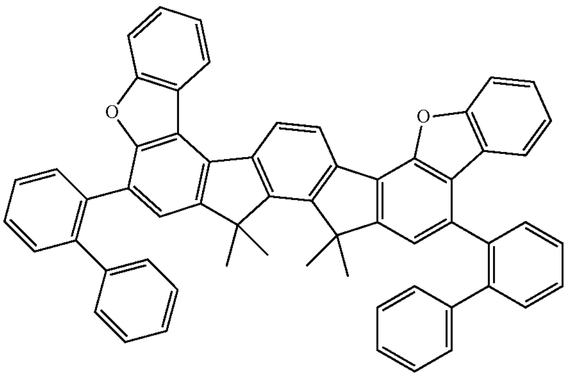

-continued
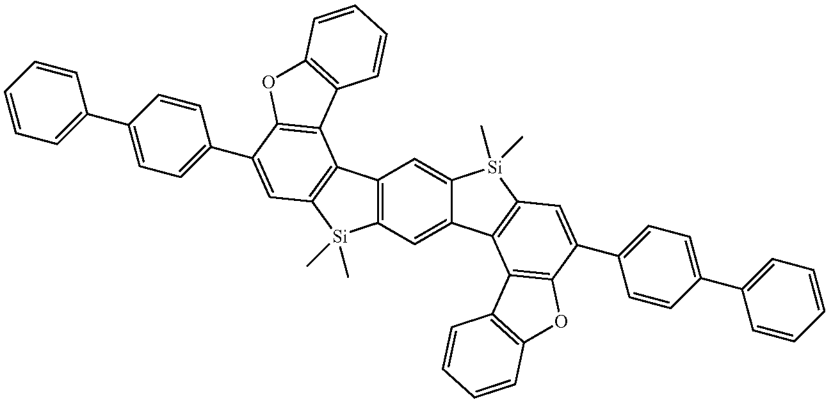
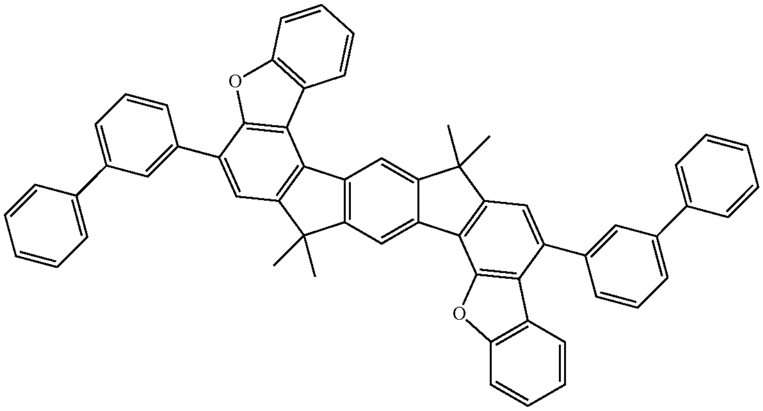
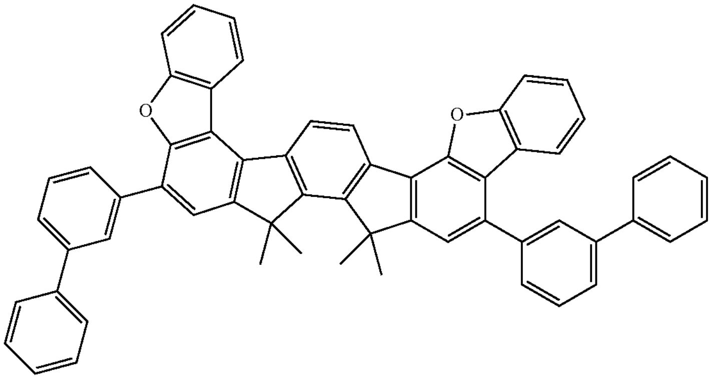
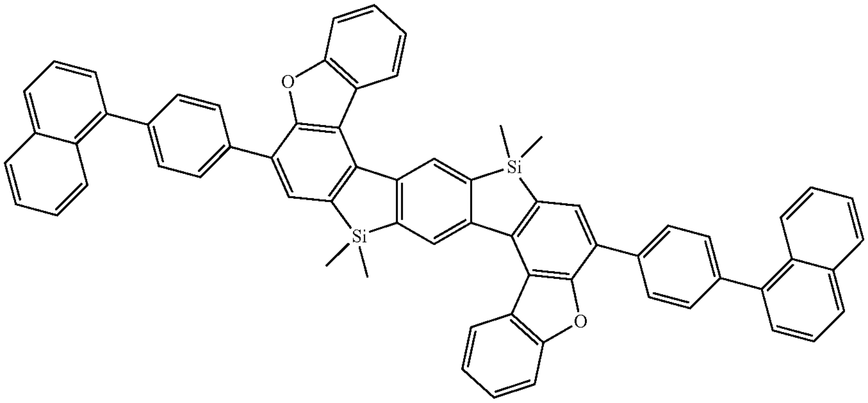

-continued
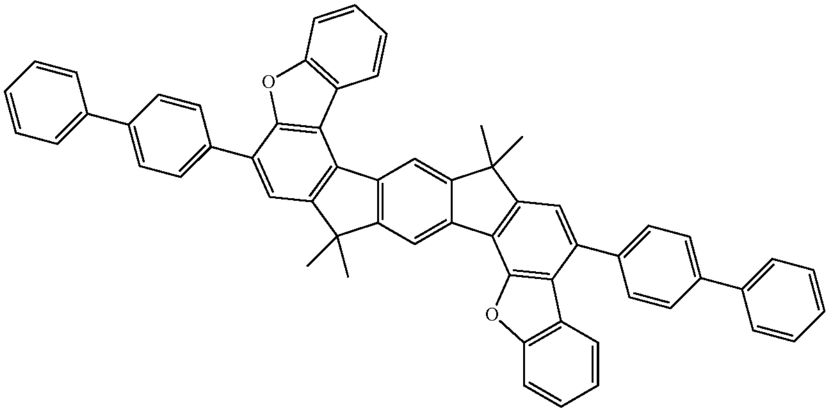
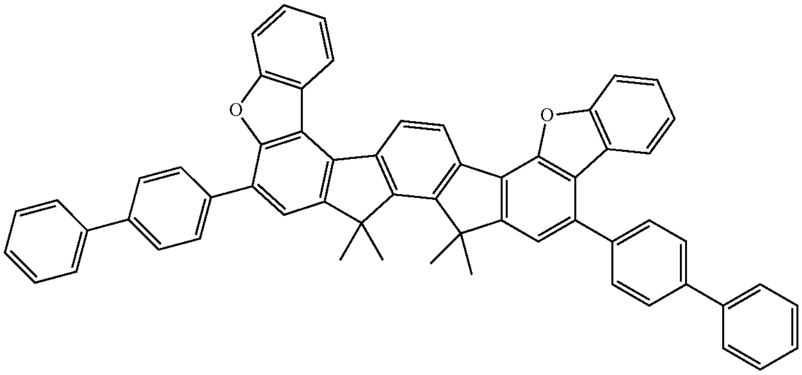
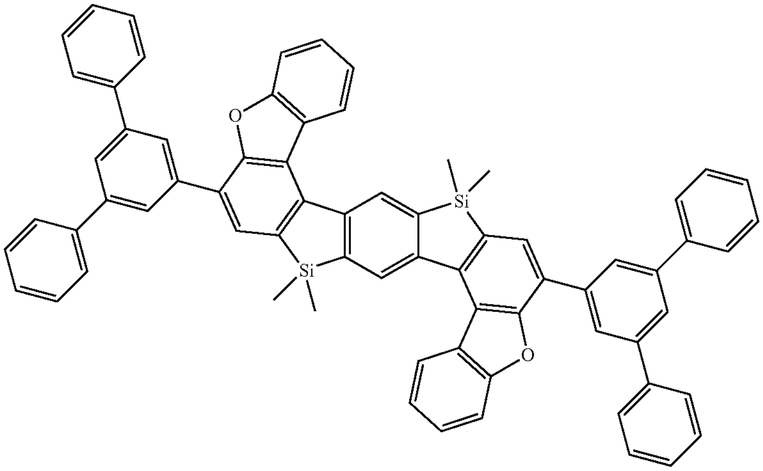
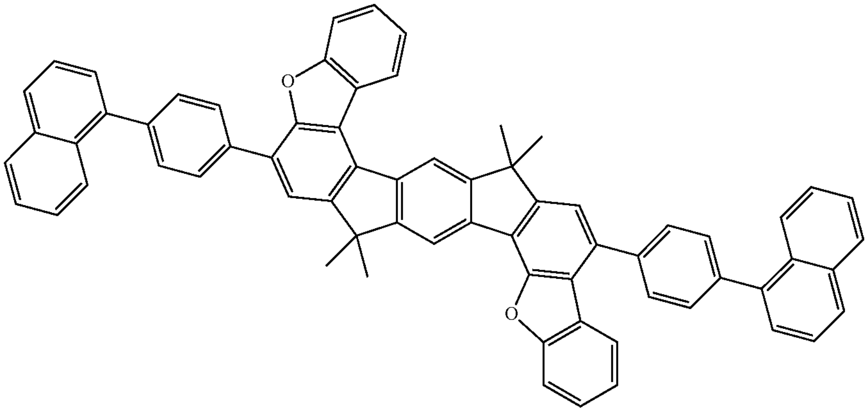

-continued
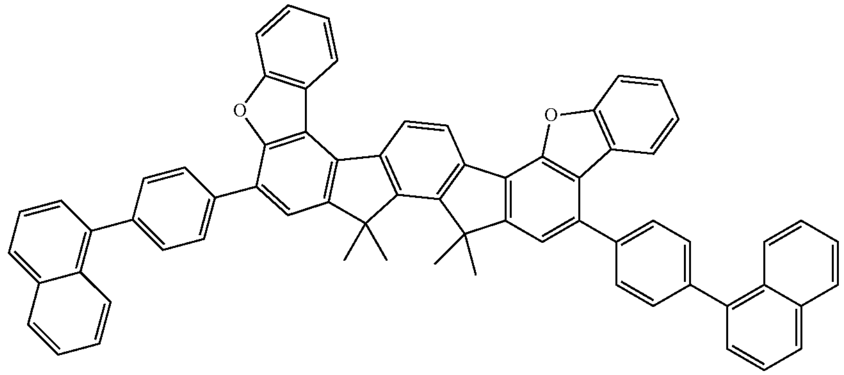
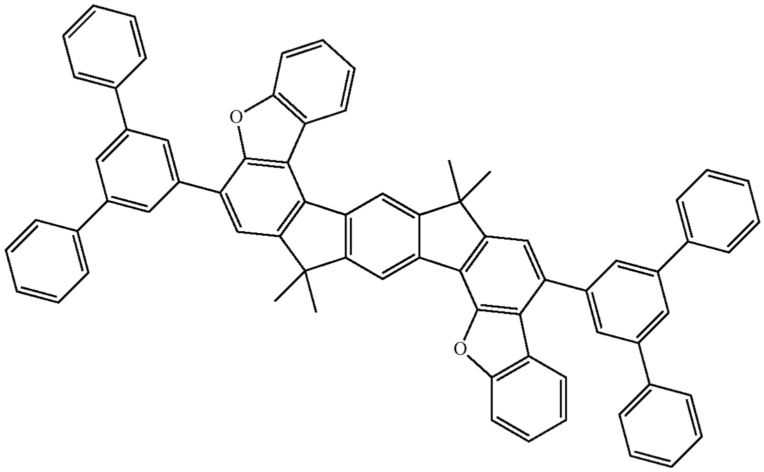
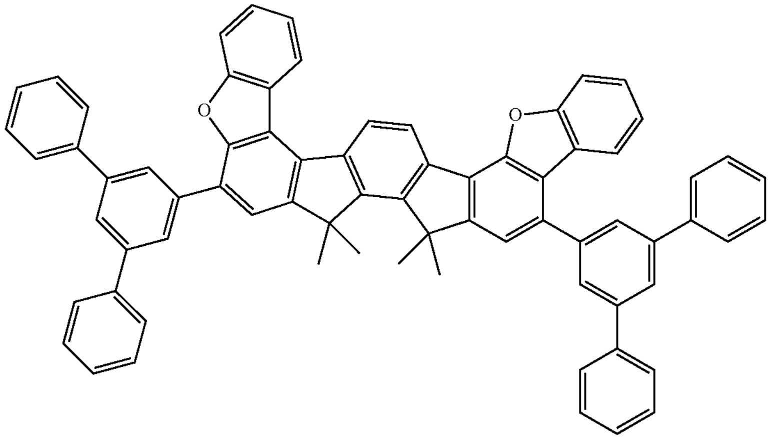
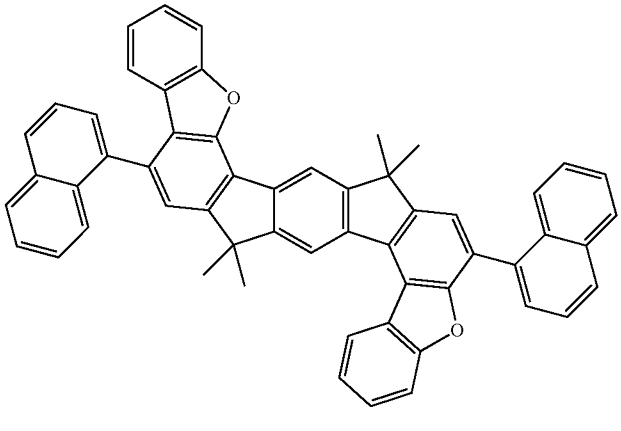
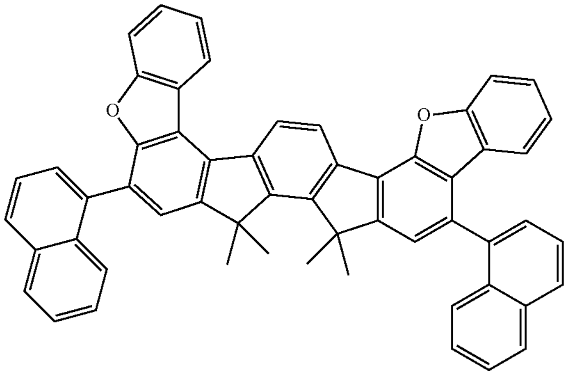

-continued
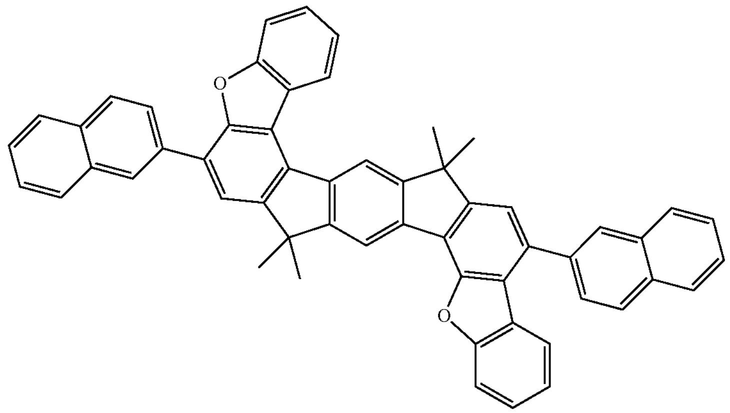
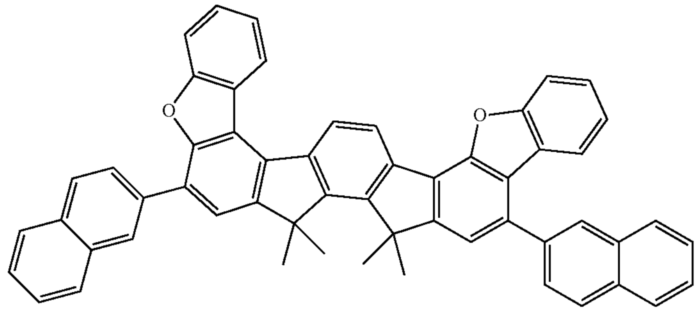
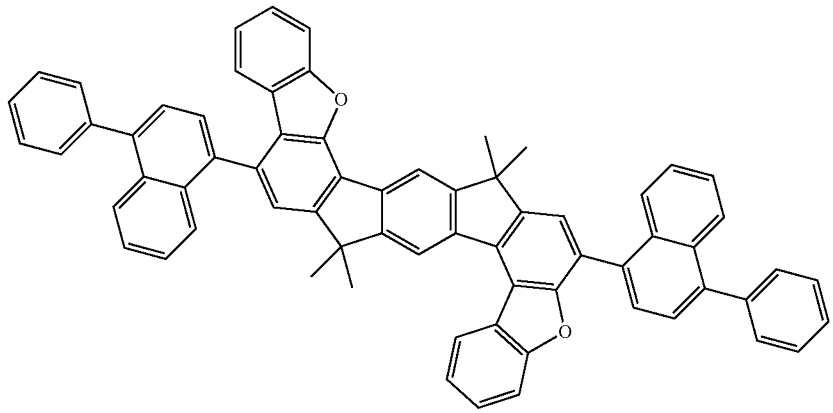
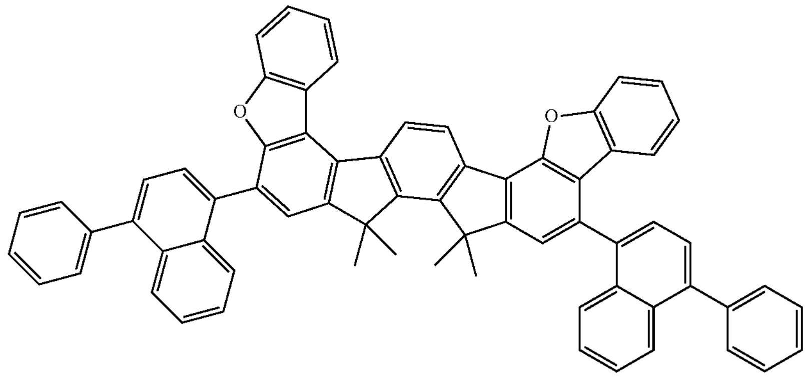

-continued
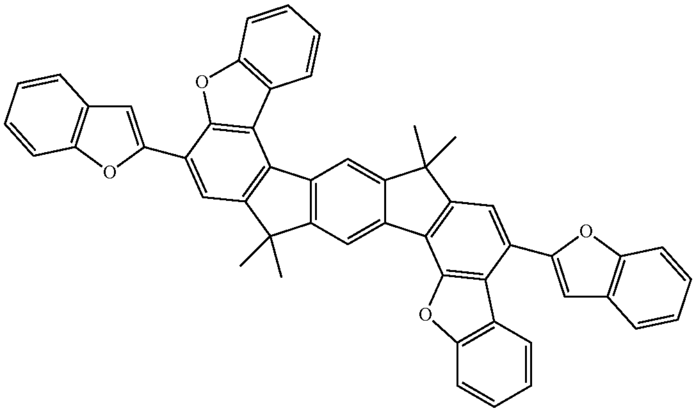
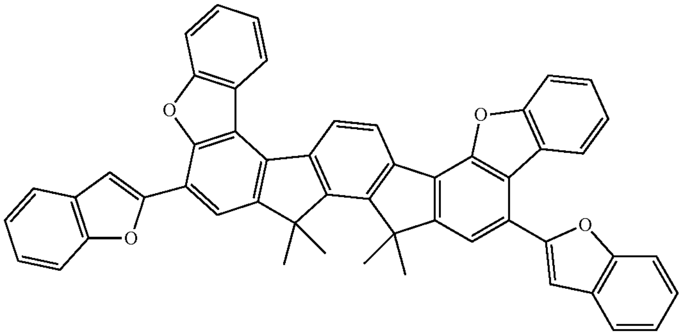
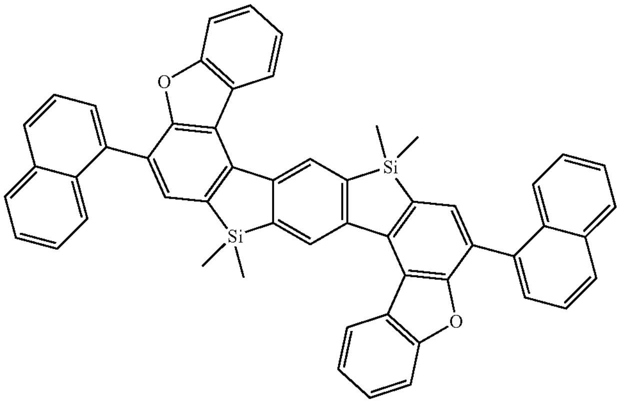
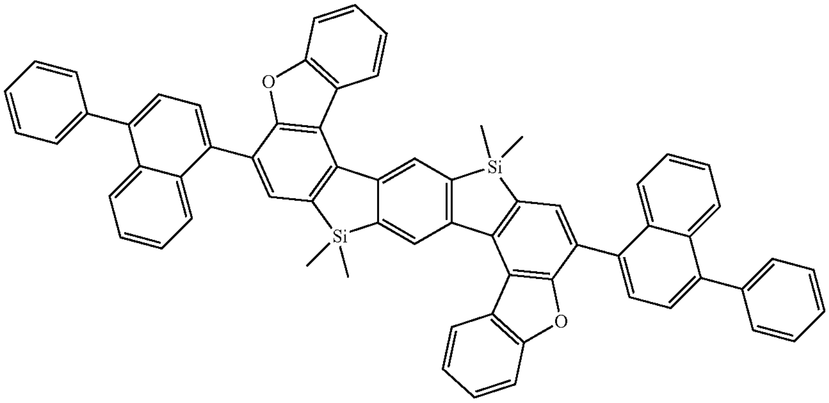

-continued
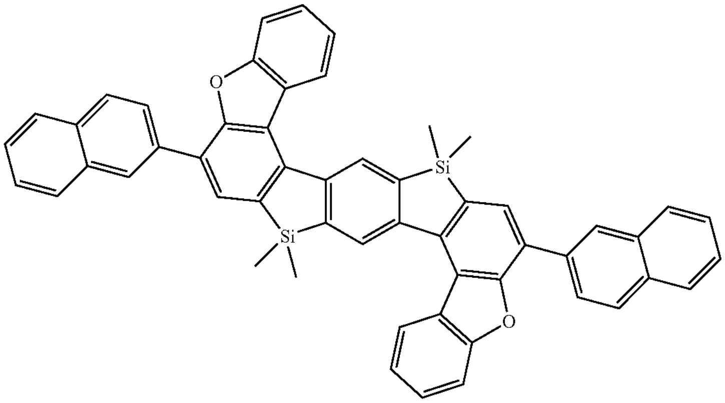
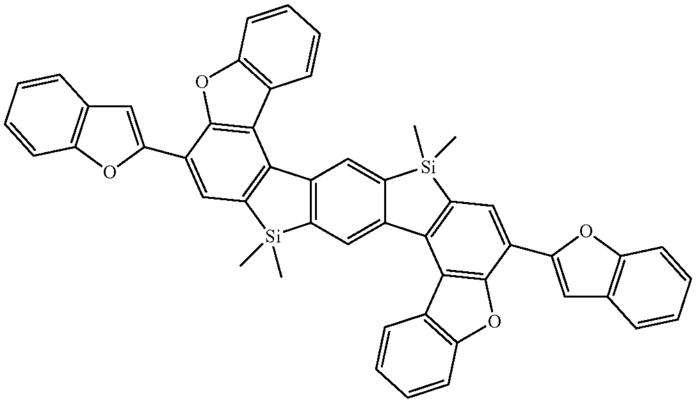
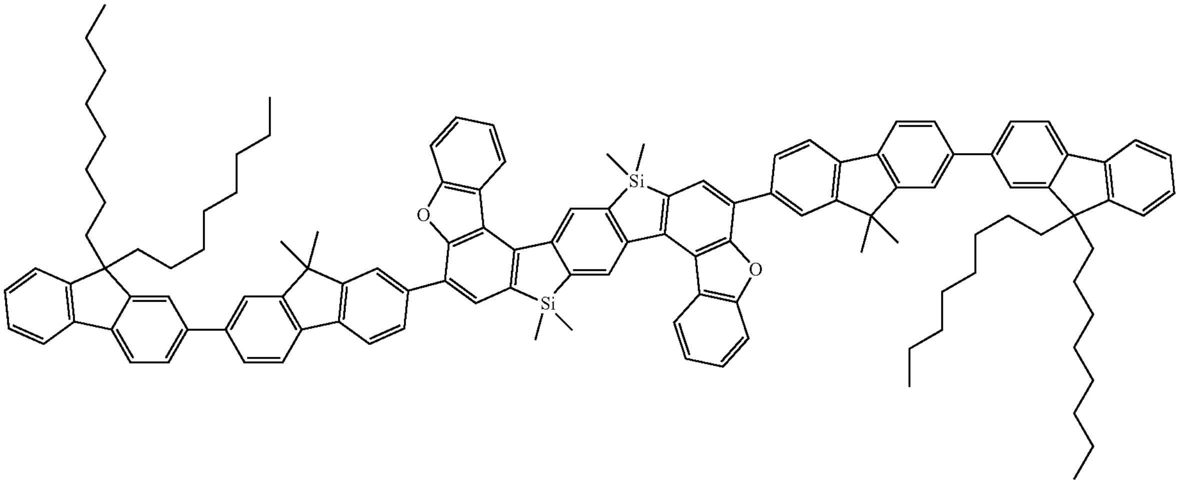

-continued
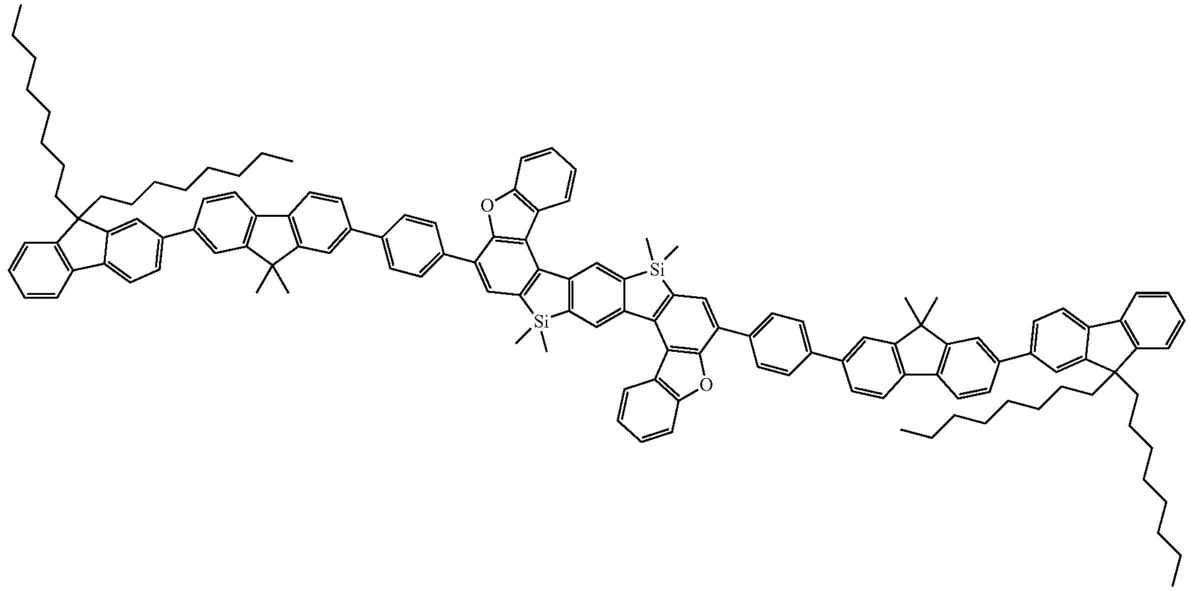
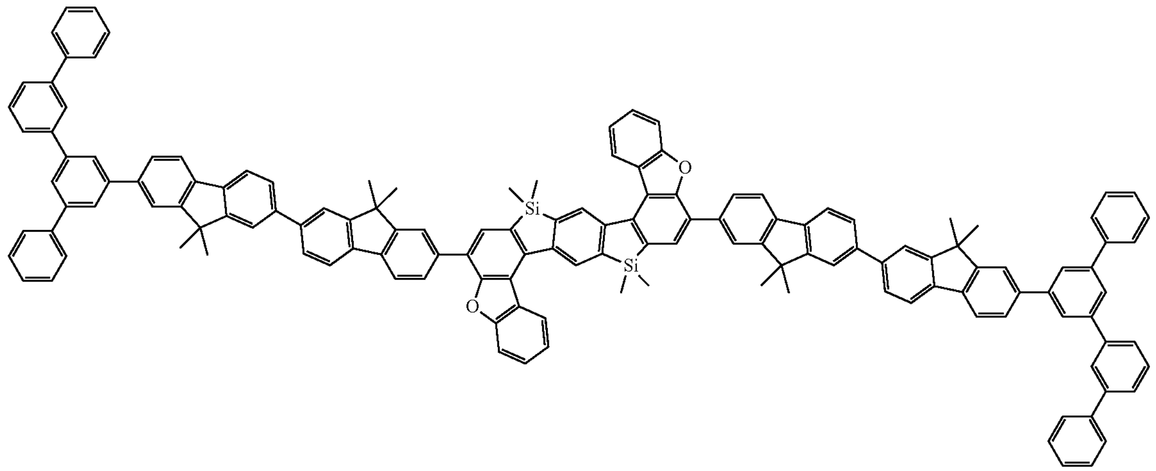
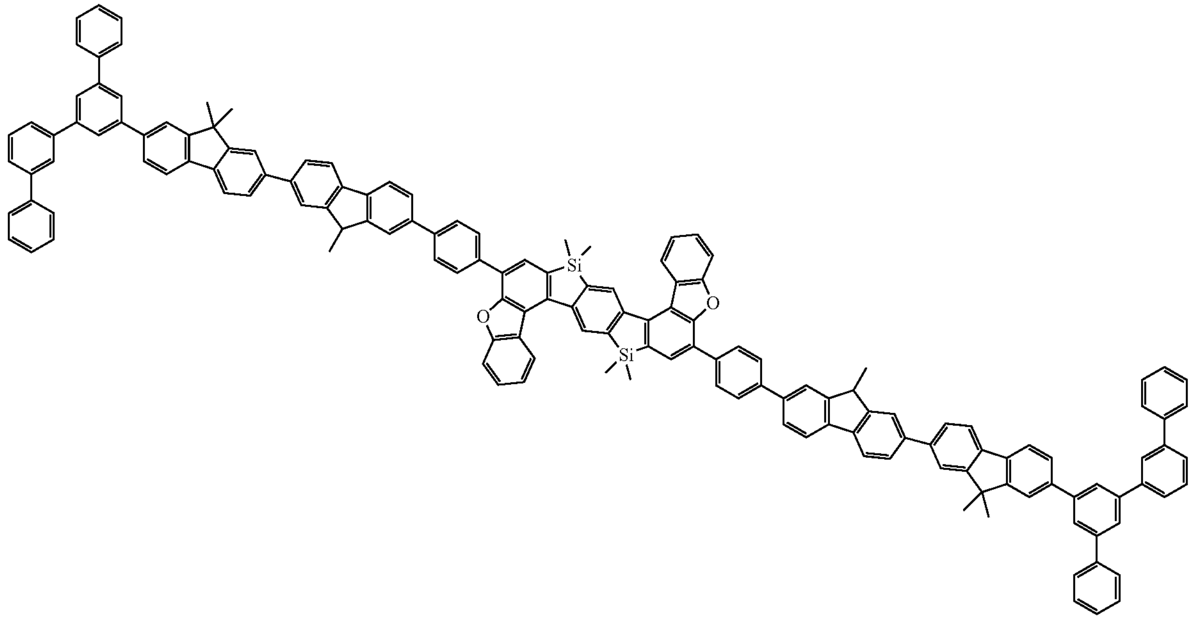

-continued
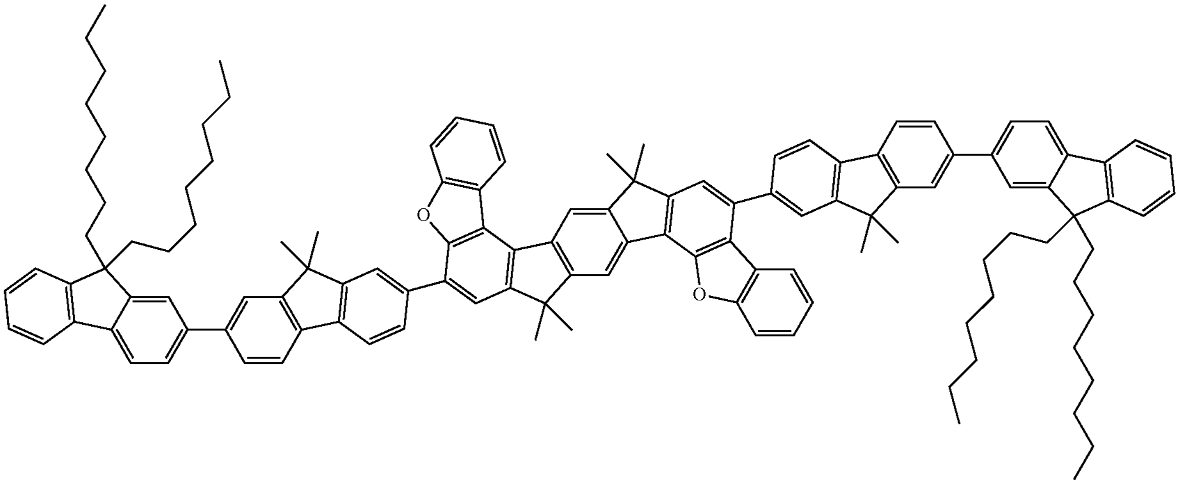
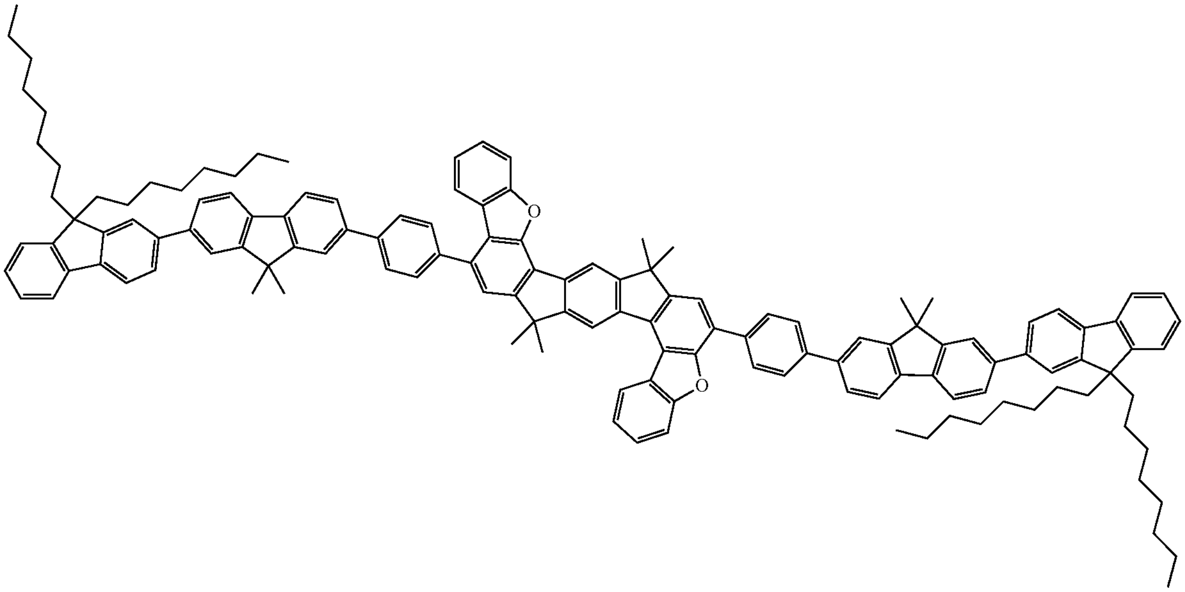
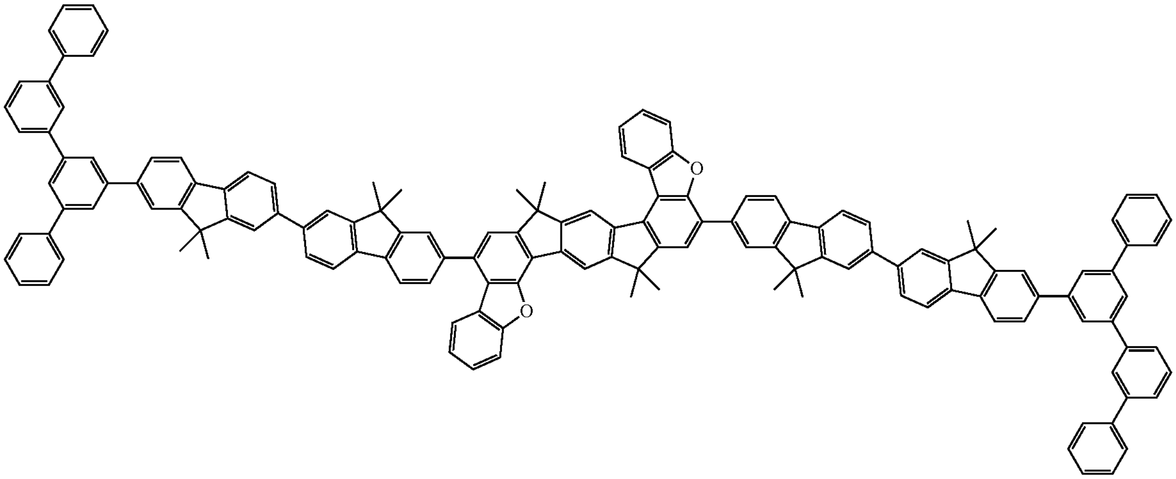

-continued
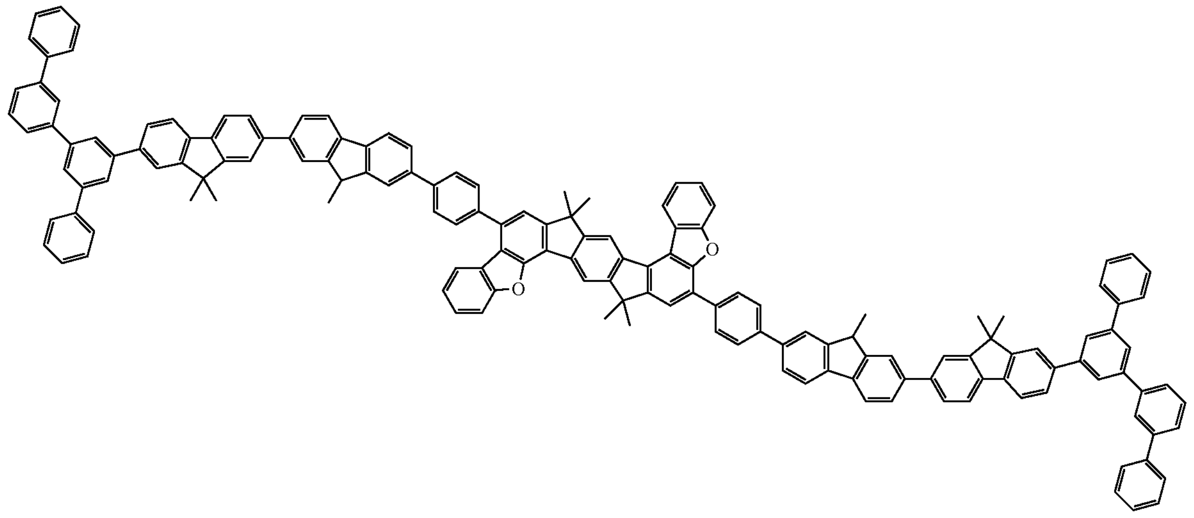
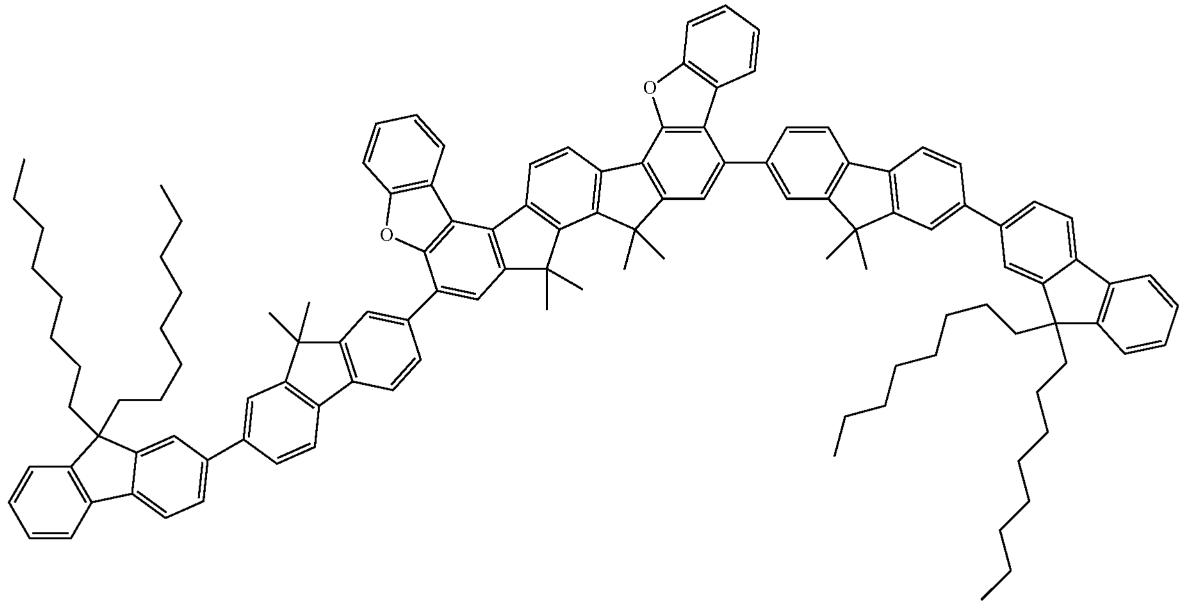
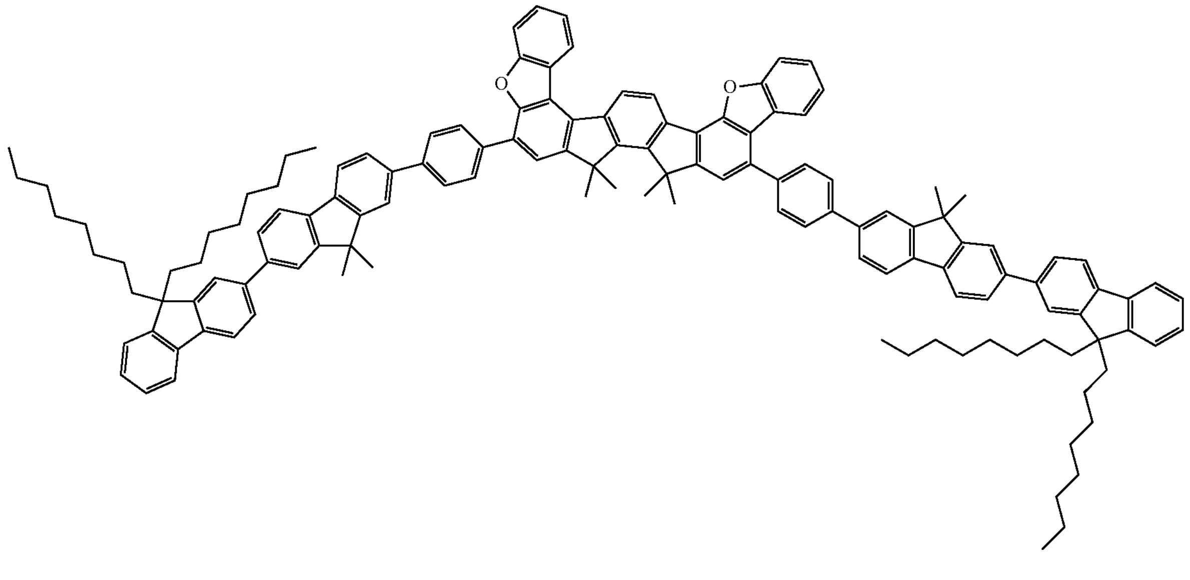

-continued
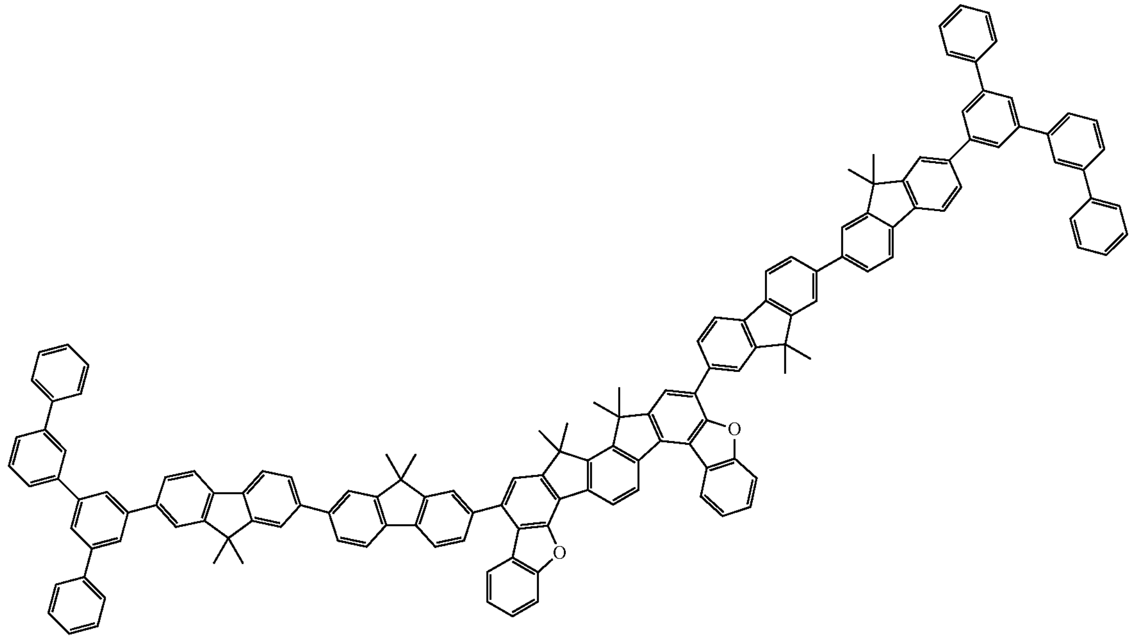
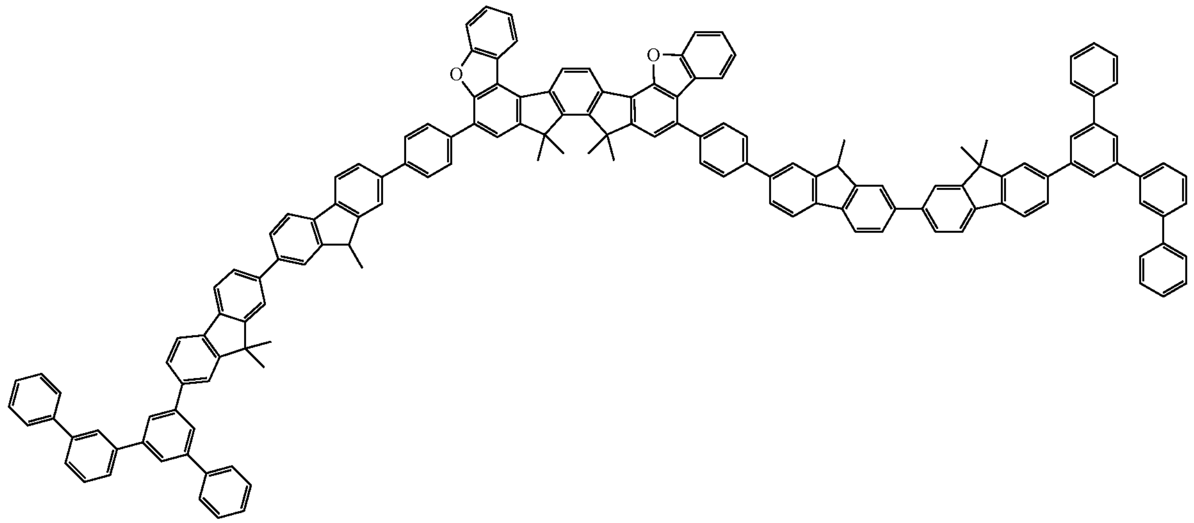
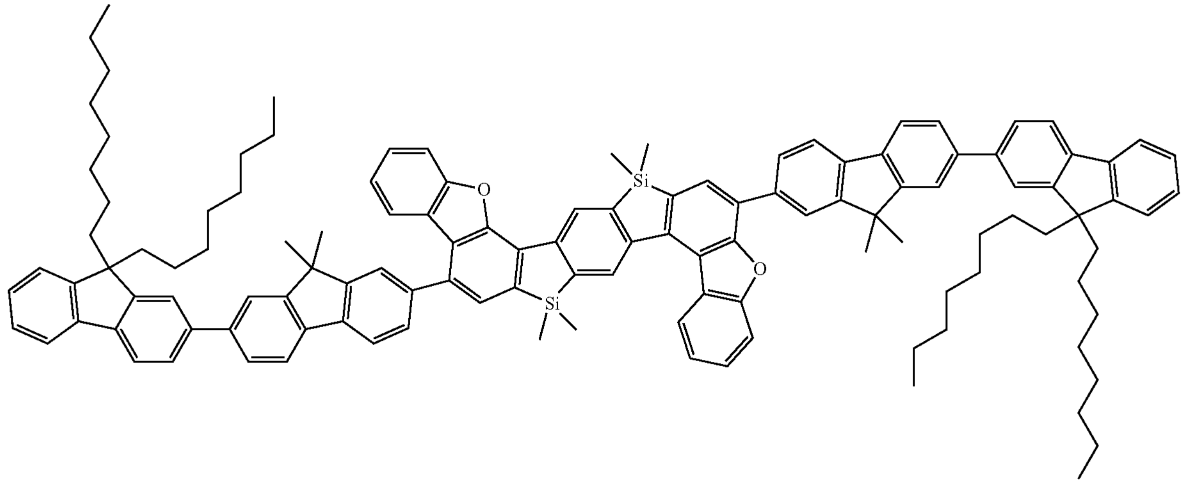

-continued
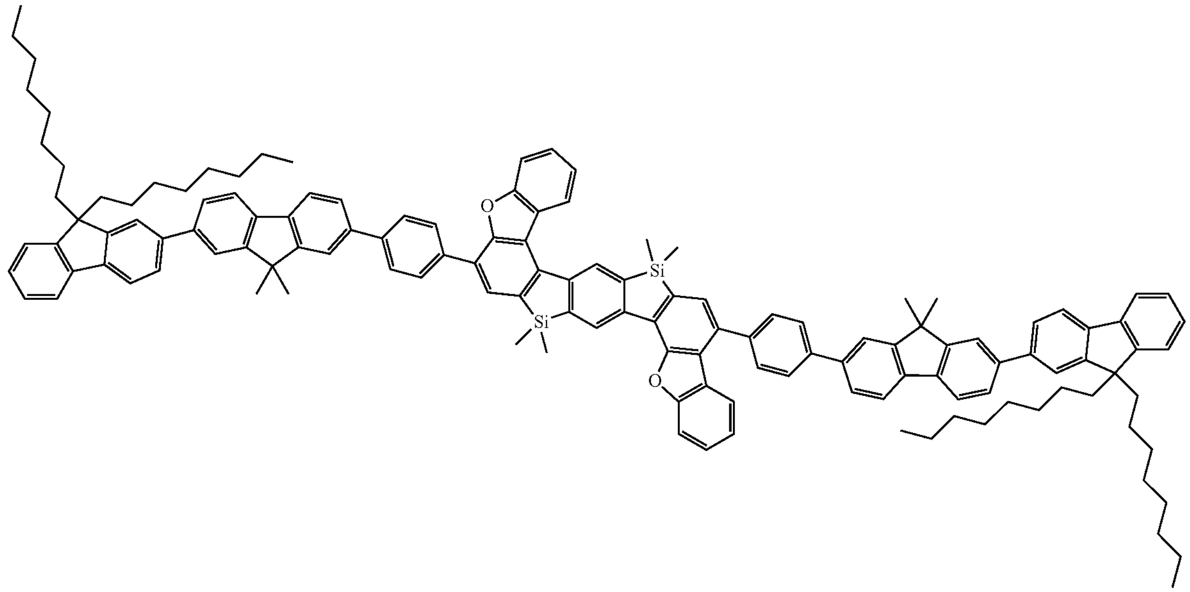
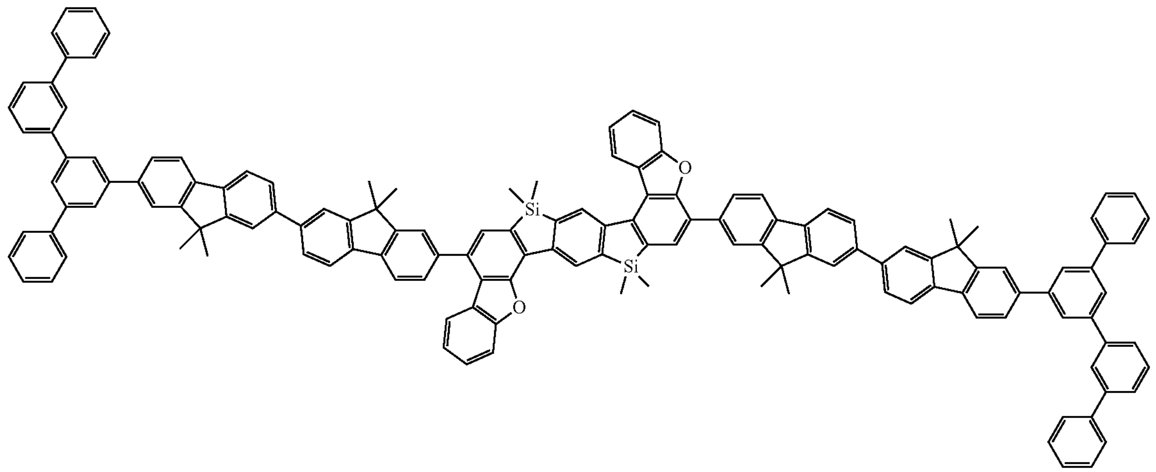
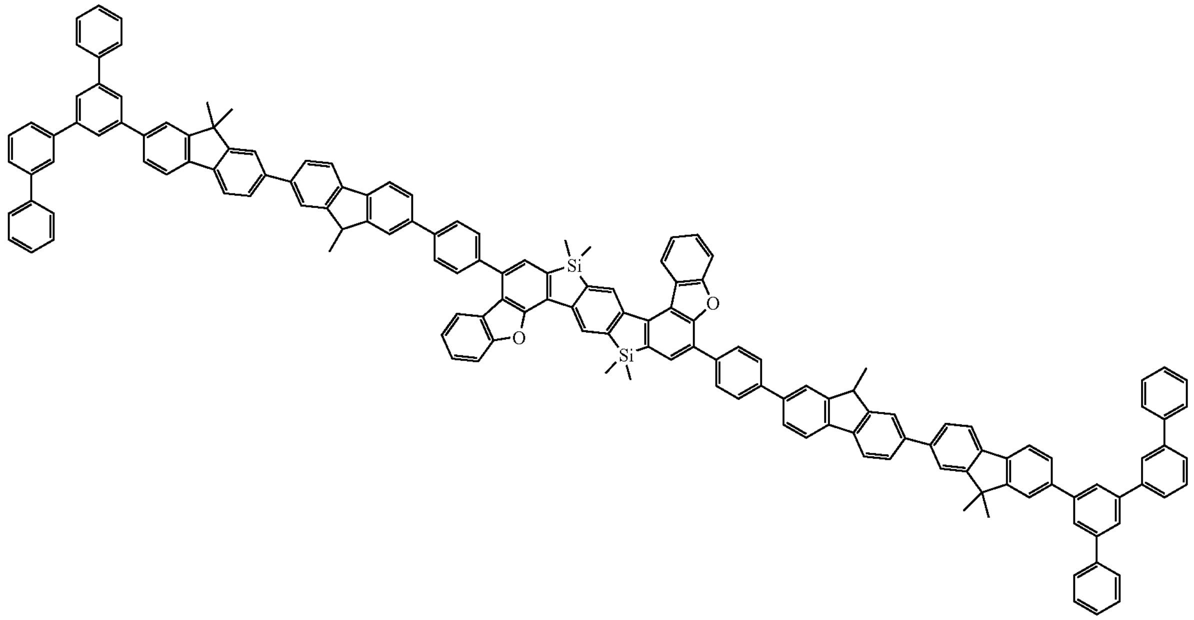

-continued
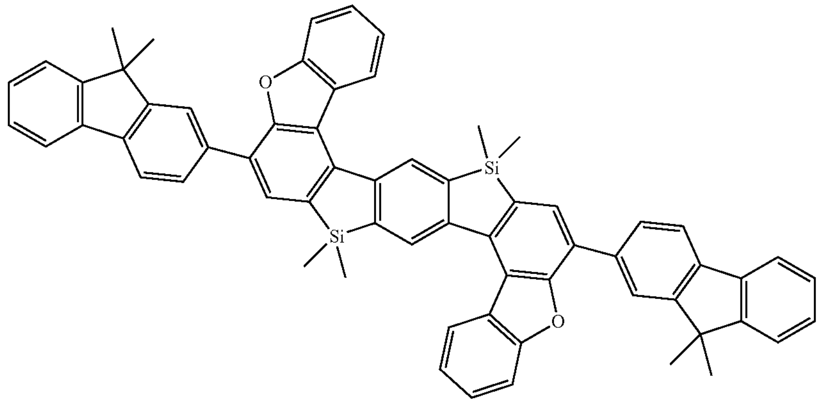
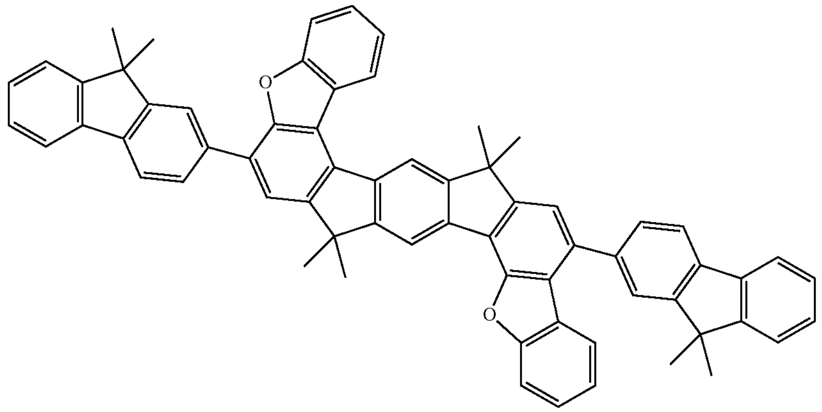
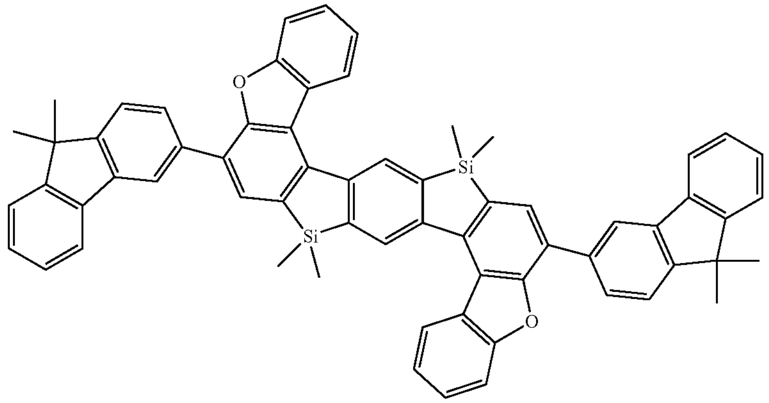
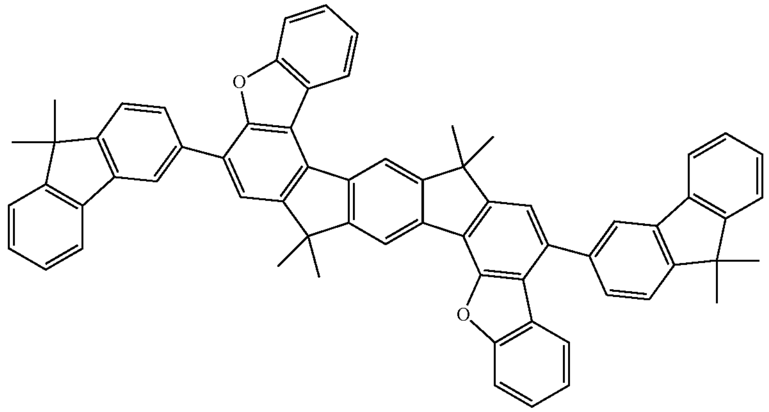

-continued
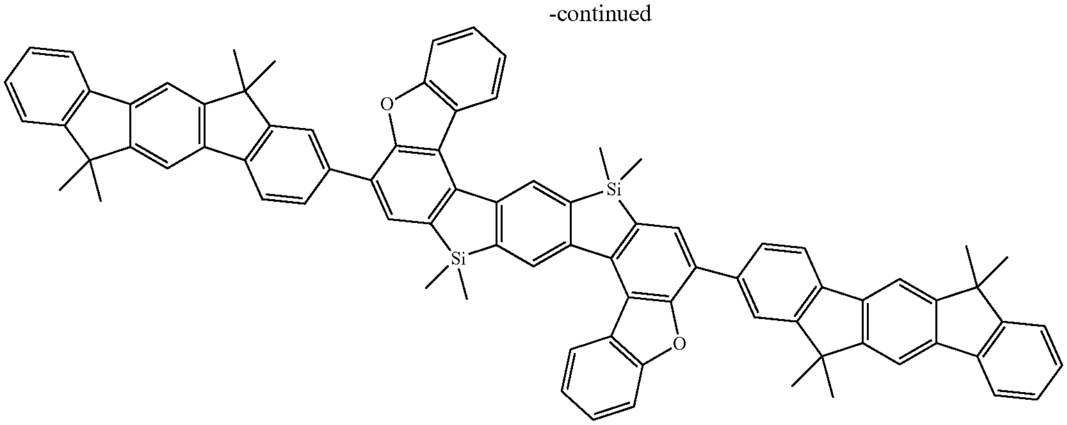
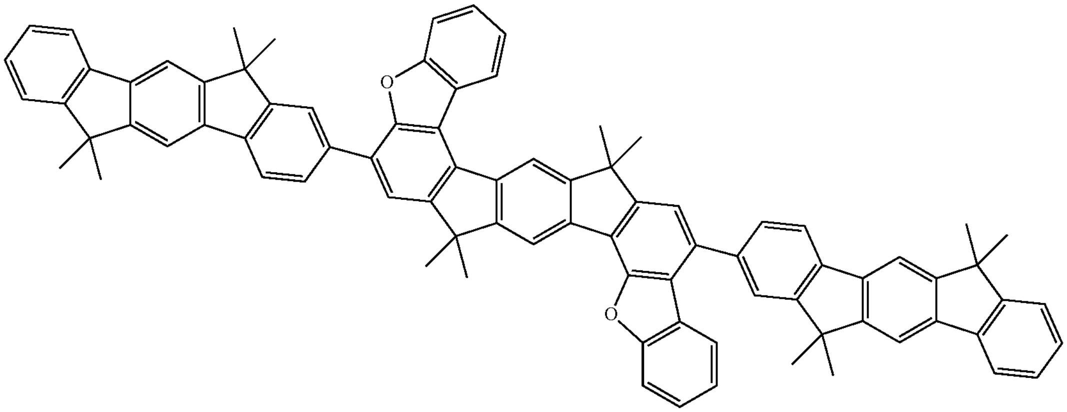
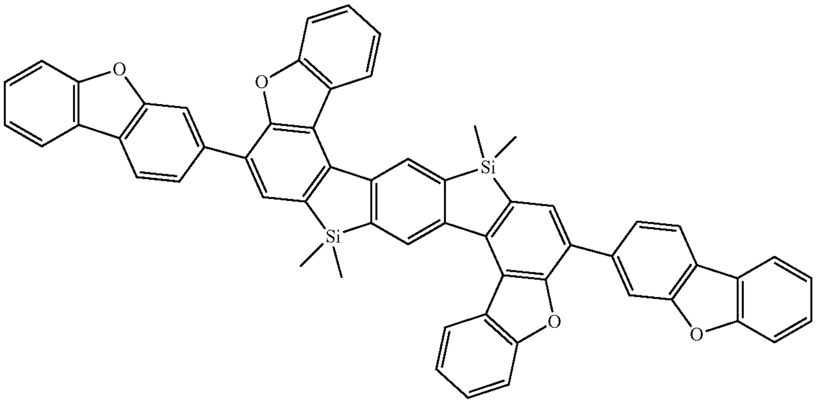
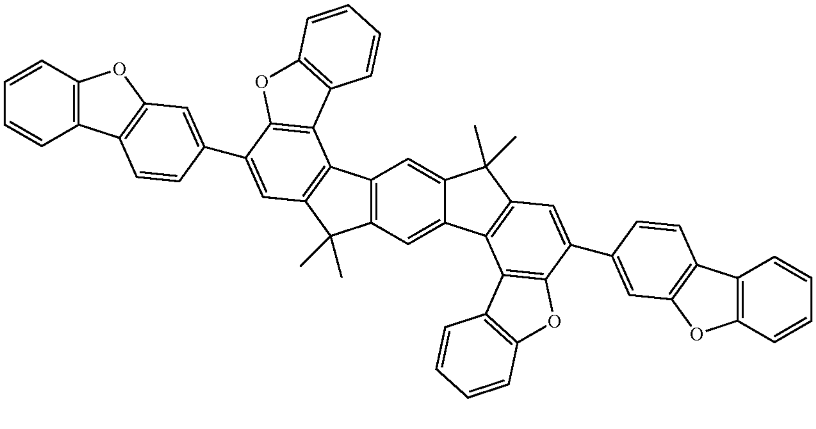

-continued
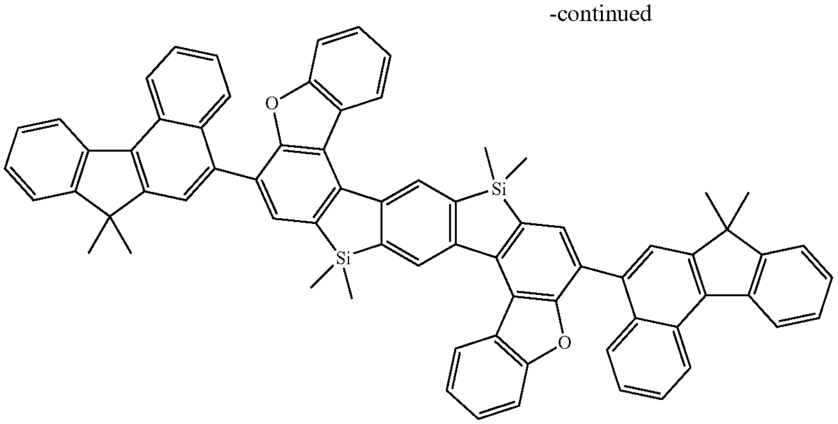
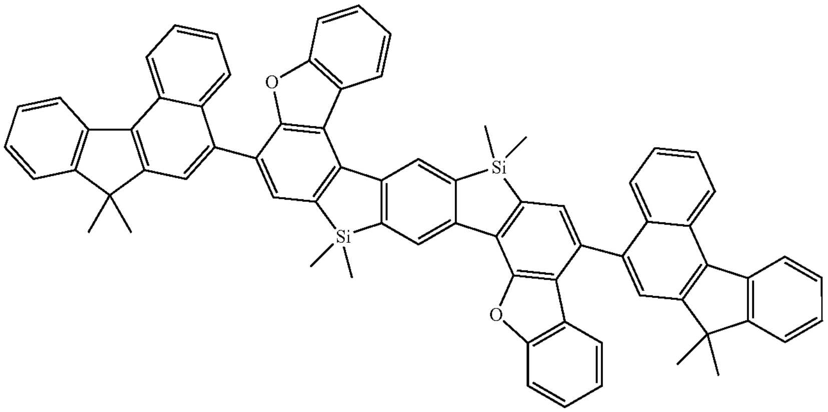
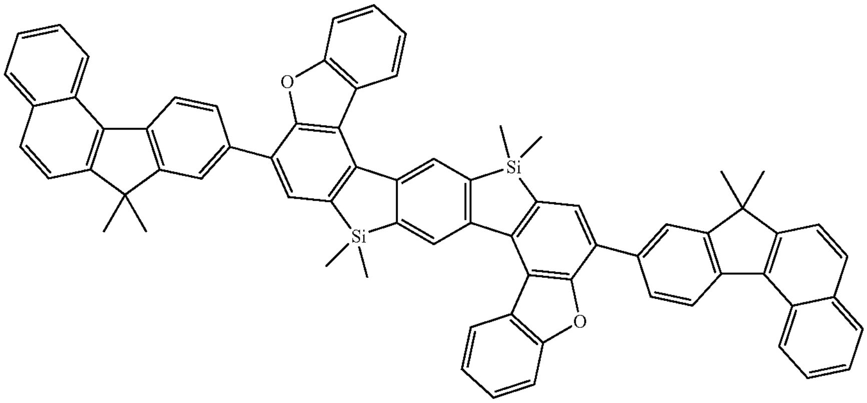
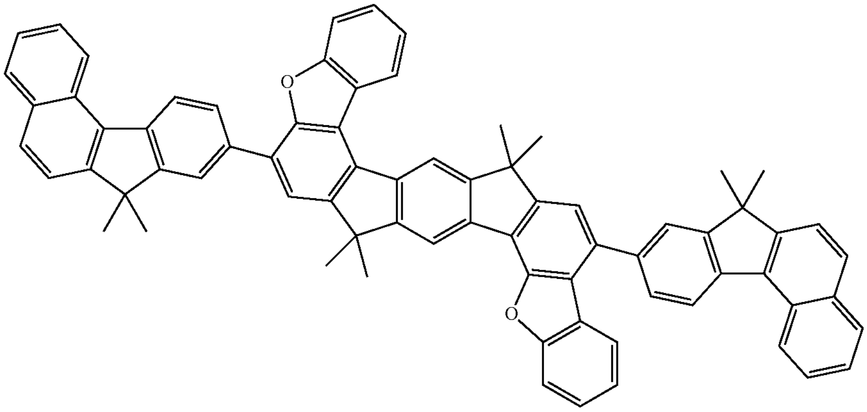

-continued
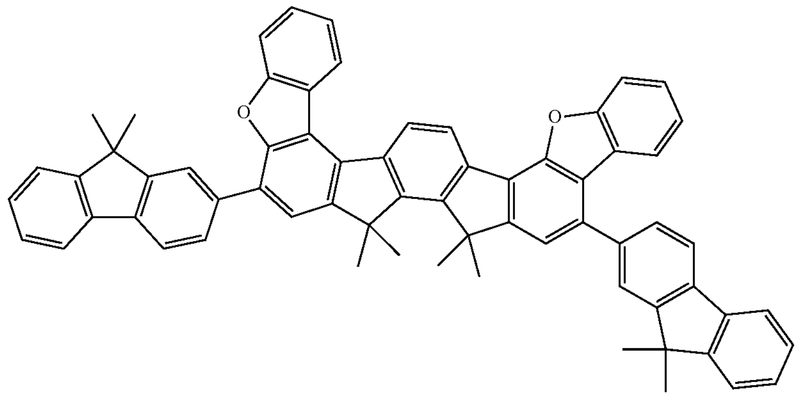
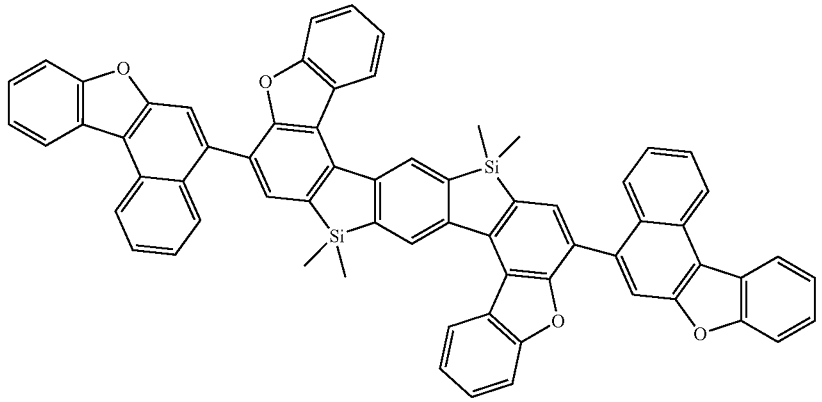
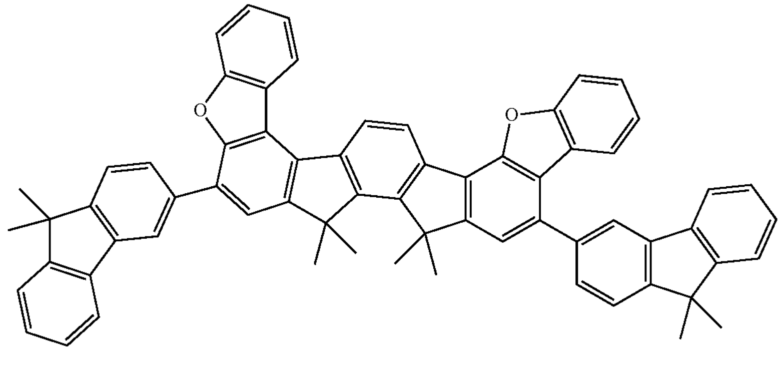
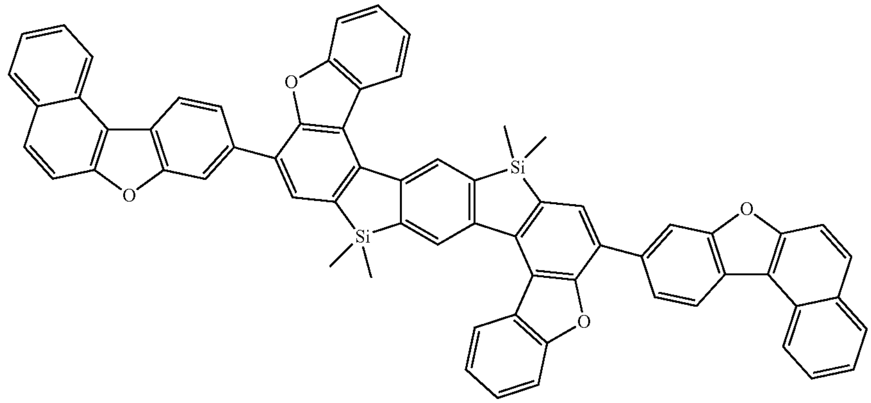

-continued
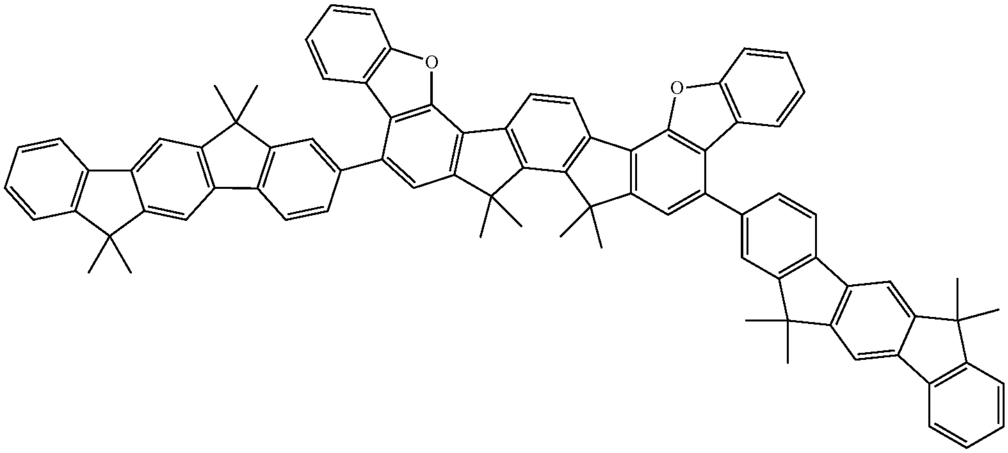
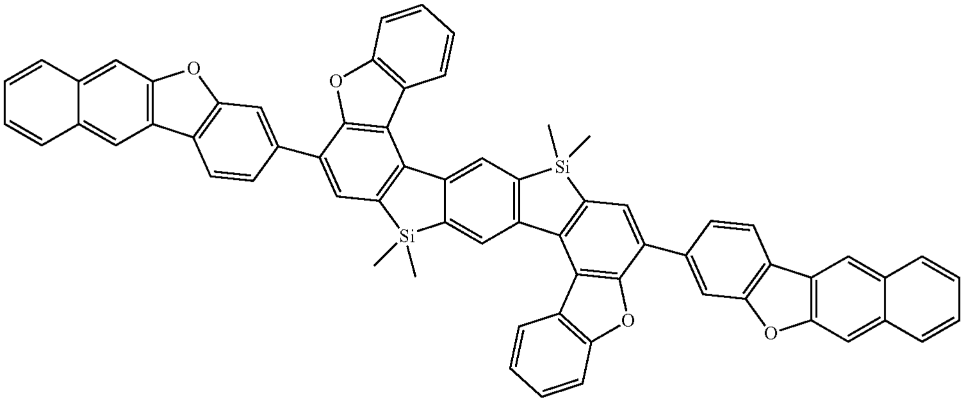
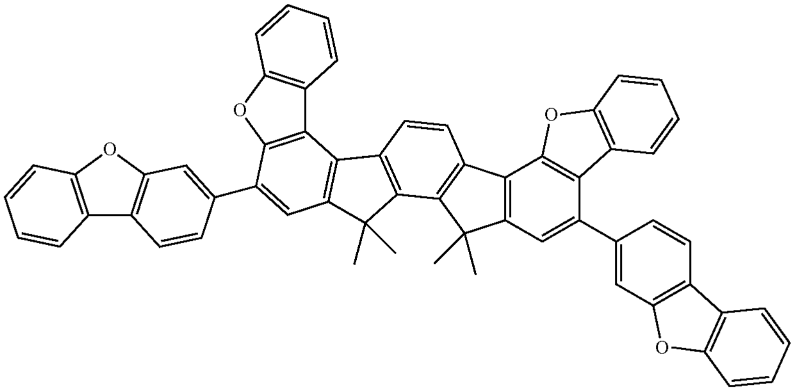
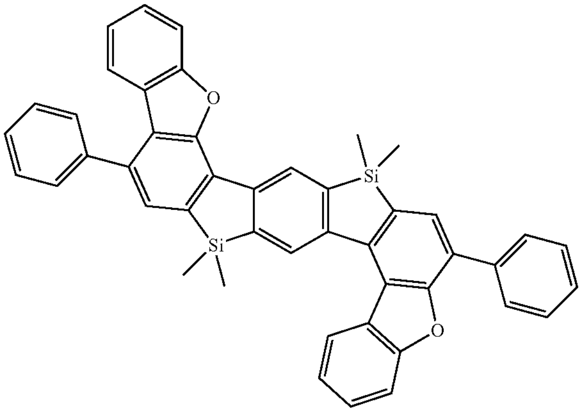

-continued
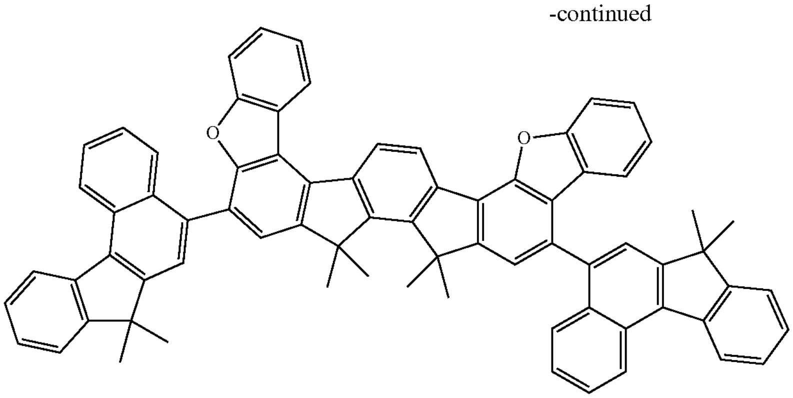
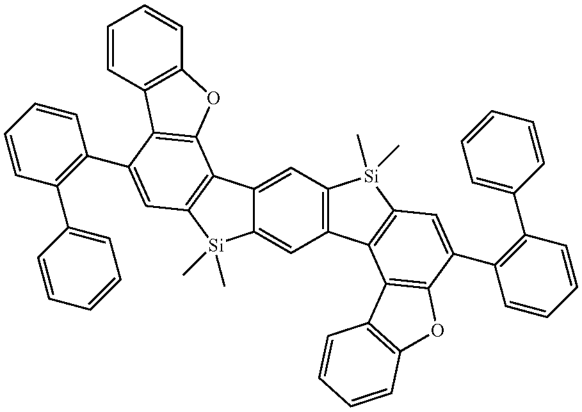
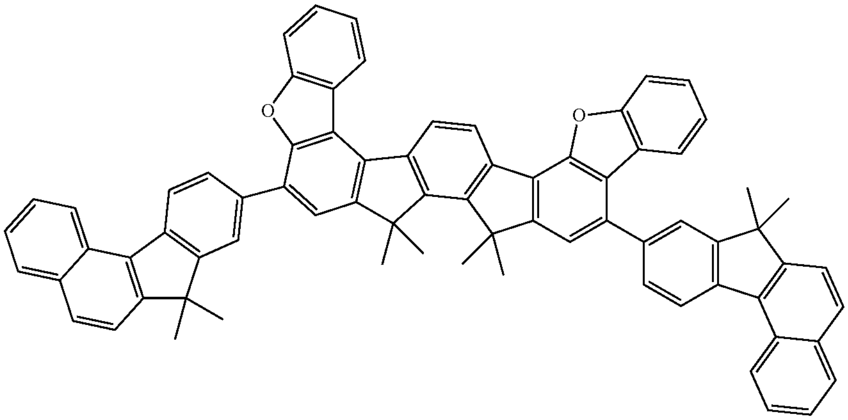
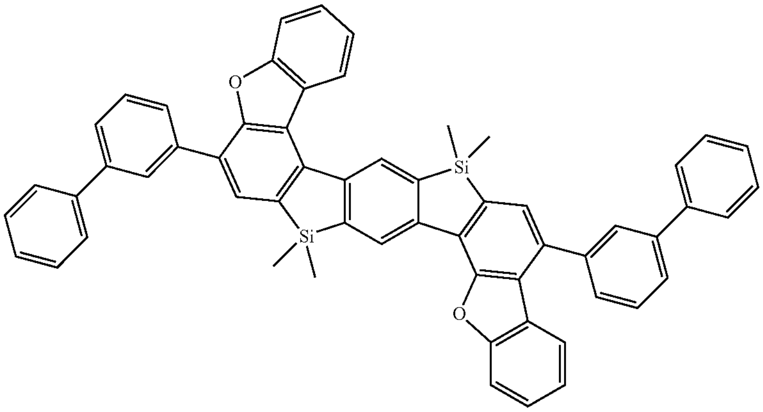

-continued
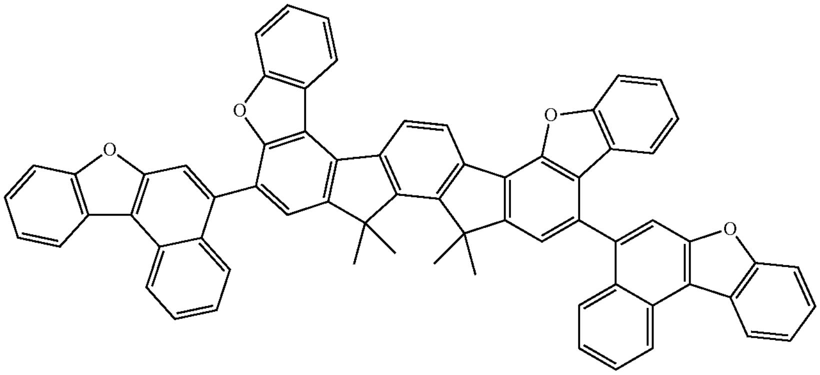
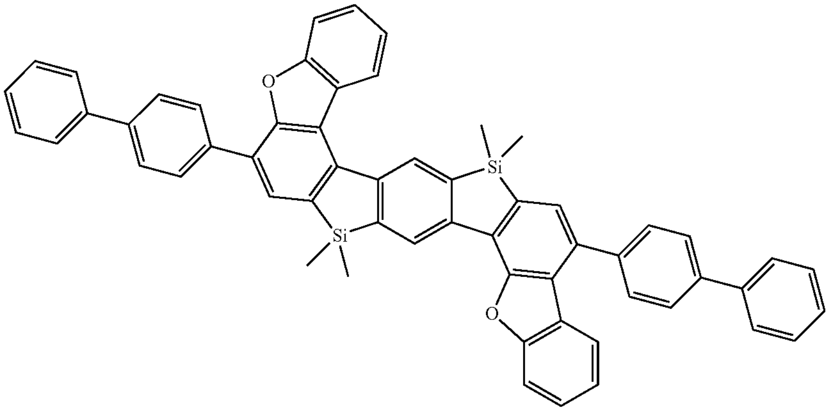
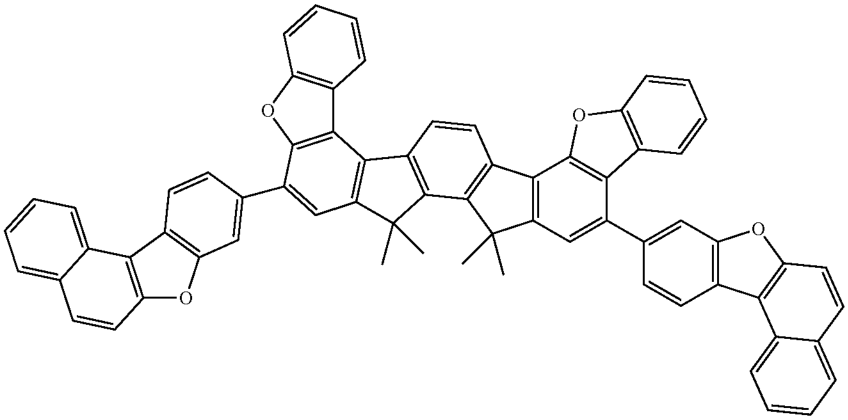
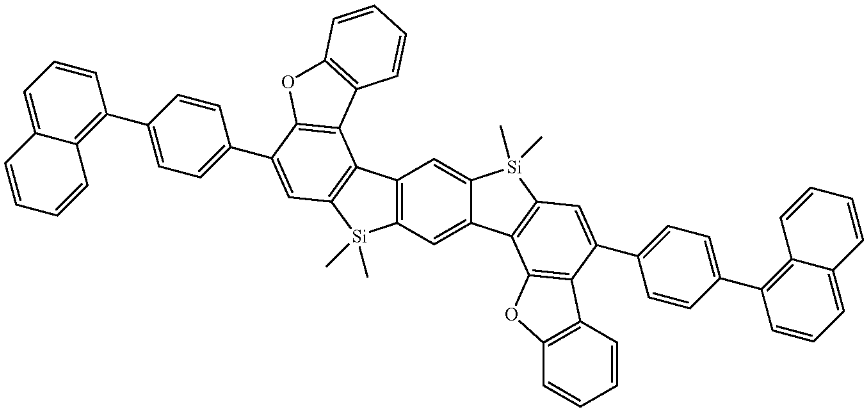

-continued
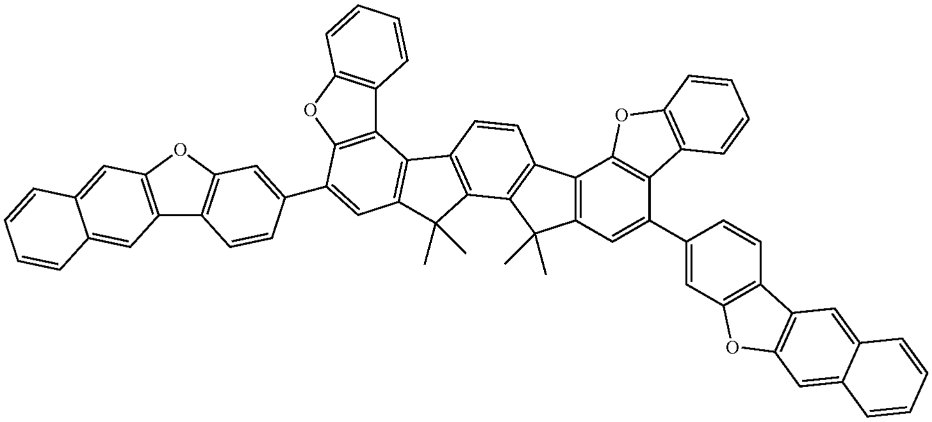
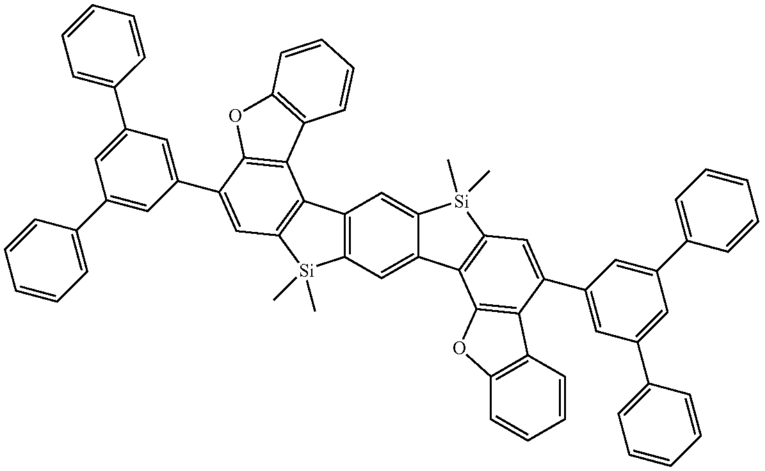
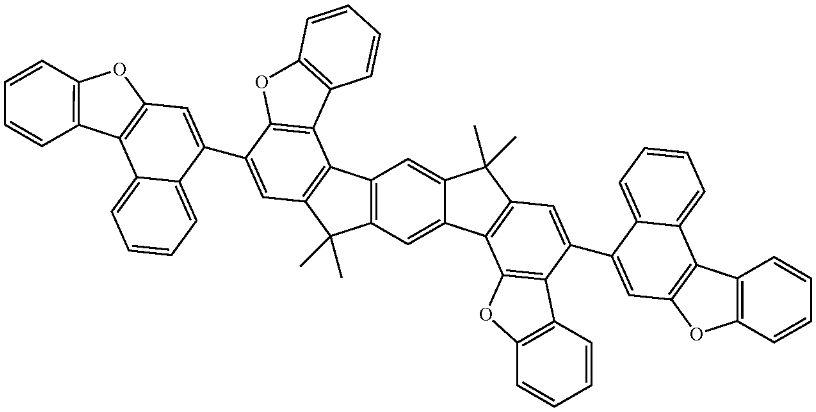
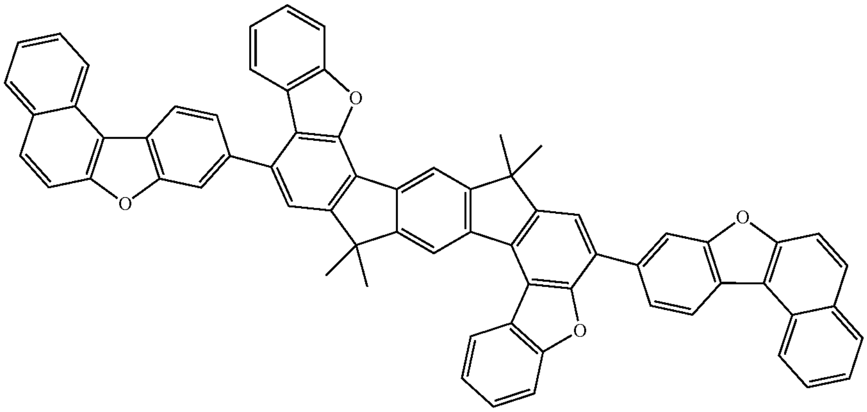

-continued
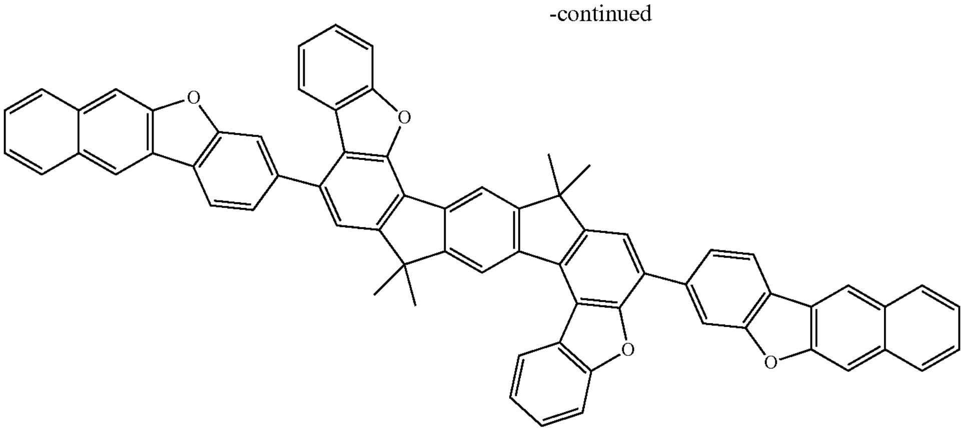
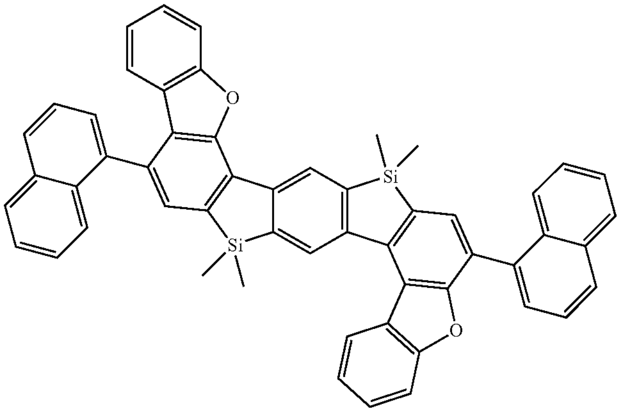
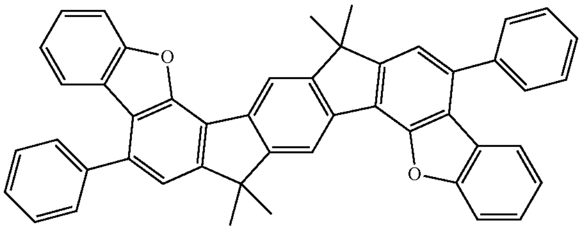
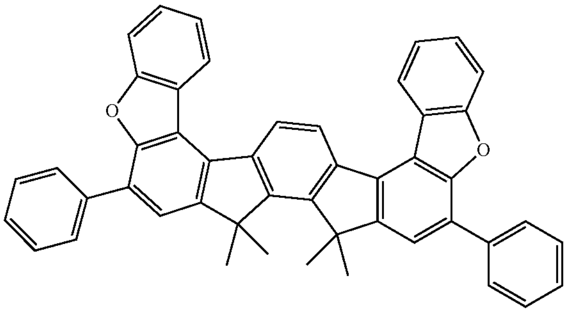
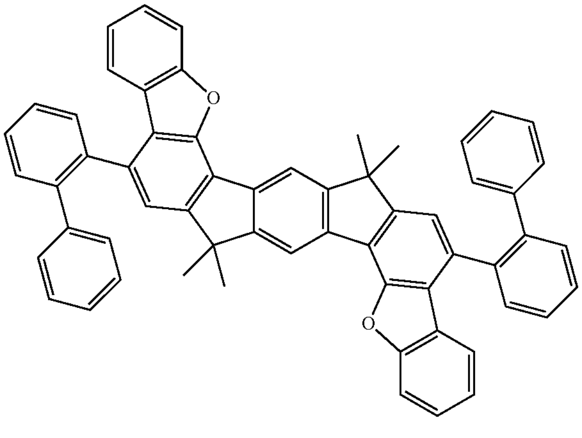
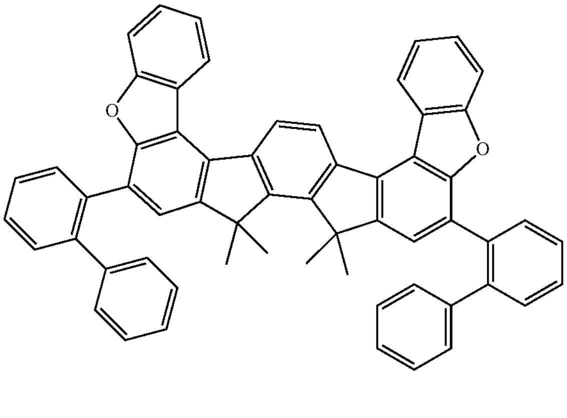

-continued
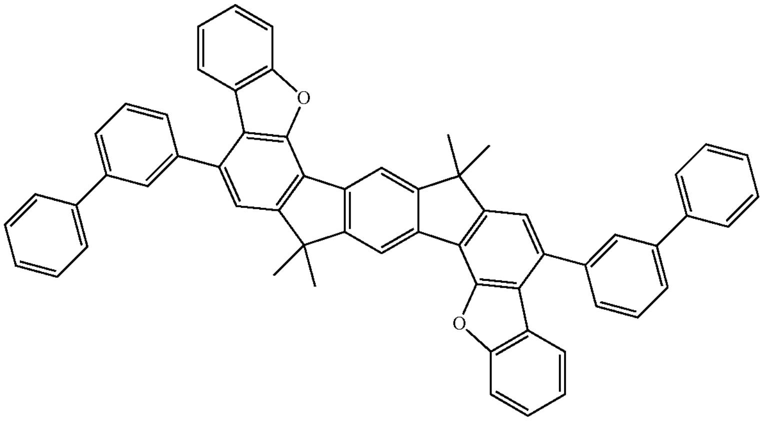
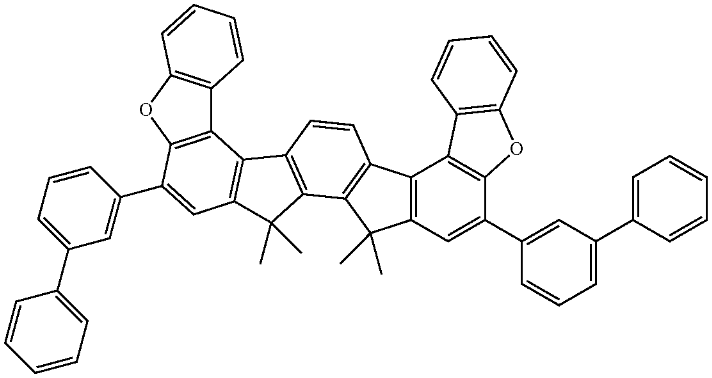
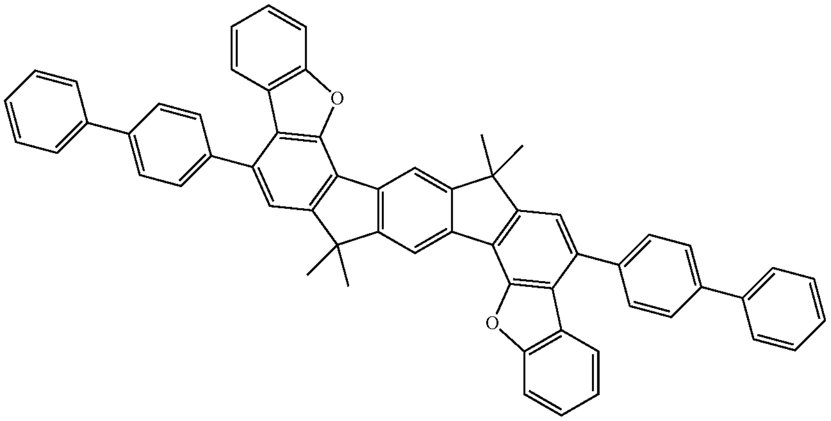
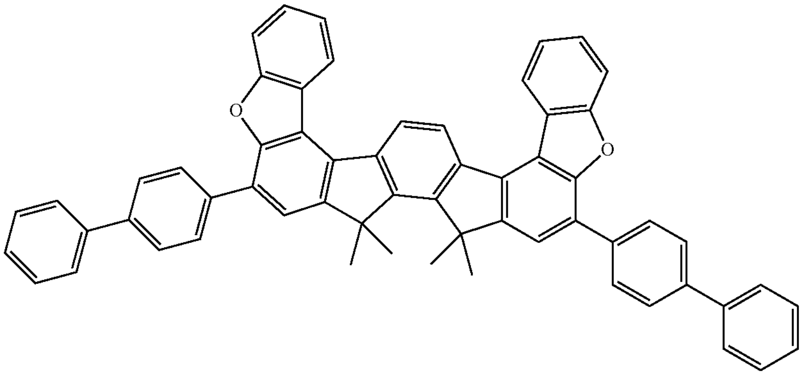

-continued
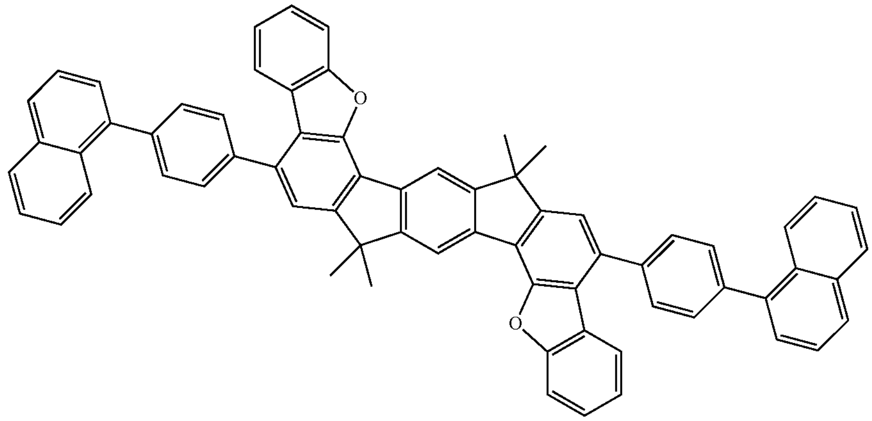
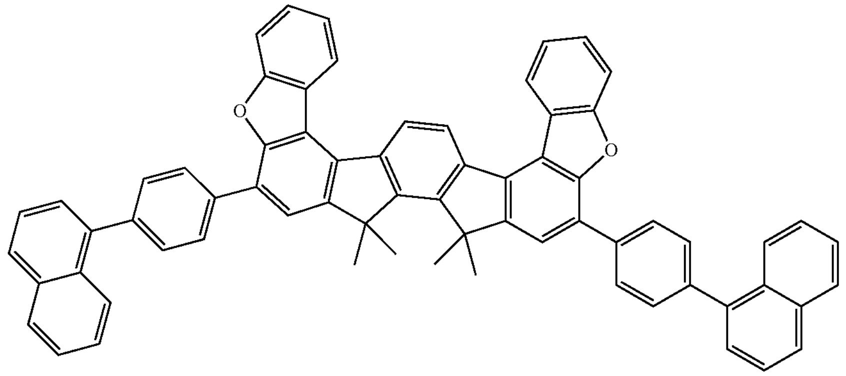
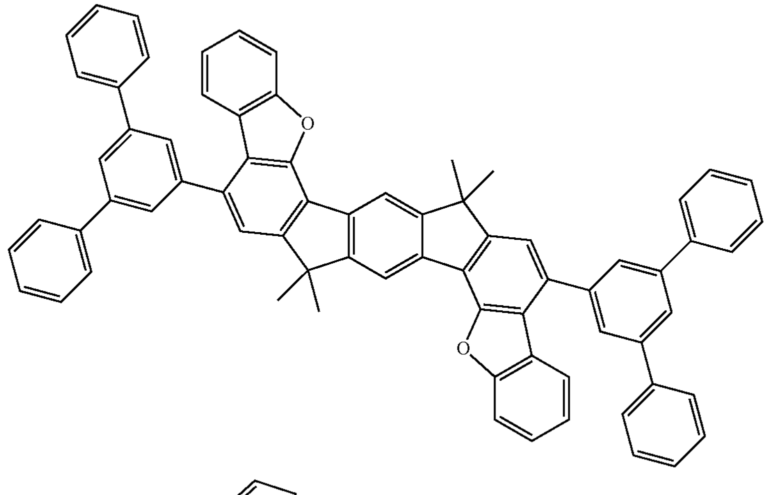
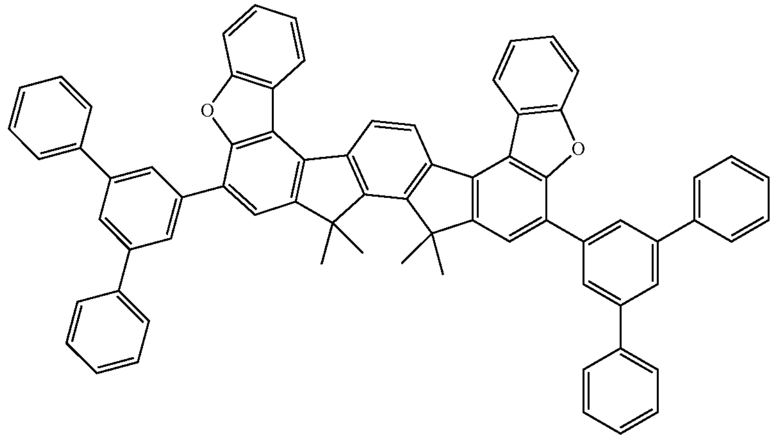

-continued
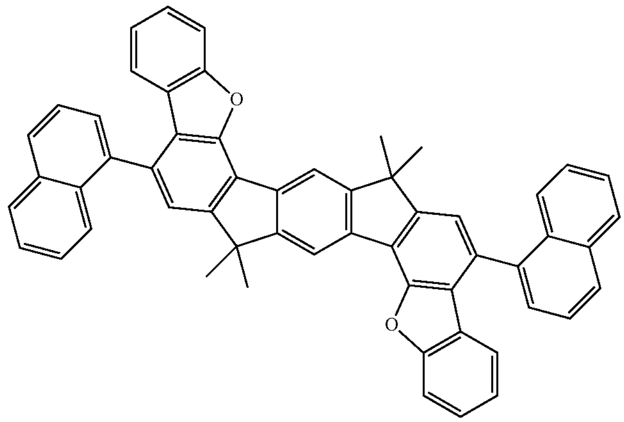
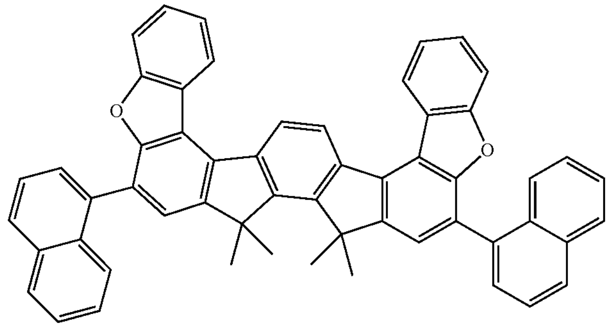
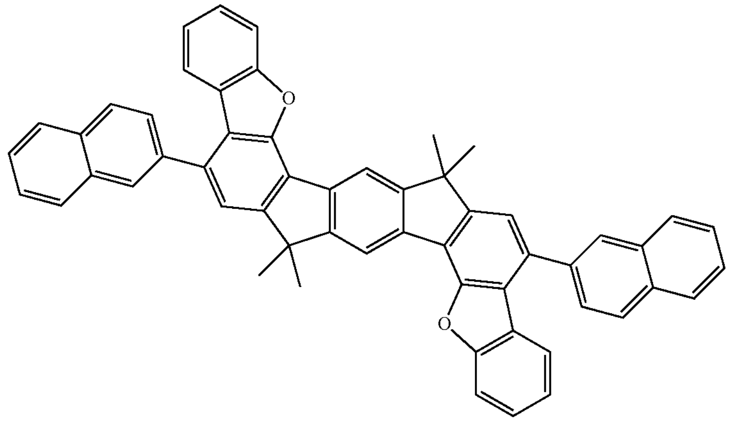
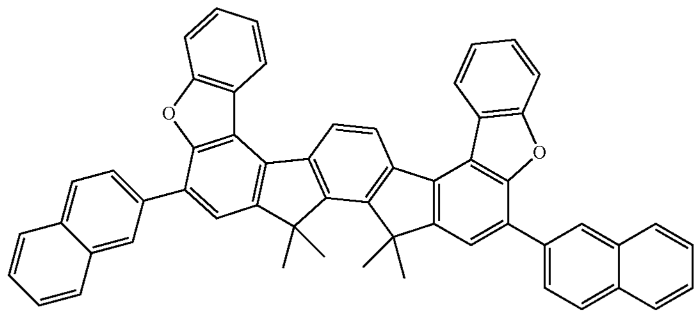

-continued
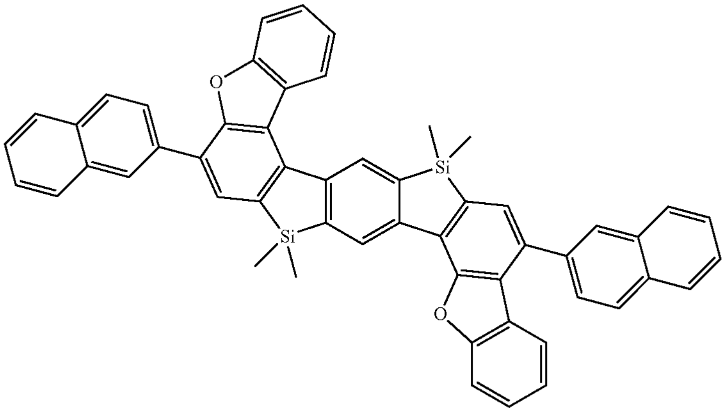
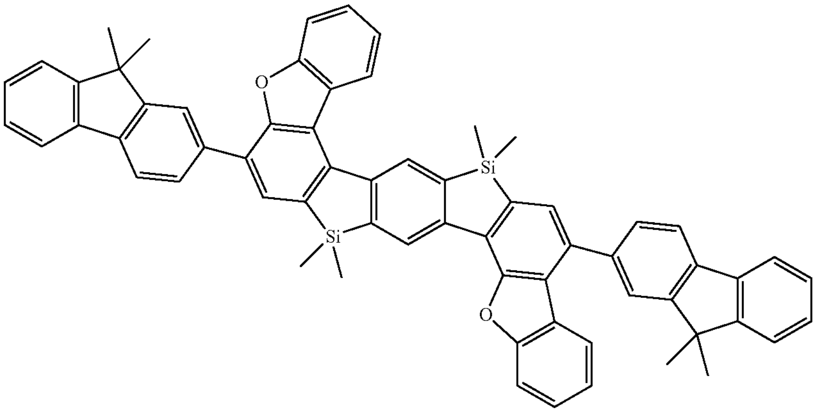
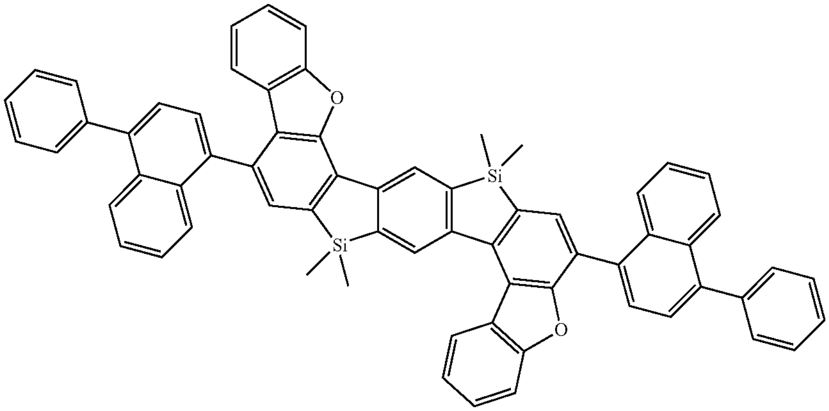
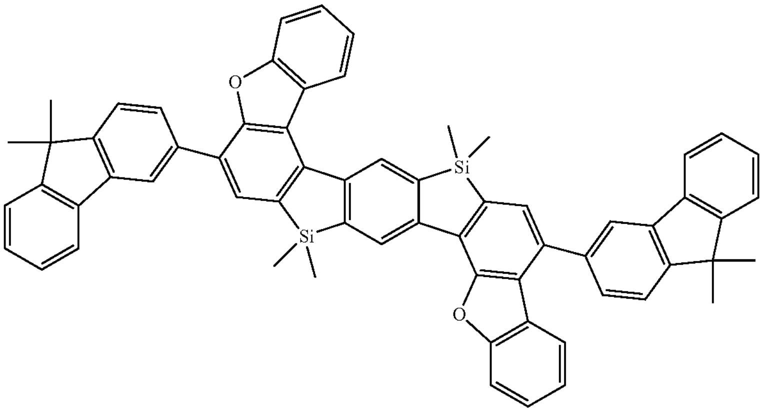

-continued
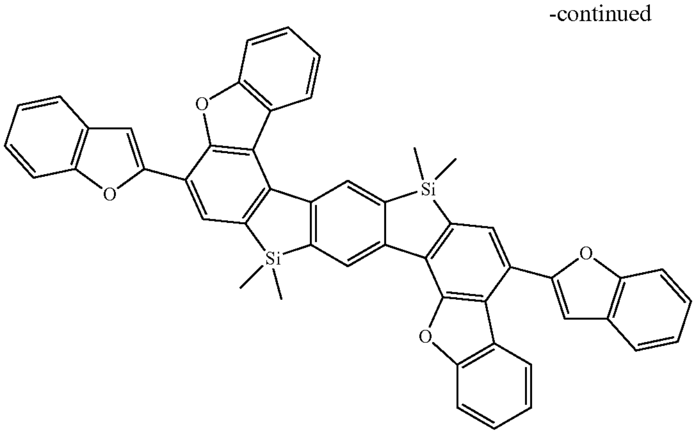
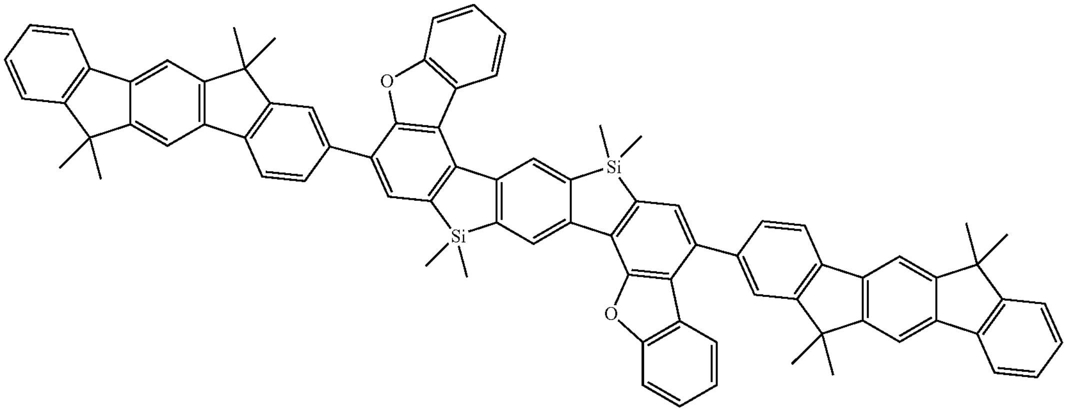
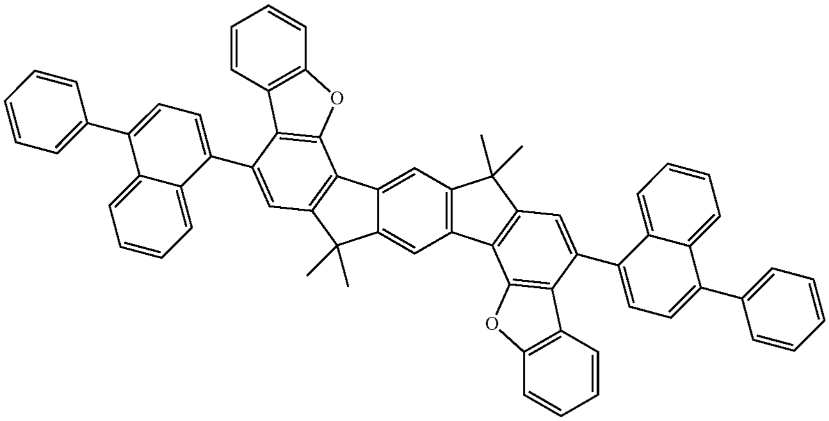
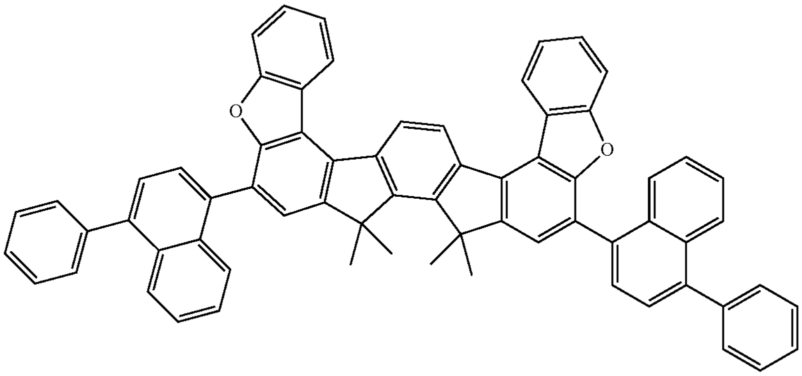

-continued
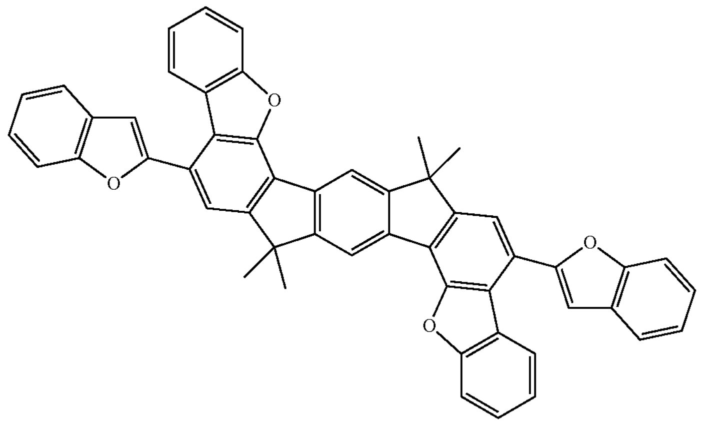
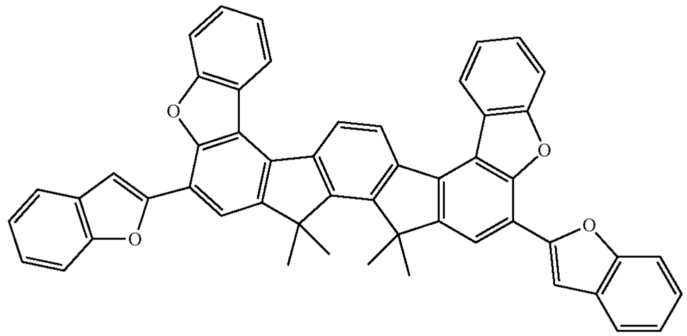
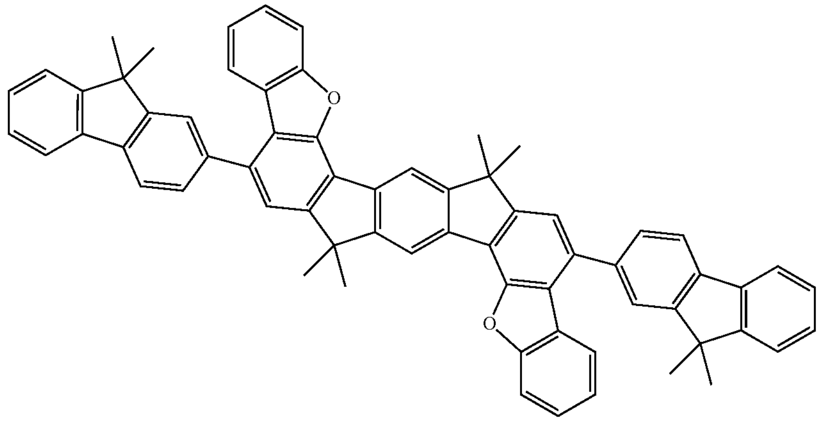
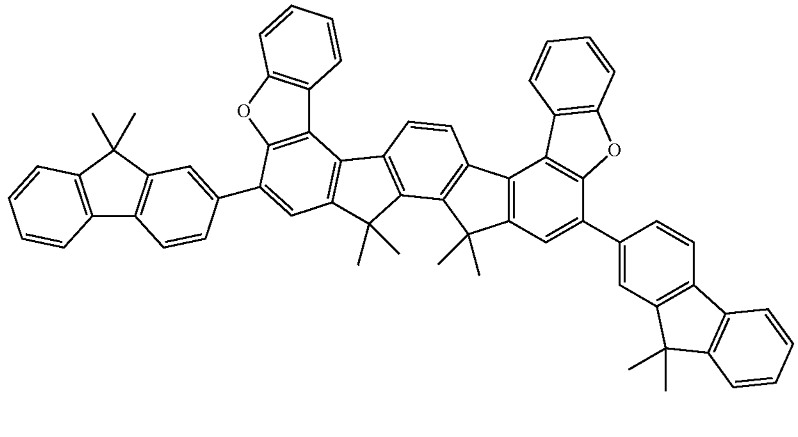

-continued
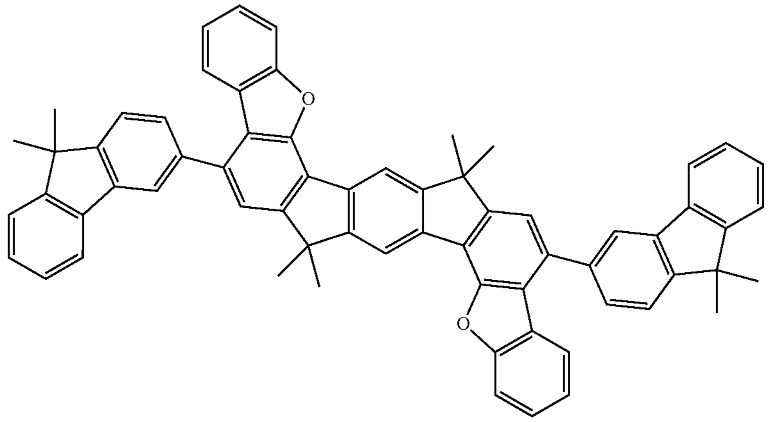
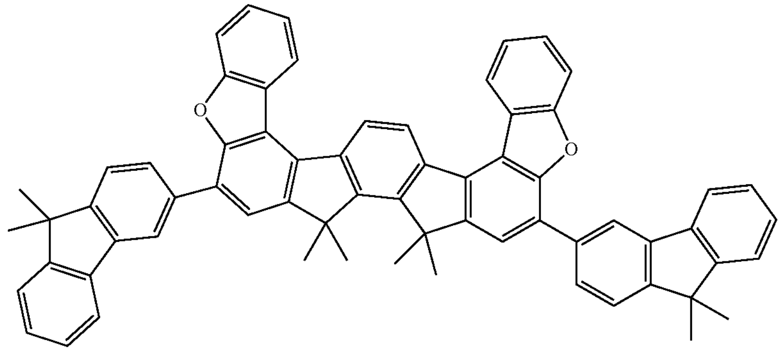
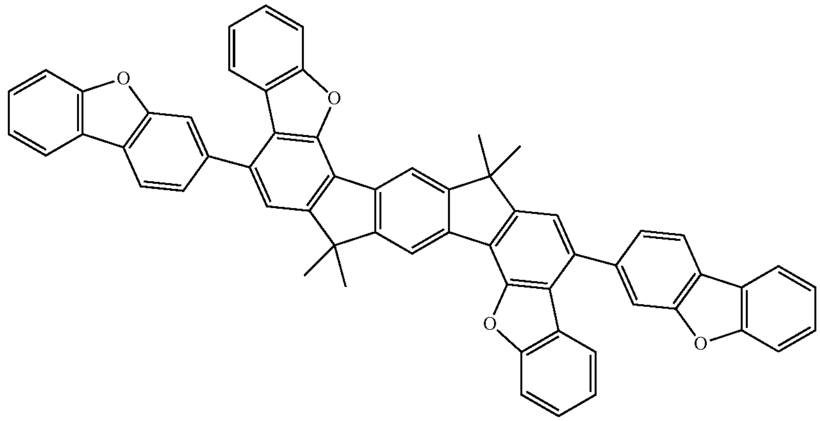
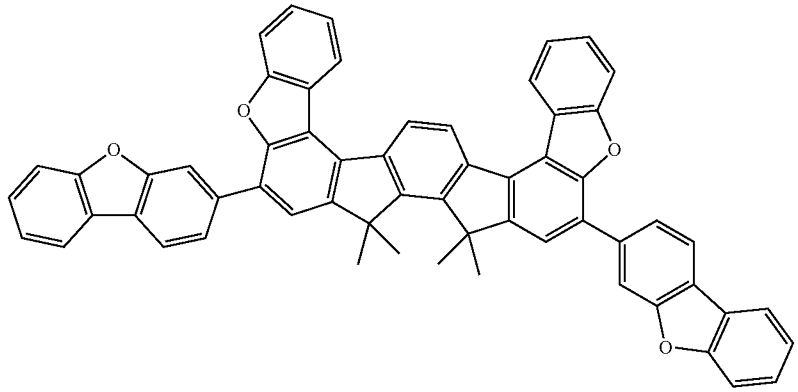

-continued
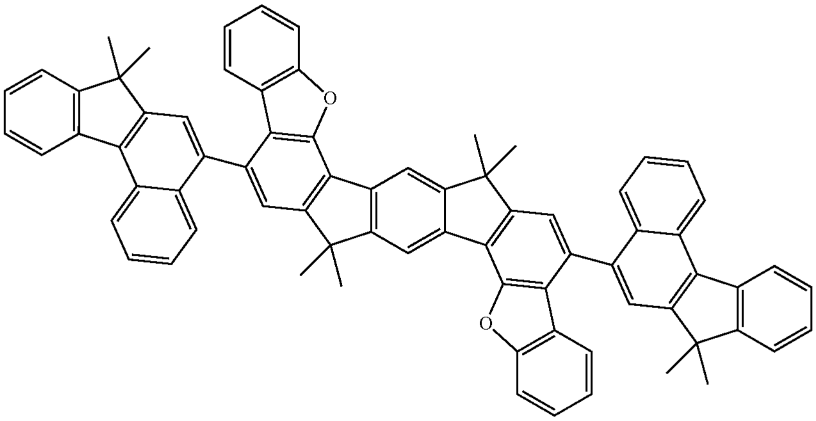
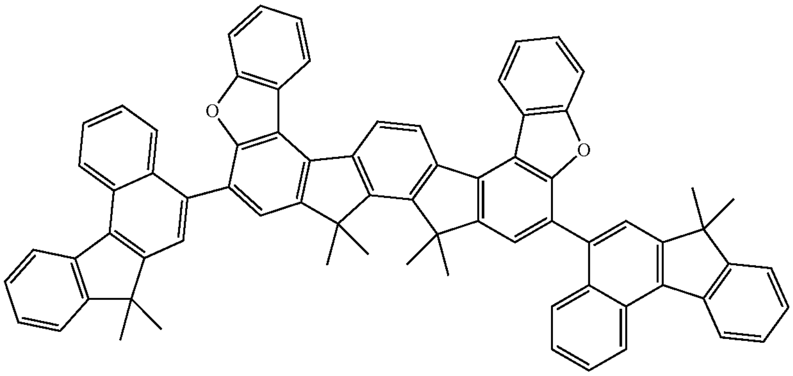
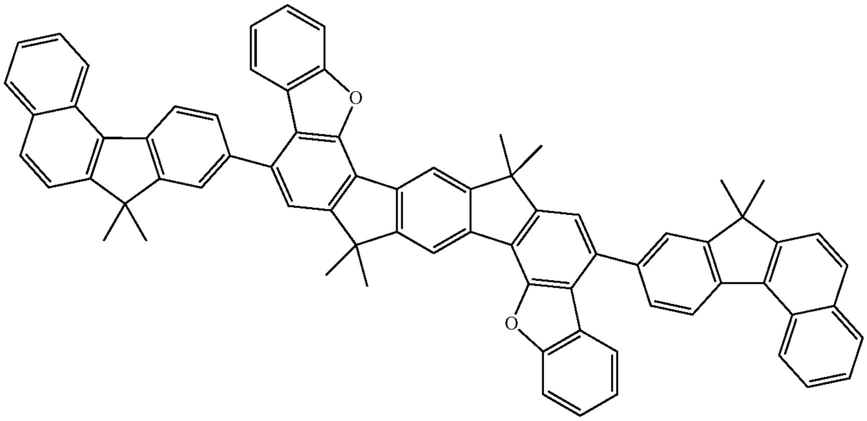
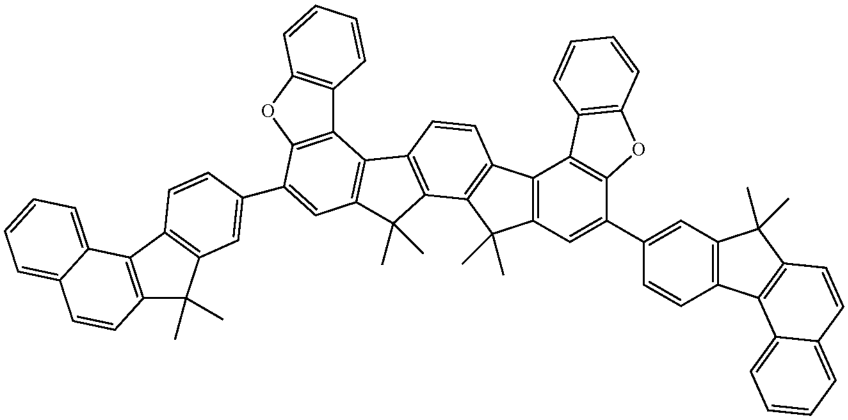

-continued
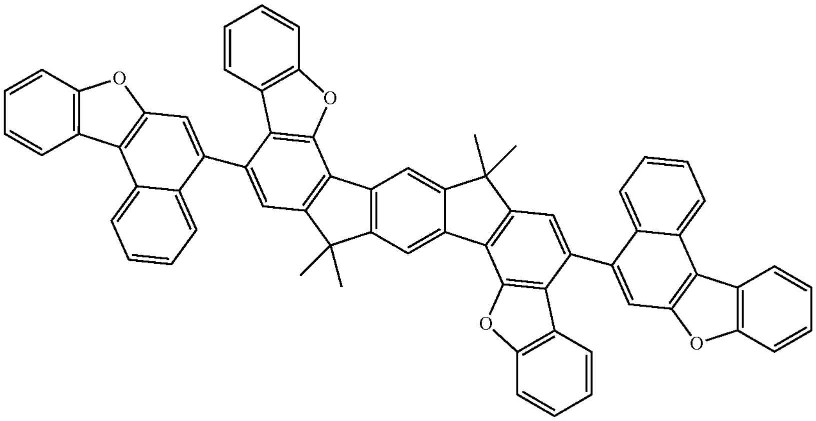
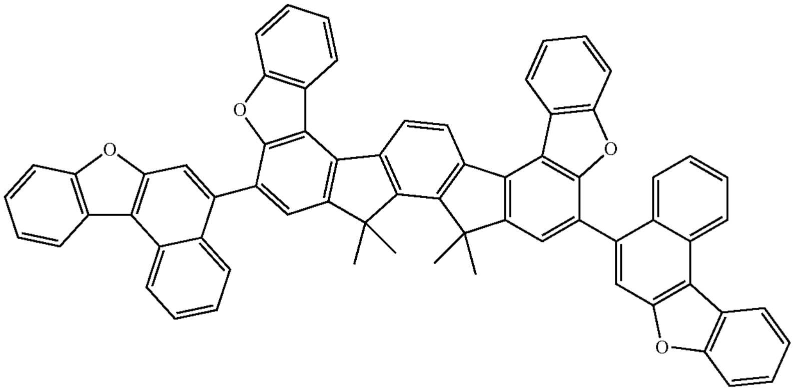
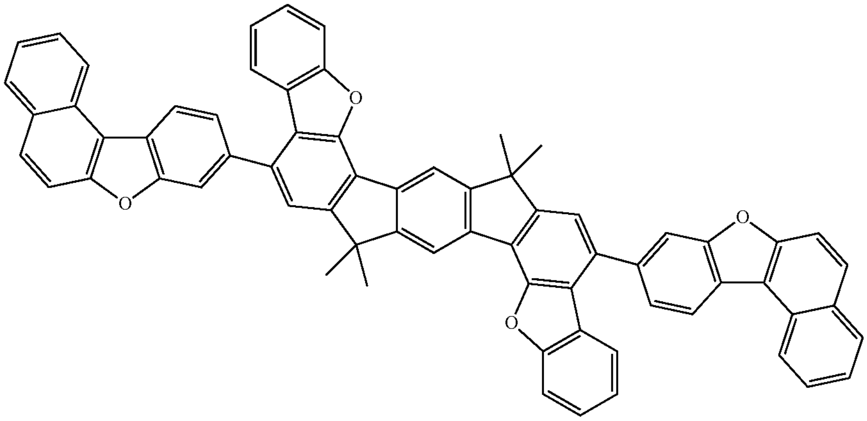
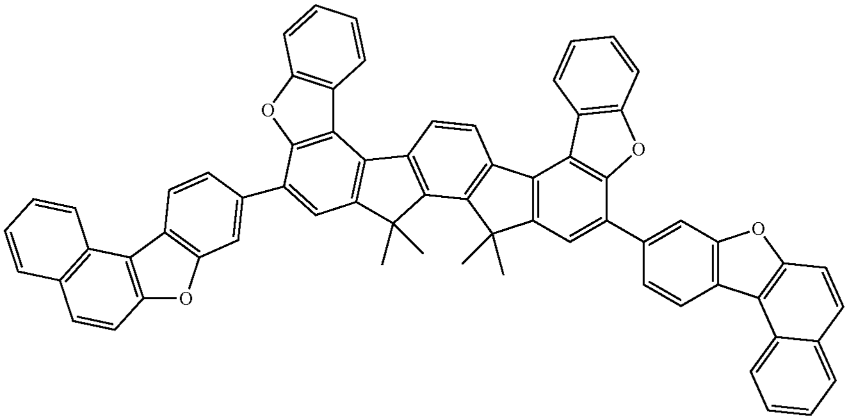

-continued
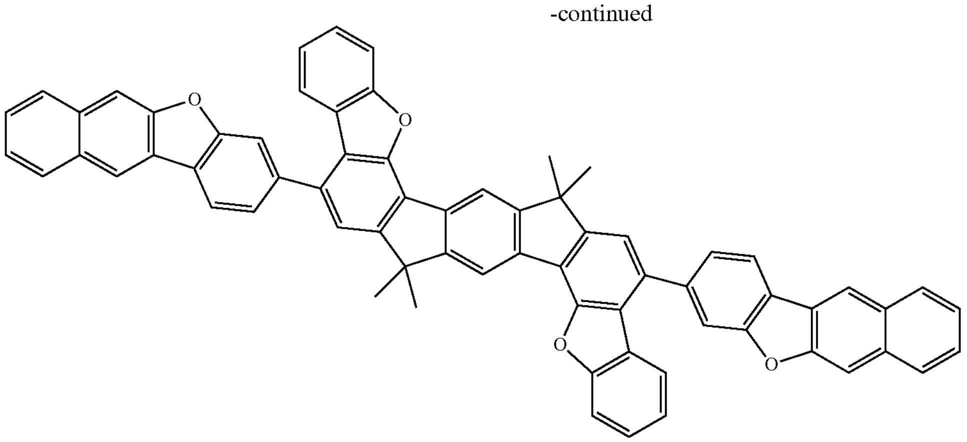
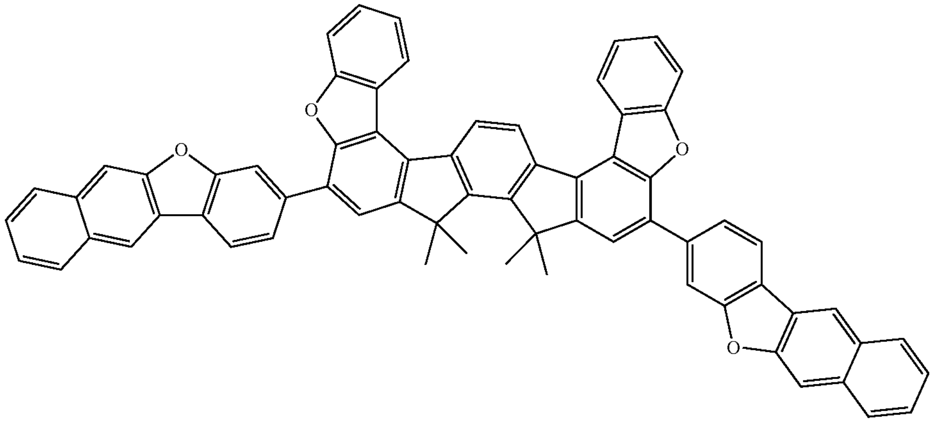
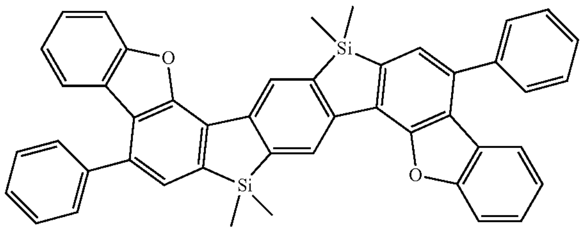
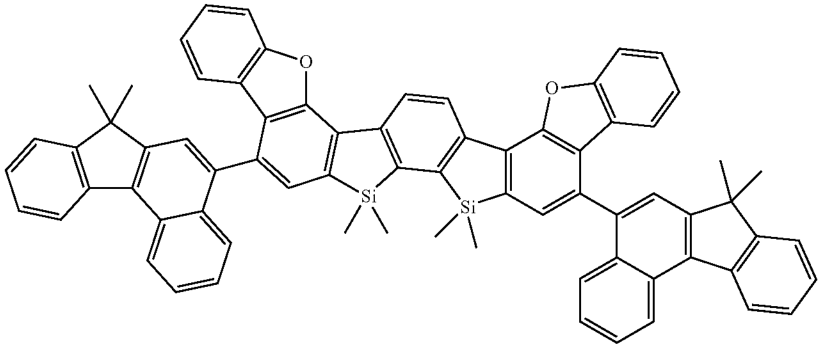
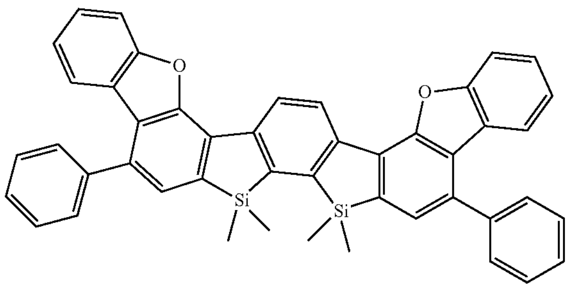
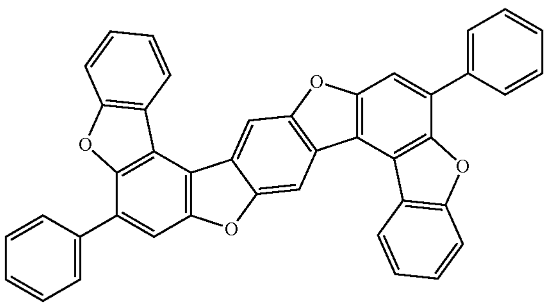

-continued
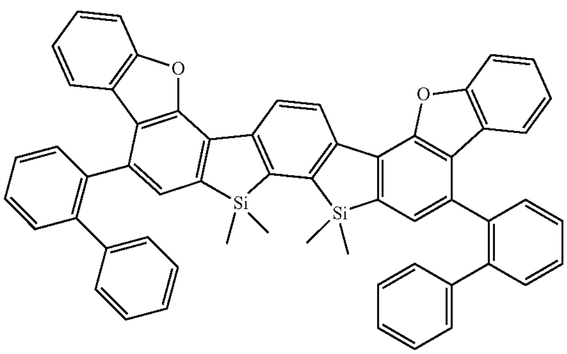
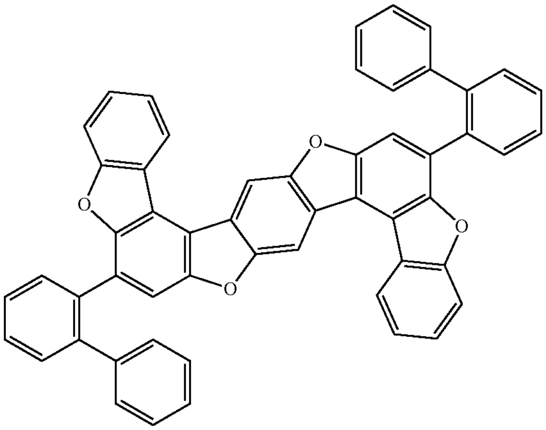
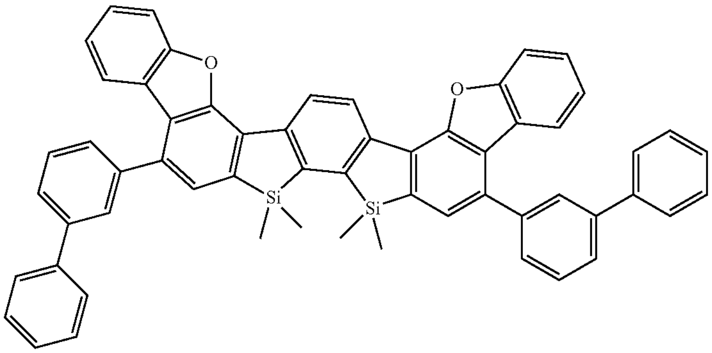
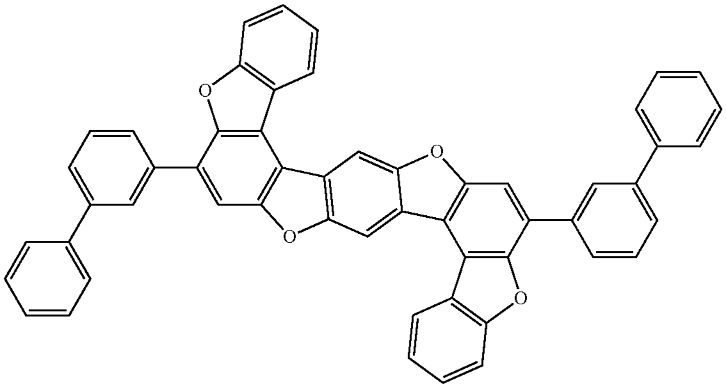
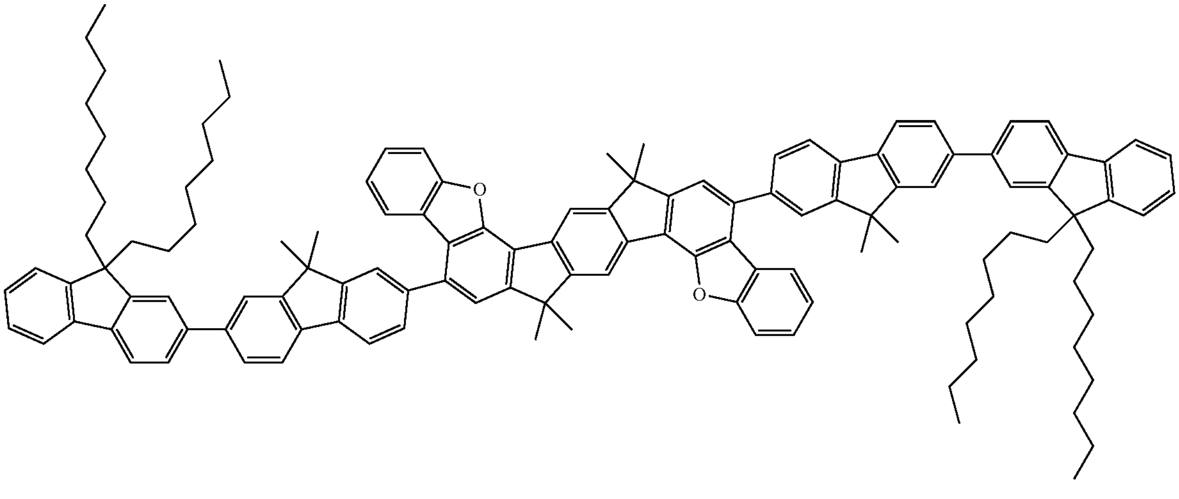

-continued
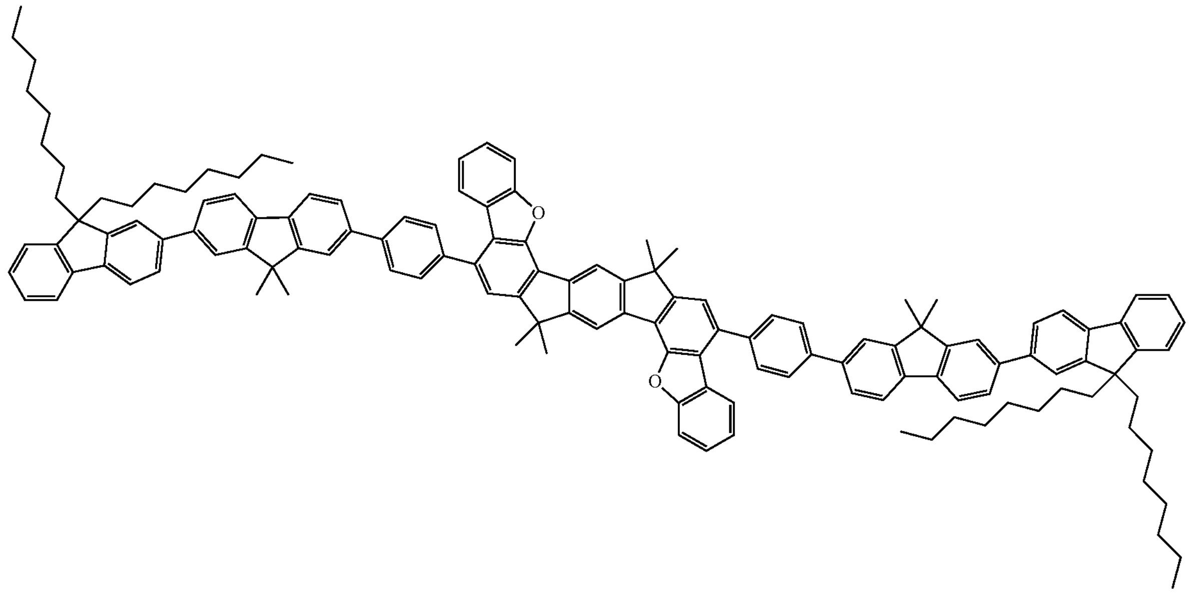
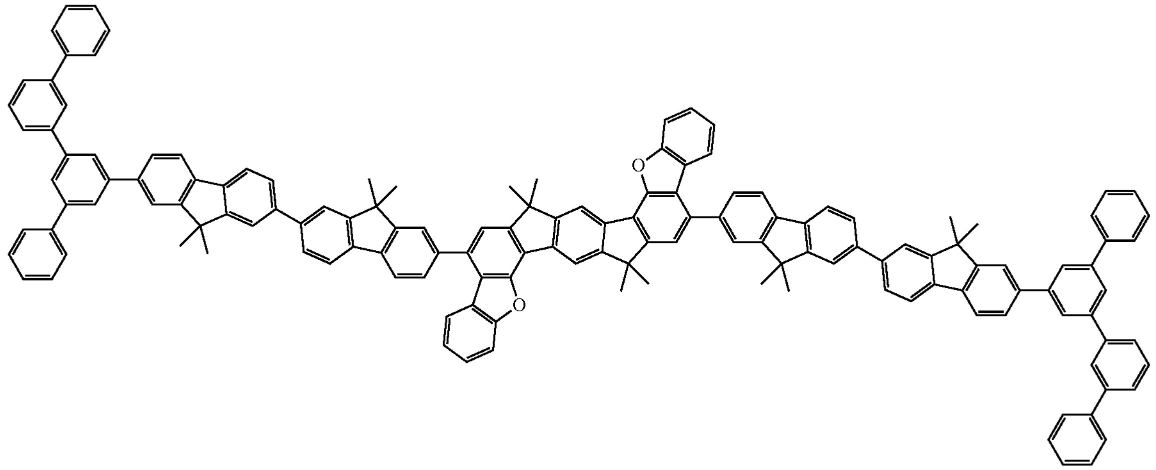
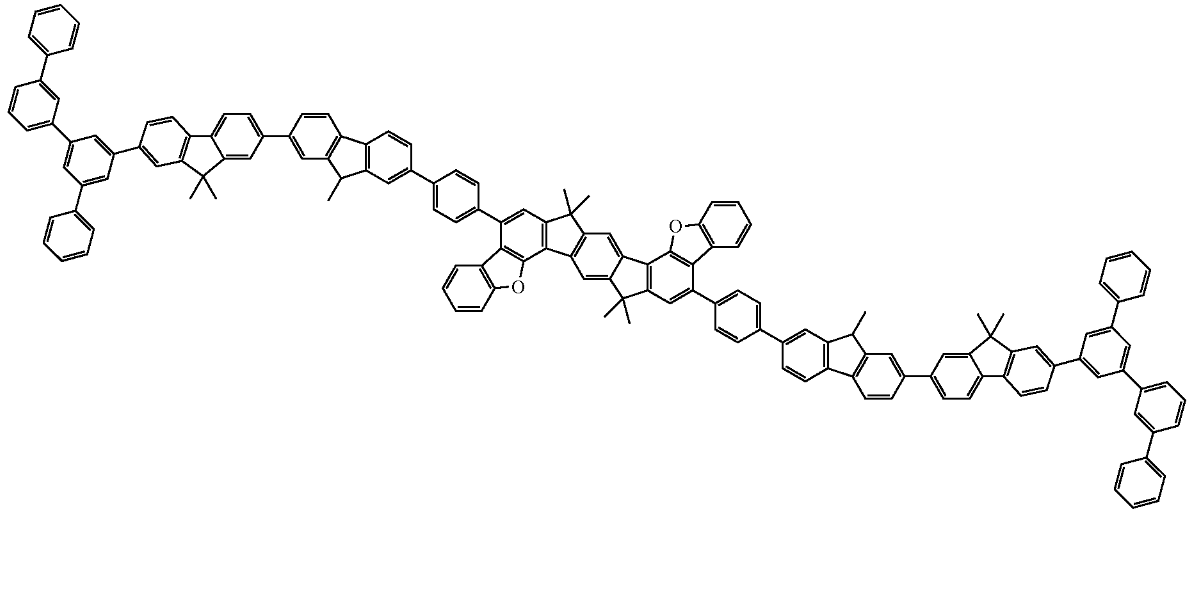

-continued
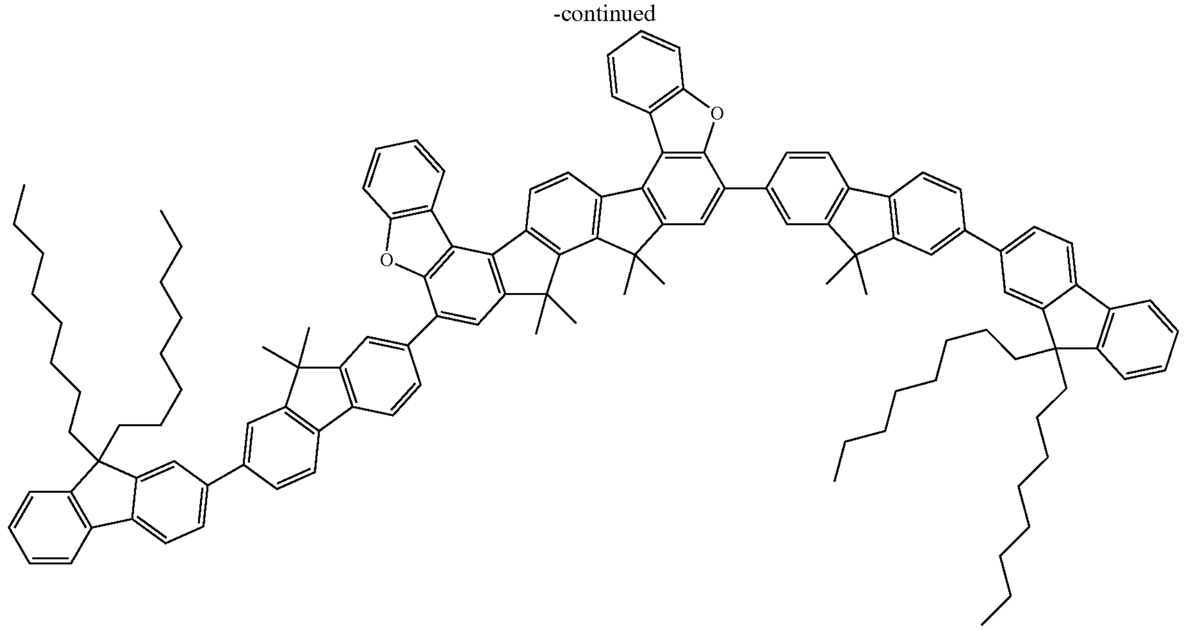
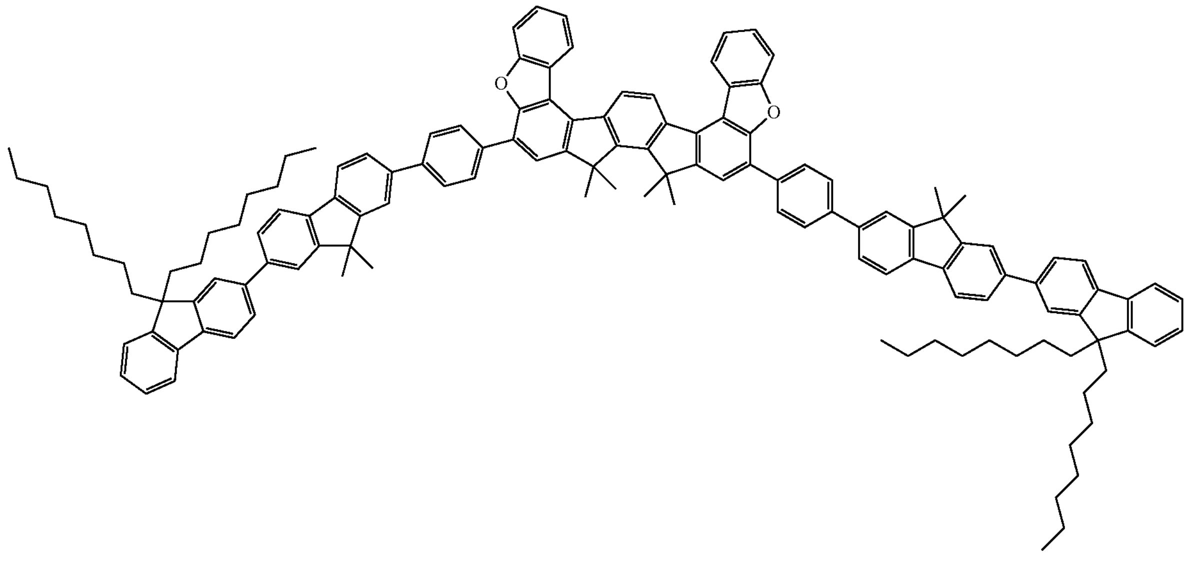

-continued
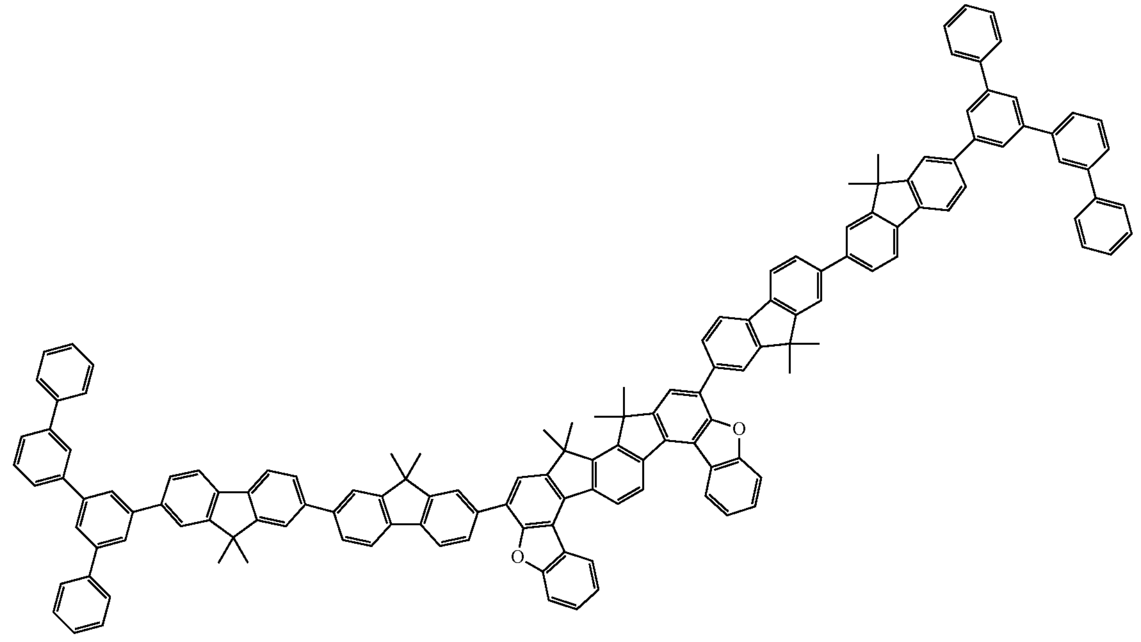
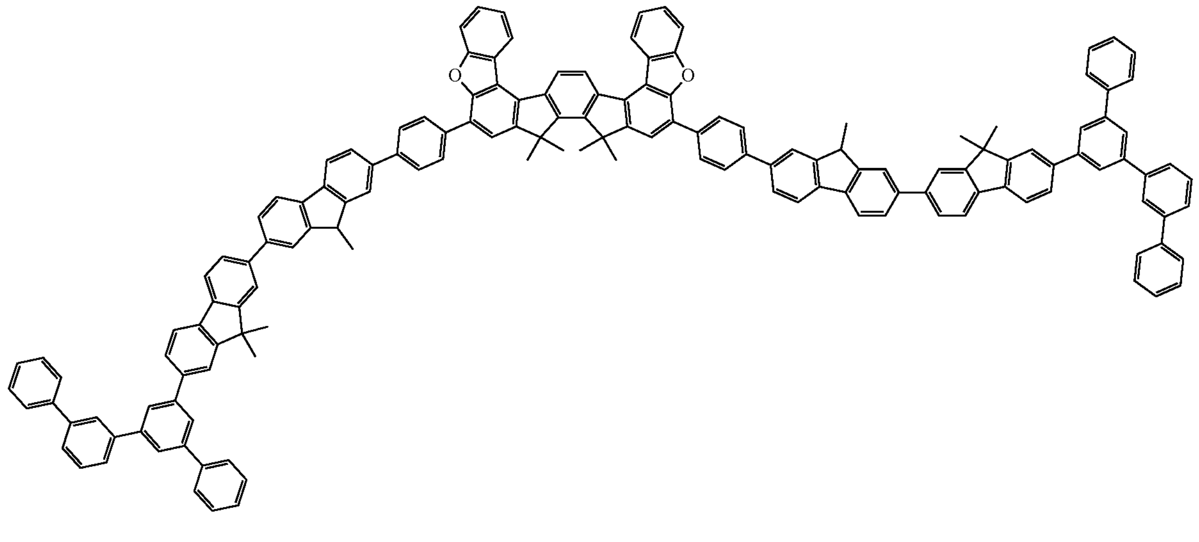
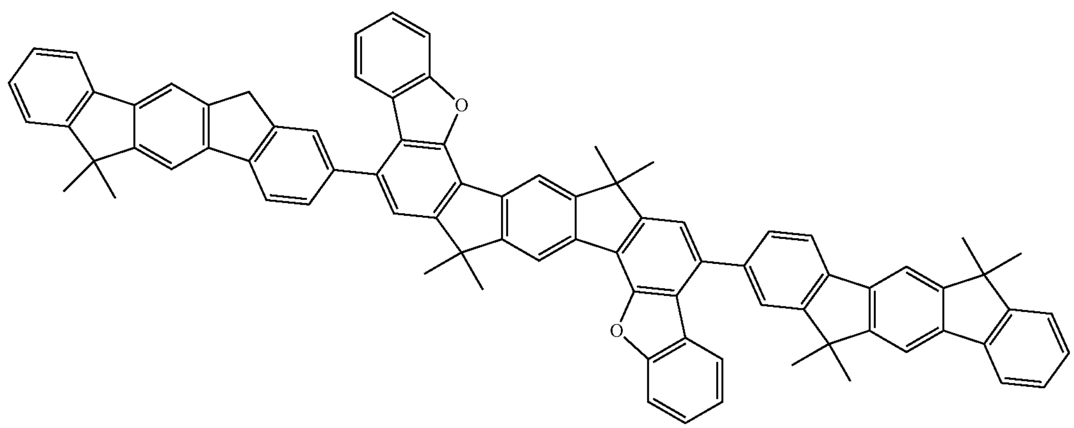

-continued
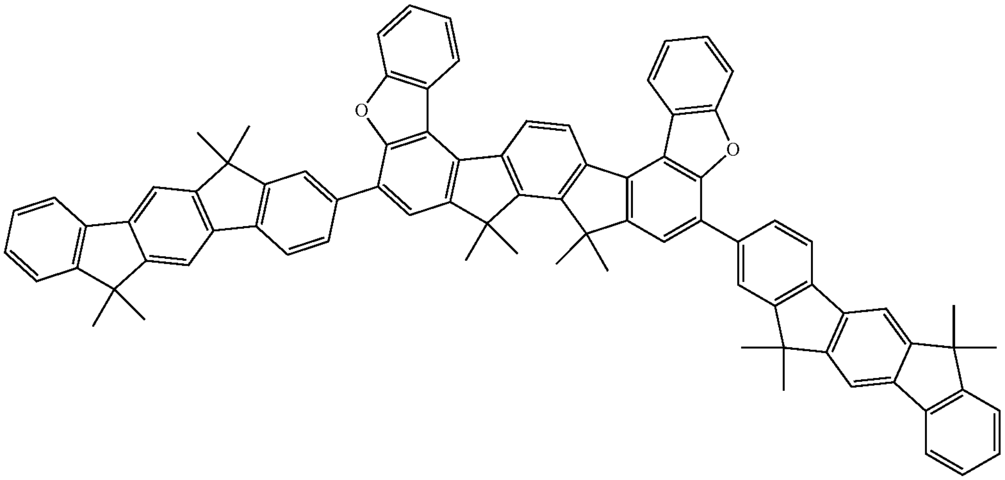
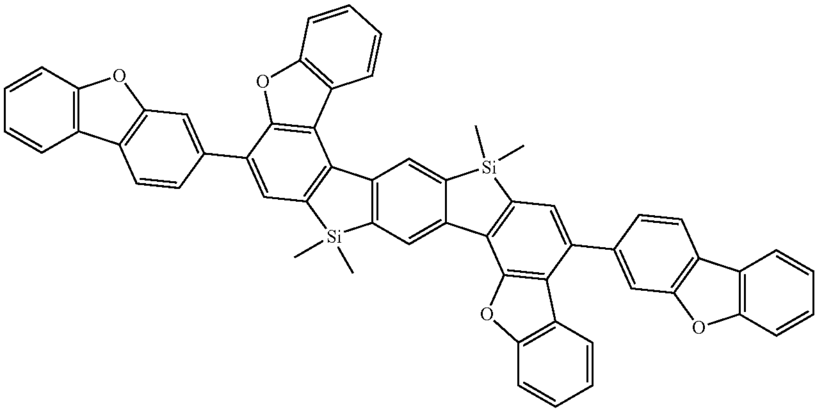
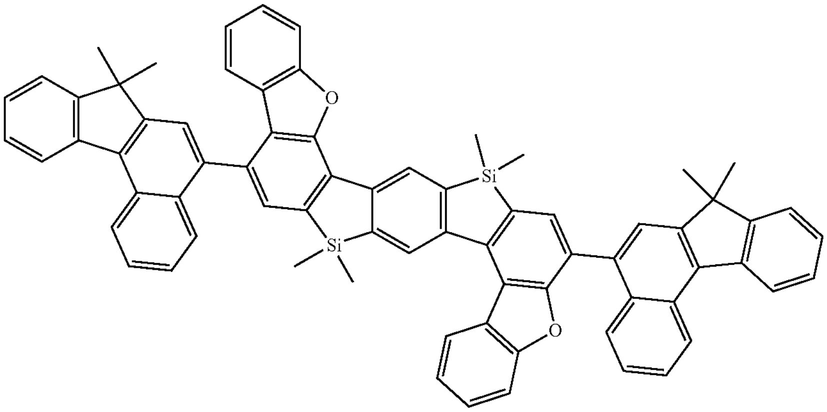
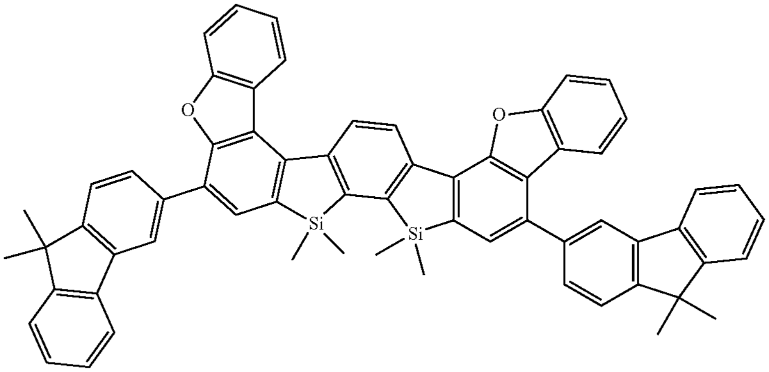

-continued
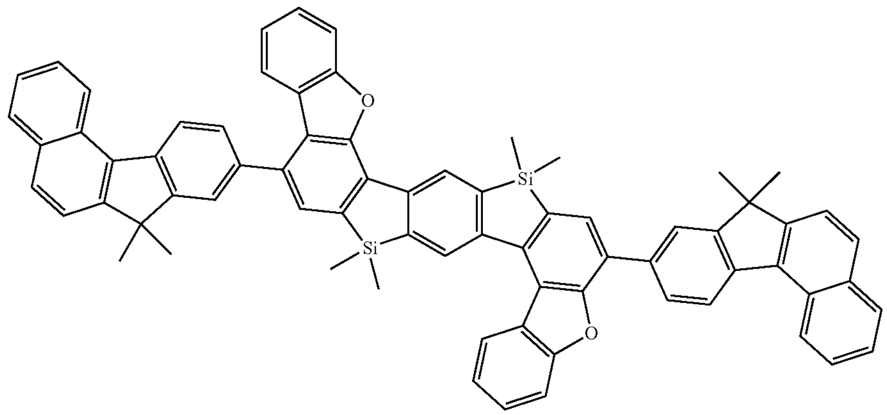
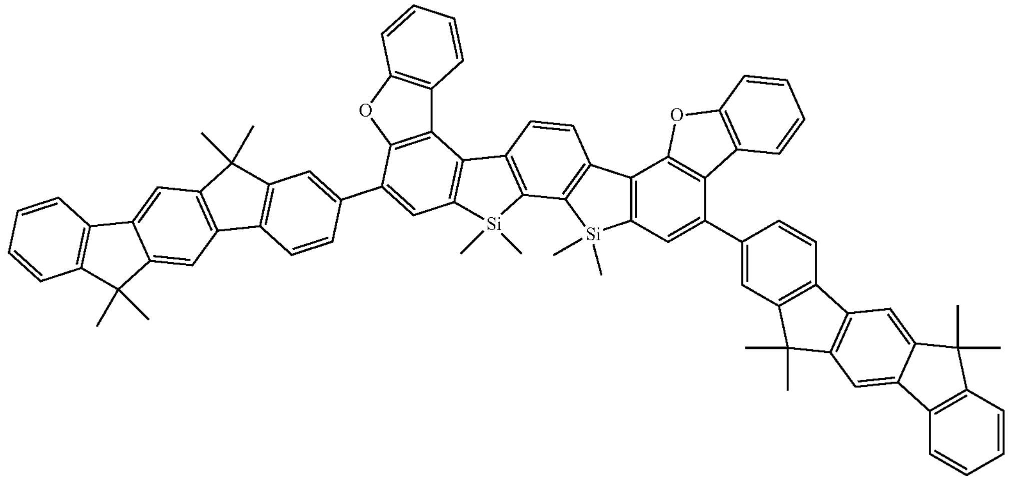
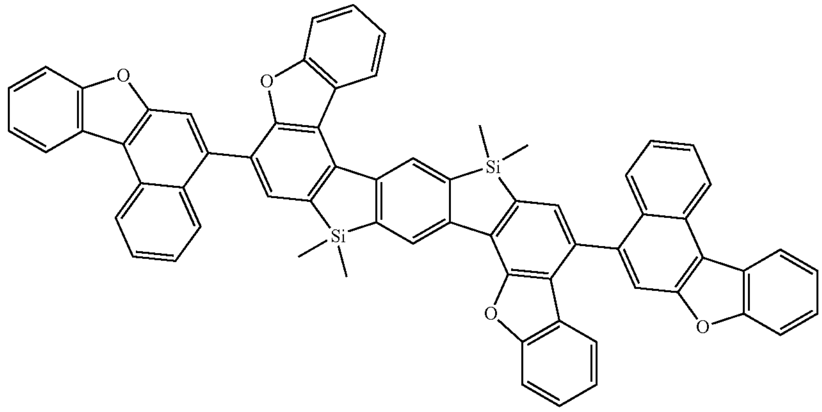
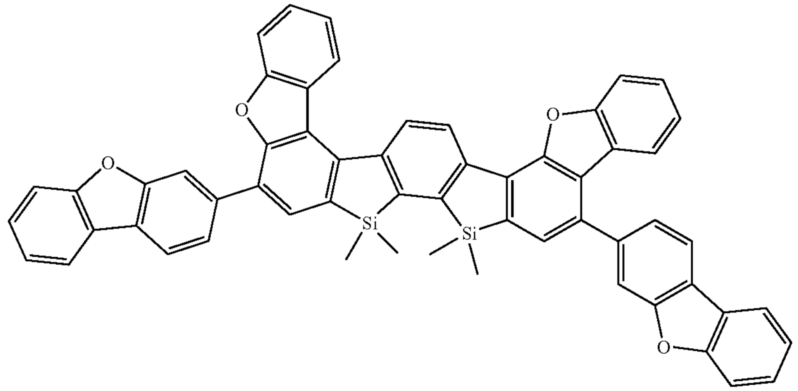

-continued
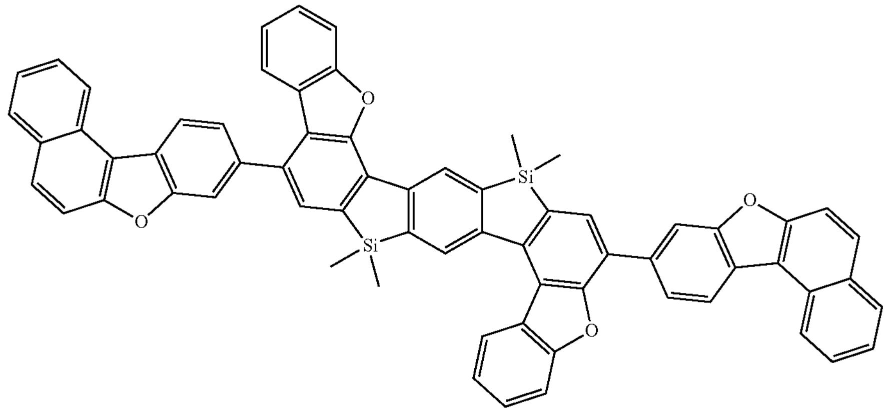
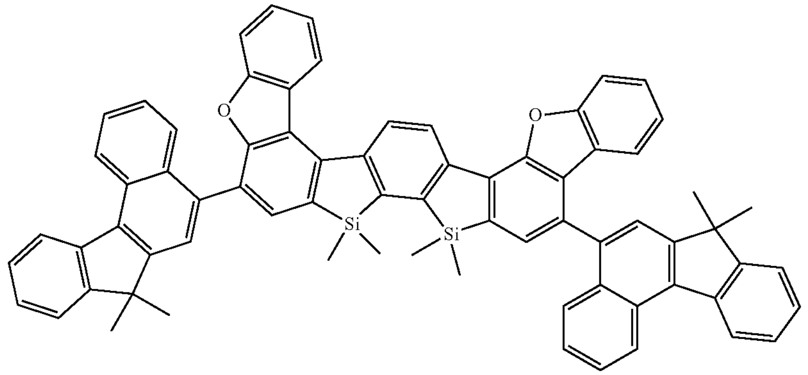
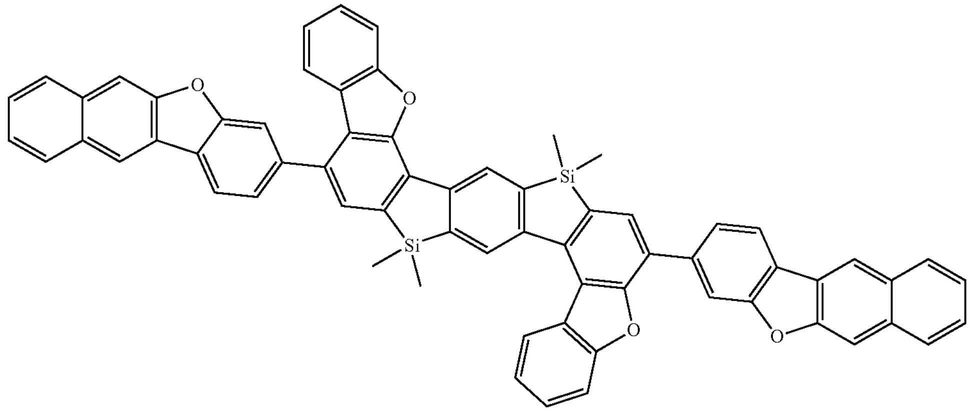
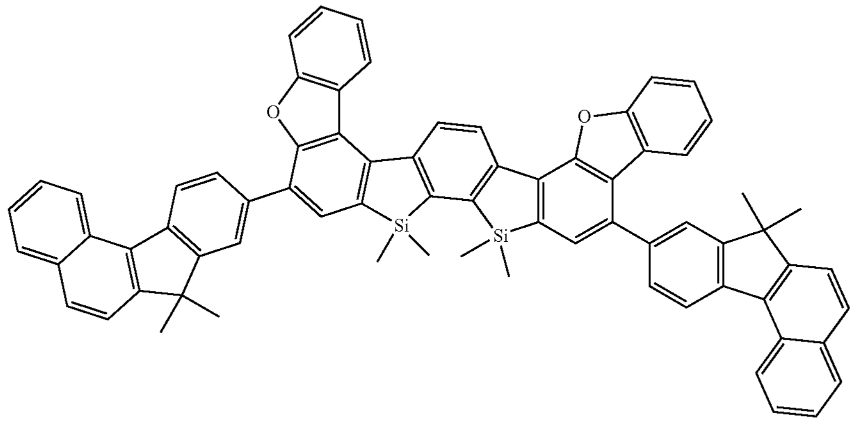

-continued
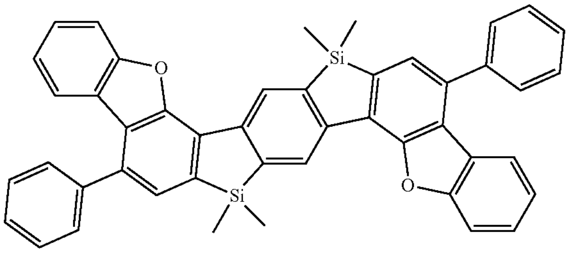
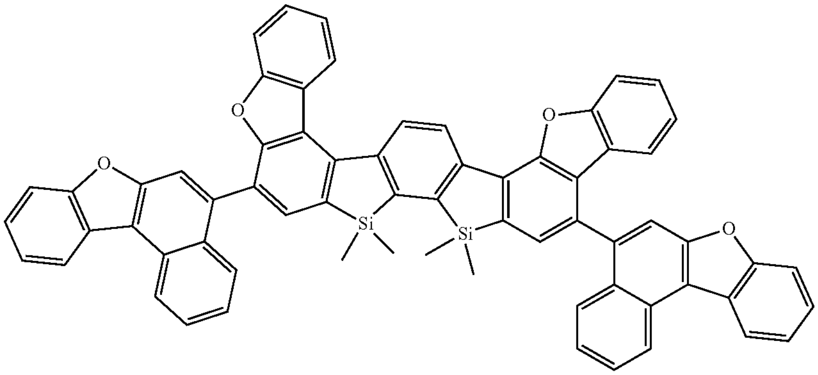
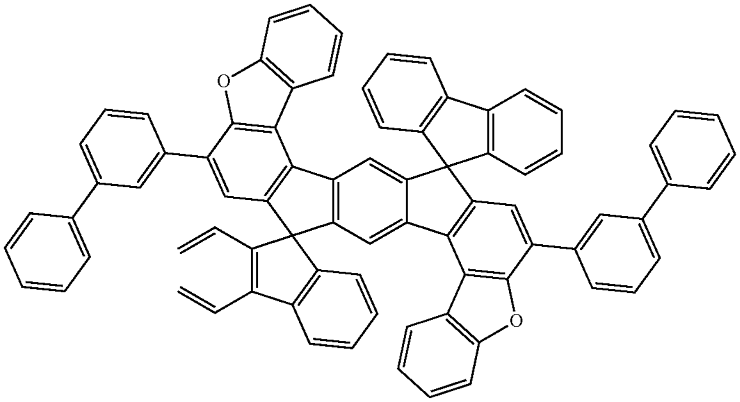
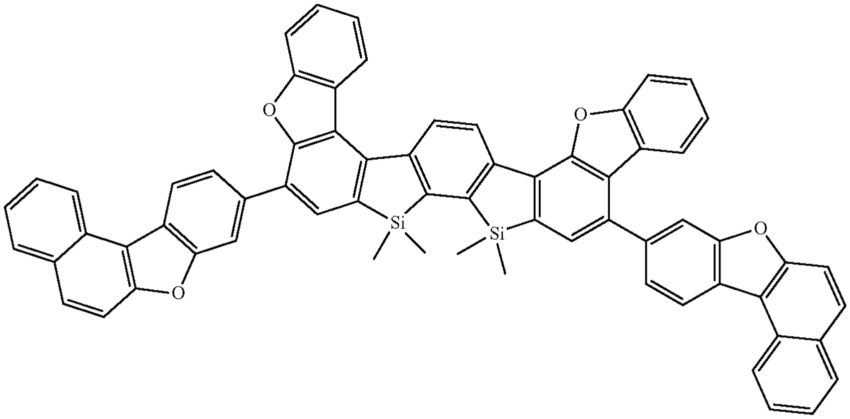

-continued
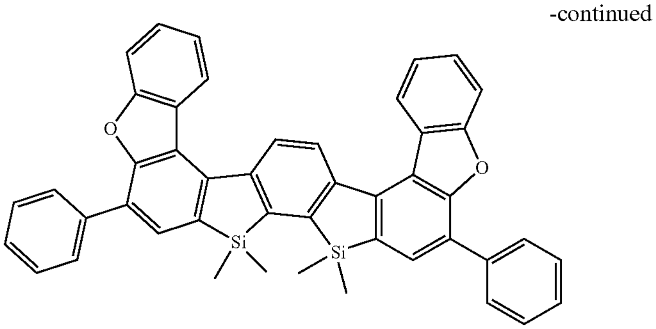
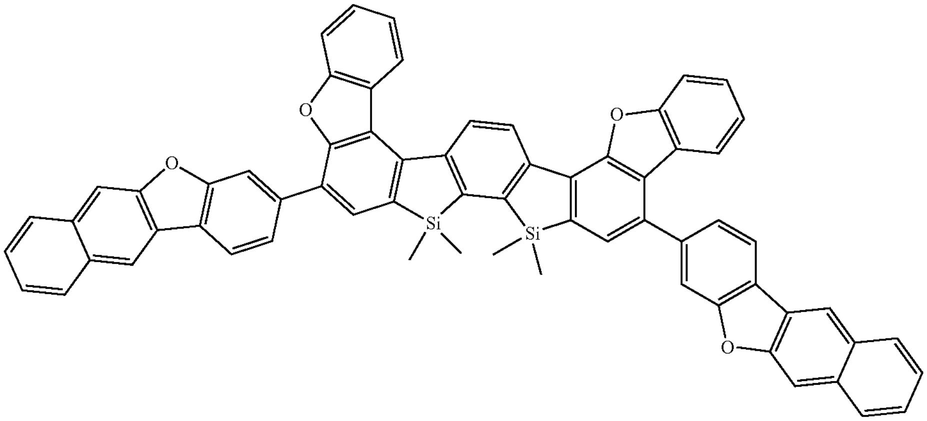
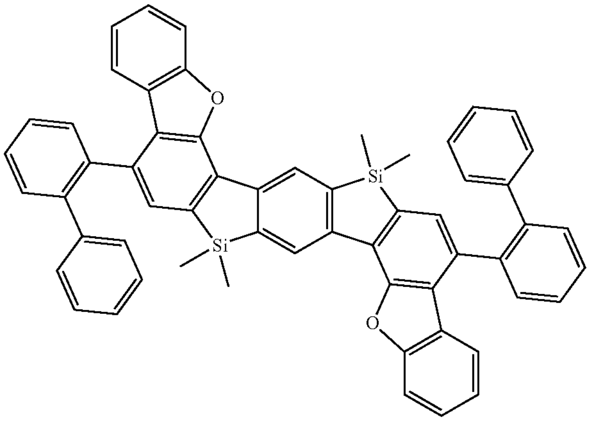
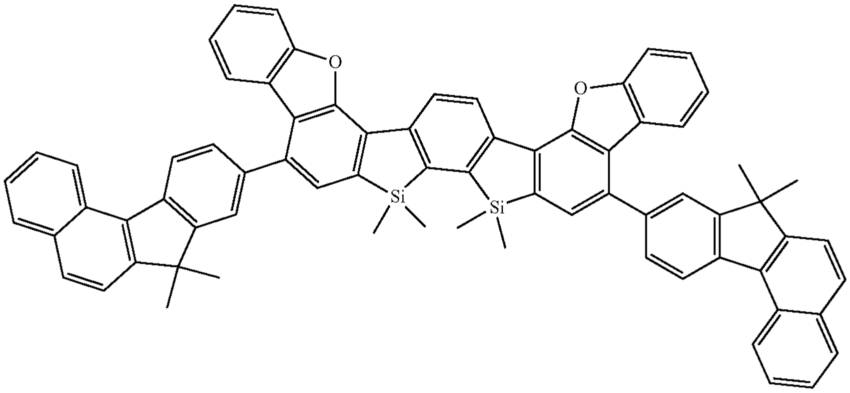

-continued
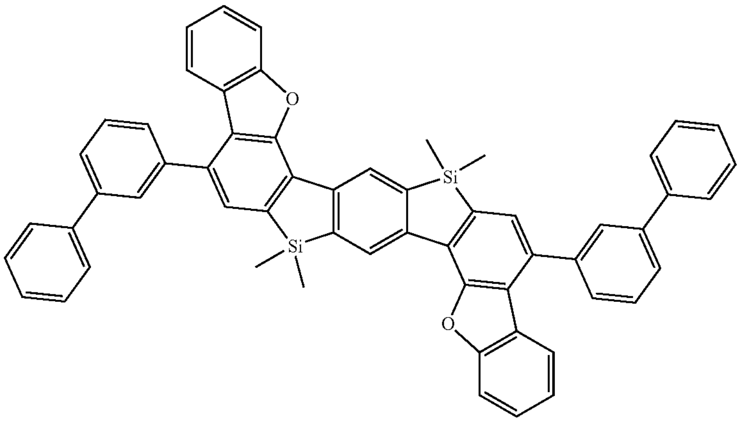
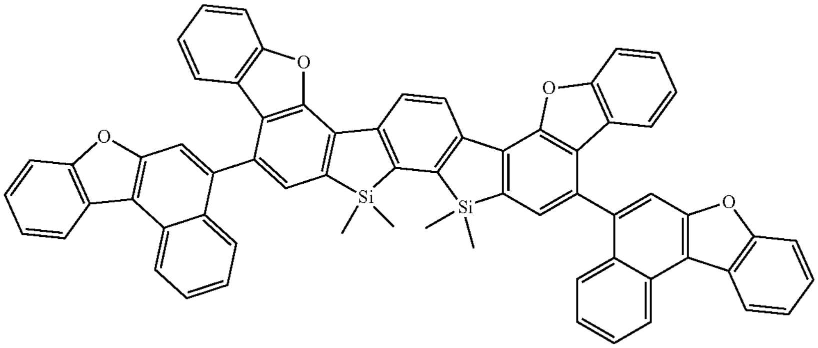
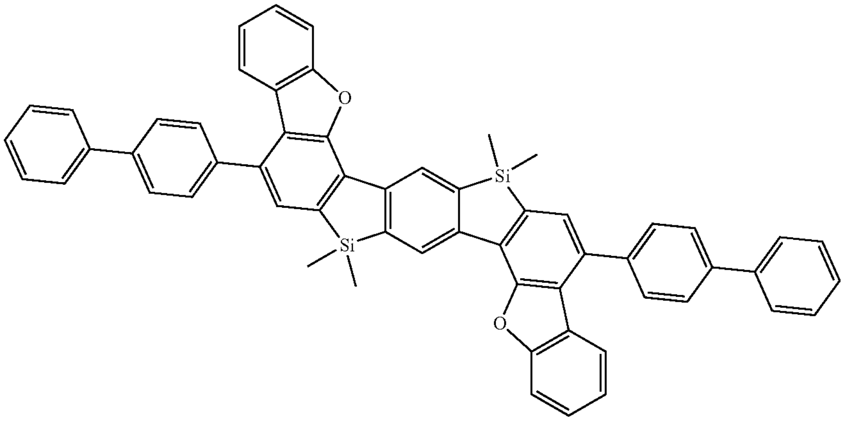
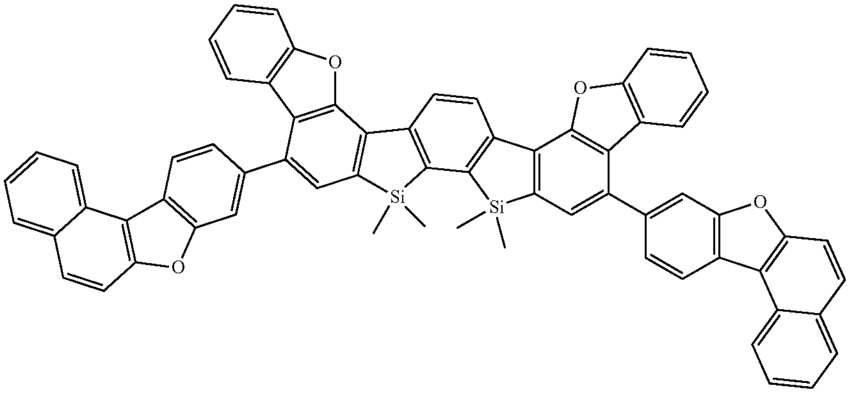

-continued
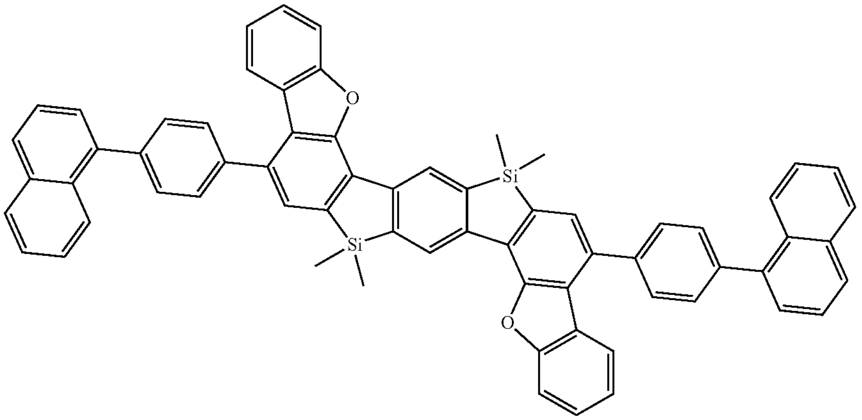
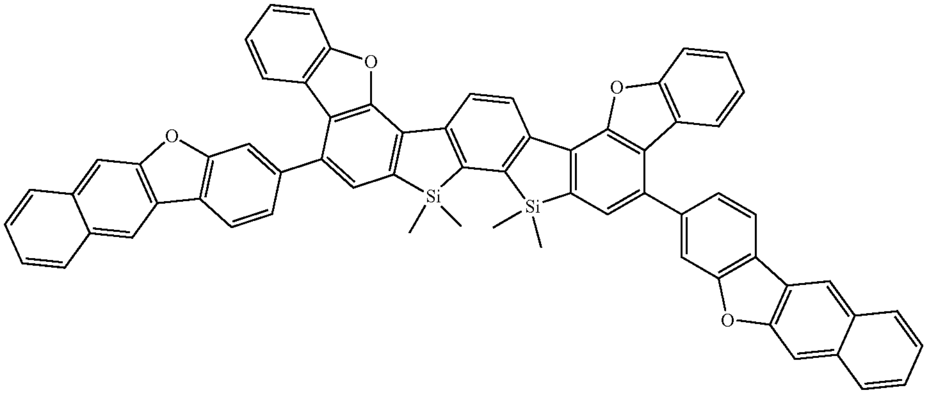
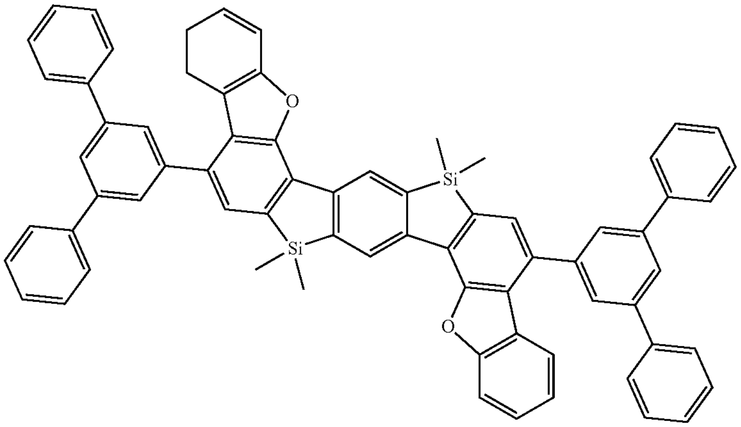
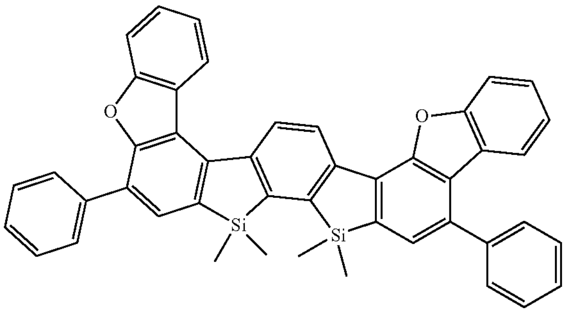

-continued
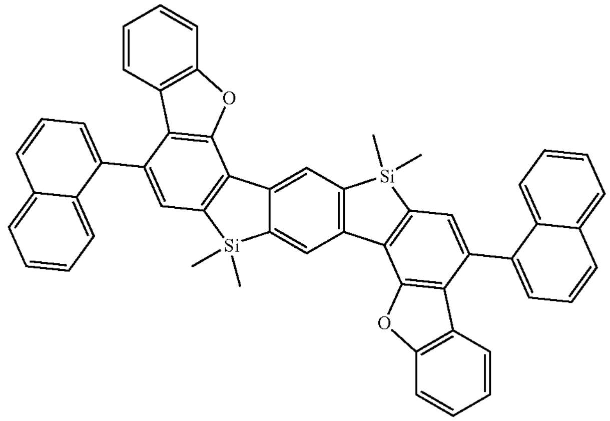
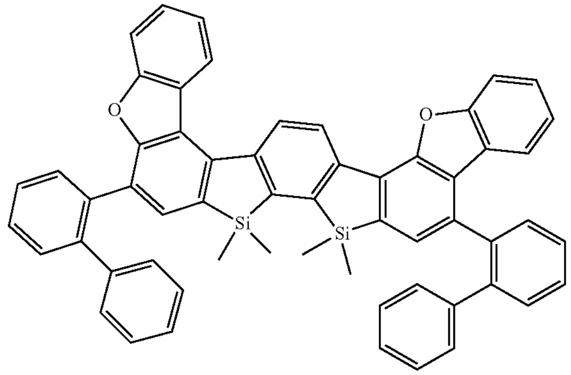
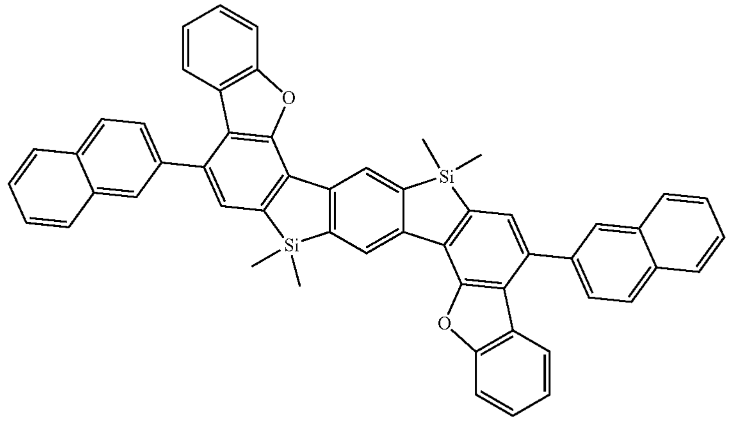
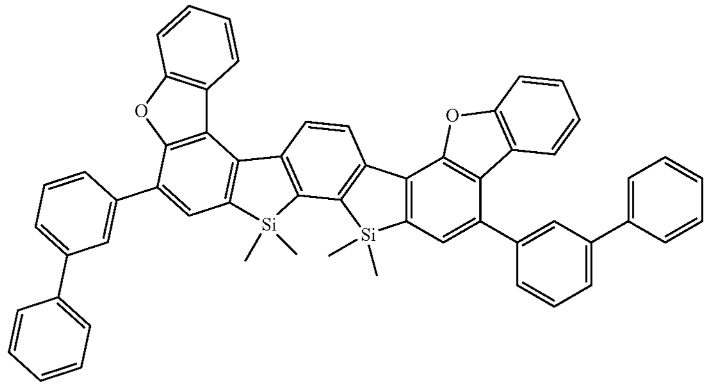

-continued
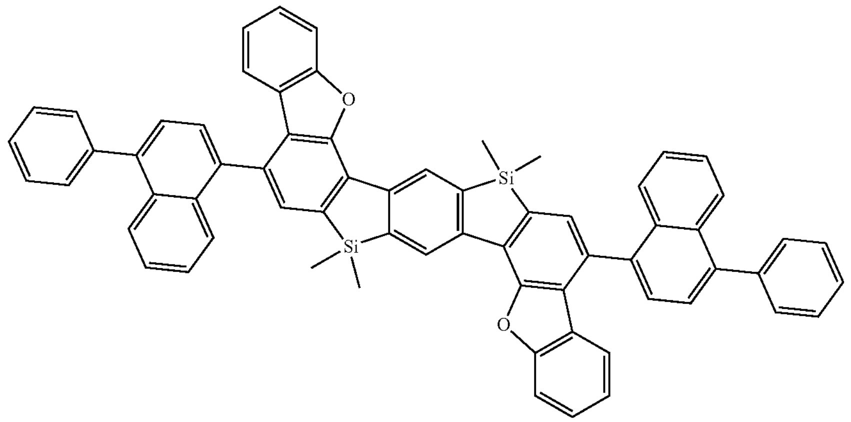
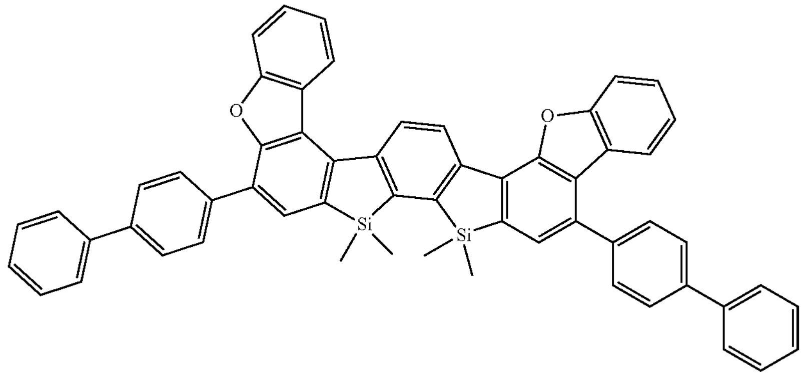
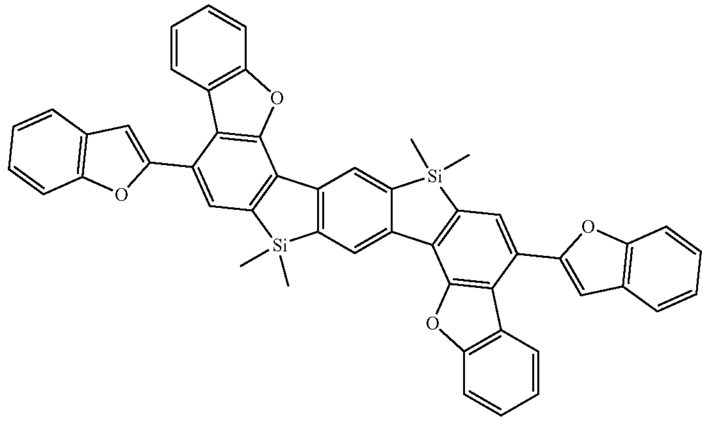
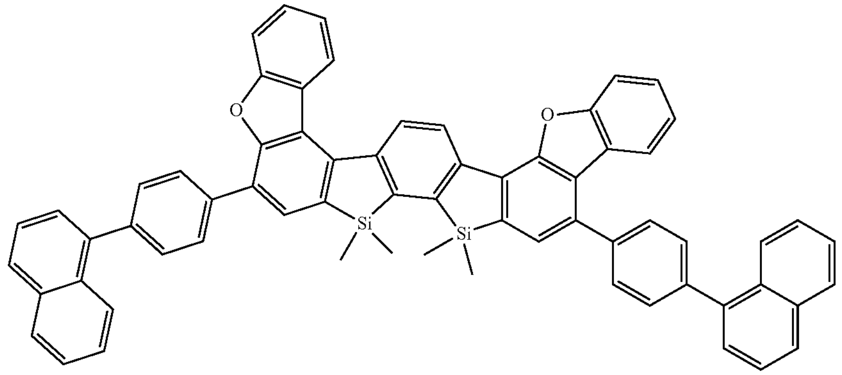

-continued
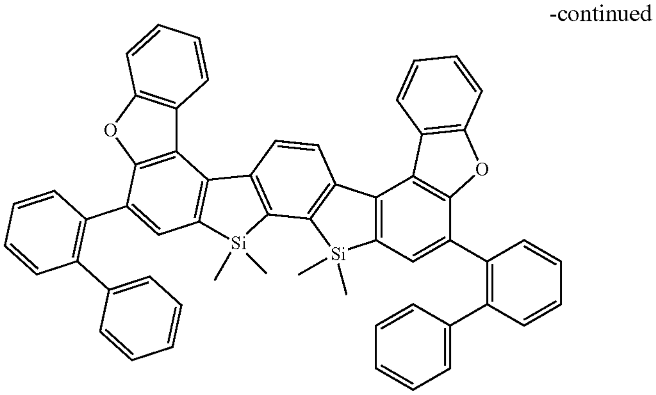
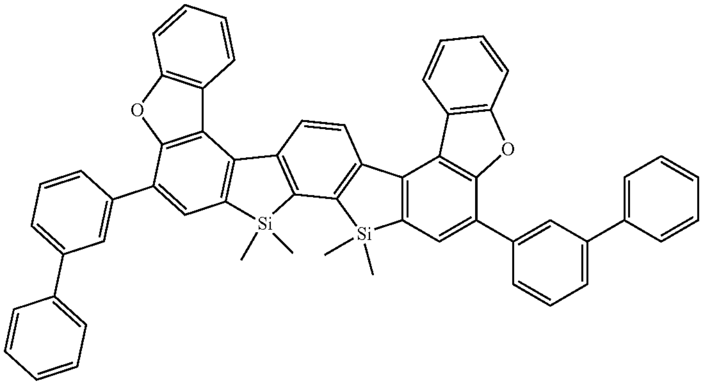
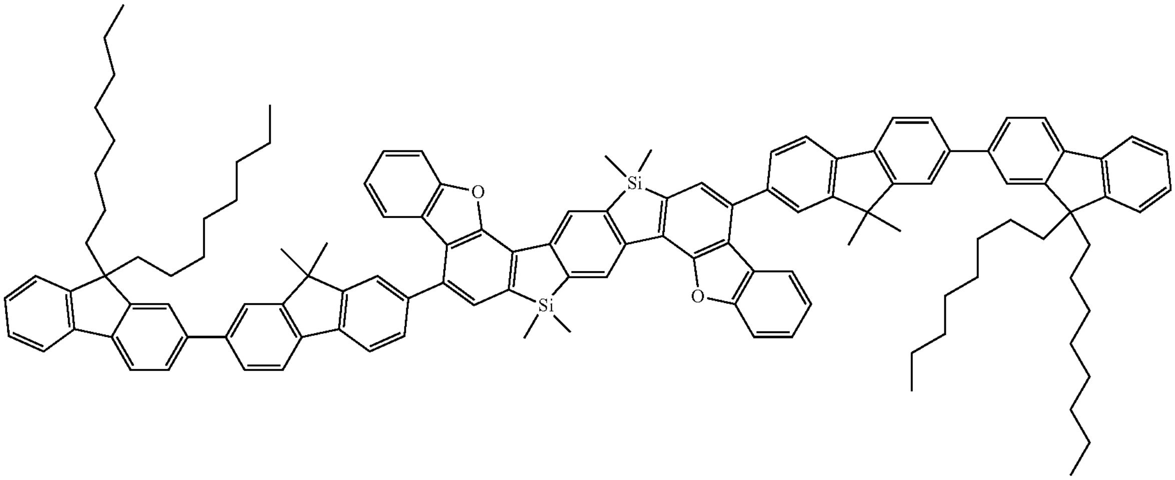
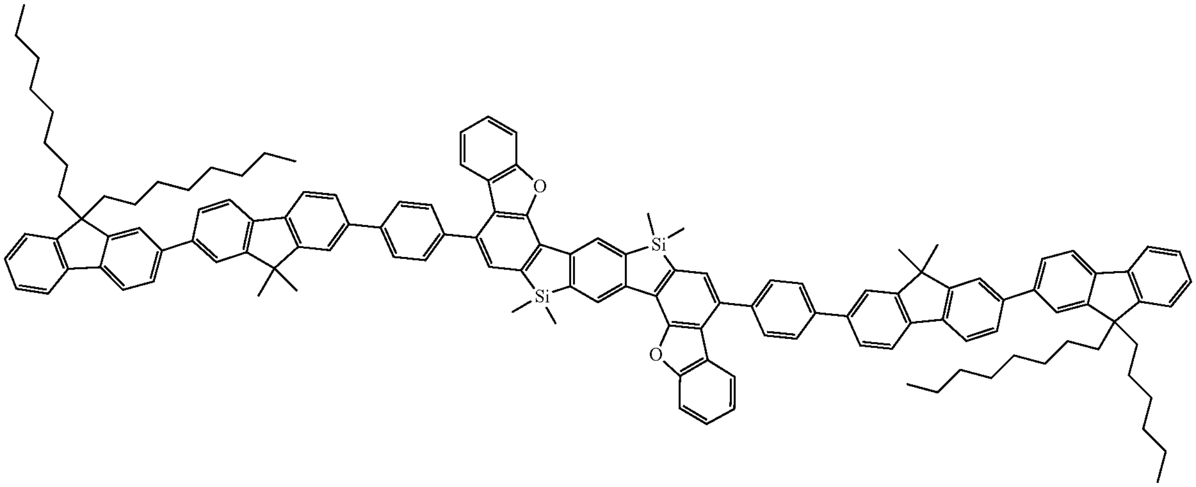

-continued
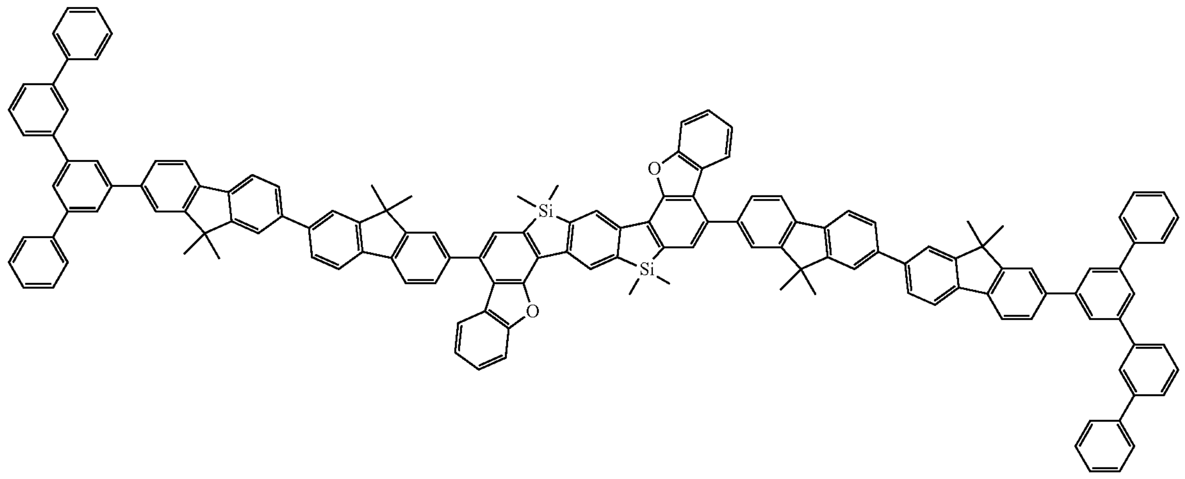
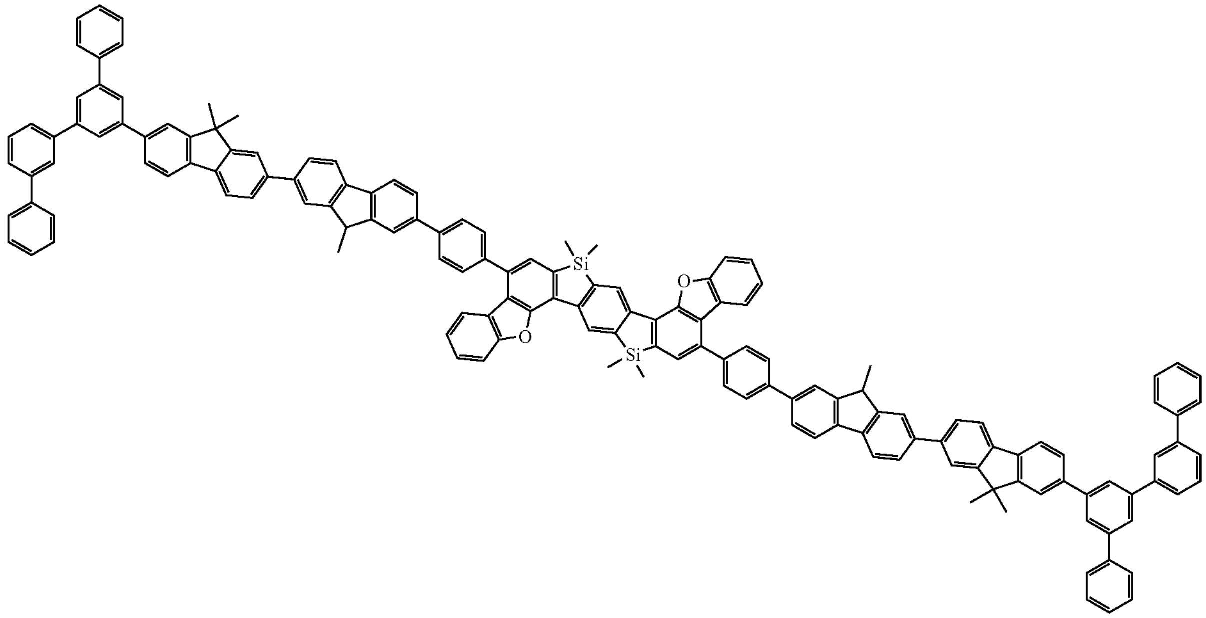
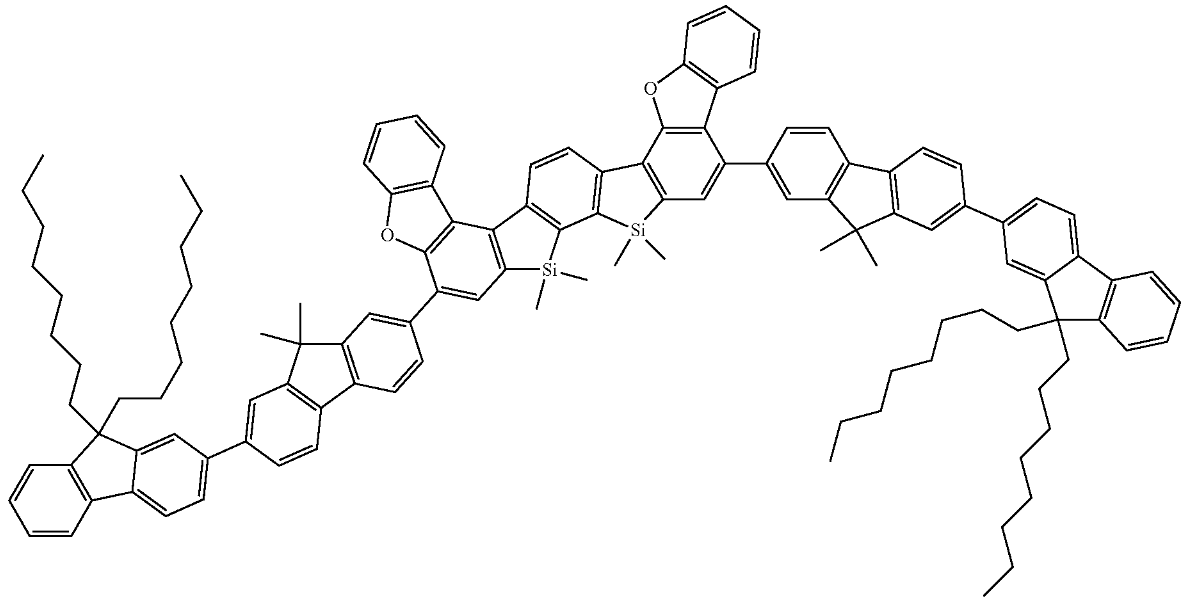

-continued
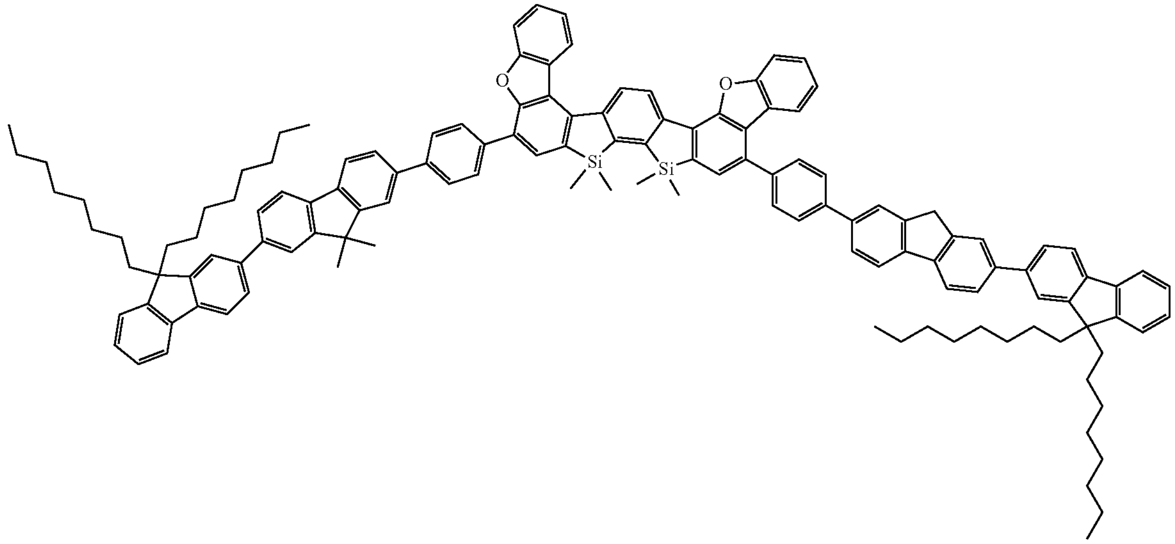
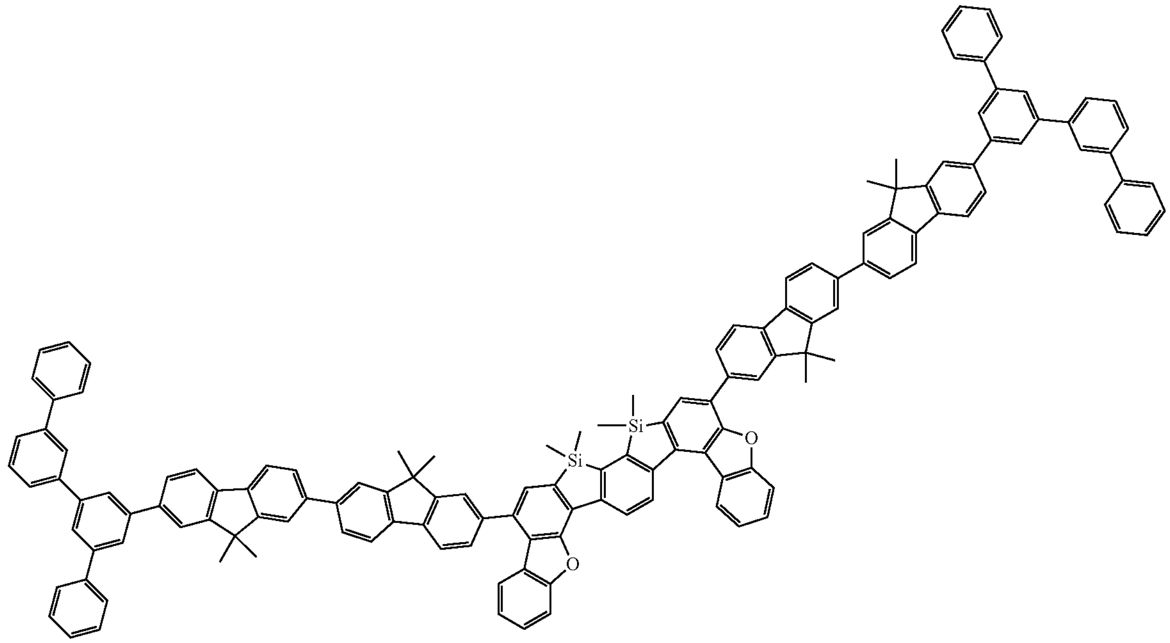
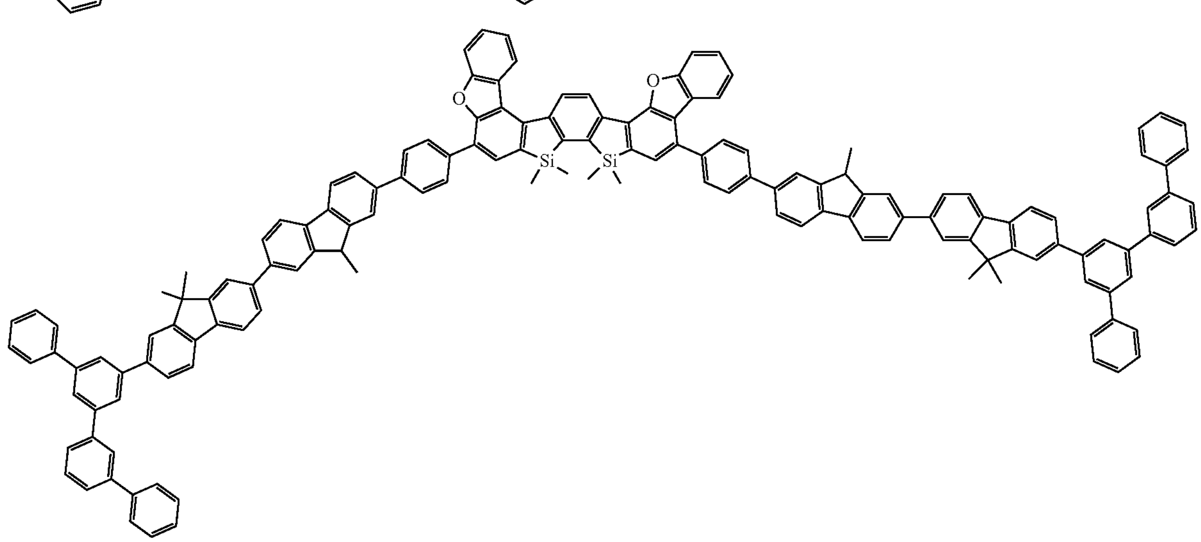

-continued
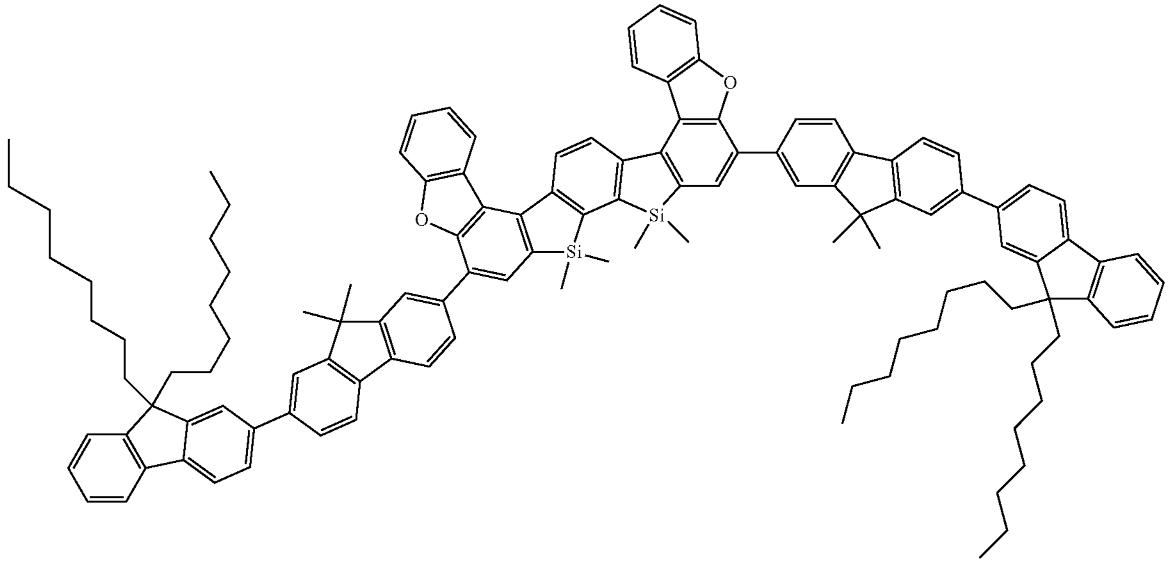
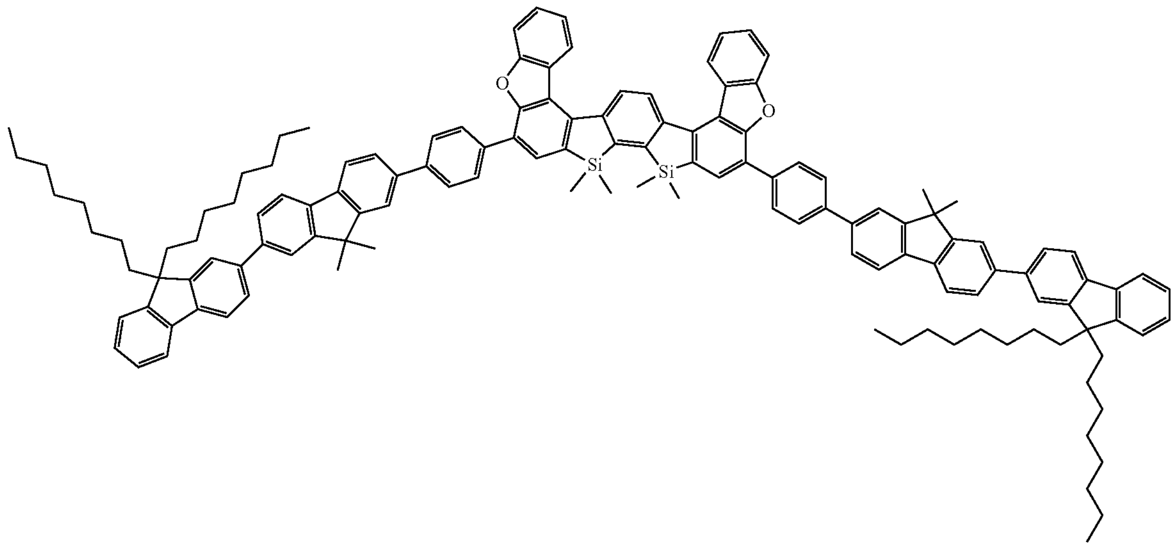

-continued
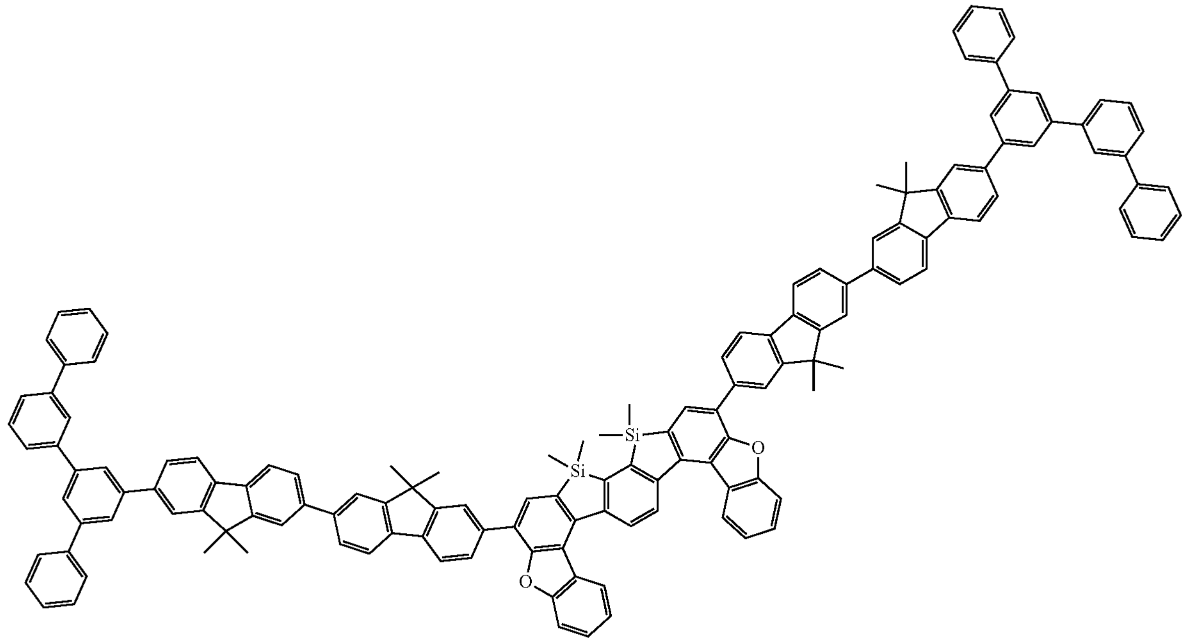
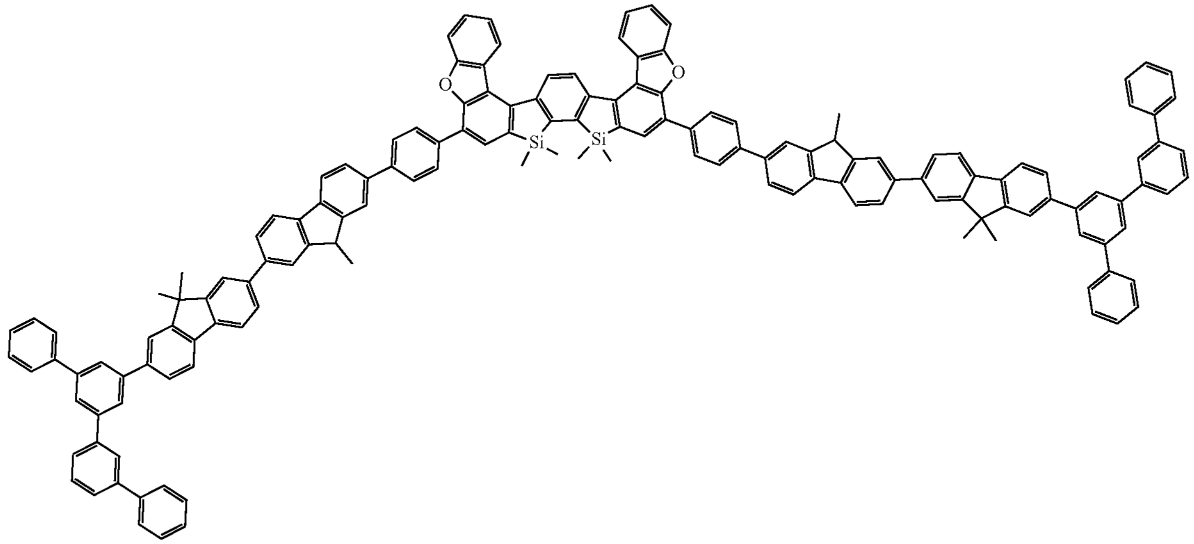
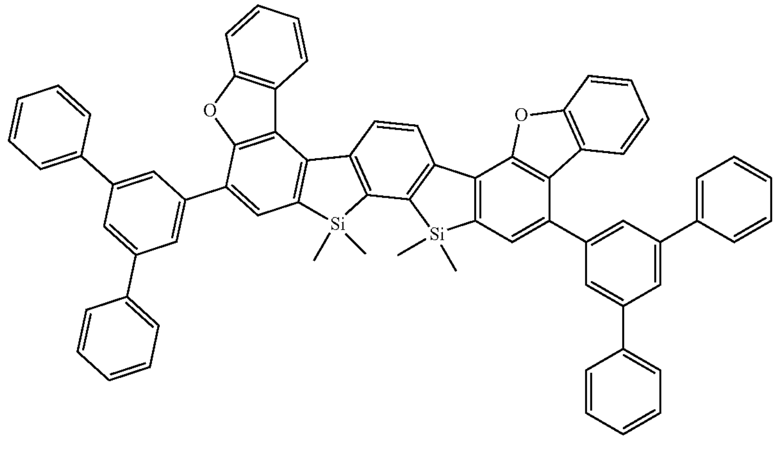

-continued
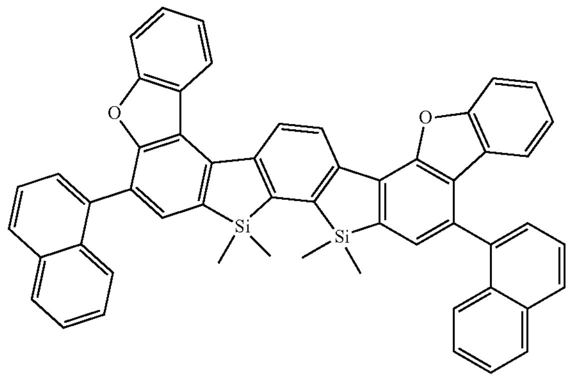
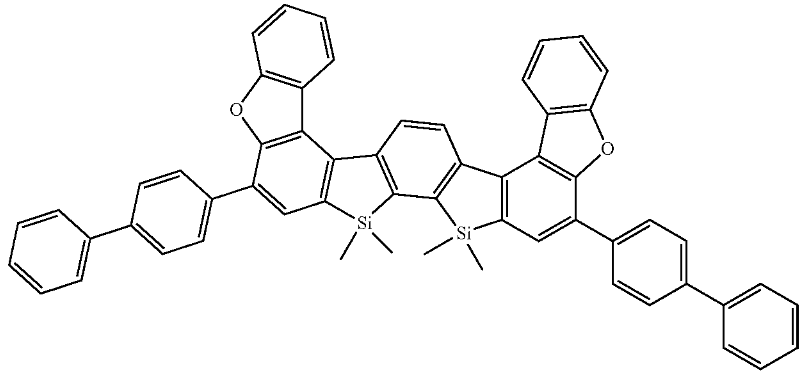
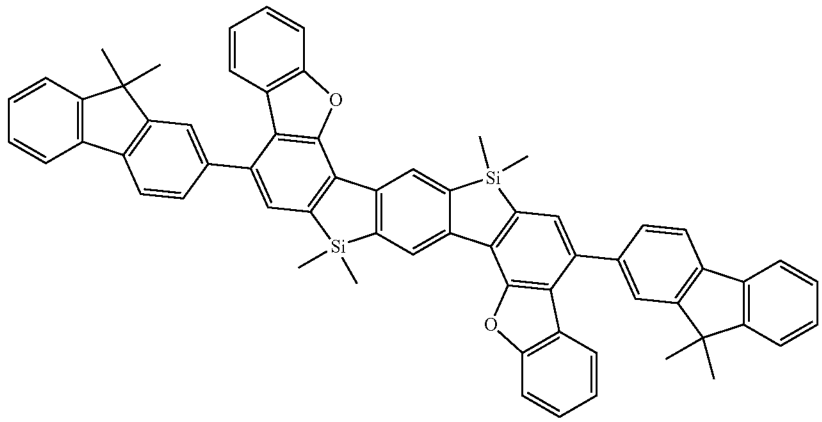
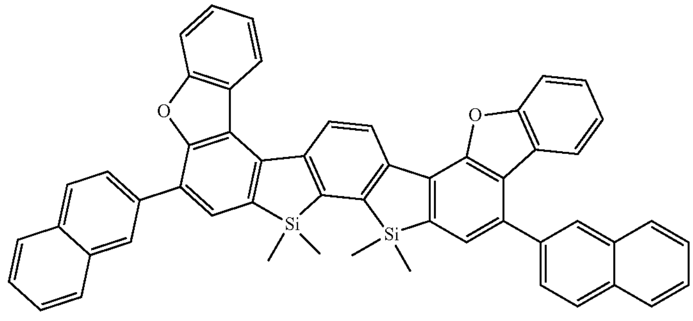

-continued
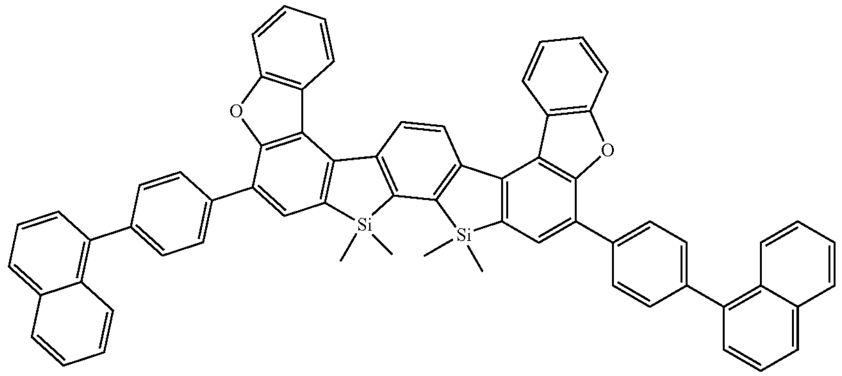
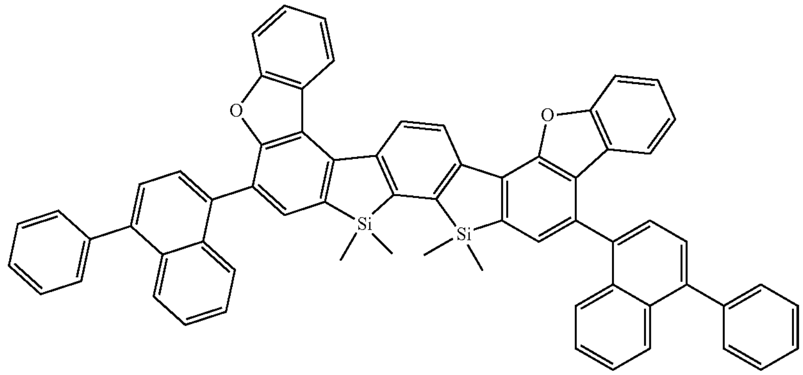
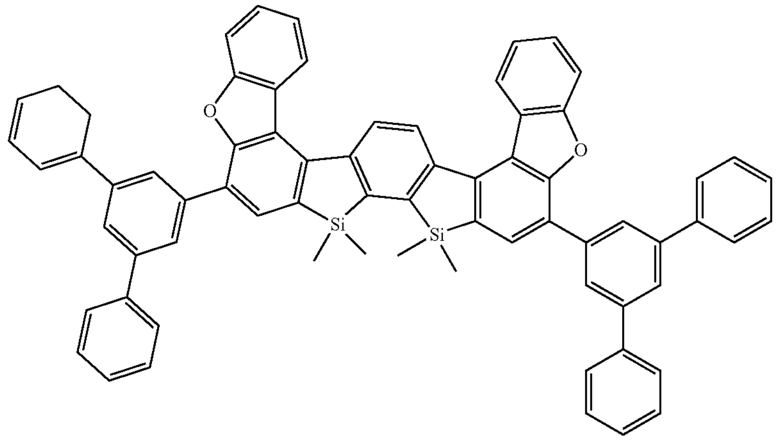
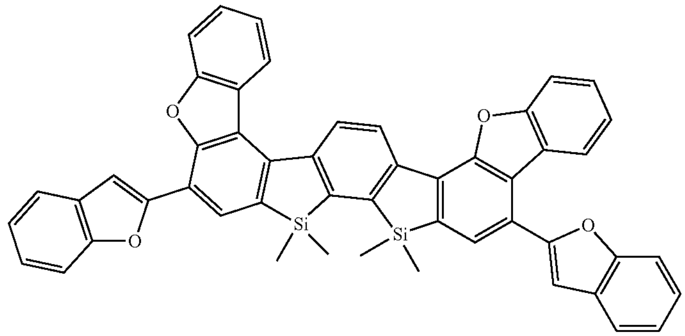

-continued
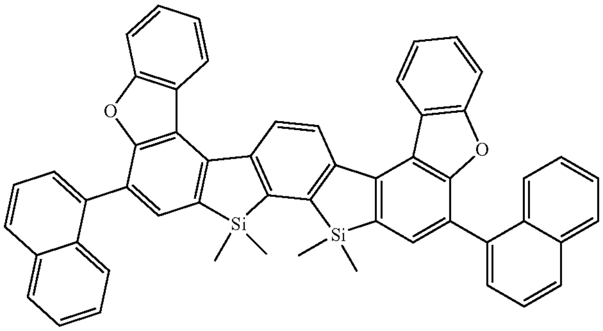
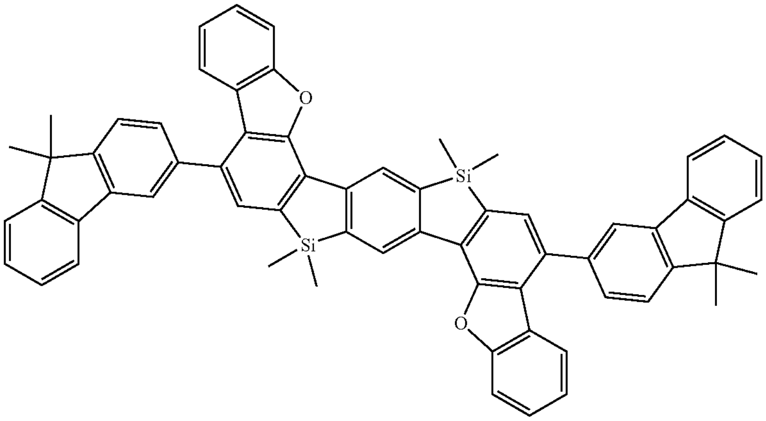
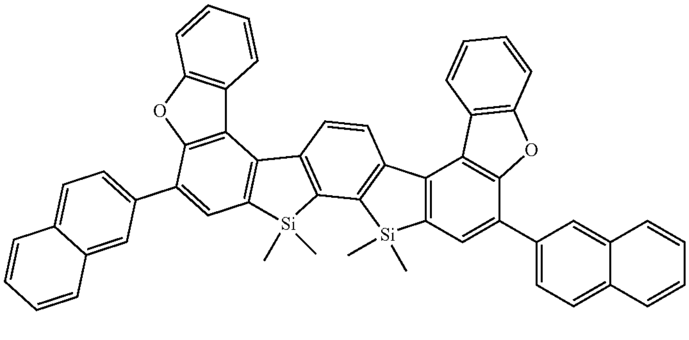
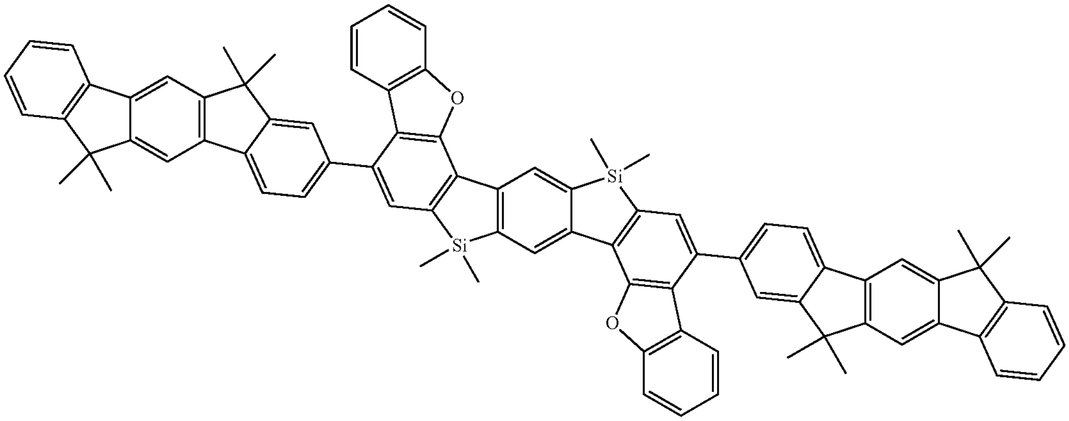

-continued
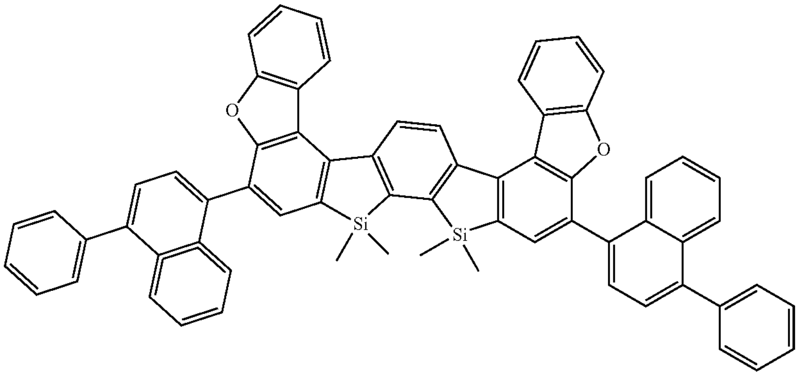
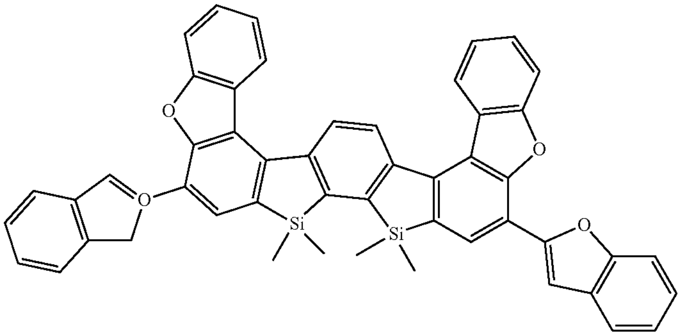
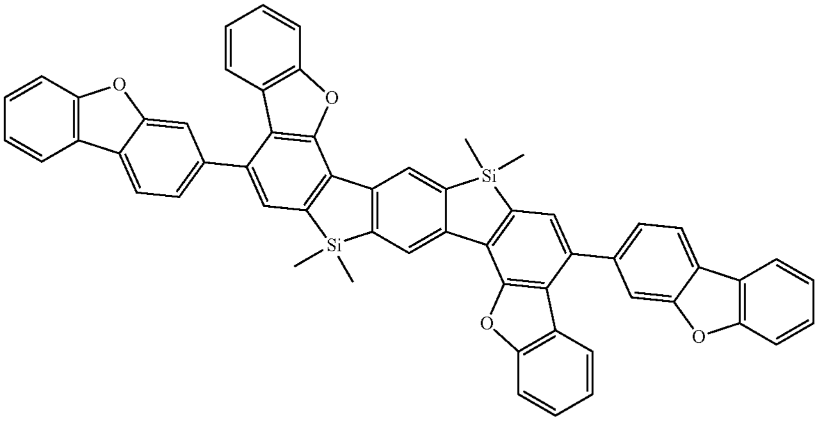
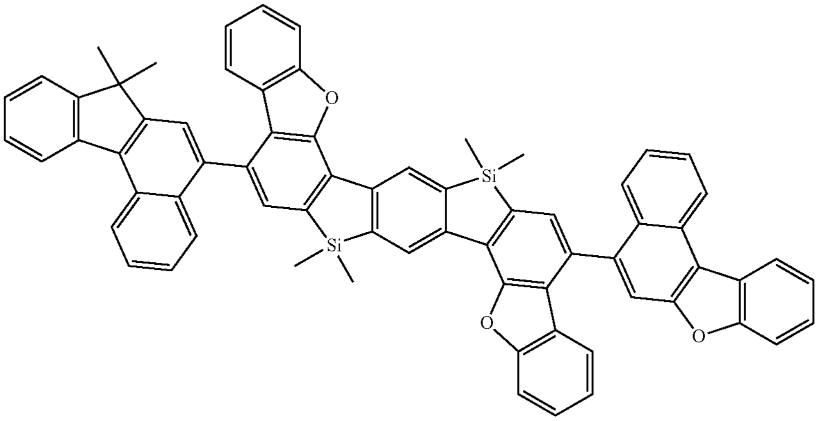

-continued
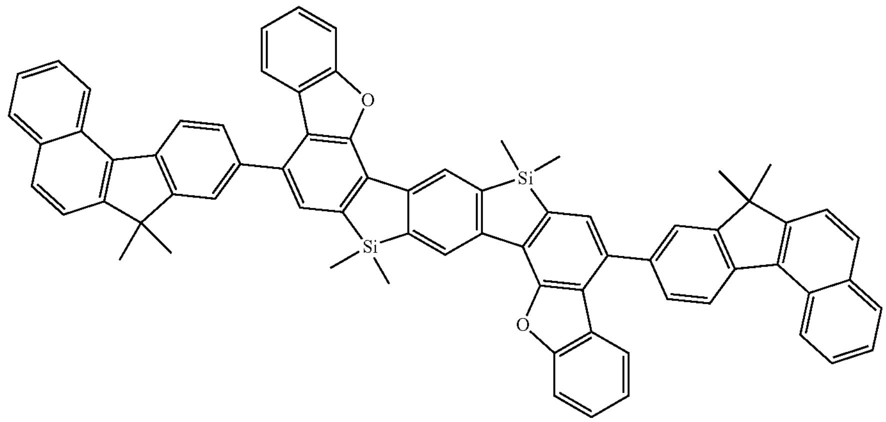
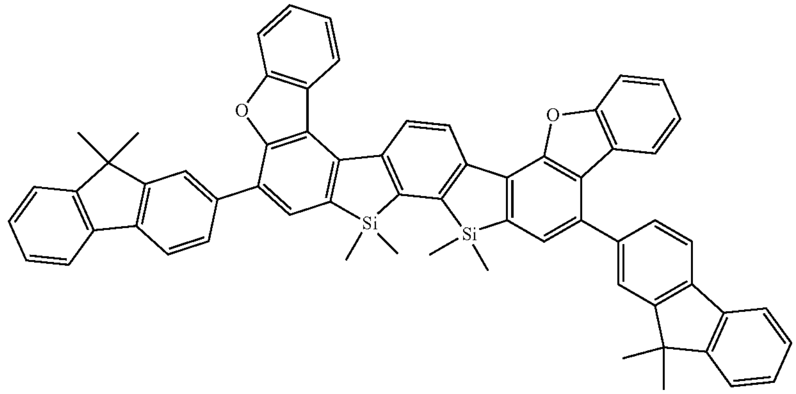
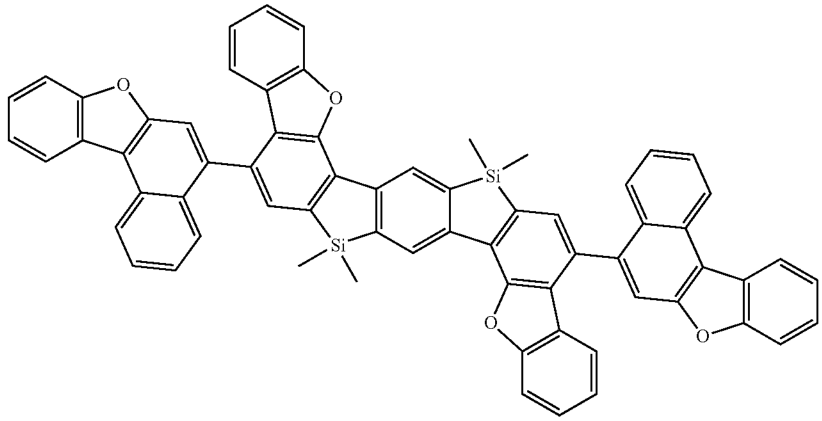
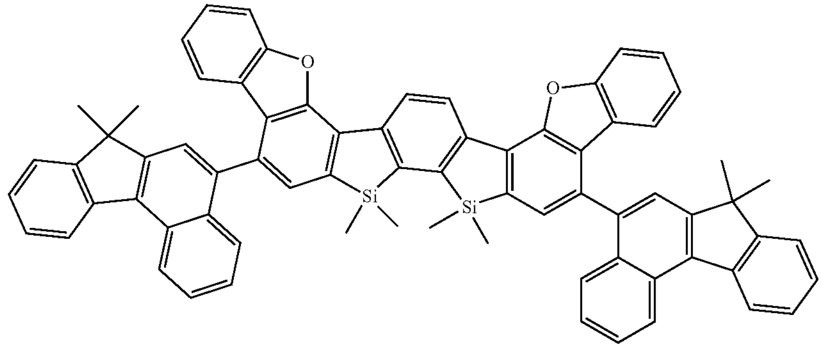

-continued
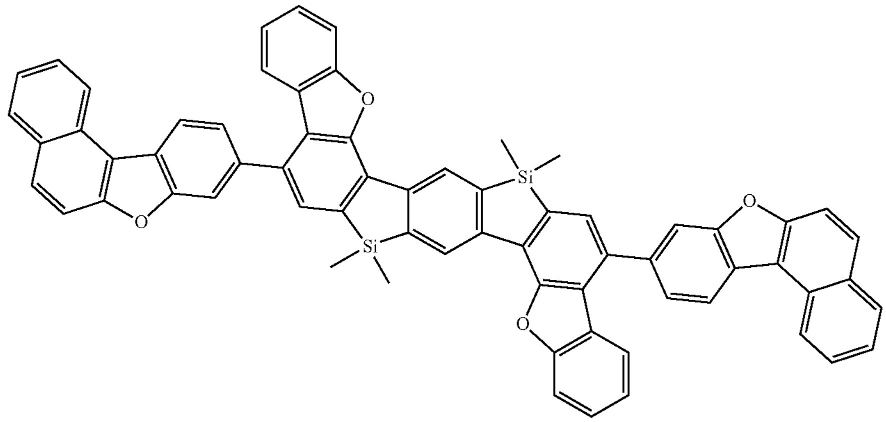
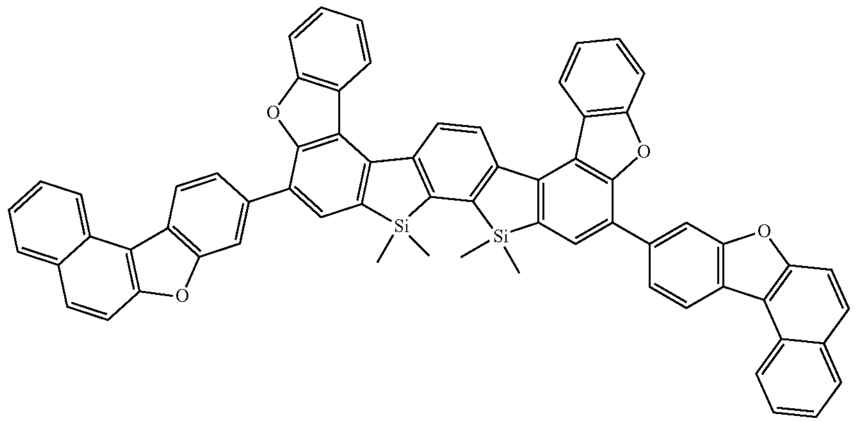
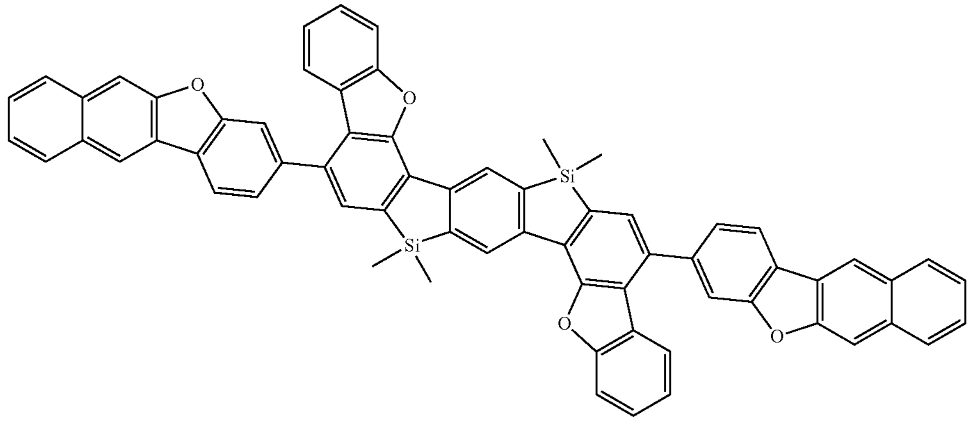
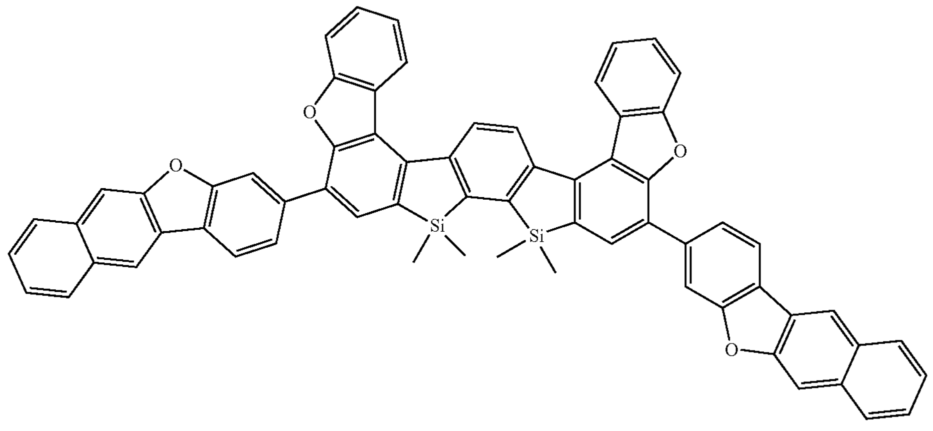

-continued
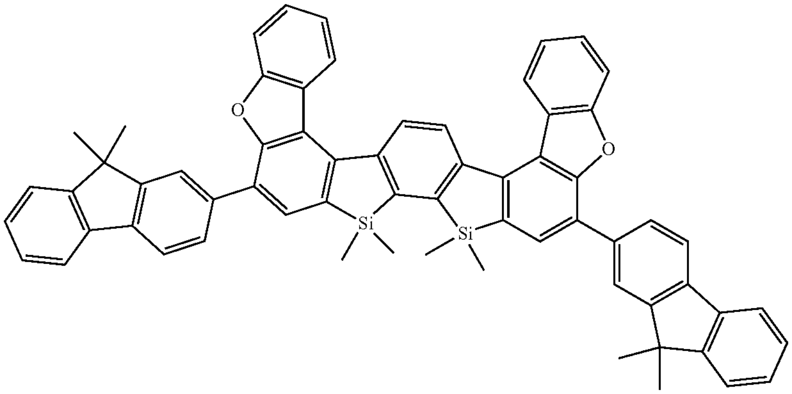
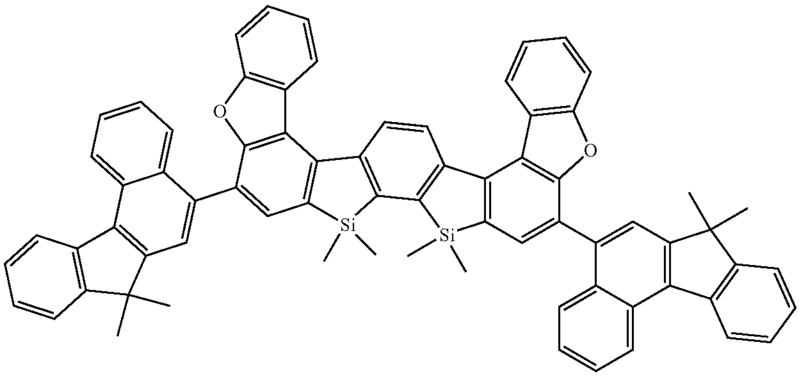
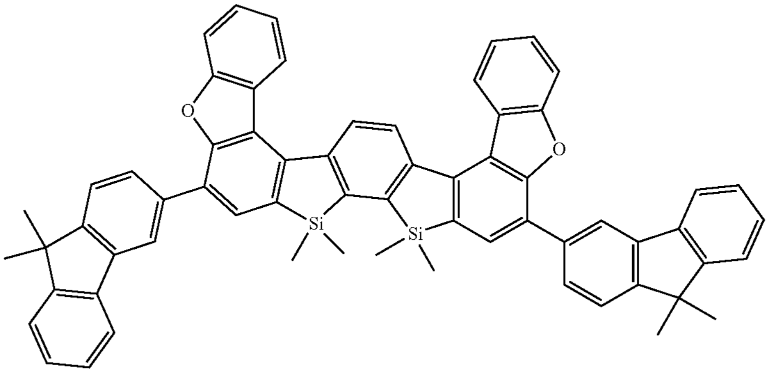
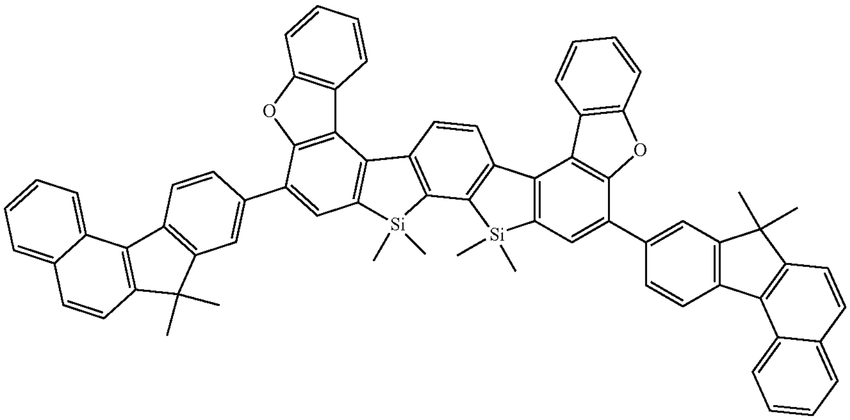

-continued
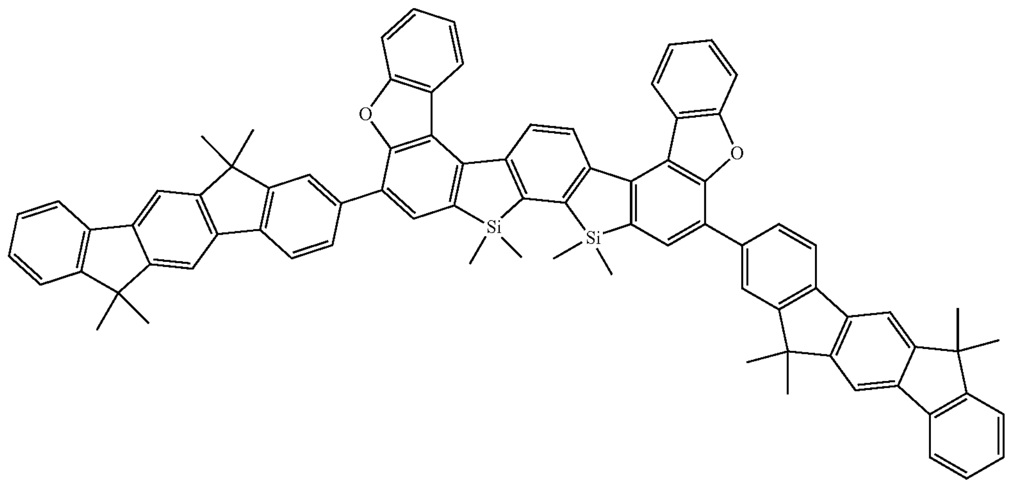
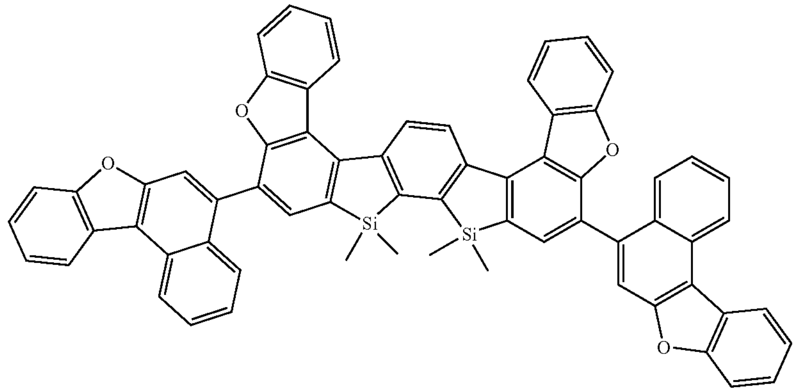
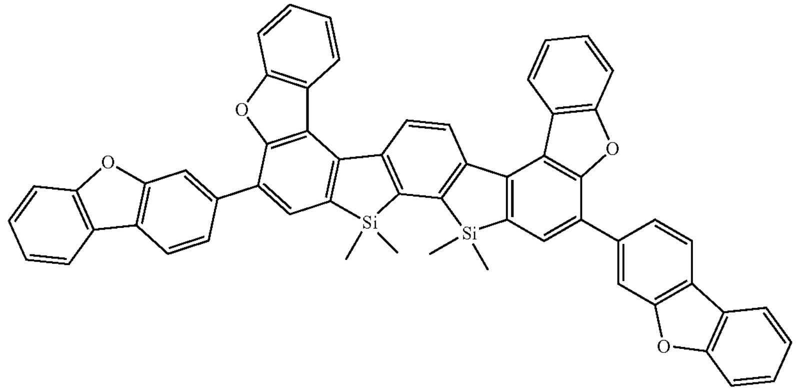
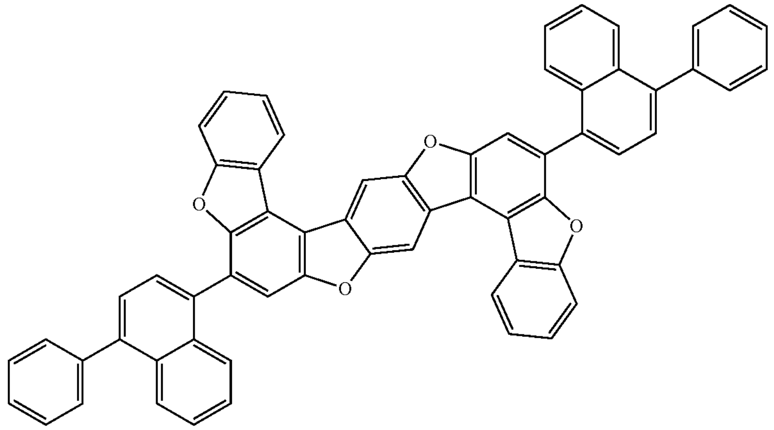

-continued
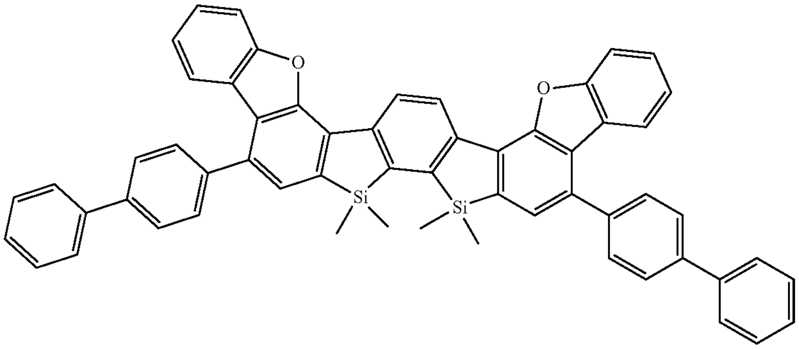
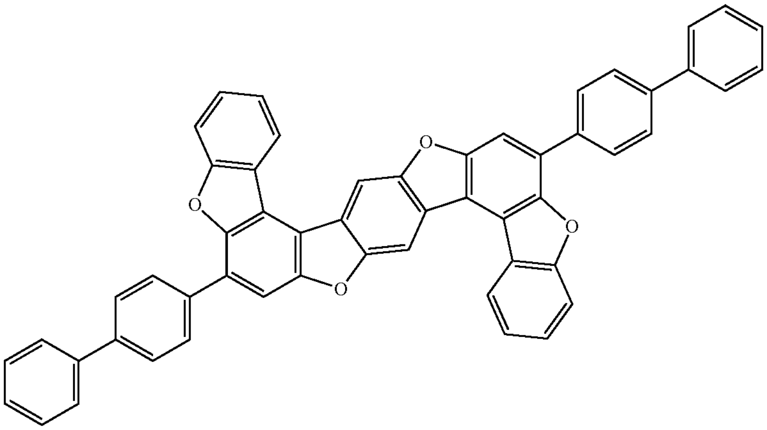
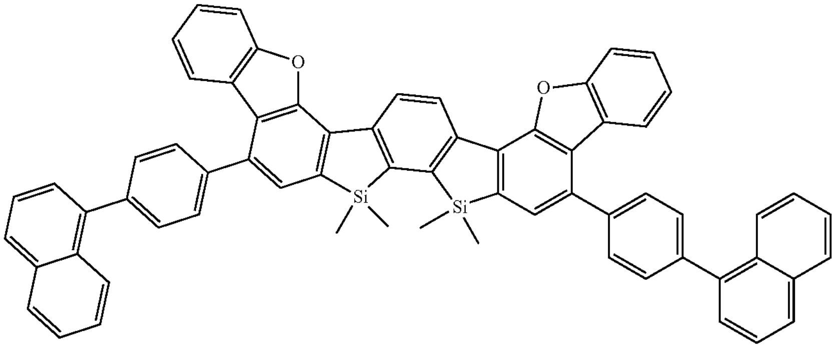
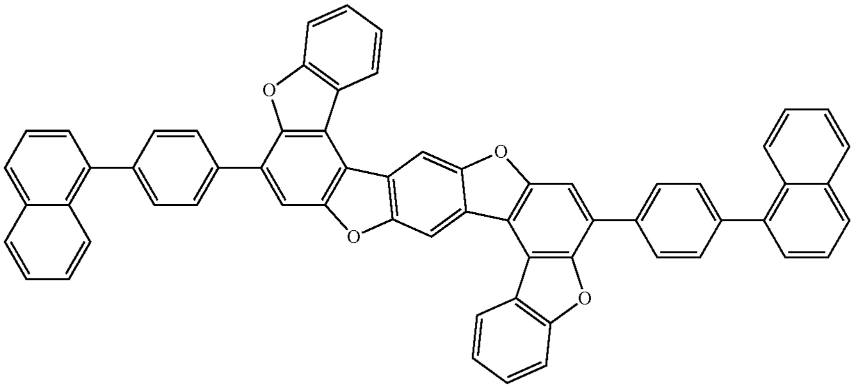

-continued
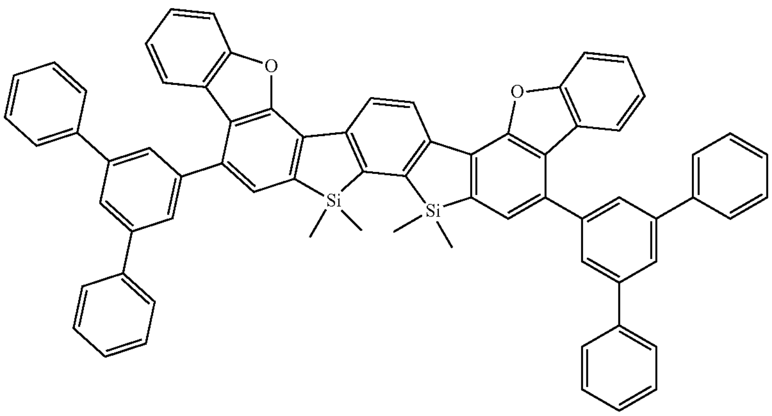
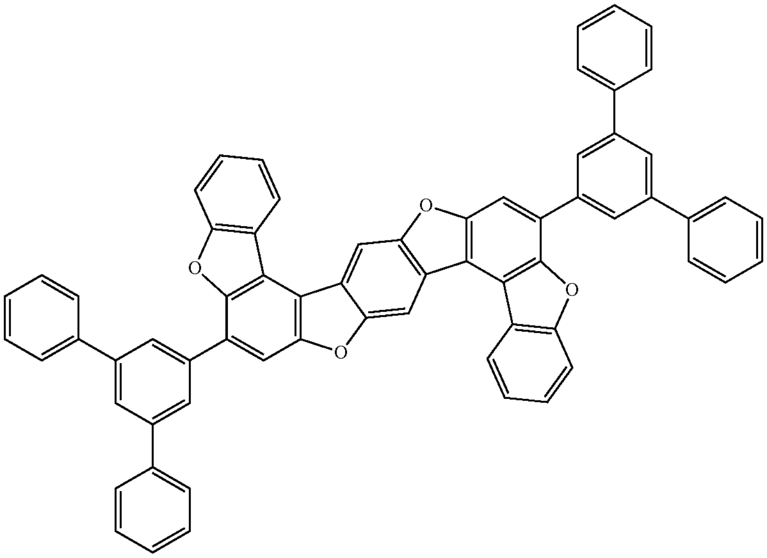
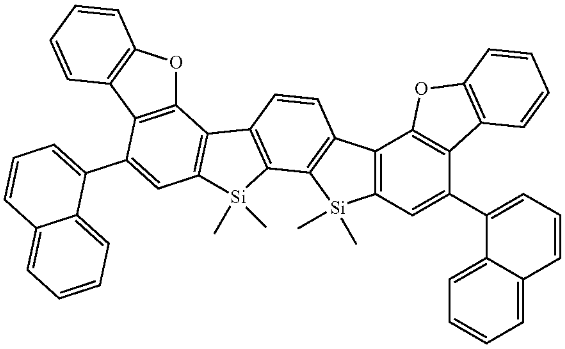
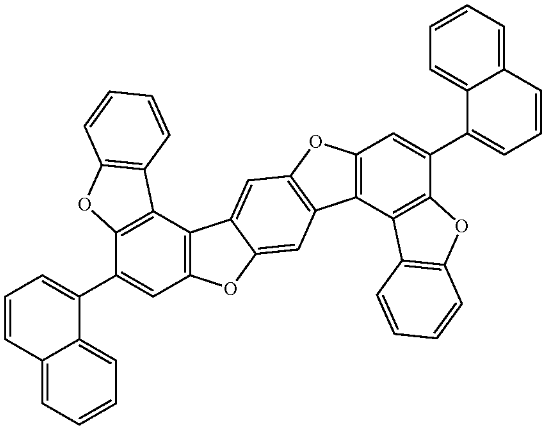
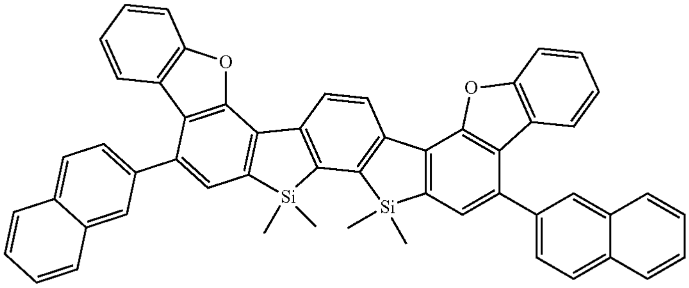

-continued
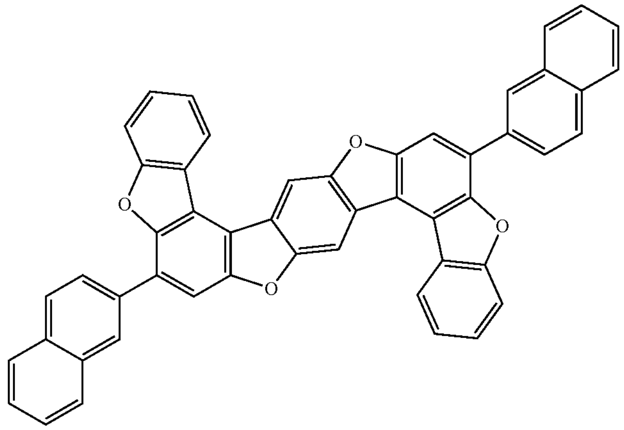
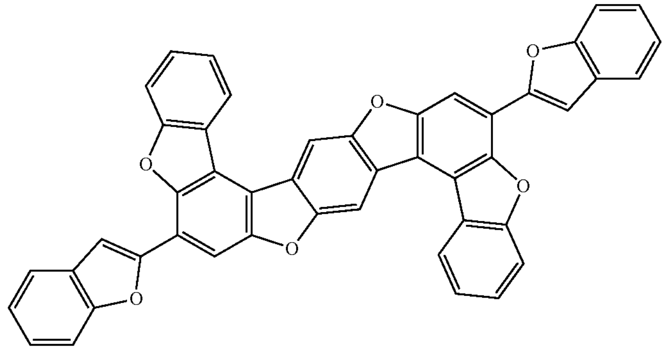
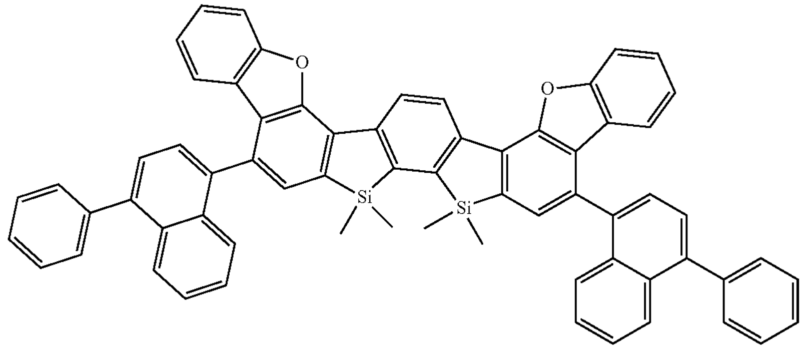
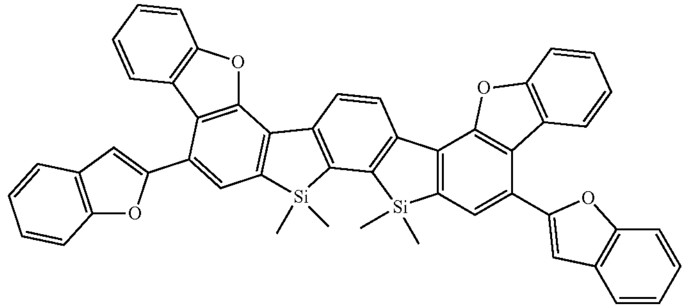

-continued
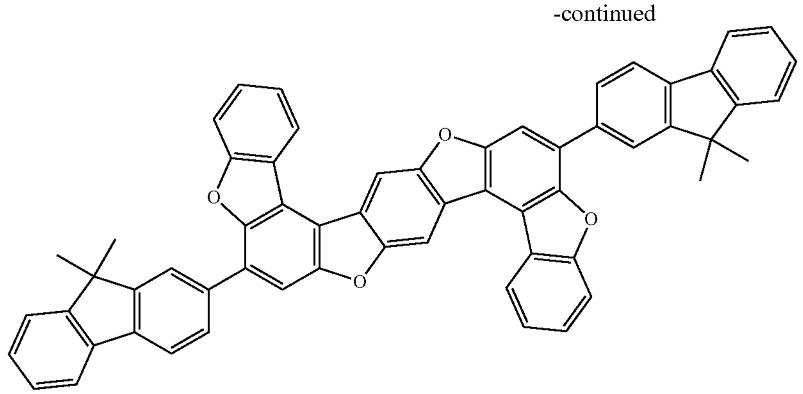
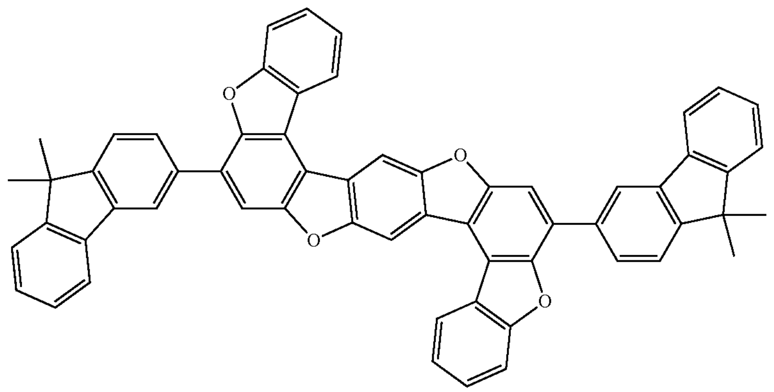
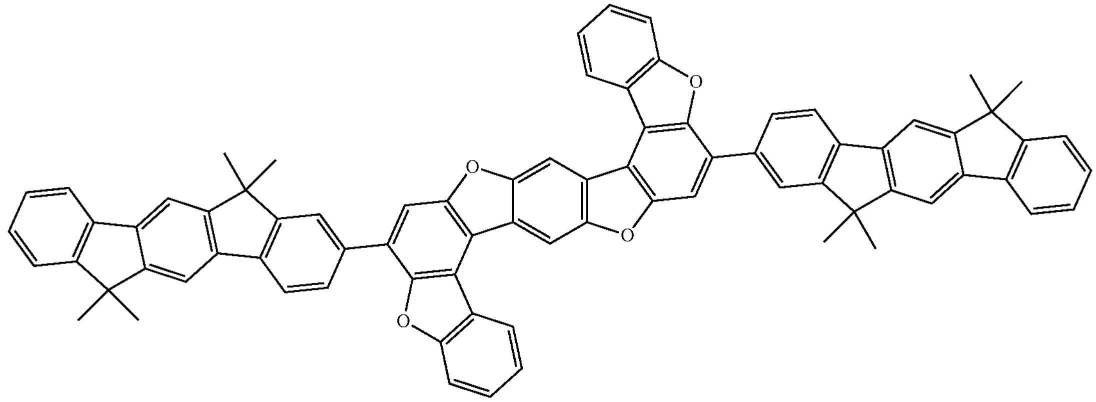
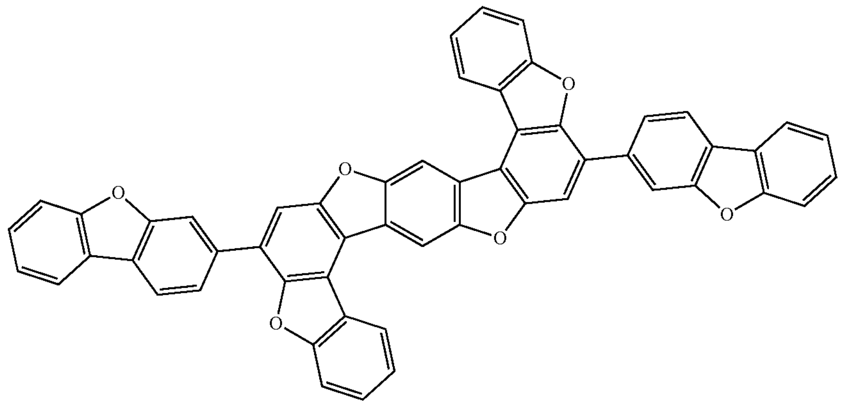

-continued
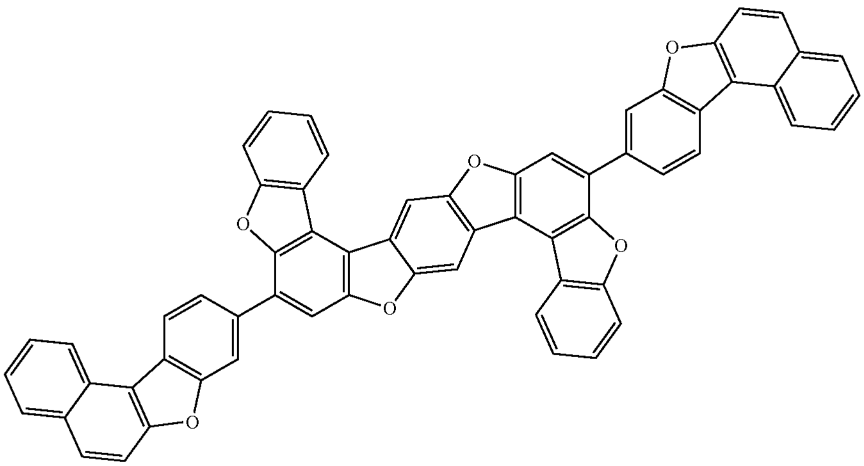
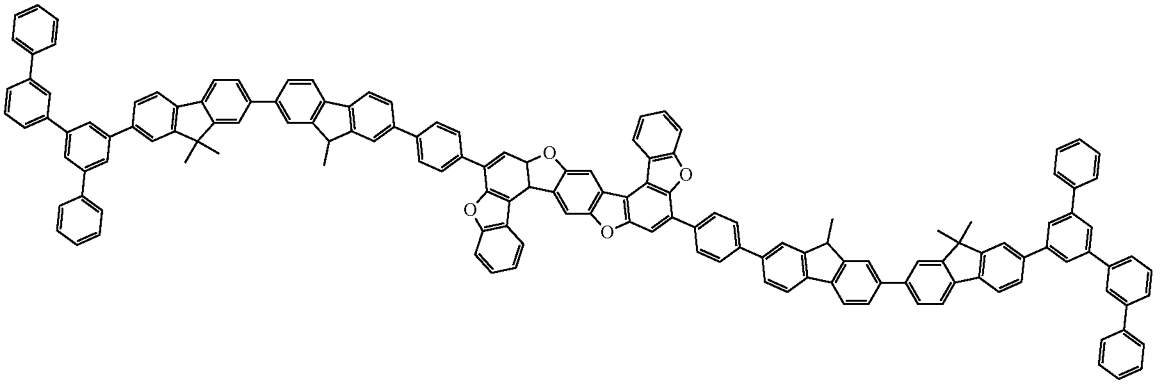
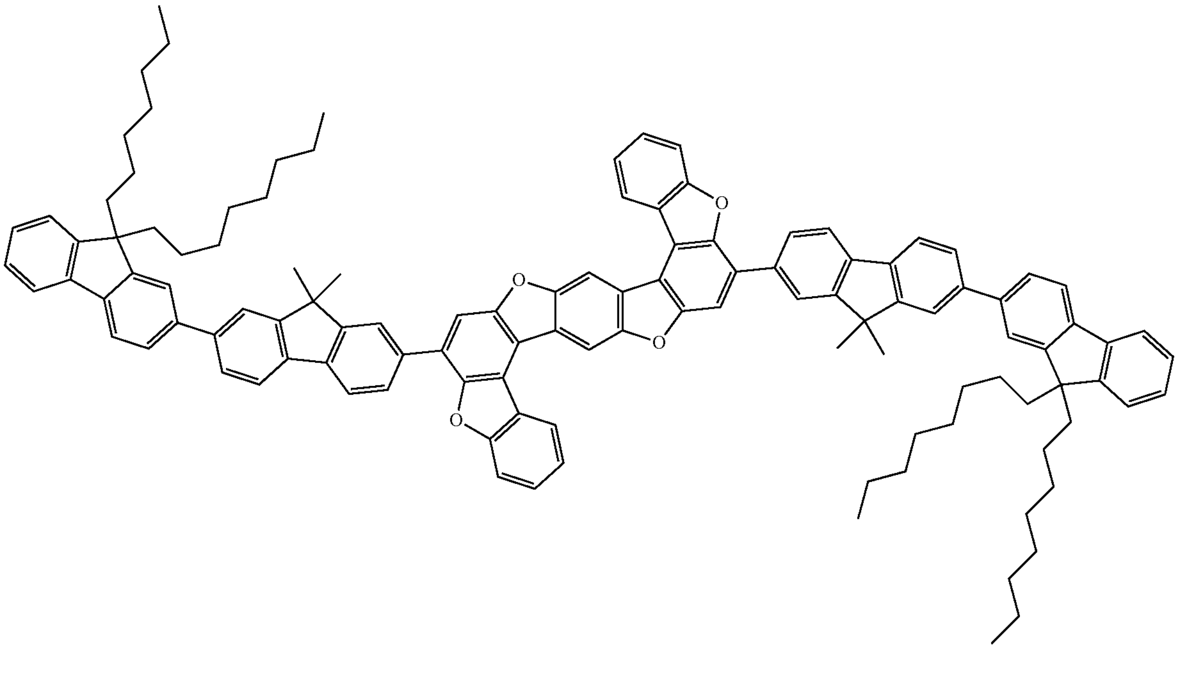

-continued
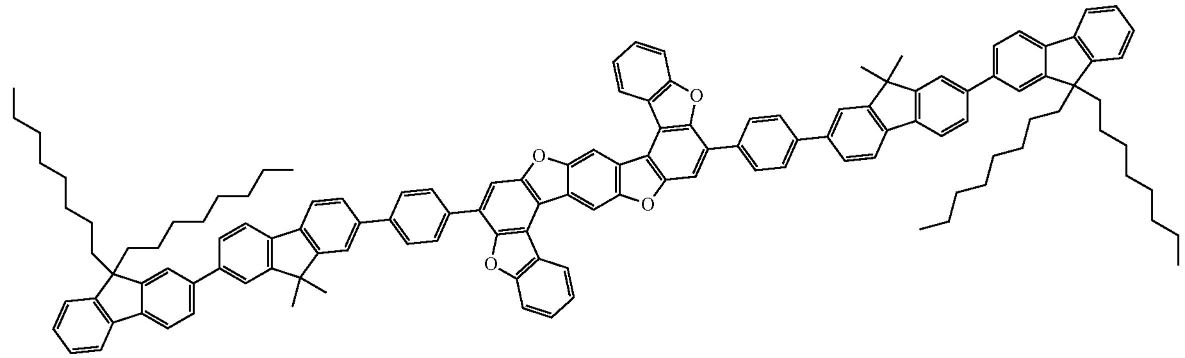
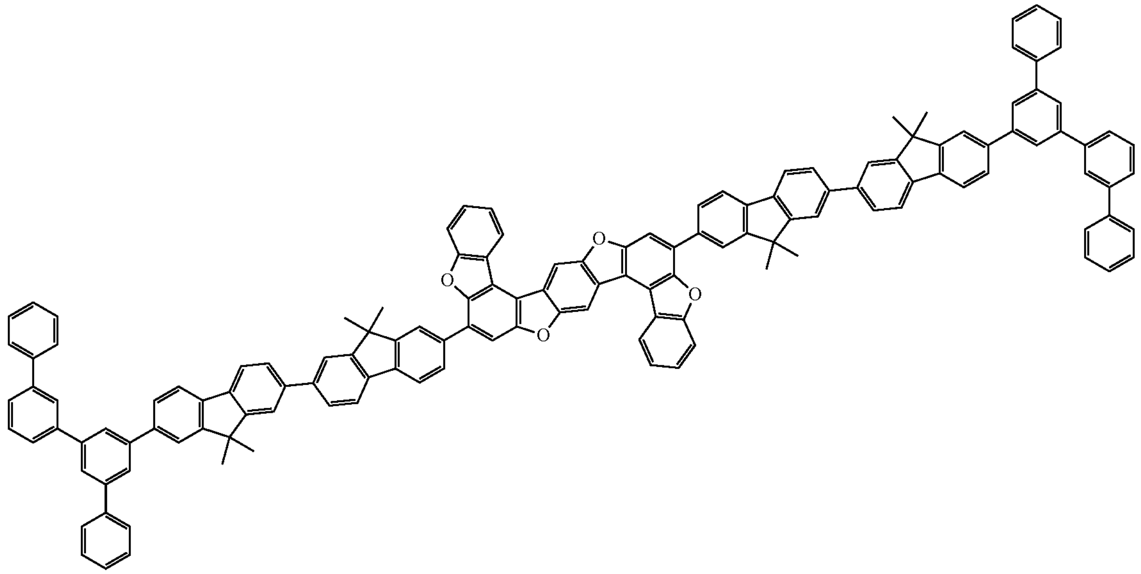
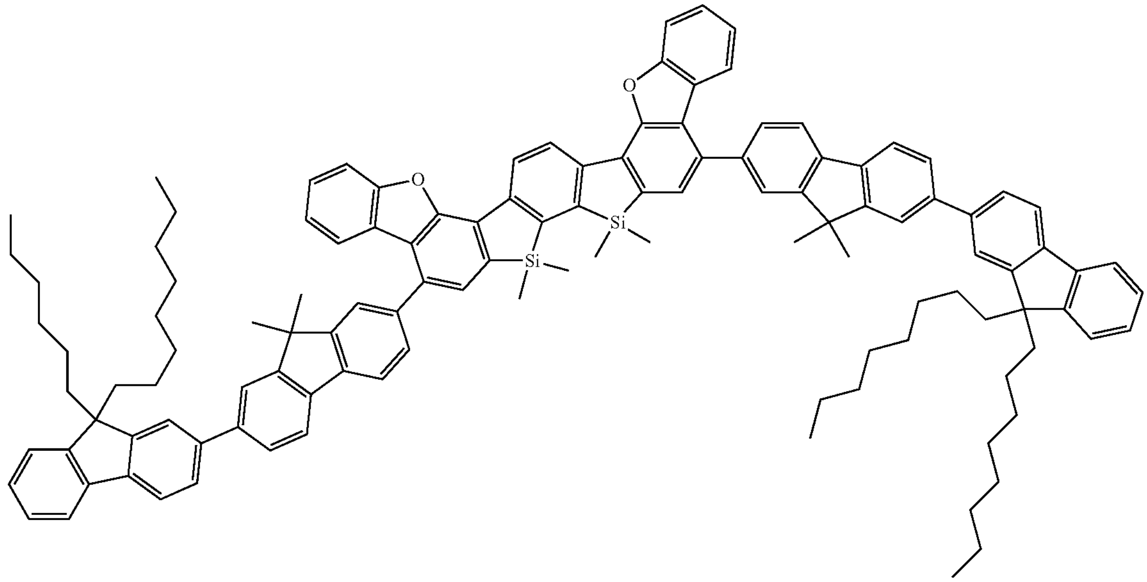

-continued
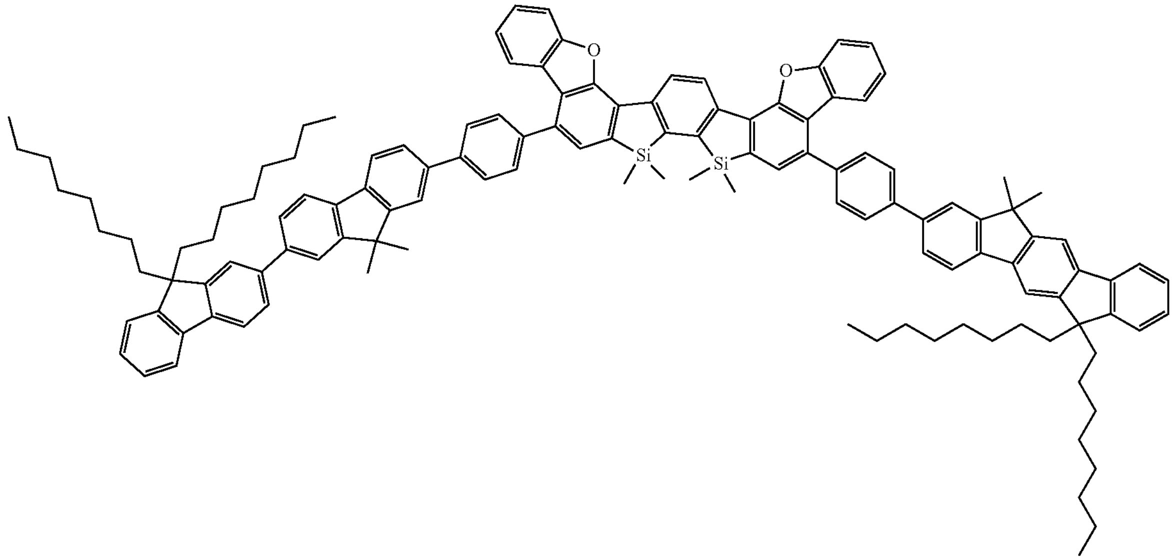
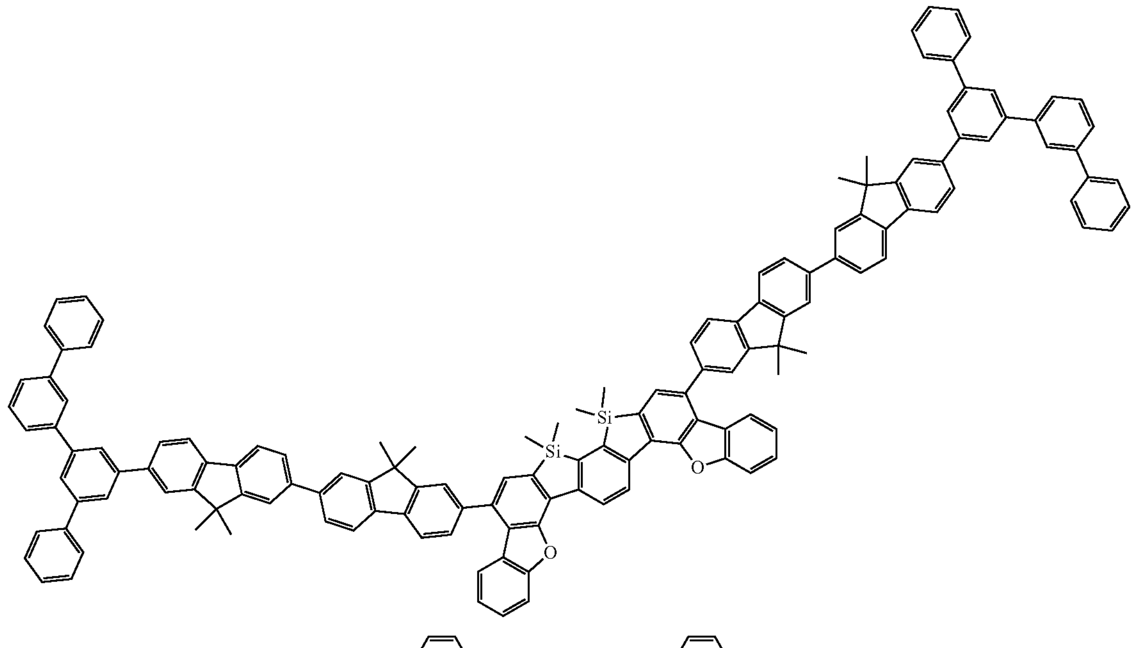
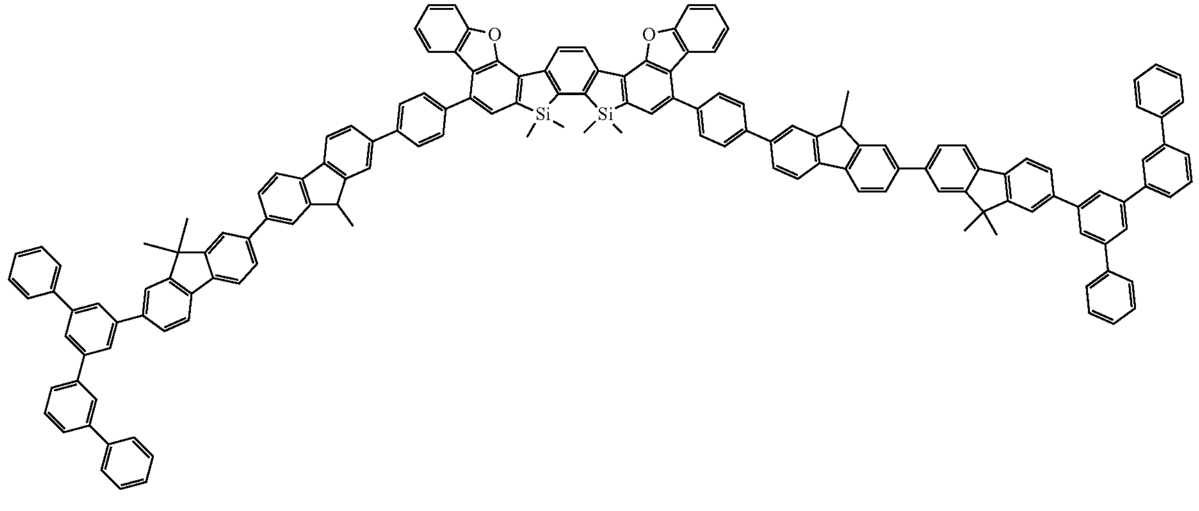

-continued
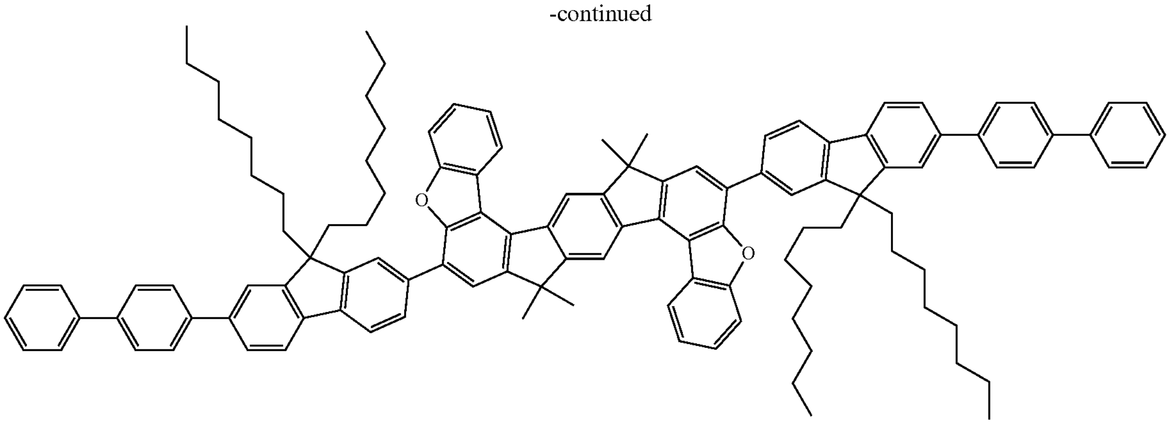
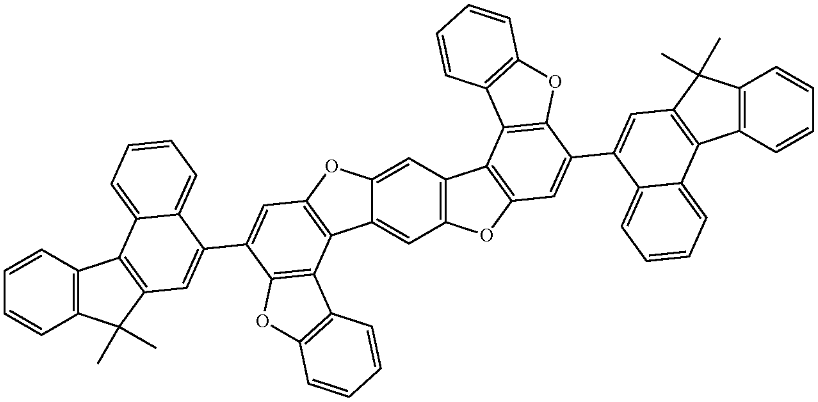
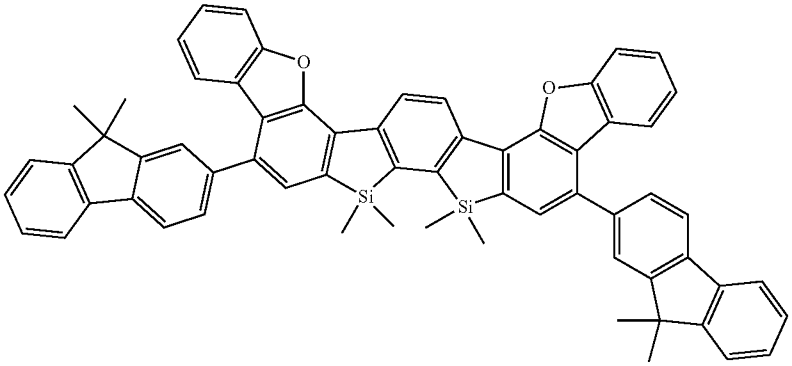
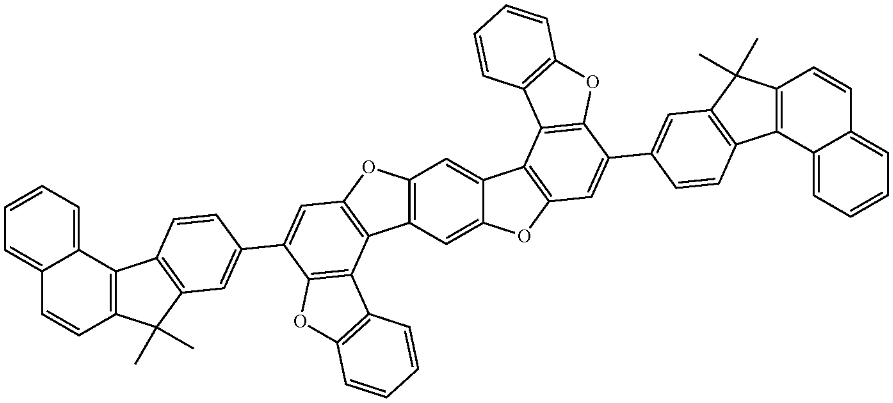

-continued
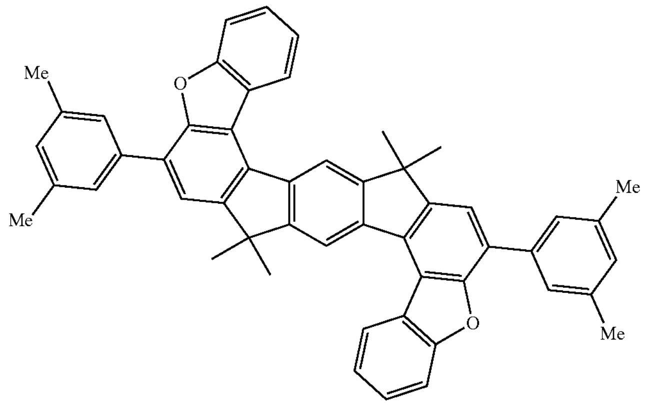
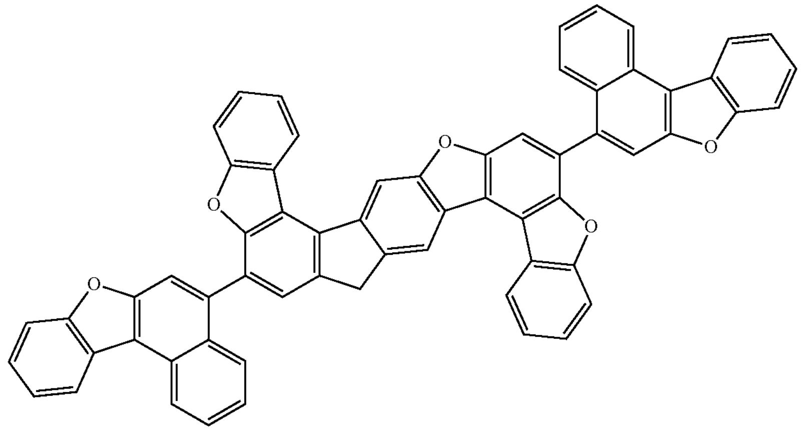
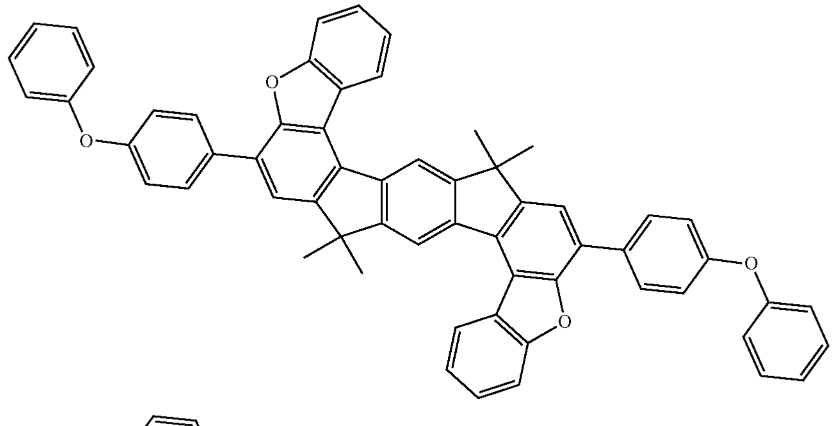
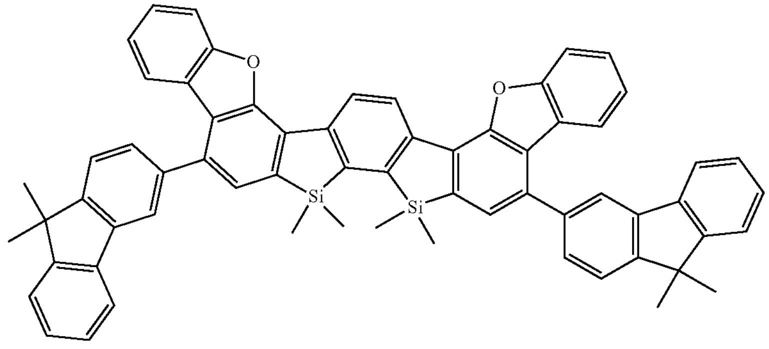

-continued
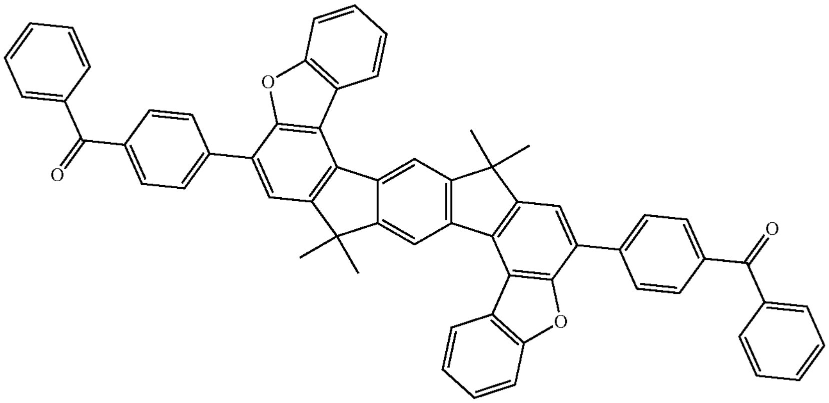
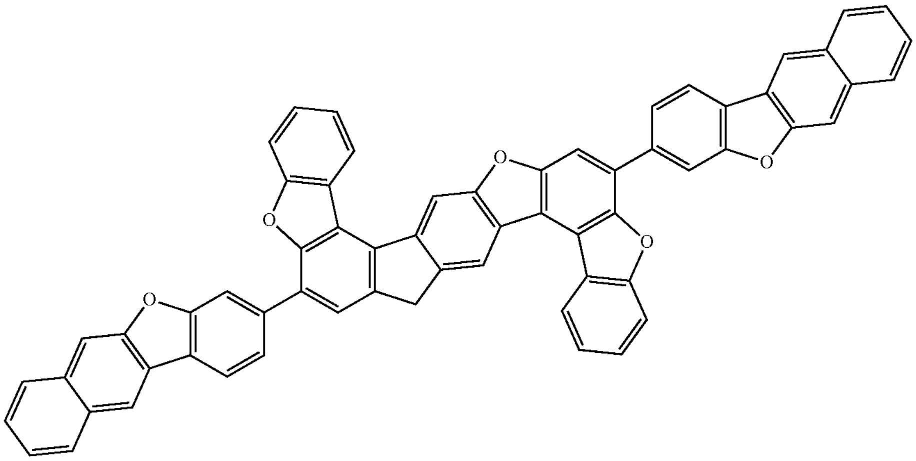
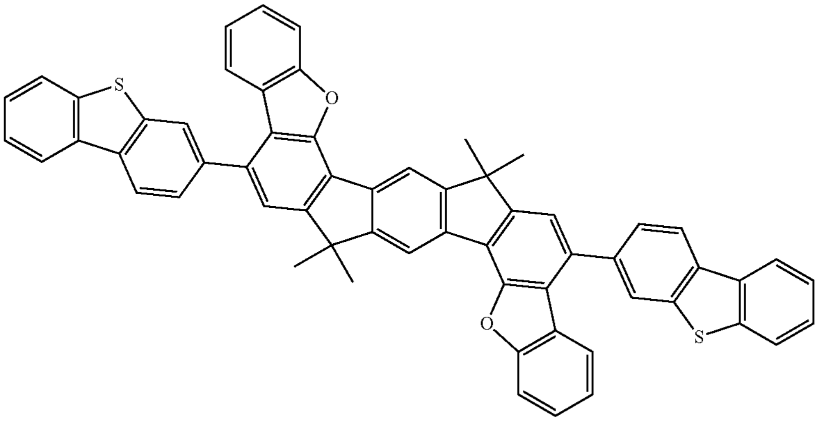
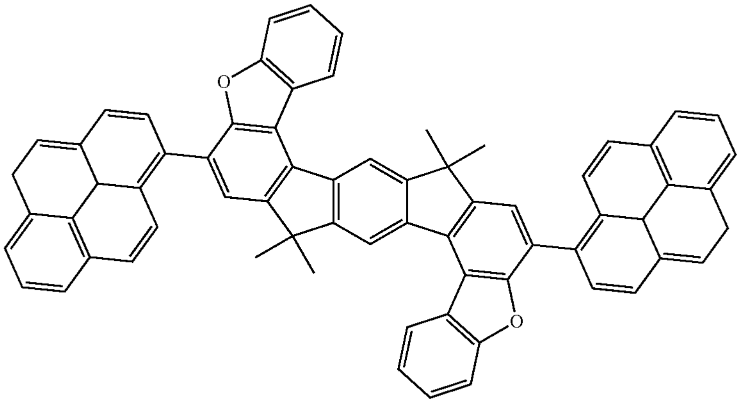

-continued
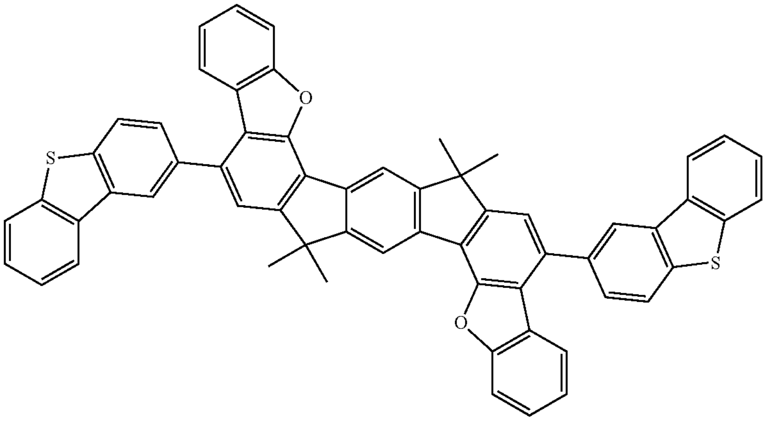
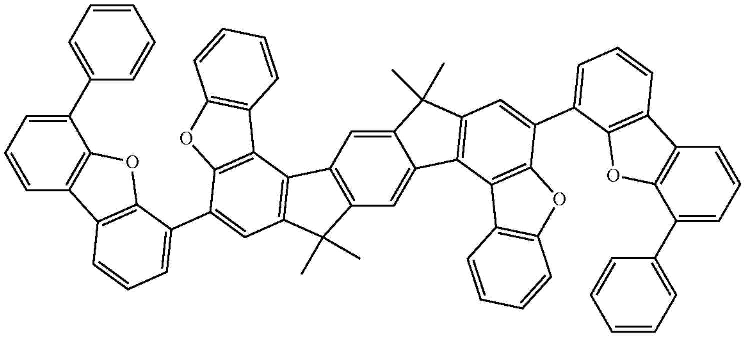
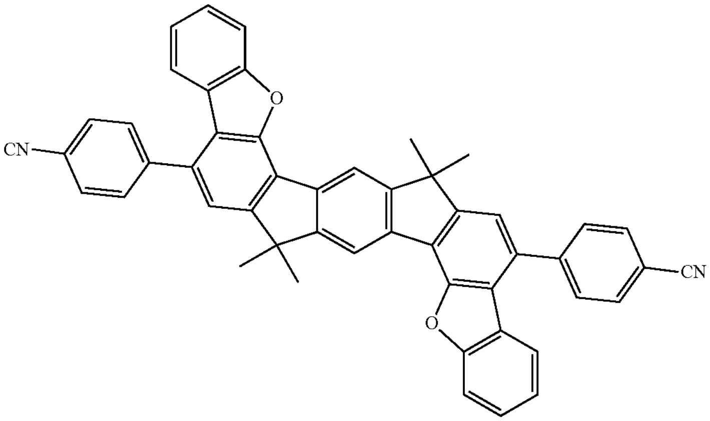
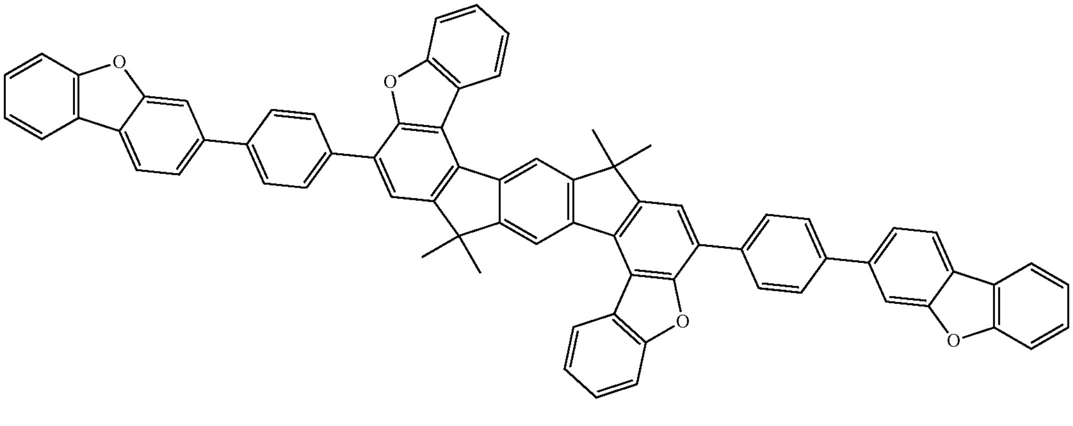

-continued
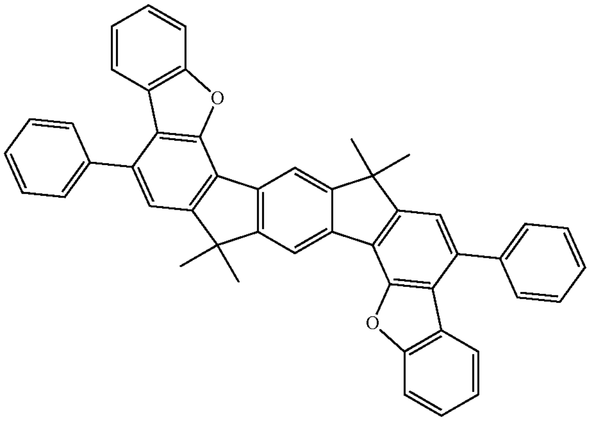
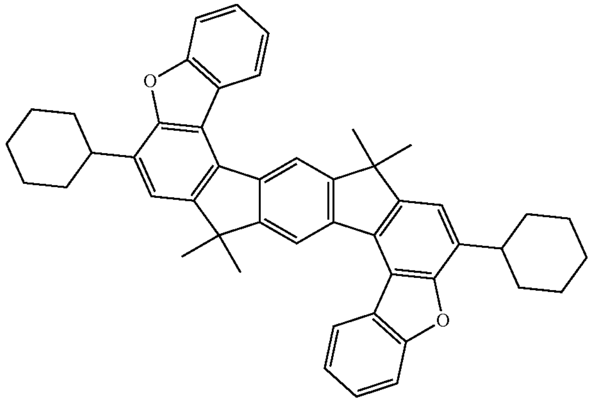
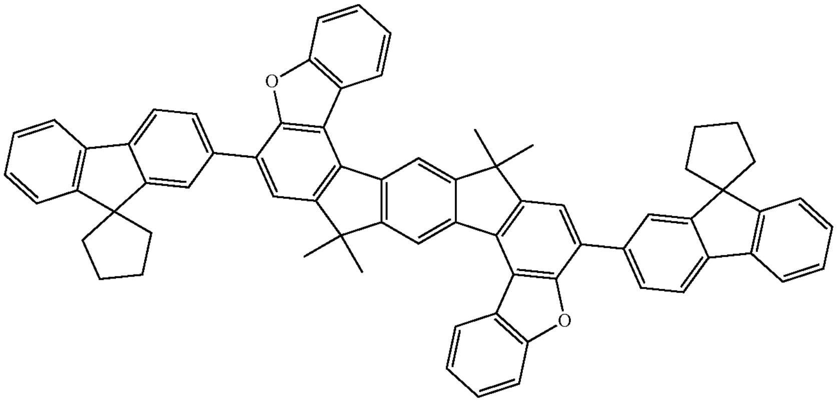
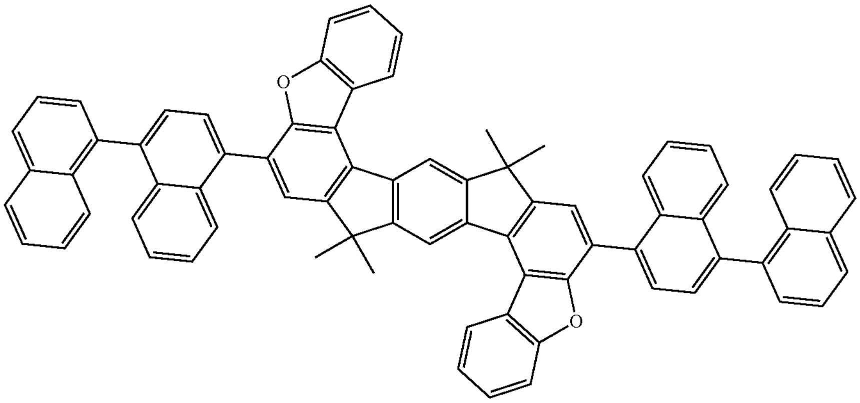
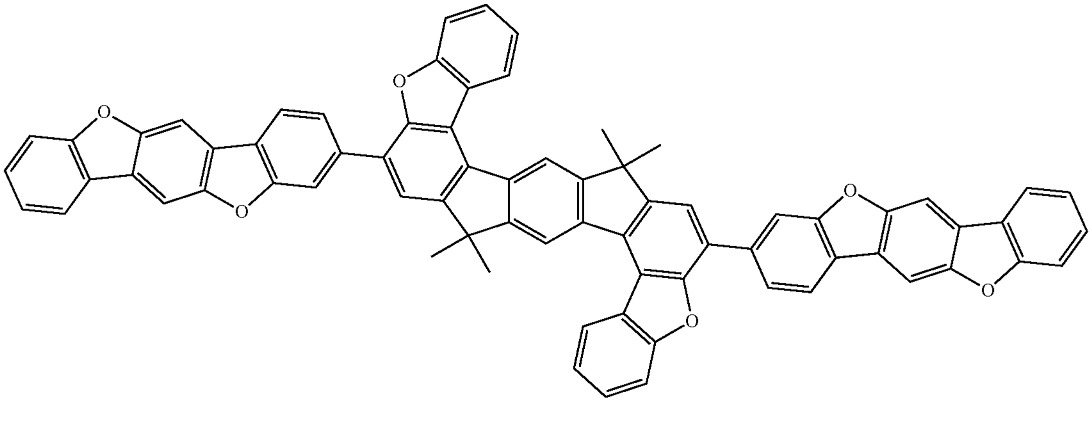

-continued
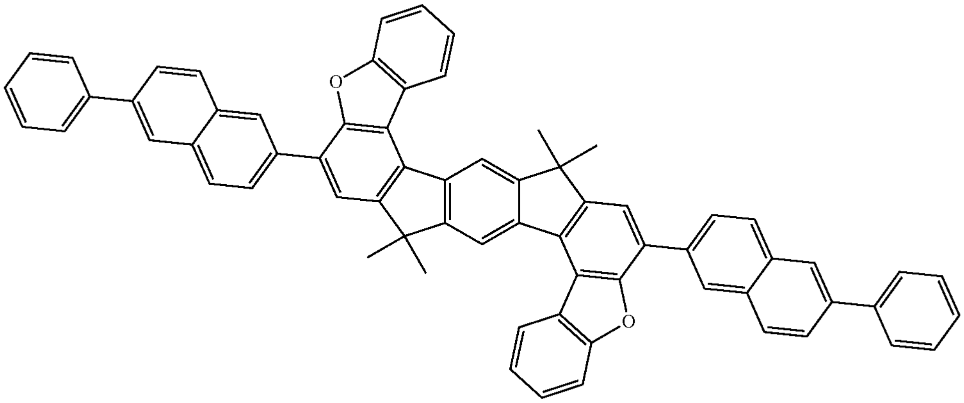
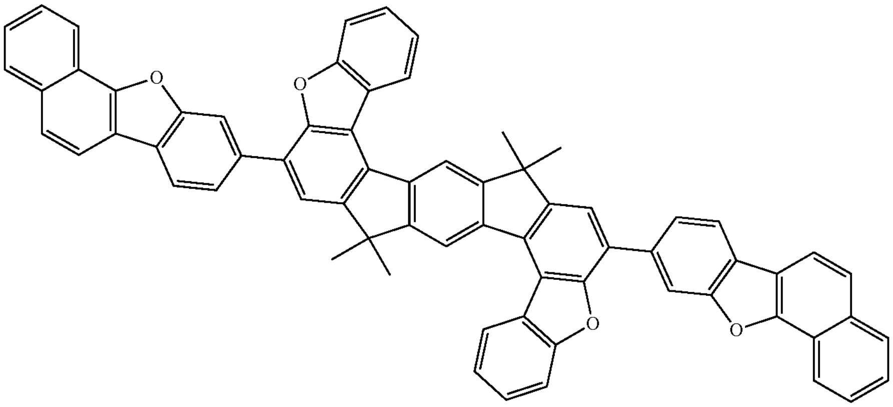
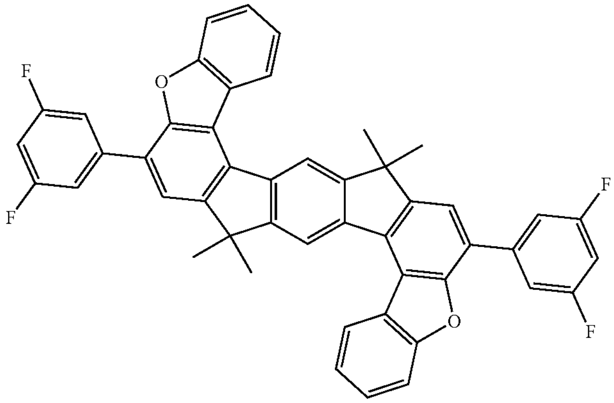
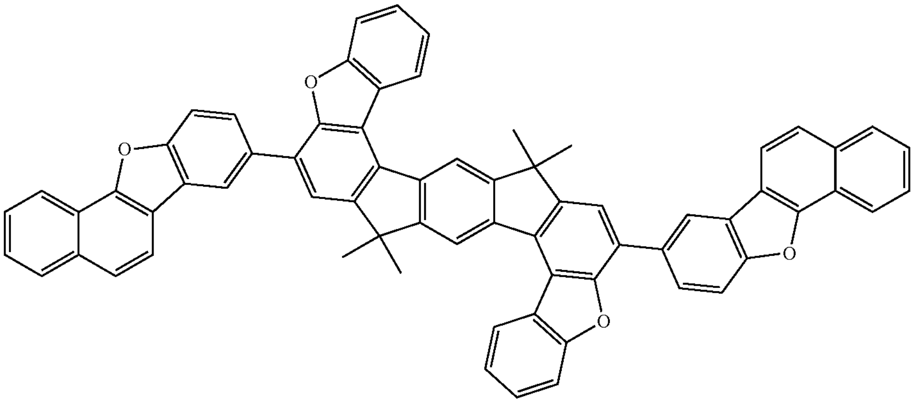

-continued
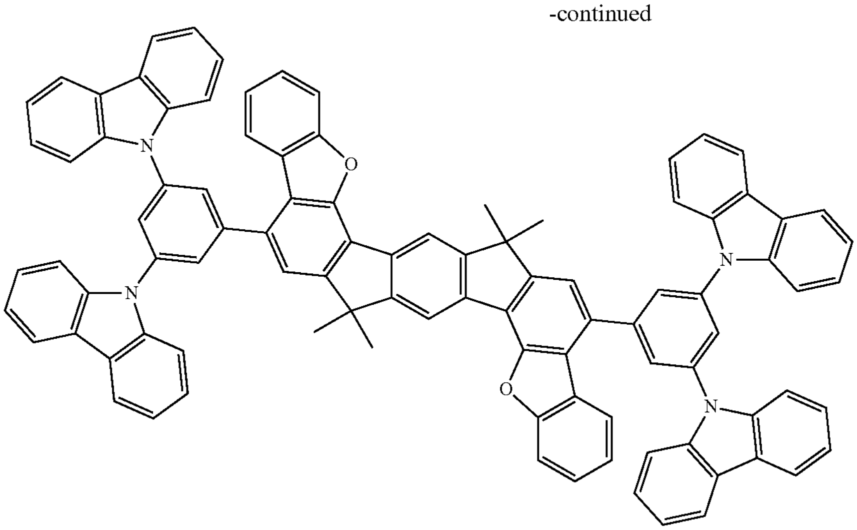
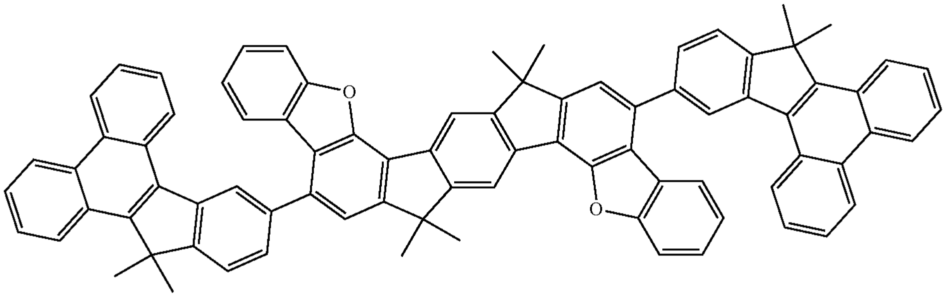
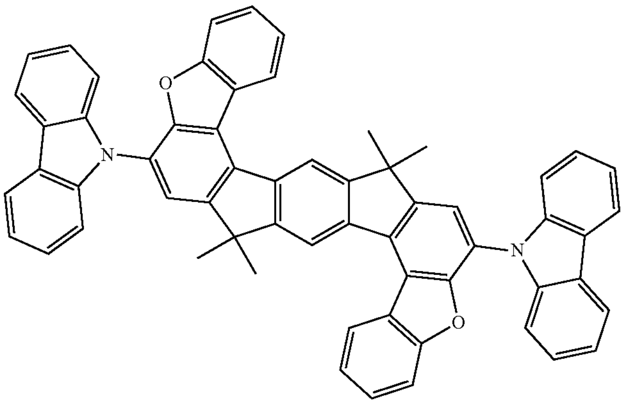
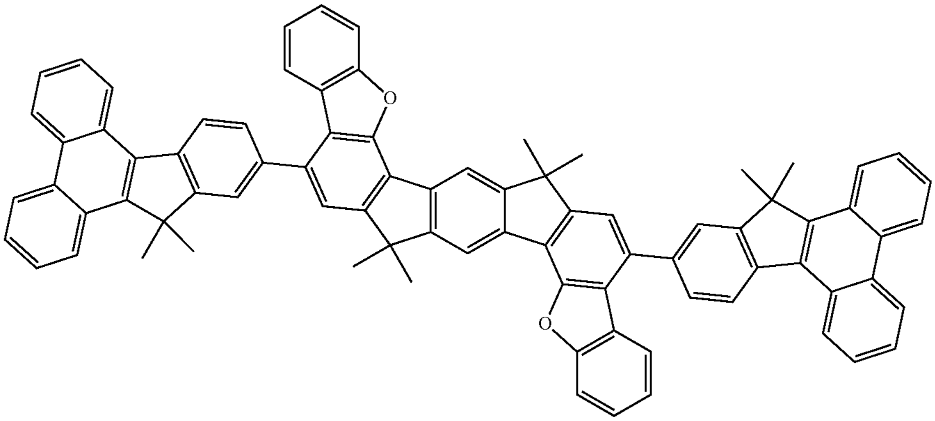

-continued
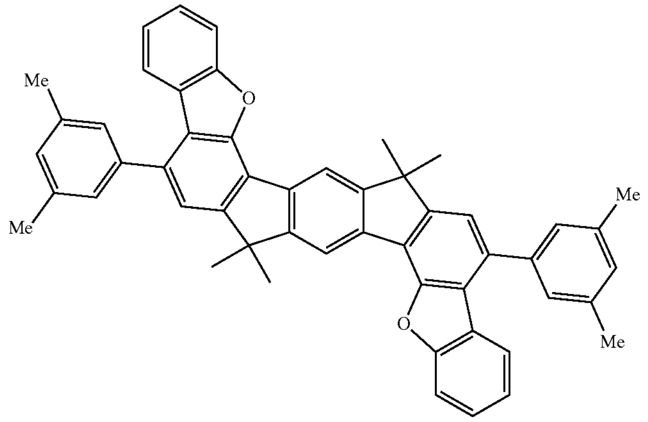
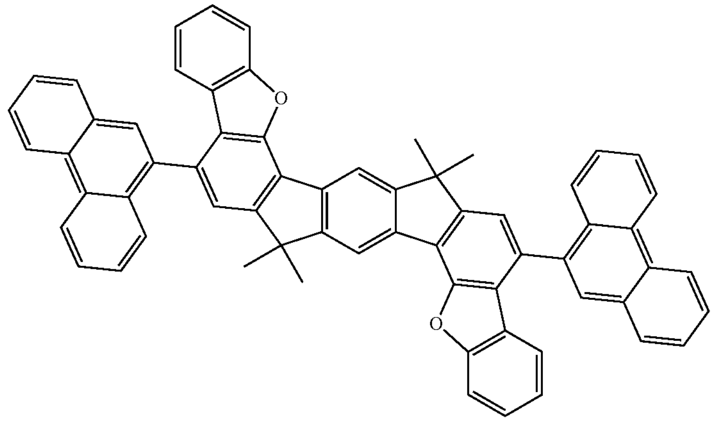
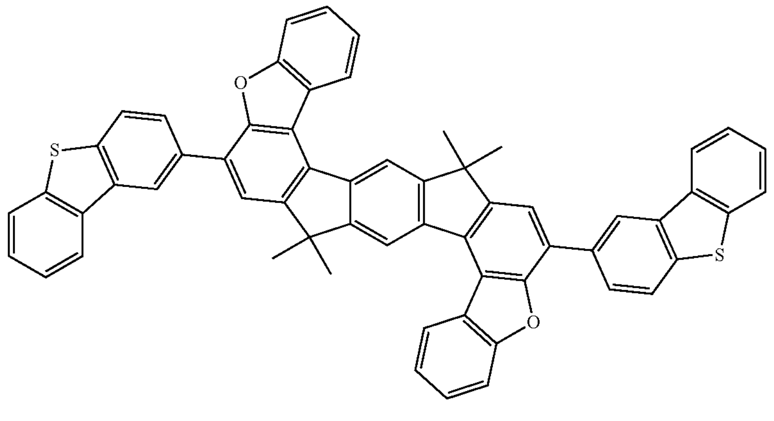
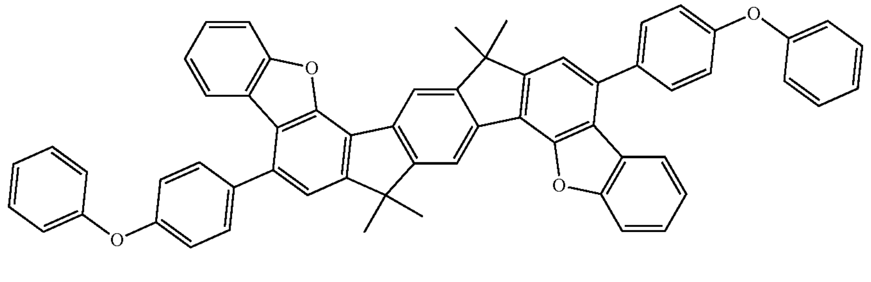

-continued
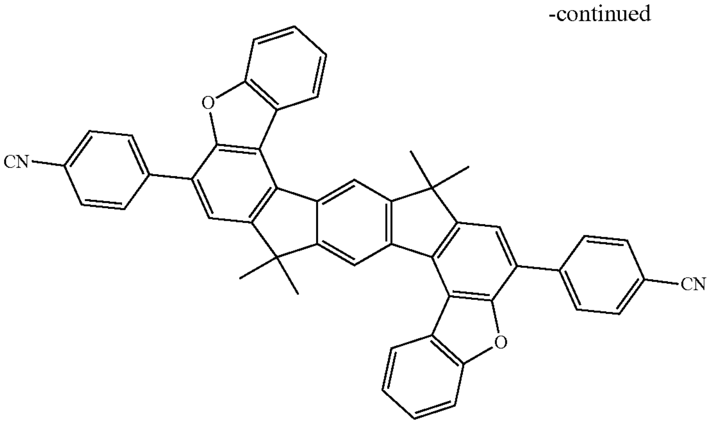
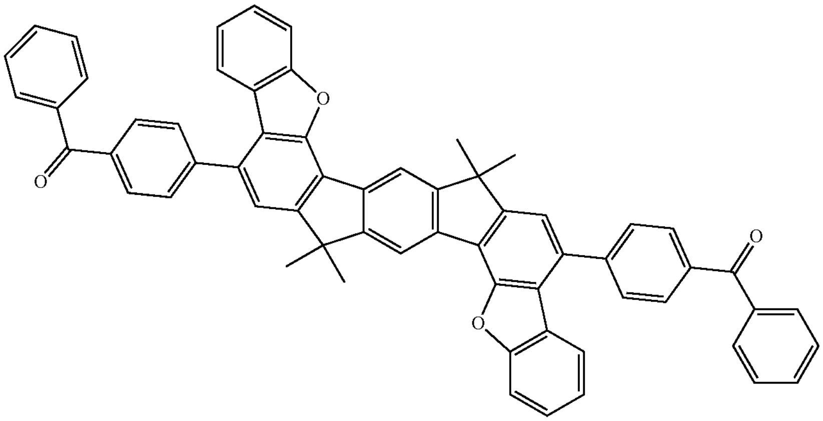
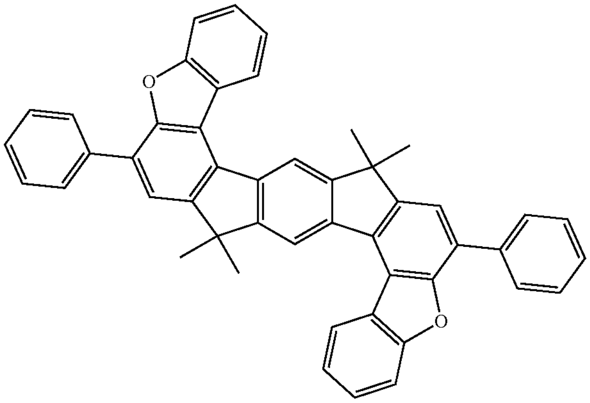
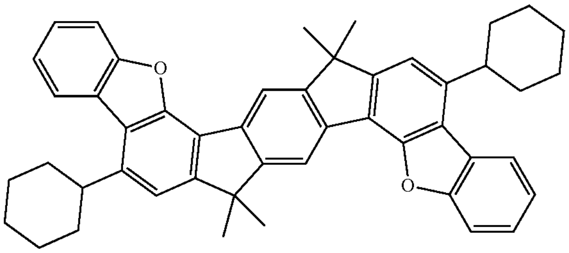
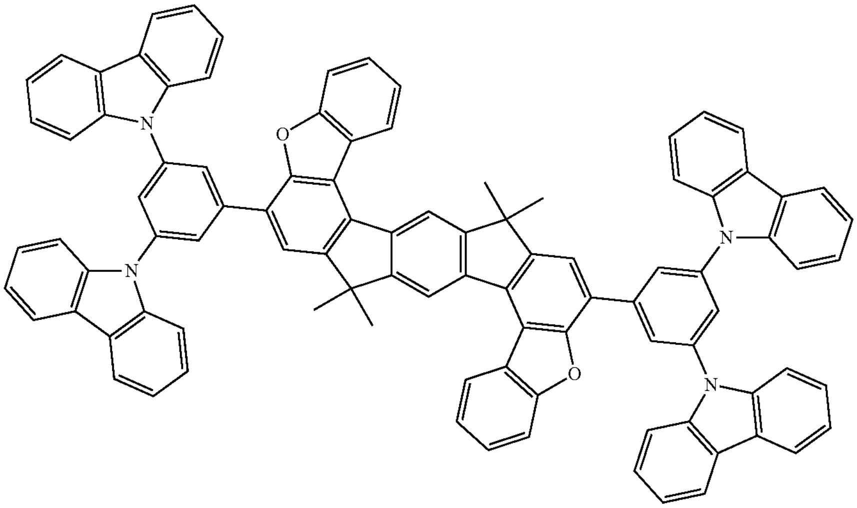

-continued
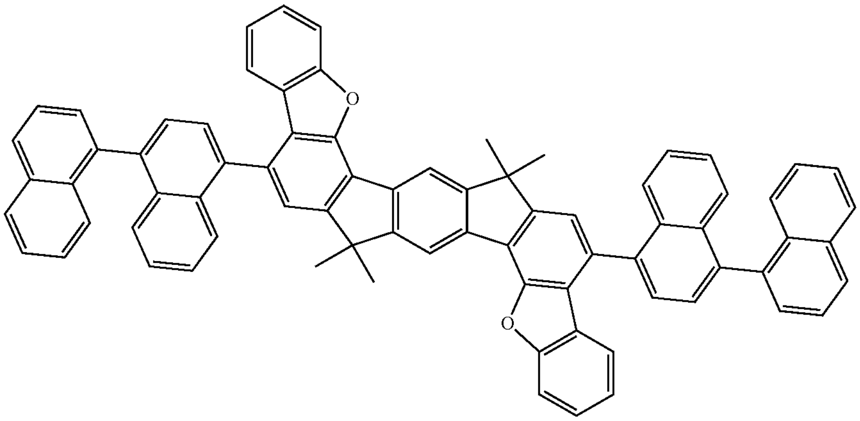
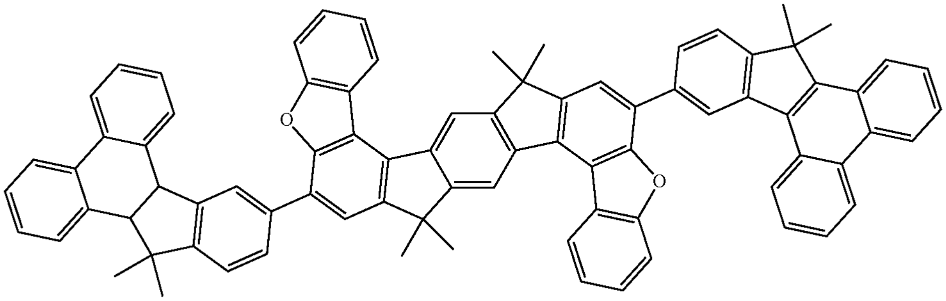
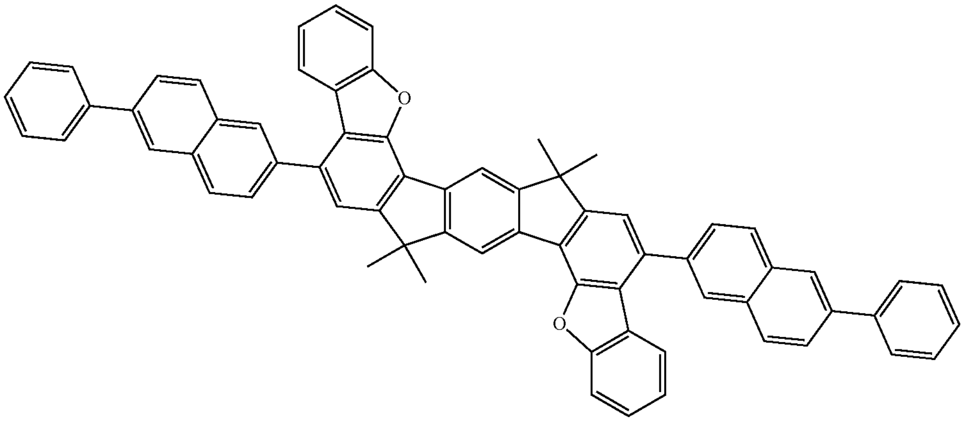
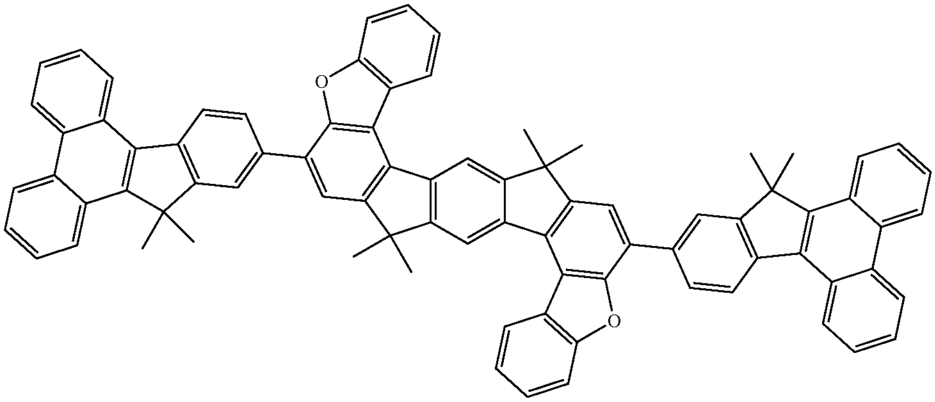

-continued
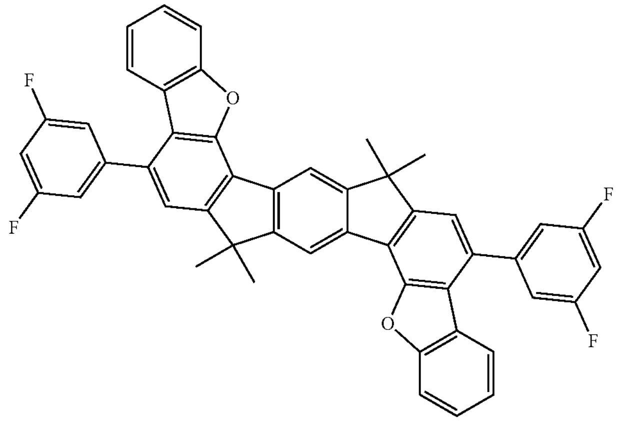
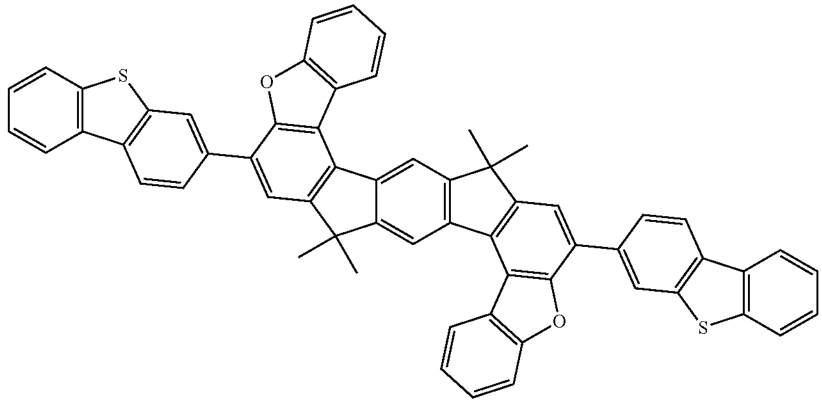
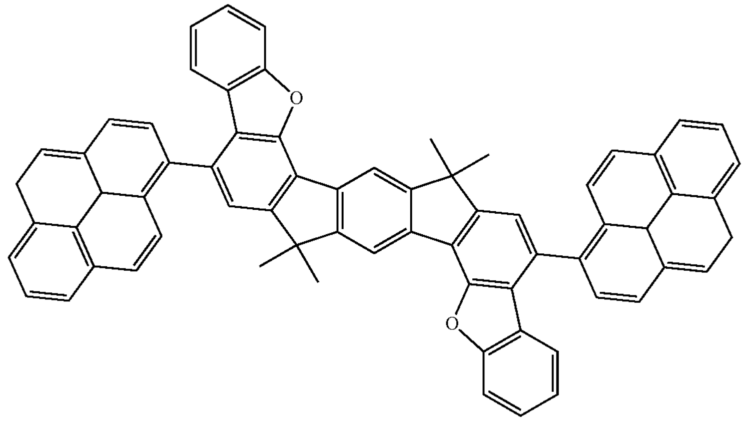
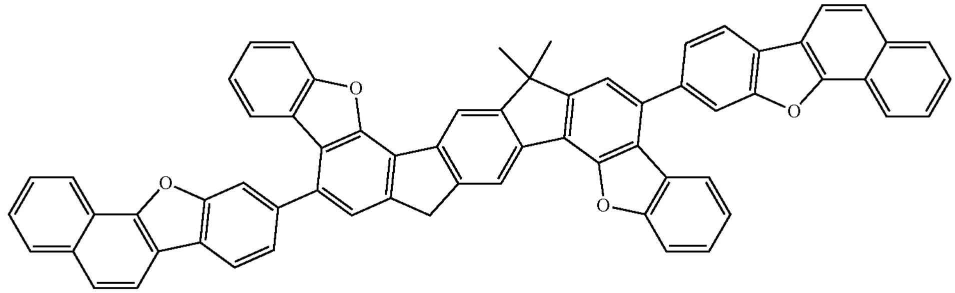

-continued
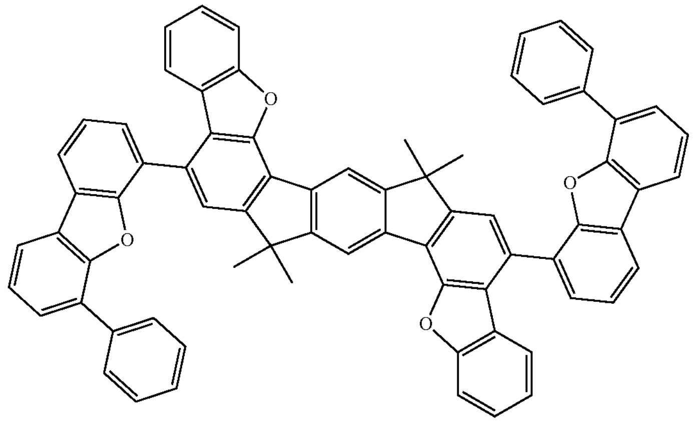
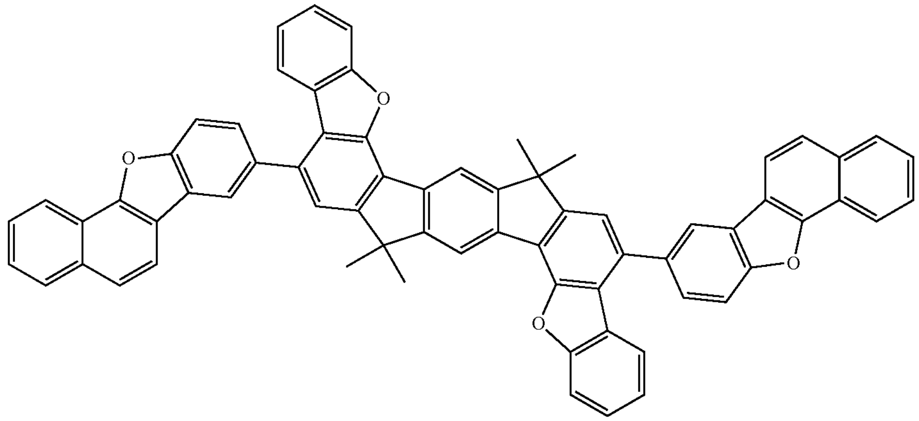
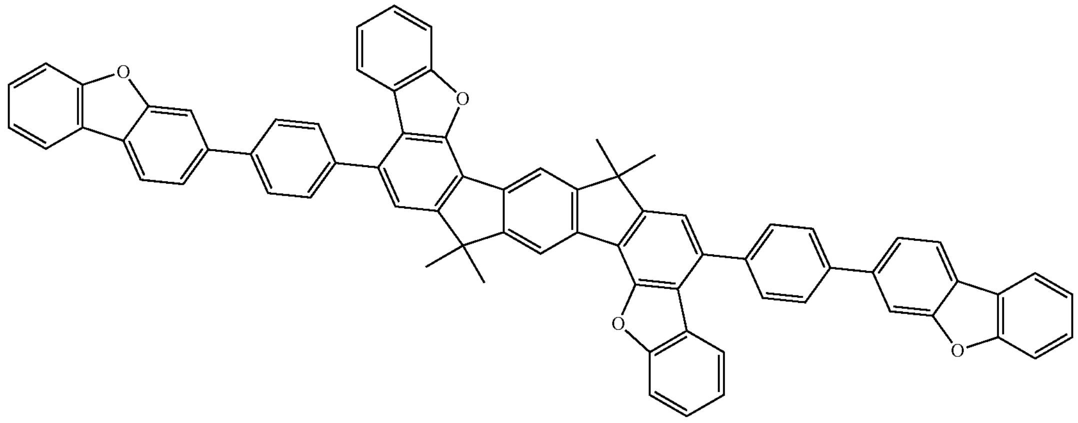
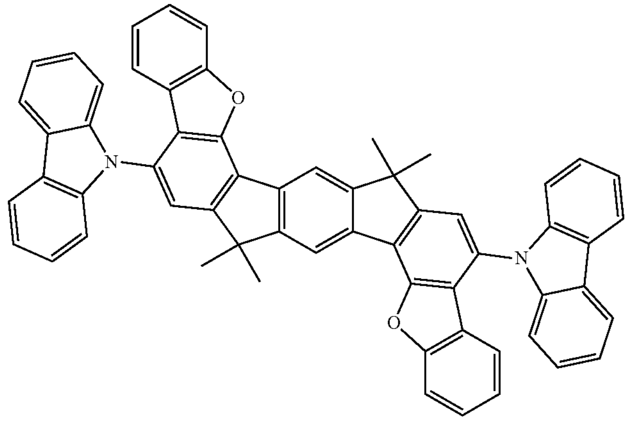

-continued
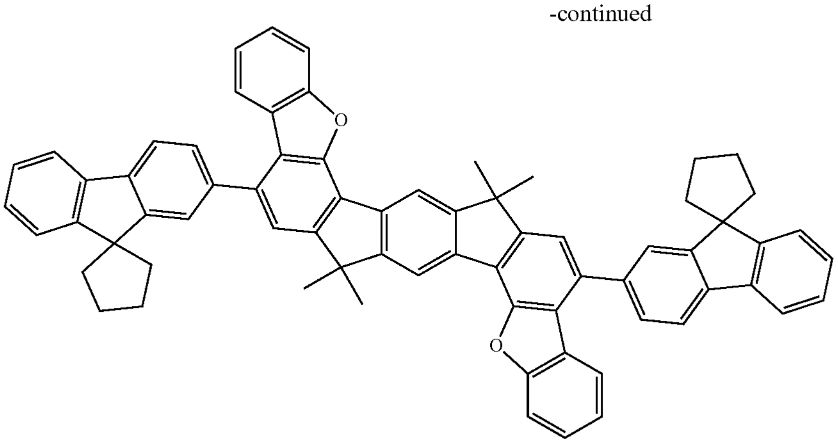
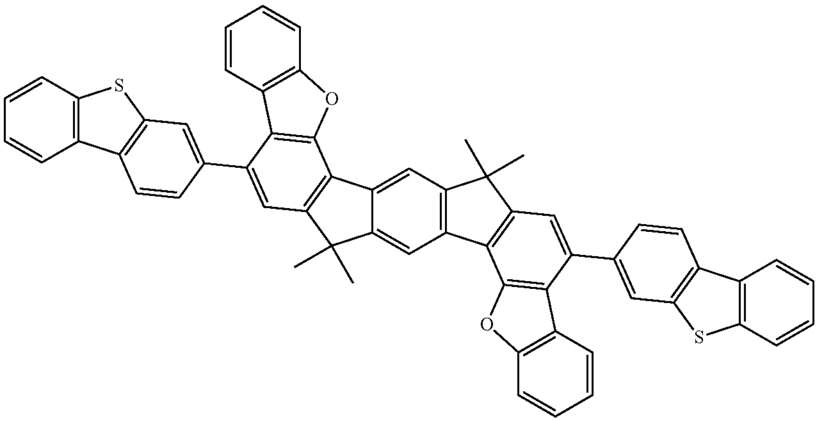
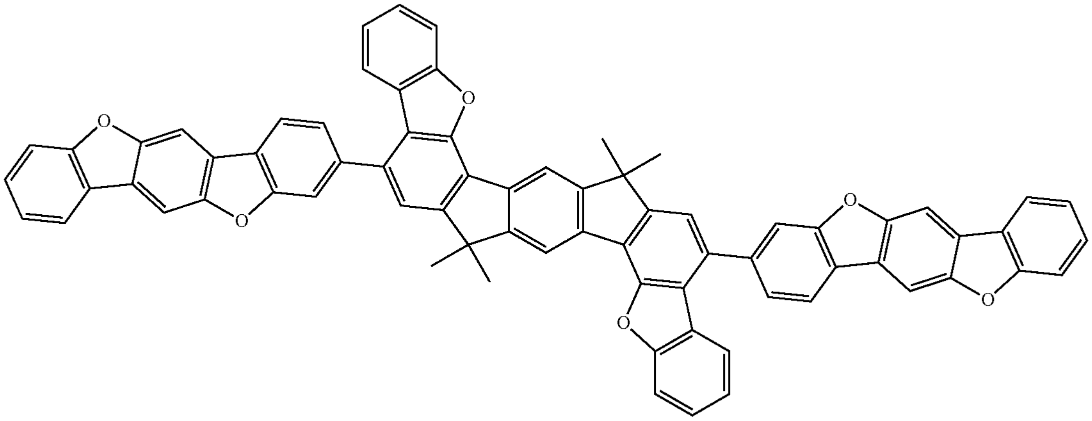
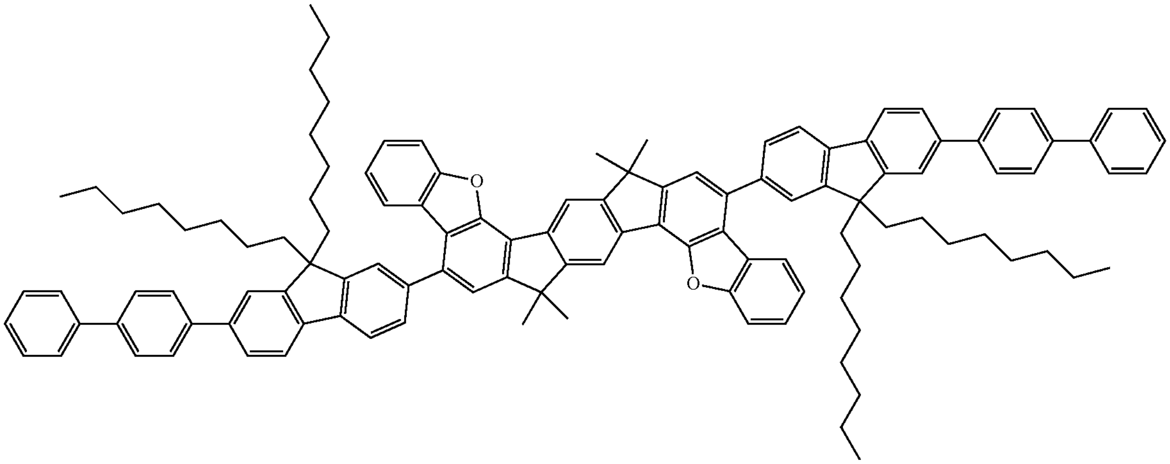

-continued
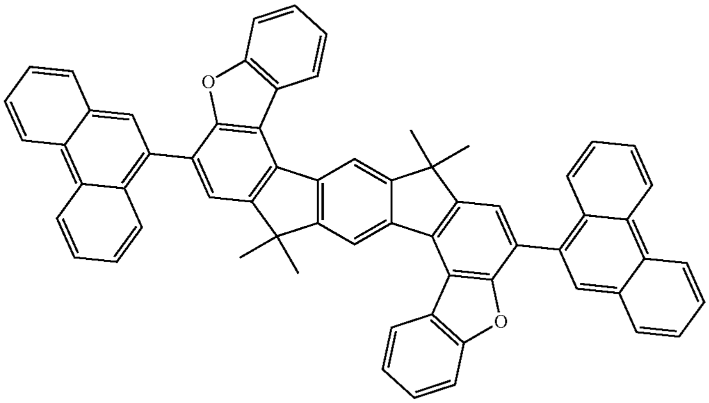
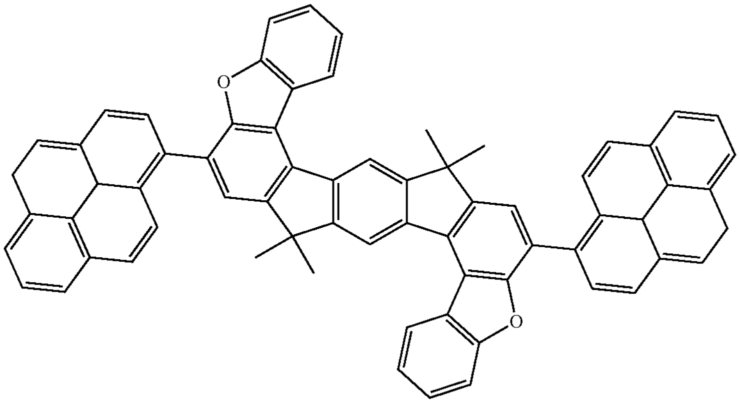
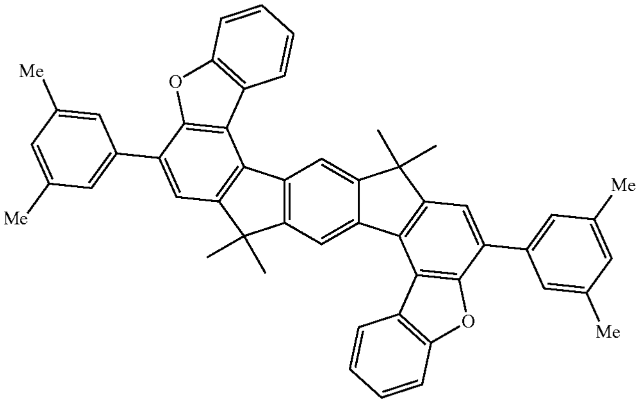
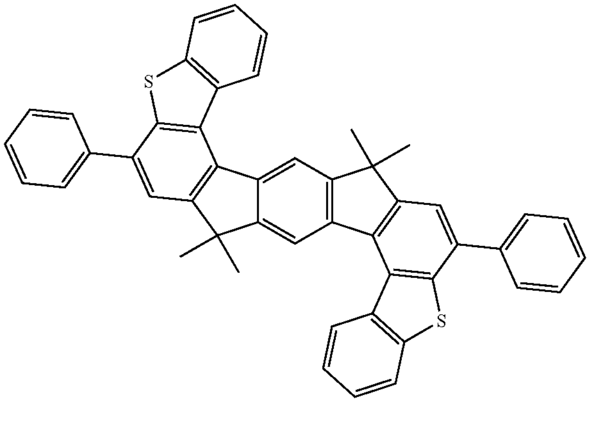

-continued
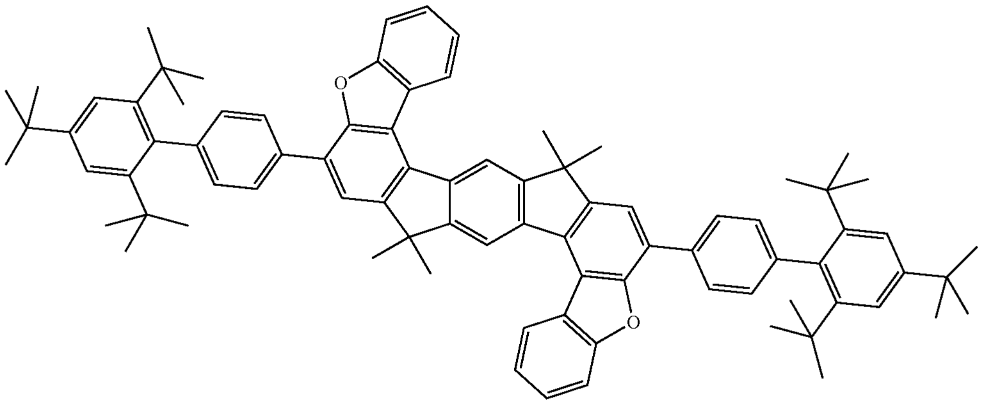
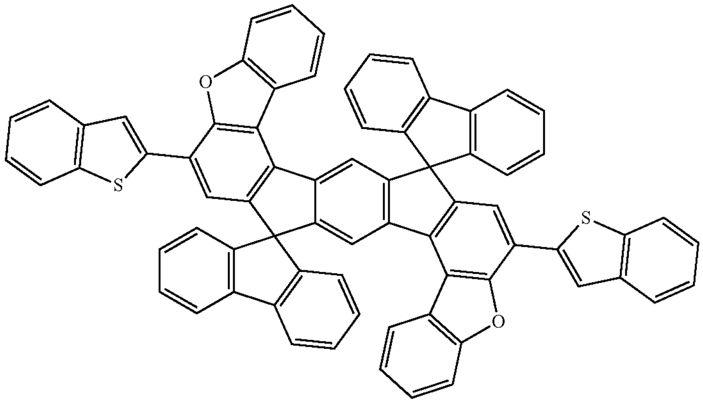
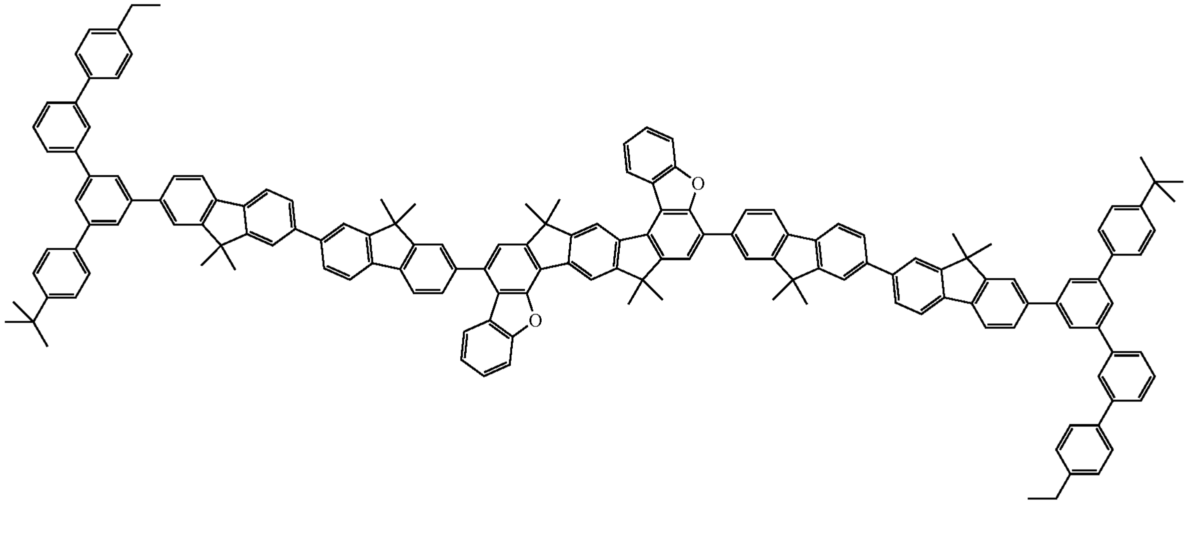

-continued
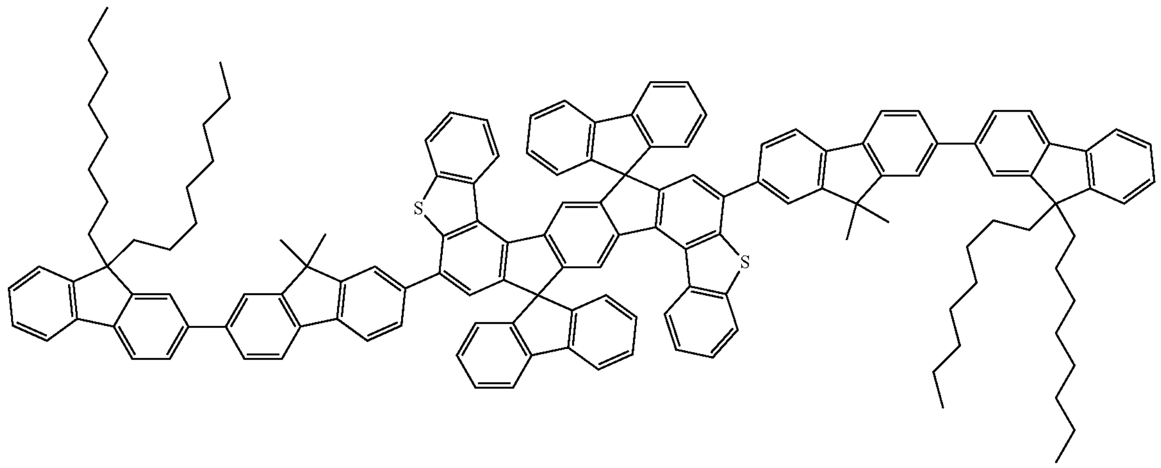
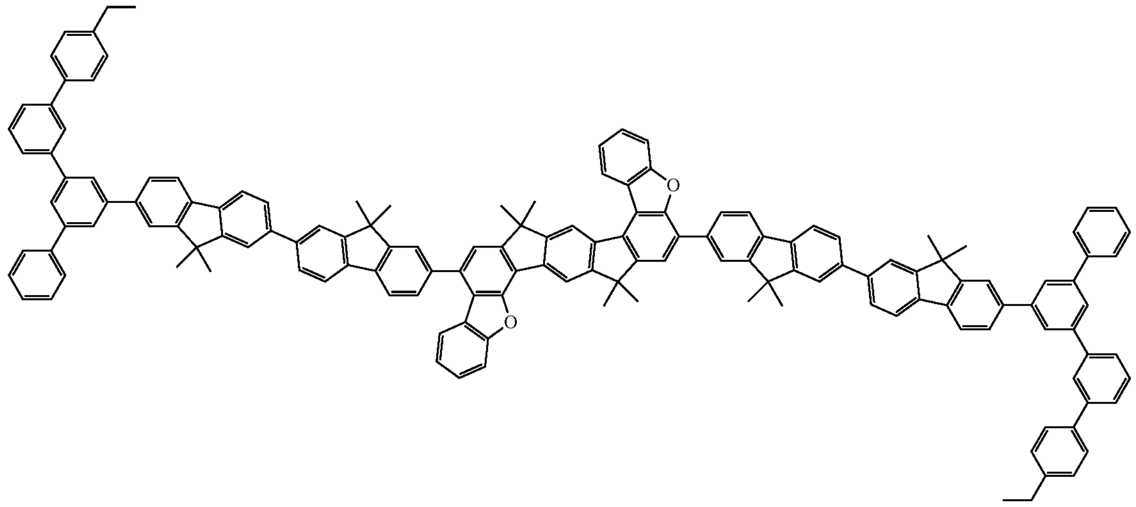
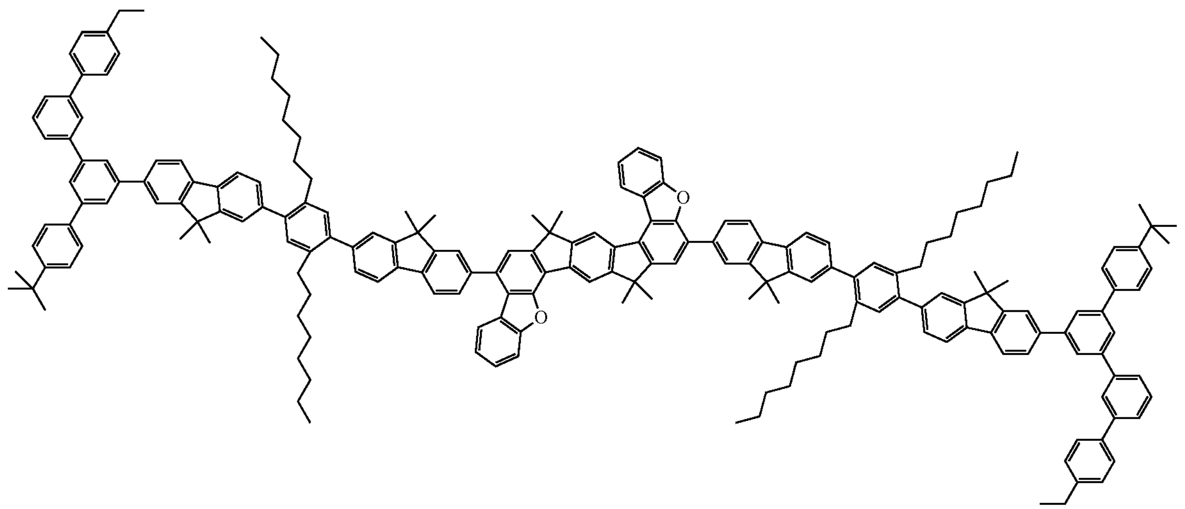

-continued
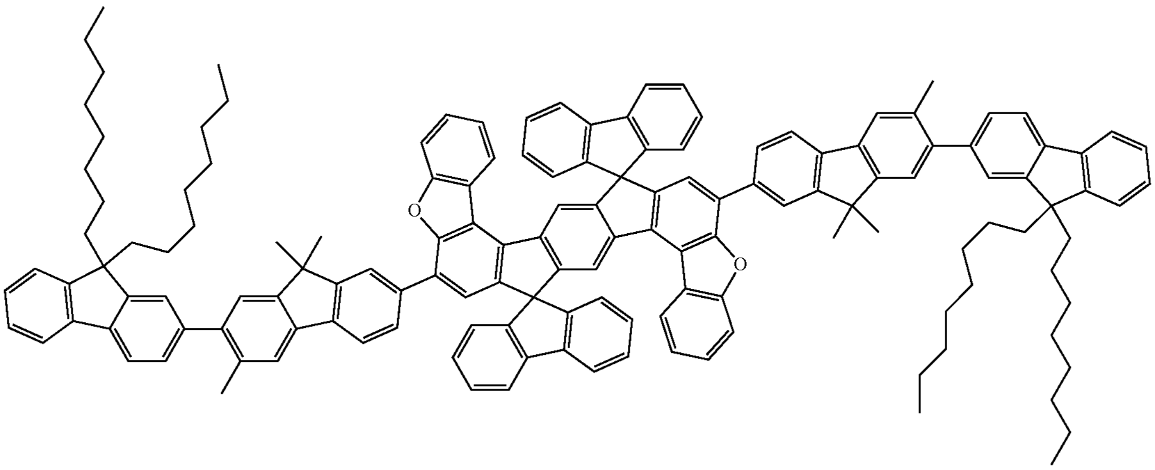
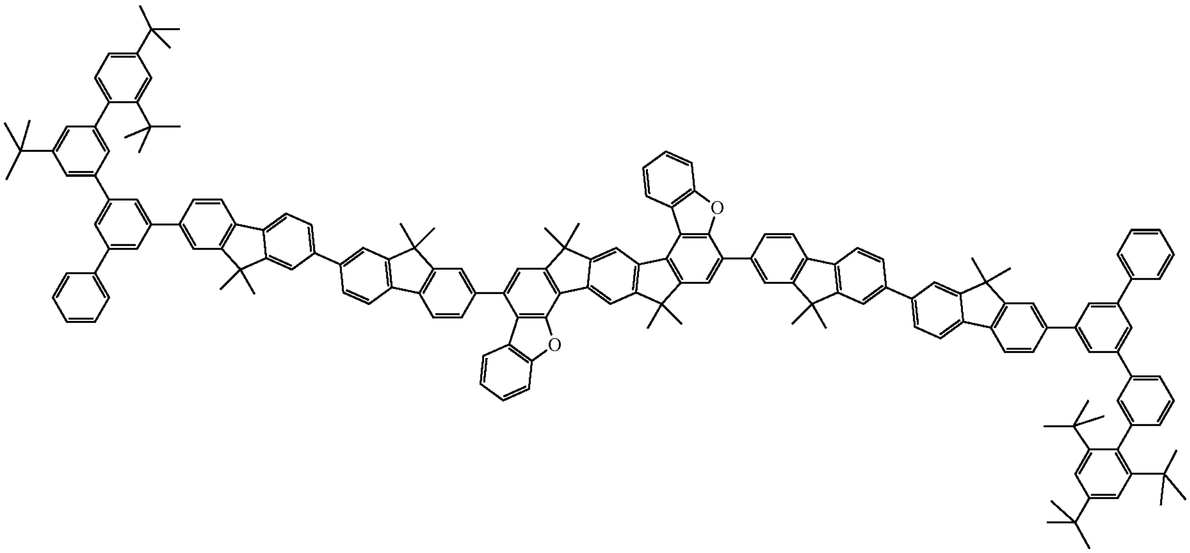
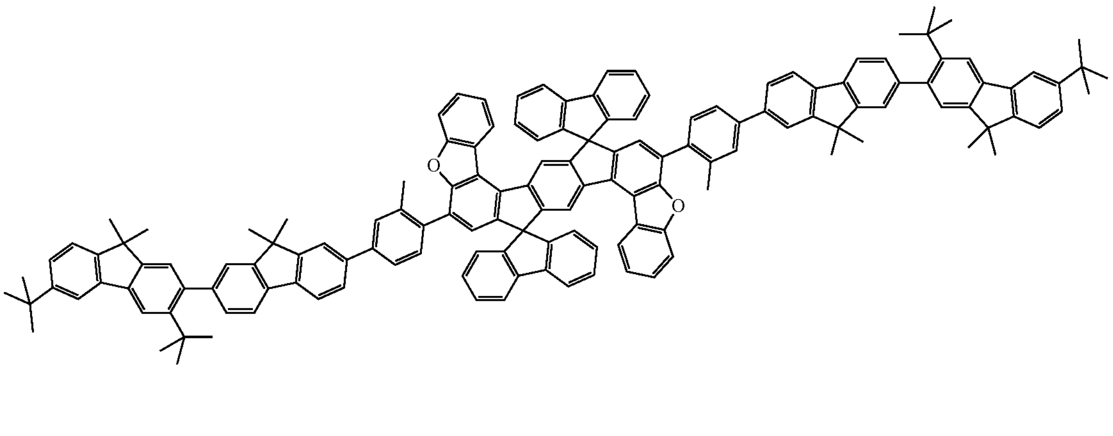

-continued
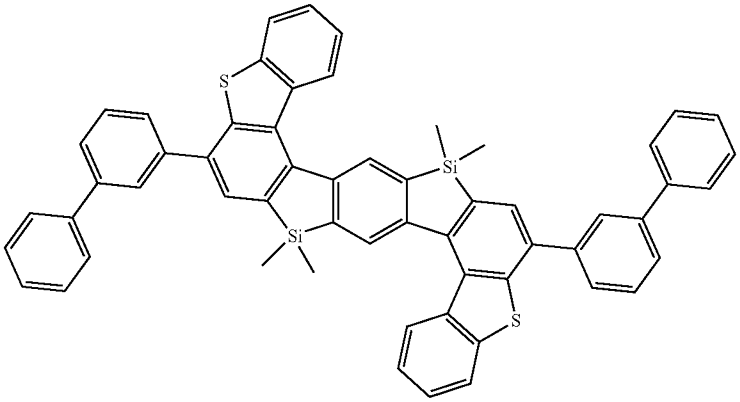
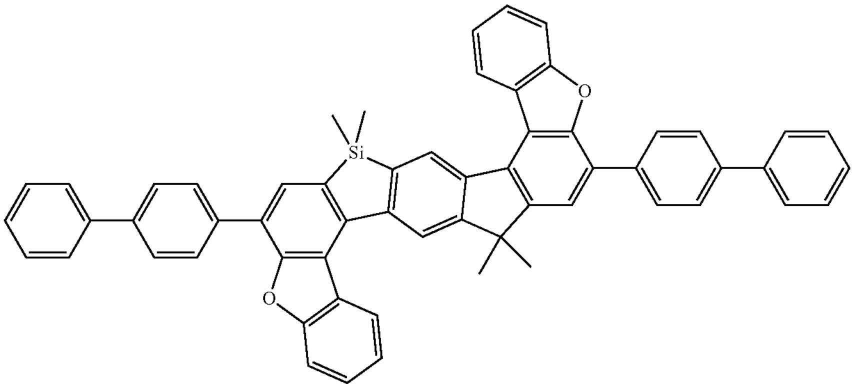
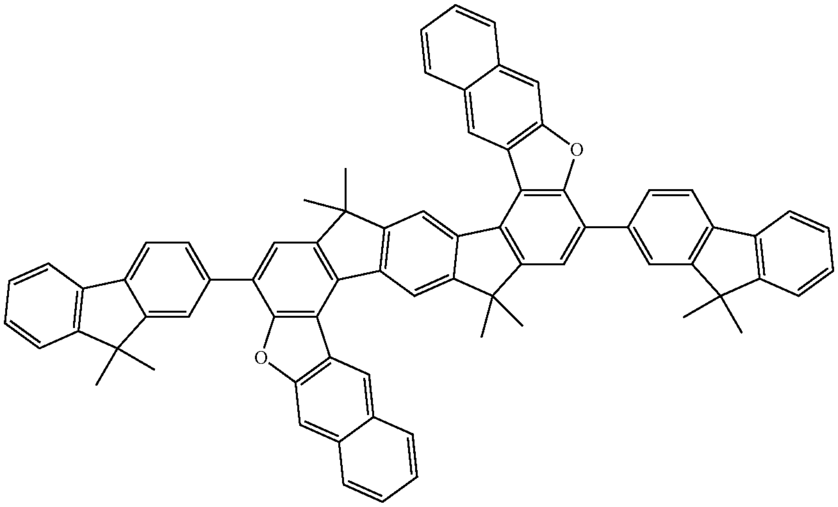
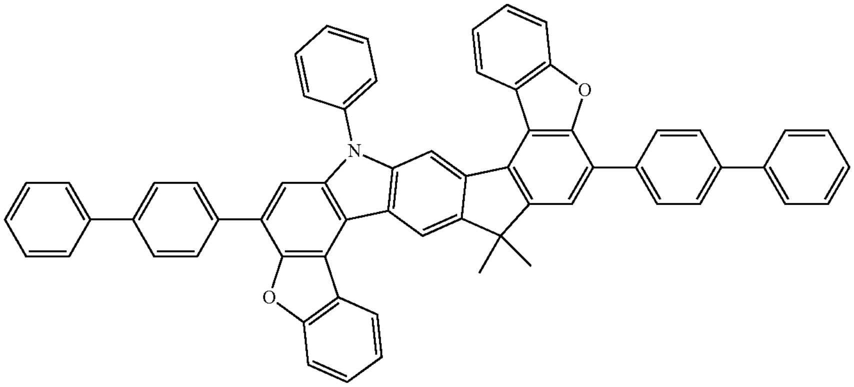

-continued
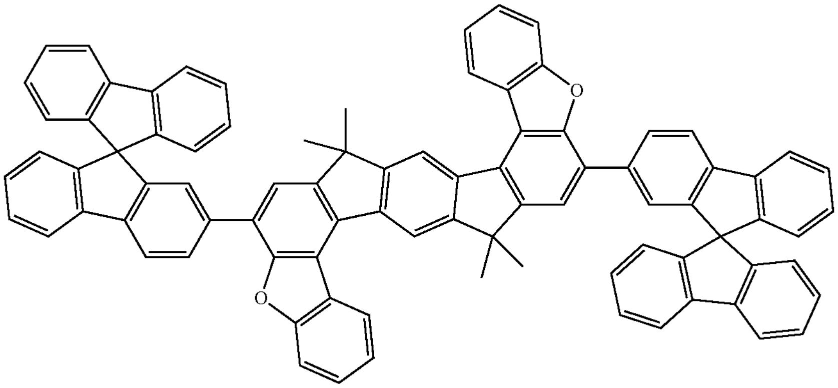
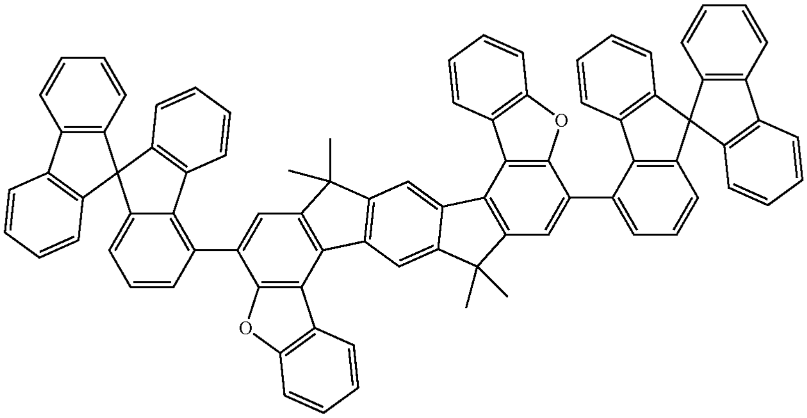
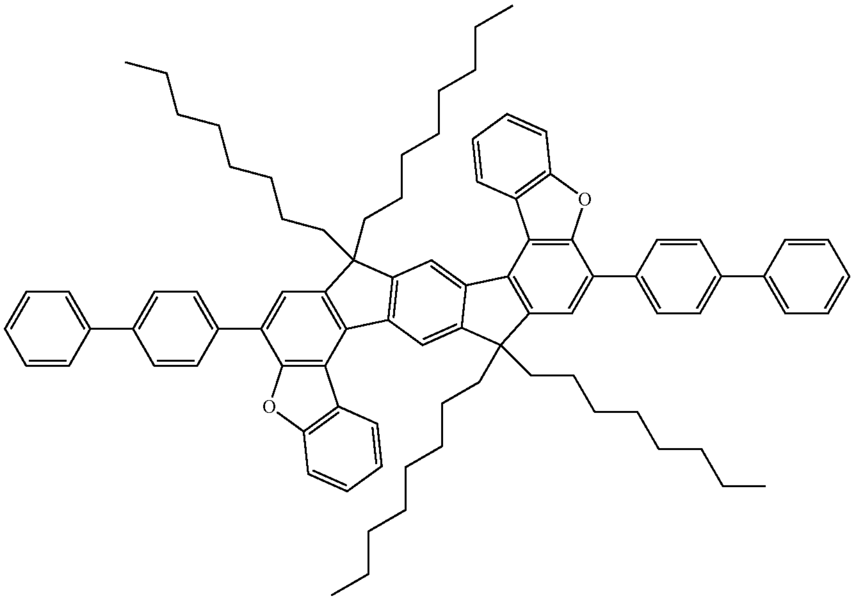

The compounds of the formula (1) can be prepared by known processes or reaction steps of organic chemistry.

A preferred process for the preparation of compounds of the formula (1) is shown below with Scheme 1 to Scheme 3:

Scheme 1

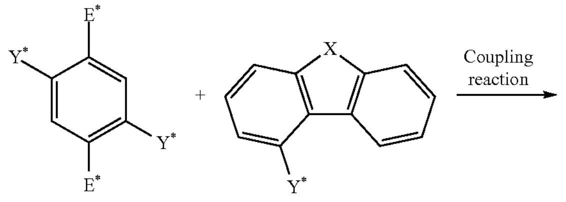

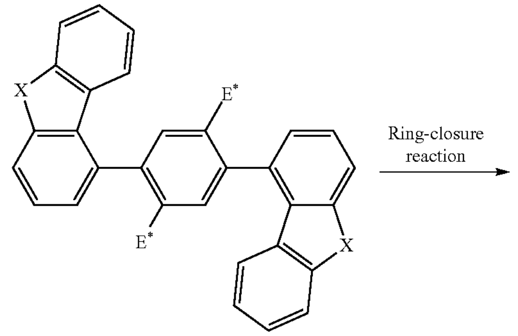

I

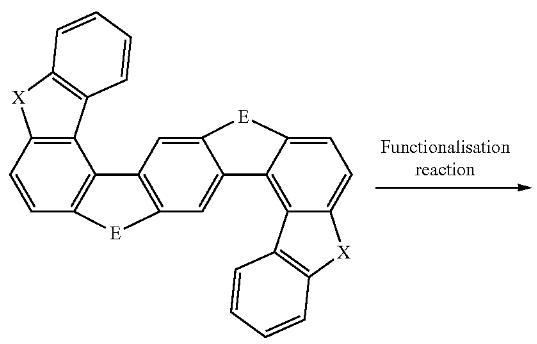

II

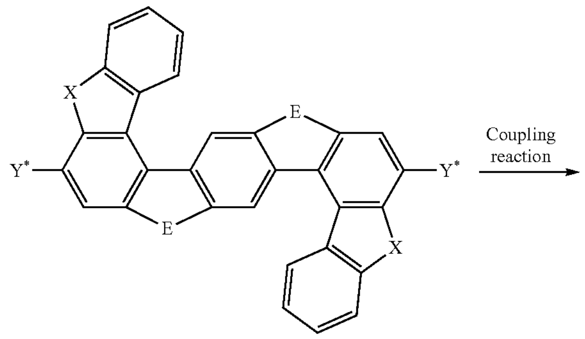

III

-continued

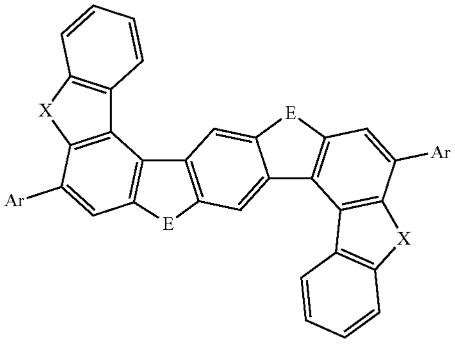

IV

X, E: bridging groups
E*: precursor of the bridging group E
Y*: reactive group, for example Cl, Br, I
Ar: Aromatic or heteroaromatic group To this end, a double coupling reaction, for example a Suzuki coupling reaction, is carried out using starting materials, which are in many cases commercially available, by means of which Compound I (see above) is obtained. Compound I contains functional group E*, which are able to carry out a ring closure with formation of bridging groups E so that Compound II is obtained. Subsequently, reactive groups Y* are introduced into Compound II, for example by bromination, or by bromination and subsequent boronation. A double coupling reaction, for example a Suzuki coupling reaction, is subsequently carried out, by means of which two further aromatic groups are introduced.

A similar process is used in Scheme 2.

Scheme 2

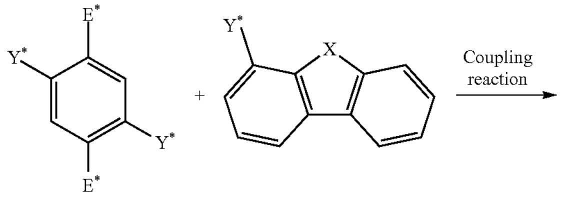

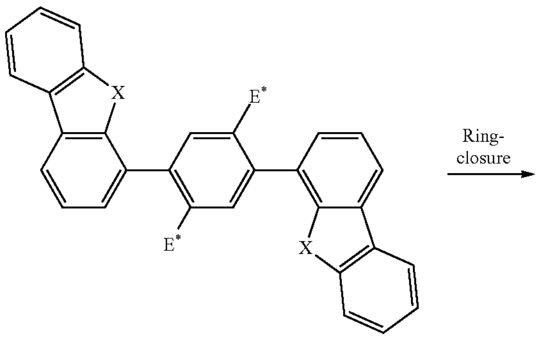

I

-continued
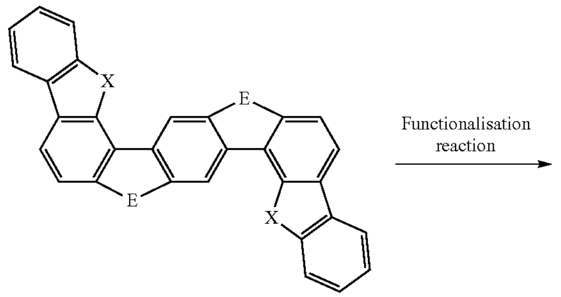
II
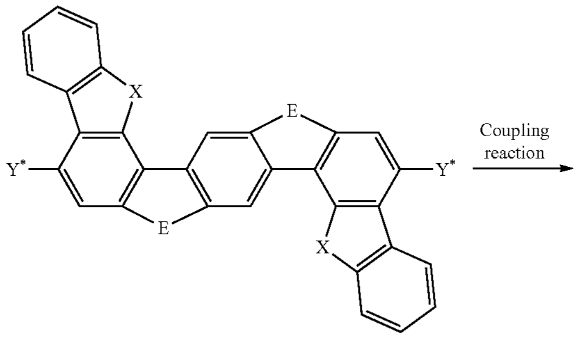
III
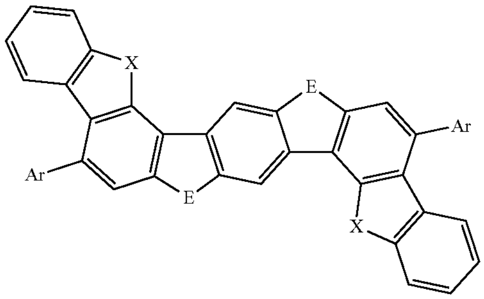
IV
X, E: bridging groups
E*: precursor of the bridging group E
Y*: reactive group, for example Cl, Br, I
Ar: Aromatic or heteroaromatic group
In Scheme 3, the compound I is obtained in two steps as follows:
Scheme 3
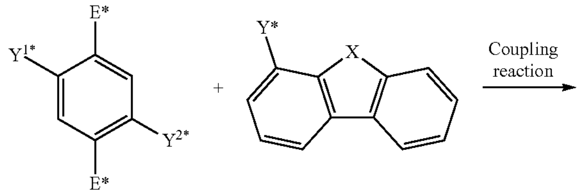
-continued
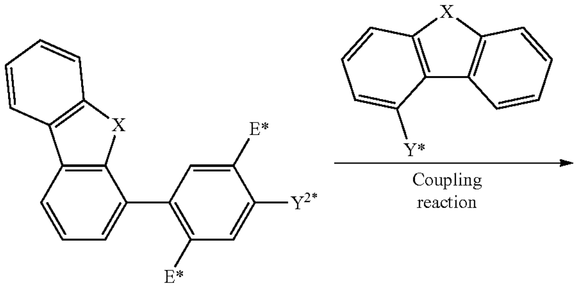
Int I
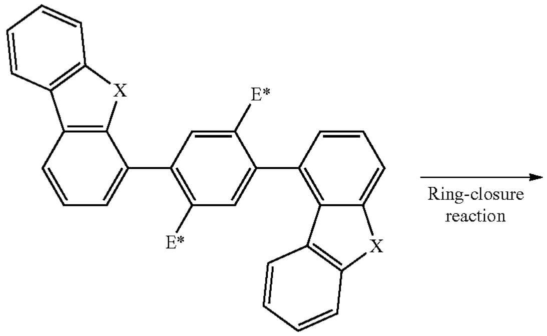
I
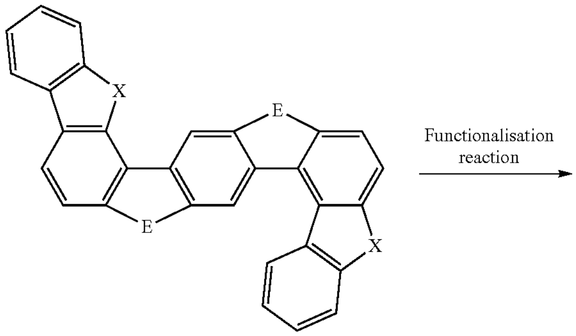
II
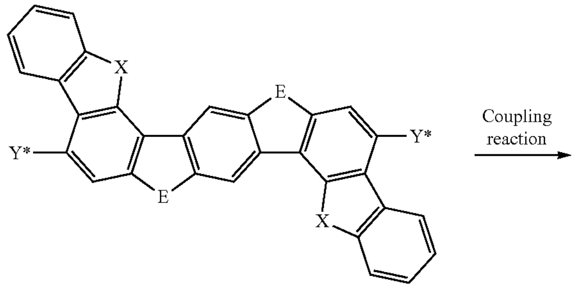
III -continued

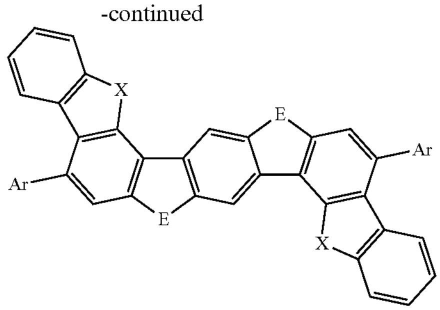

IV

X, E: bridging groups
E*: precursor of the bridging group E
Y*: reactive group, for example Cl, Br, I
Ar: Aromatic or heteroaromatic group Details on the processes indicated schematically above can be obtained from the working examples.

The person skilled in the art will be able to deviate from the processes indicated schematically above or modify them in order to obtain compounds of the formula (1), if this is necessary. This is carried out within the scope of the usual abilities of the person skilled in the art.

The present application thus relates to a process for the preparation of a compound of the formula (1), characterised in that it comprises at least one metal-catalysed coupling reaction and at least one ring-closure reaction.

The metal-catalysed coupling reaction here is preferably a transition-metal-catalysed coupling reaction, particularly preferably a Suzuki reaction.

The compounds according to the invention described above, in particular compounds which are substituted by reactive leaving groups, such as bromine, iodine, chlorine, boronic acid or boronic acid ester, can be used as monomers for the preparation of corresponding oligomers, dendrimers or polymers. Suitable reactive leaving groups are, for example, bromine, iodine, chlorine, boronic acids, boronic acid esters, amines, alkenyl or alkynyl groups containing a terminal C—C double or triple bond respectively, oxiranes, oxetanes, groups which undergo a cycloaddition, for example a 1,3-dipolar cycloaddition, such, as, for example, dienes or azides, carboxylic acid derivatives, alcohols and silanes.

The invention therefore furthermore relates to oligomers, polymers or dendrimers comprising one or more compounds of the formula (1), where the bond(s) to the polymer, oligomer or dendrimer may be localised at any desired positions in formula (1) which are substituted by R, $R^1$ or $R^2$. Depending on the linking of the compound of the formula (1), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (1) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (1) may, for example, be linked via a trivalent or polyvalent group, for example via a trivalent or polyvalent aromatic or heteroaromatic group, to give a branched or dendritic oligomer or polymer.

The same preferences as described above for compounds of the formula (1) apply to the recurring units of the formula (1) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 1992/18552), carbazoles (for example in accordance with WO 04/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (1) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, dichlorobenzene, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (1) or at least one polymer, oligomer or dendrimer containing at least one unit of the formula (1), and at least one solvent, preferably an organic solvent. The way in which solutions of this type can be prepared is known to the person skilled in the art and is described, for example, in WO 2002/072714, WO 2003/019694 and the literature cited therein.

The compounds of the formula (1) are suitable for use in electronic devices, in particular in organic electroluminescent devices (OLEDs). Depending on the substitution, the compounds are employed in various functions and layers.

The compound of the formula (1) can be employed in any function in the organic electroluminescent device, for example as hole-transporting material, as matrix material, as emitting material, or as electron-transporting material.

The invention therefore furthermore relates to the use of a compound of the formula (1) in an electronic device. The electronic device here is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention furthermore relates to an electronic device comprising at least one compound of the formula (1). The electronic device is preferably selected from the devices indicated above. Particular preference is given to an organic electroluminescent device comprising anode, cathode and at least one emitting layer, characterised in that at least one organic layer comprises at least one compound of the formula (1).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, chargegeneration layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of the organic electroluminescent device is preferably as follows: anode-hole-injection layer-hole-transport layer-emitting layer-electron-transport layer-electron-injection layer-cathode. It is not necessary for all of the said layers to be present, and further layers may additionally be present, for example an electron-blocking layer adjacent to the emitting layer on the anode side, or a hole-blocking layer adjacent to the emitting layer on the cathode side The organic electroluminescent device according to the invention may comprise a plurality of emitting layers. In this case, these emission layers particularly preferably have in total a plurality of emission maxima between 380 nm and 750 nm, resulting overall in white emission, i.e. various emitting compounds which are able to fluoresce or phosphoresce and which emit blue, green, yellow, orange or red light are used in the emitting layers. Particular preference is given to three-layer systems, i.e. systems having three emitting layers, where at least one of these layers preferably comprises at least one compound of the formula (1) and where the three layers exhibit blue, green, yellow, orange or red emission (for the basic structure see, for example, WO 2005/011013). It should be noted that, for the generation of white light, an emitter compound used individually which emits in a broad wavelength range may also be suitable instead of a plurality of emitter compounds emitting in colour. Alternatively and/or additionally, the compounds according to the invention may also be present in the hole-transport layer or in another layer in an organic electroluminescent device of this type. The various emitting layers may be directly adjacent to one another, or they may be separated from one another by non-emitting layers. According to a preferred embodiment of the invention, a white-emitting OLED is a so-called tandem OLED, i.e. two or more complete OLED layer sequences are present in the OLED, where the OLED layer sequences in each case comprise hole-transport layer, emitting layer and electron-transport layer, which are each separated from one another by a chargegeneration layer.

It is preferred for the compound of the formula (1) to be employed in an emitting layer. The compound of the formula (1) is particularly suitable for use as emitting compound or as matrix material in an emitting layer.

The compound according to the invention is particularly suitable for use as blue-emitting emitter compound or as matrix compound for a blue-emitting emitter compound.

If the compound according to the invention is employed as emitting compound in an emitting layer, it is preferably employed in combination with one or more matrix materials. A matrix material here is taken to mean a material which is present in the emitting layer, preferably as the principal component, and which does not emit light on operation of the device.

The proportion of the emitting compound in the mixture of the emitting layer is between 0.1 and 50.0%, preferably between 0.5 and 20.0%, particularly preferably between 1.0 and 10.0%. Correspondingly, the proportion of the matrix material or matrix materials is between 50.0 and 99.9%, preferably between 80.0 and 99.5%, particularly preferably between 90.0 and 99.0%.

The specifications of the proportions in % are, for the purposes of the present application, taken to mean % by vol. if the compounds are applied from the gas phase and % by weight if the compounds are applied from solution.

If the compound according to the invention is employed as matrix material, it can be employed in combination with all known emitting compounds. It is preferably employed in combination with the preferred emitting compounds indicated below, particularly the preferred fluorescent compounds indicated below.

If the compound of the formula (1) is employed as matrix material in combination with a phosphorescent emitter in an emitting layer, the phosphorescent emitter is preferably selected from the embodiments of phosphorescent emitters indicated below. In this case, one or more further matrix materials are furthermore preferably present in the emitting layer.

So-called mixed-matrix systems of this type preferably comprise two or three different matrix materials, particularly preferably two different matrix materials. One of the two materials here is preferably a material having hole-transporting properties and the other material is a material having electron-transporting properties. The compound of the formula (1) preferably represents the material having hole-transporting properties.

However, the desired electron-transporting and hole-transporting properties of the mixed-matrix components may also be combined principally or completely in a single mixed-matrix components, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

Particularly suitable matrix materials which can be used in combination with the compounds according to the invention as matrix components of a mixed-matrix system are selected from the preferred matrix materials indicated below for phosphorescent emitting compounds or the preferred matrix materials for fluorescent emitting compounds, depending on what type of emitting compound is employed in the mixed-matrix system.

The compounds according to the invention can also be employed in layers other than the emitting layer, for example as hole-transport materials in a hole-injection or hole-transport layer or electron-blocking layer.

If the compound of the formula (1) is employed as hole-transport material, for example in a hole-transport layer, a hole-injection layer or an electron-blocking layer, the compound can be employed as pure material, i.e. in a proportion of 100%, in the hole-transport layer, or it can be employed in combination with one or more further compounds. According to a preferred embodiment, the organic layer comprising the compound of the formula (1) then additionally comprises one or more p-dopants. Preferred p-dopants employed in accordance with the present invention are organic electron-acceptor compounds which are able to oxidise one or more of the other compounds in the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600 and WO 2012/095143.

It is furthermore preferred in this case for the electronic device to have a plurality of hole-transporting layers between the anode and the emitting layer. The case may occur that all these layers comprise a compound of the formula (1), or that only individual layers thereof comprise a compound of the formula (1).

If the compound of the formula (1) is employed as hole-transport material, it is preferred for it to have a large separation between the HOMO and LUMO energy levels. It is furthermore preferred for it to contain no amino groups as substituents. It is furthermore preferred for it to contain absolutely no substituents on the aromatic rings, i.e. for $R^1$ and $R^2$ to be equal to H or D, particularly preferably equal to H.

The compound of the formula (1) can furthermore be employed as electron-transporting compound in an electron-transport layer, a hole-blocking layer or an electron-injection layer. It is preferred for this purpose for the compound of the formula (1) to contain one or more substituents selected from electron-deficient heteroaryl groups, such as, for example, triazine, pyrimidine or benzimidazole.

Generally preferred classes of material for use as corresponding functional materials in the organic electroluminescent devices according to the invention are indicated below.

Suitable phosphorescent emitting compounds are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitting compounds used are preferably compounds which contain copper, molybdenum, tungsten, rhenium, ruthenium, osmium, rhodium, iridium, palladium, platinum, silver, gold or europium, in particular compounds which contain iridium, platinum or copper.

All luminescent iridium, platinum or copper complexes are regarded as phosphorescent compounds in the sense of the present invention.

Examples of the phosphorescent emitting compounds described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as are used in accordance with the prior art for phosphorescent OLEDs and as are known to the person skilled in the art in the area of organic electroluminescent devices are suitable for use in the devices according to the invention. The person skilled in the art will also be able, without inventive step, to employ further phosphorescent complexes in combination with the compounds according to the invention in OLEDs.

Preferred fluorescent emitters, besides the compounds according to the invention, are selected from the class of the arylamines. An arylamine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position.

Aromatic pyrenamines, pyrenediamines, chrysenamines and chrysenediamines are defined analogously thereto, where the diarylamino groups are preferably bonded to the pyrene in the 1-position or in the 1,6-position. Further preferred emitters are indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847, and the indenofluorene derivatives containing condensed aryl groups which are disclosed in WO 2010/012328. Preference is likewise given to the pyrenarylamines disclosed in WO 2012/048780 and WO 2013/185871. Preference is likewise given to the benzoindenofluorenamines disclosed in WO 2014/037077, the benzofluorenamines disclosed in the as yet unpublished EP 13000012.8 and the indenofluorenes disclosed in the as yet unpublished EP13004921.6.

Preferred fluorescent emitting compounds, besides the compounds according to the invention, are depicted in the following table:

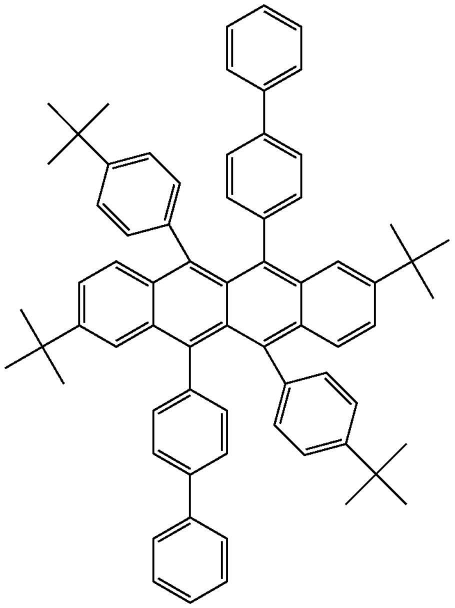 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]

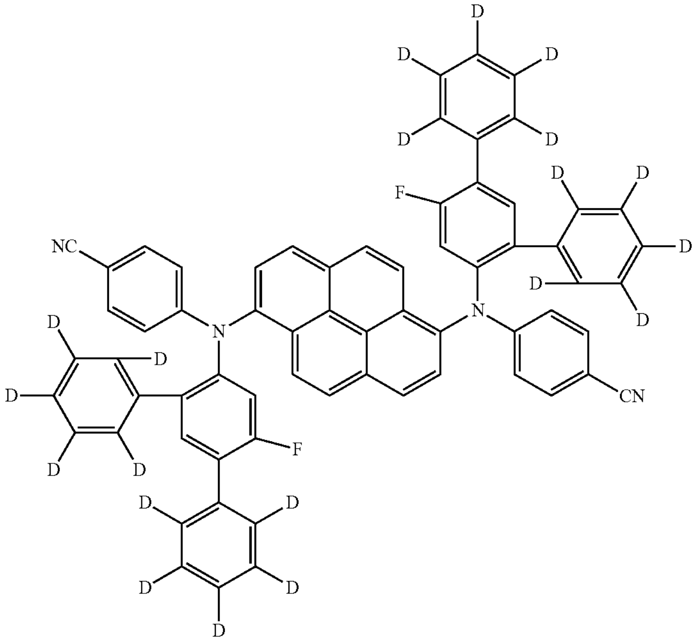 [SMILES: [2H]c1c([2H])c([2H])c(-c2cc(-c3c([2H])c([2H])c([2H])c([2H])c3[2H])c(N(c3ccc(C#N)cc3)c3ccc4ccc5c(N(c6ccc(C#N)cc6)c6cc(F)c(-c7c([2H])c([2H])c([2H])c([2H])c7[2H])cc6-c6c([2H])c([2H])c([2H])c([2H])c6[2H])ccc6ccc3c4c65)cc2F)c([2H])c1[2H]]

-continued
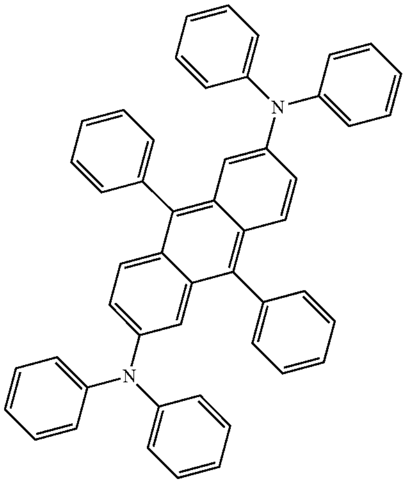 [SMILES: c1ccc(-c2c3ccc(N(c4ccccc4)c4ccccc4)cc3c(-c3ccccc3)c3ccc(N(c4ccccc4)c4ccccc4)cc23)cc1]
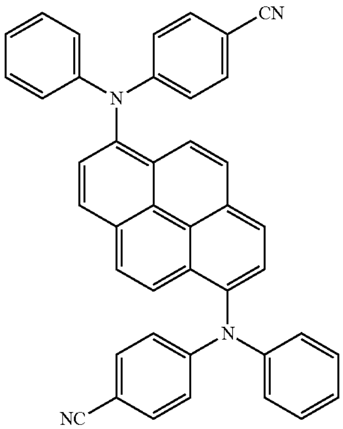 [SMILES: N#Cc1ccc(N(c2ccccc2)c2ccc3ccc4c(N(c5ccccc5)c5ccc(C#N)cc5)ccc5ccc2c3c54)cc1]
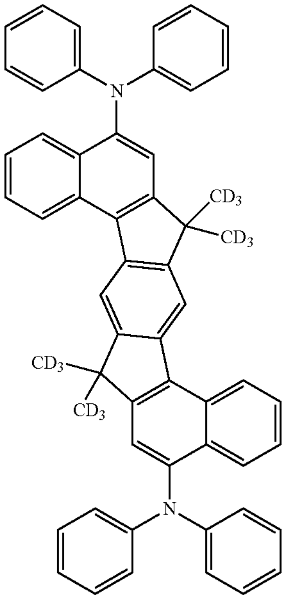 [SMILES: [2H]C([2H])([2H])C1(C([2H])([2H])[2H])c2cc3c(cc2-c2c1cc(N(c1ccccc1)c1ccccc1)c1ccccc21)C(C([2H])([2H])[2H])(C([2H])([2H])[2H])c1cc(N(c2ccccc2)c2ccccc2)c2ccccc2c1-3]

-continued
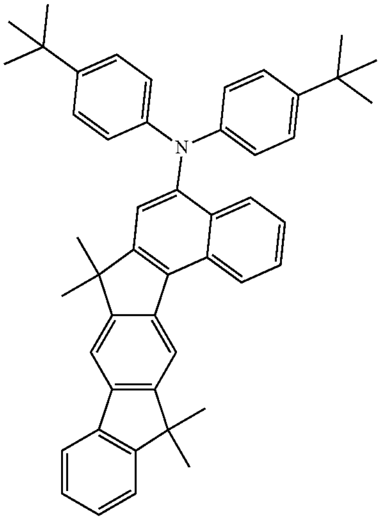 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]
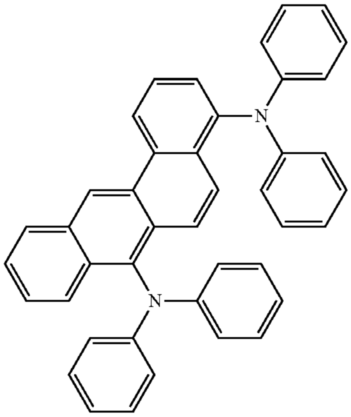 [SMILES: c1ccc(N(c2ccccc2)c2cccc3c2ccc2c(N(c4ccccc4)c4ccccc4)c4ccccc4cc23)cc1]
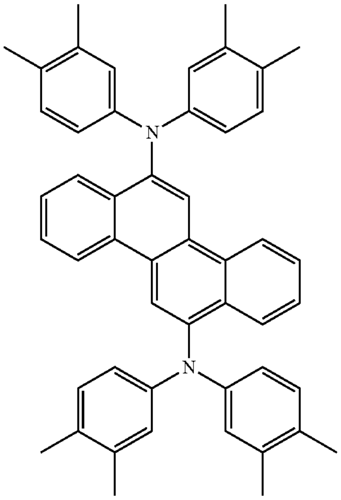

-continued
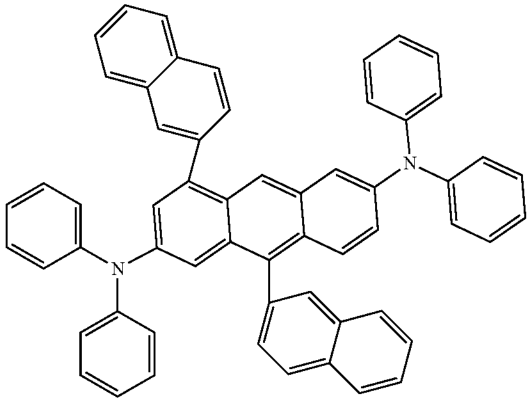 [SMILES: c1ccc(N(c2ccccc2)c2ccc3c(-c4ccc5ccccc5c4)c4cc(N(c5ccccc5)c5ccccc5)cc(-c5ccc6ccccc6c5)c4cc3c2)cc1]
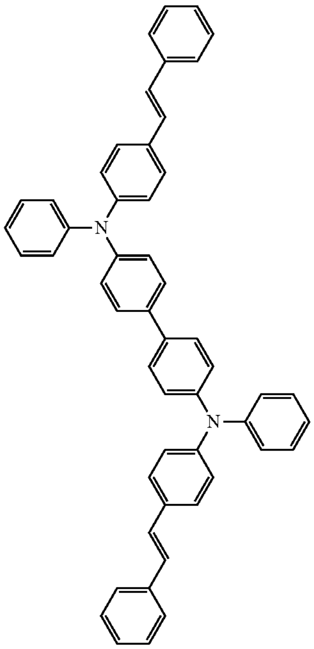 [SMILES: C(=C\c1ccc(N(c2ccccc2)c2ccc(-c3ccc(N(c4ccccc4)c4ccc(/C=C/c5ccccc5)cc4)cc3)cc2)cc1)/c1ccccc1]
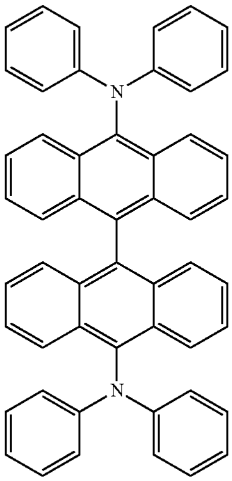 [SMILES: c1ccc(N(c2ccccc2)c2c3ccccc3c(-c3c4ccccc4c(N(c4ccccc4)c4ccccc4)c4ccccc34)c3ccccc23)cc1]

-continued
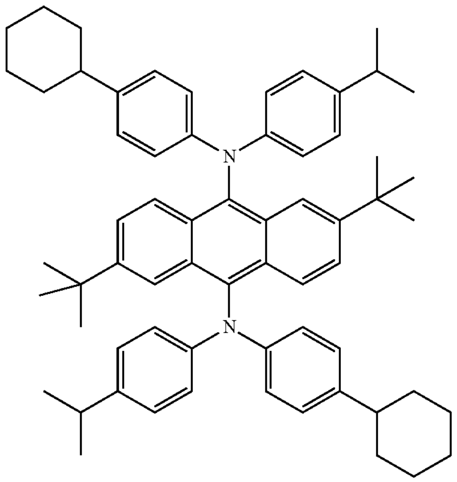 [SMILES: CC(C)c1ccc(N(c2ccc(C3CCCCC3)cc2)c2c3ccc(C(C)(C)C)cc3c(N(c3ccc(C(C)C)cc3)c3ccc(C4CCCCC4)cc3)c3ccc(C(C)(C)C)cc23)cc1]
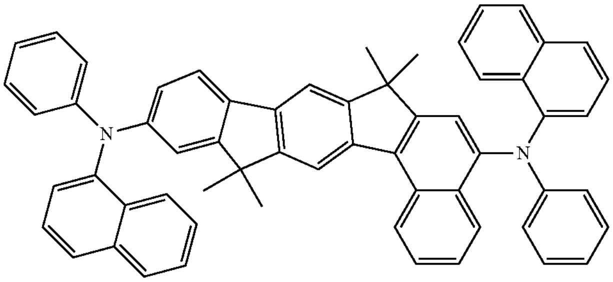 [SMILES: CC1(C)c2cc(N(c3ccccc3)c3cccc4ccccc34)ccc2-c2cc3c(cc21)-c1c(cc(N(c2ccccc2)c2cccc4ccccc24)c2ccccc12)C3(C)C]
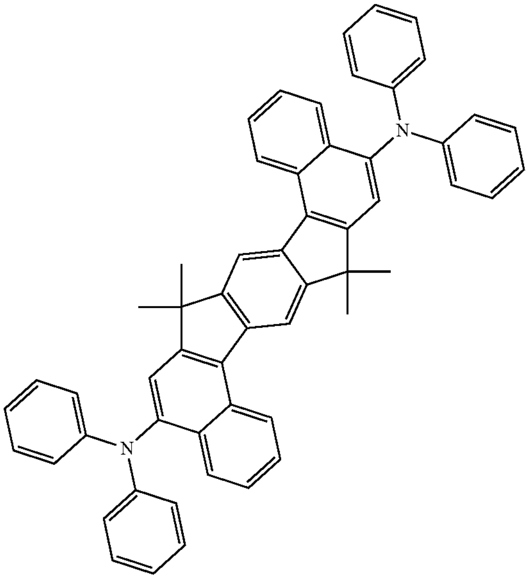 [SMILES: CC1(C)c2cc3c(cc2-c2c1cc(N(c1ccccc1)c1ccccc1)c1ccccc21)C(C)(C)c1cc(N(c2ccccc2)c2ccccc2)c2ccccc2c1-3]

-continued
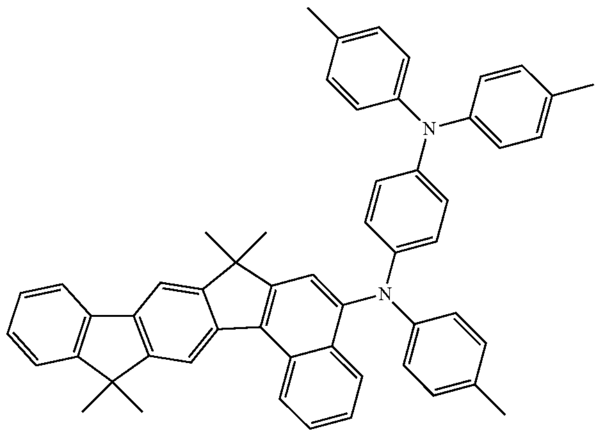 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]
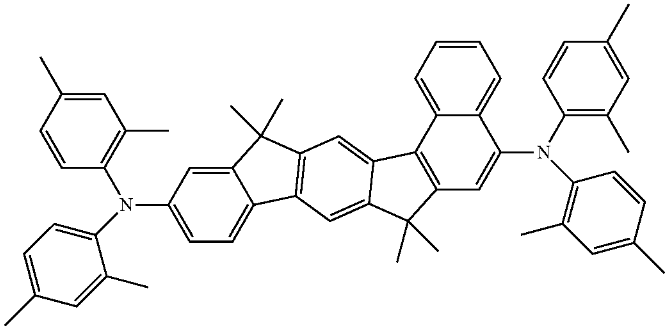
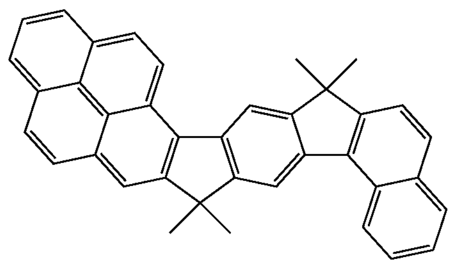 [SMILES: CC1(C)c2cc3c(cc2-c2c1ccc1ccccc21)C(C)(C)c1cc2ccc4cccc5ccc(c1-3)c2c45]
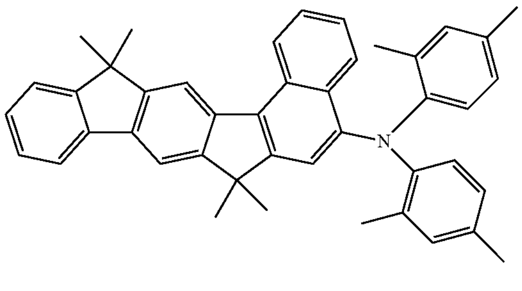 [SMILES: Cc1ccc(N(c2ccc(C)cc2C)c2cc3c(c4ccccc24)-c2cc4c(cc2C3(C)C)-c2ccccc2C4(C)C)c(C)c1]

-continued
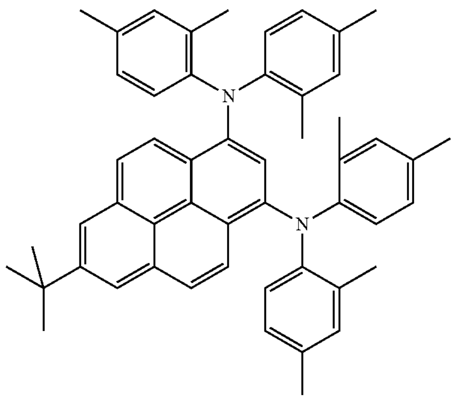 [SMILES: Cc1ccc(N(c2ccc(C)cc2C)c2cc(N(c3ccc(C)cc3C)c3ccc(C)cc3C)c3ccc4cc(C(C)(C)C)cc5ccc2c3c54)c(C)c1]
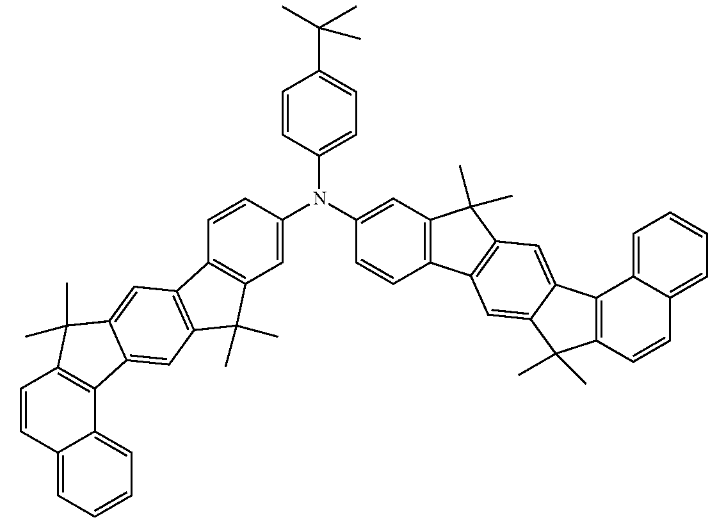 [SMILES: CC(C)(C)c1ccc(N(c2ccc3c(c2)C(C)(C)c2cc4c(cc2-3)C(C)(C)c2ccc3ccccc3c2-4)c2ccc3c(c2)C(C)(C)c2cc4c(cc2-3)C(C)(C)c2ccc3ccccc3c2-4)cc1]
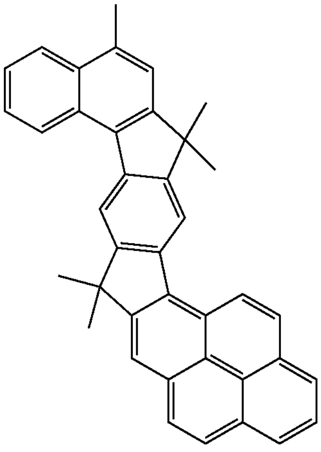 [SMILES: Cc1cc2c(c3ccccc13)-c1cc3c(cc1C2(C)C)-c1c(cc2ccc4cccc5ccc1c2c45)C3(C)C]

-continued
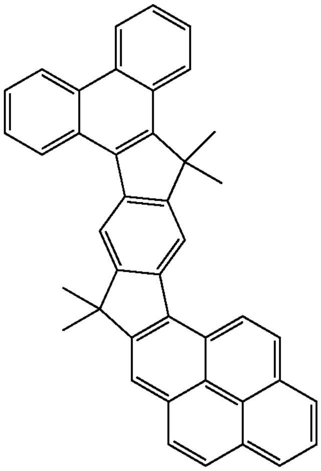 [SMILES: CC1(C)c2cc3c(cc2-c2c1cc1ccc4cccc5ccc2c1c45)C(C)(C)c1c-3c2ccccc2c2ccccc12]
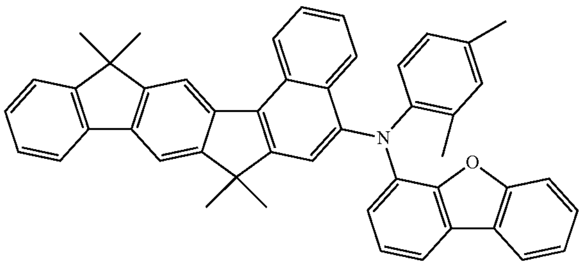 [SMILES: Cc1ccc(N(c2cc3c(c4ccccc24)-c2cc4c(cc2C3(C)C)-c2ccccc2C4(C)C)c2cccc3c2oc2ccccc23)c(C)c1]
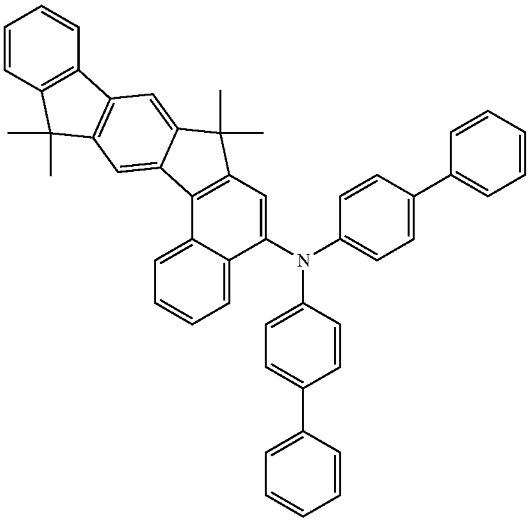 [SMILES: CC1(C)c2ccccc2-c2cc3c(cc21)-c1c(cc(N(c2ccc(-c4ccccc4)cc2)c2ccc(-c4ccccc4)cc2)c2ccccc12)C3(C)C]

-continued
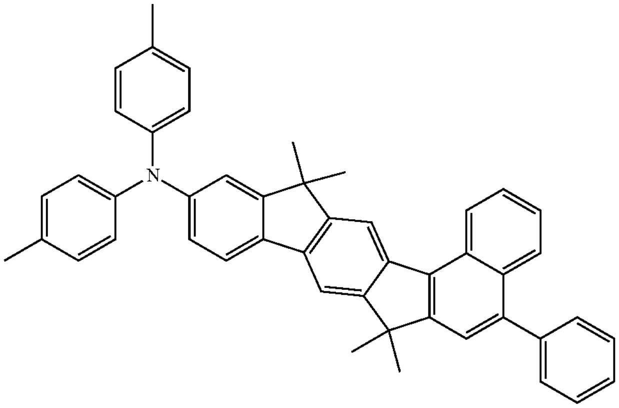 [SMILES: Cc1ccc(N(c2ccc(C)cc2)c2ccc3c(c2)C(C)(C)c2cc4c(cc2-3)C(C)(C)c2cc(-c3ccccc3)c3ccccc3c2-4)cc1]
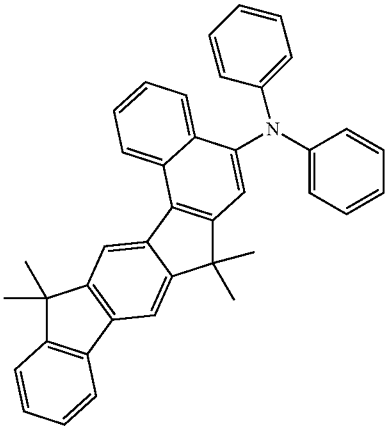 [SMILES: CC1(C)c2ccccc2-c2cc3c(cc21)-c1c(cc(N(c2ccccc2)c2ccccc2)c2ccccc12)C3(C)C]
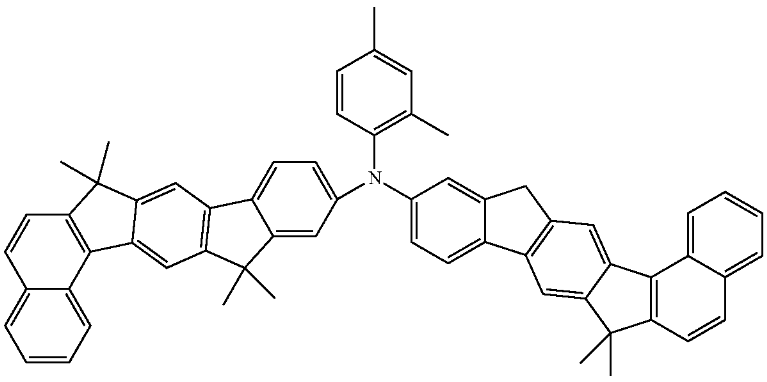 [SMILES: Cc1ccc(N(c2ccc3c(c2)Cc2cc4c(cc2-3)C(C)(C)c2ccc3ccccc3c2-4)c2ccc3c(c2)C(C)(C)c2cc4c(cc2-3)C(C)(C)c2ccc3ccccc3c2-4)c(C)c1]

-continued
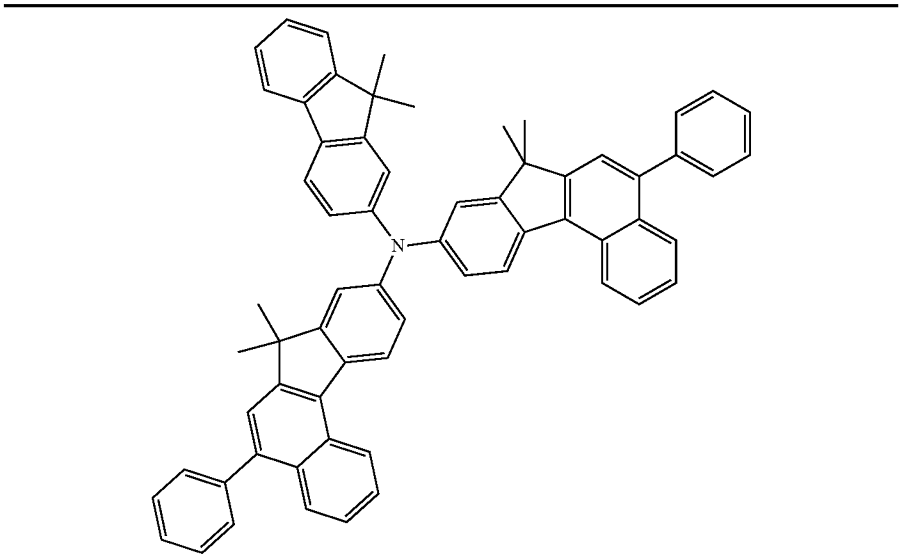
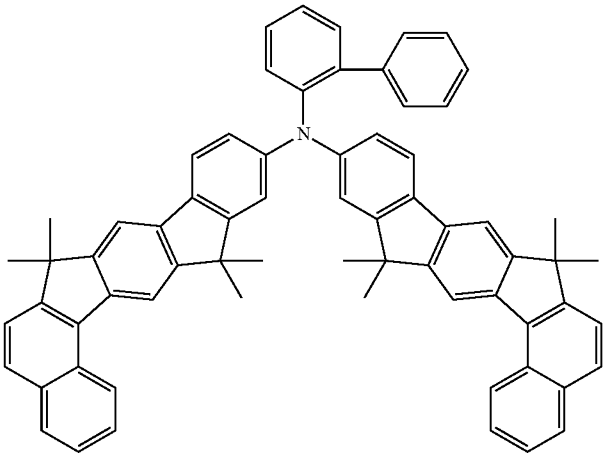 [SMILES: CC1(C)c2cc(N(c3ccc4c(c3)C(C)(C)c3cc5c(cc3-4)C(C)(C)c3ccc4ccccc4c3-5)c3ccccc3-c3ccccc3)ccc2-c2cc3c(cc21)-c1c(ccc2ccccc12)C3(C)C]
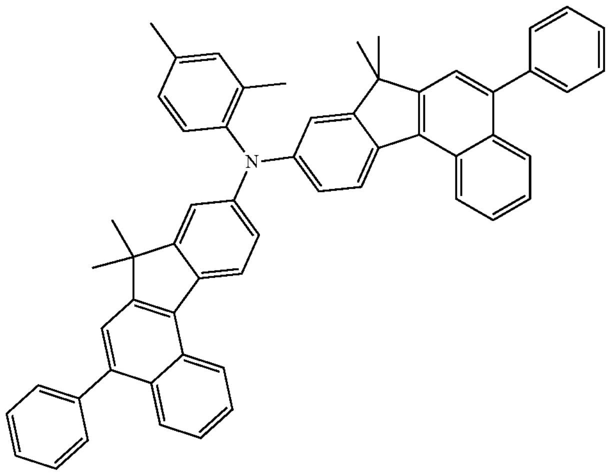 [SMILES: Cc1ccc(N(c2ccc3c(c2)C(C)(C)c2cc(-c4ccccc4)c4ccccc4c2-3)c2ccc3c(c2)C(C)(C)c2cc(-c4ccccc4)c4ccccc4c2-3)c(C)c1]

-continued
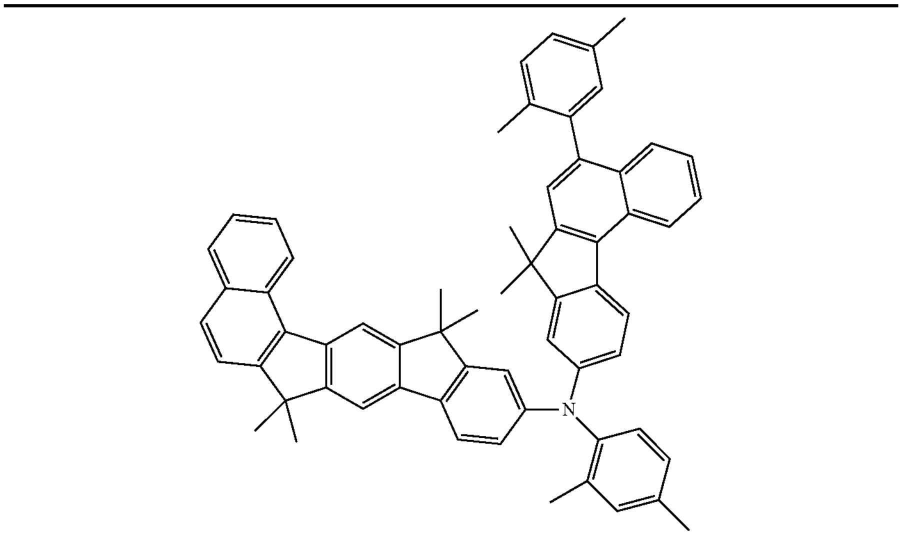
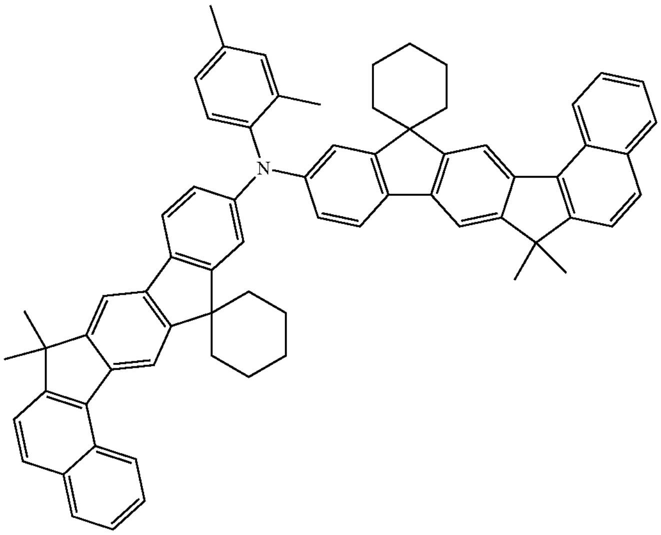 [SMILES: Cc1ccc(N(c2ccc3c(c2)C2(CCCCC2)c2cc4c(cc2-3)C(C)(C)c2ccc3ccccc3c2-4)c2ccc3c(c2)C2(CCCCC2)c2cc4c(cc2-3)C(C)(C)c2ccc3ccccc3c2-4)c(C)c1]
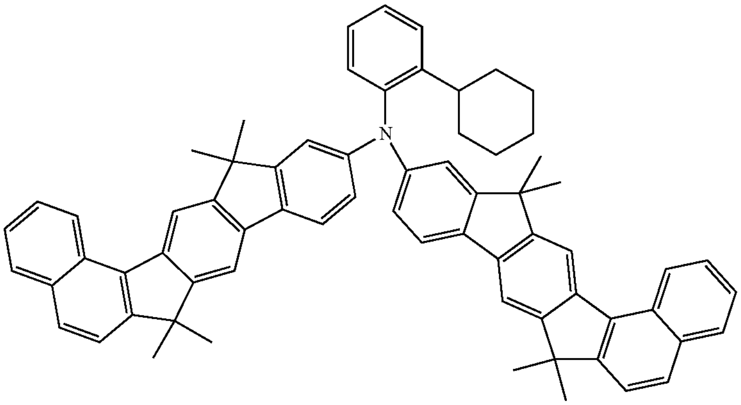 [SMILES: CC1(C)c2cc(N(c3ccc4c(c3)C(C)(C)c3cc5c(cc3-4)C(C)(C)c3ccc4ccccc4c3-5)c3ccccc3C3CCCCC3)ccc2-c2cc3c(cc21)-c1c(ccc2ccccc12)C3(C)C]

-continued
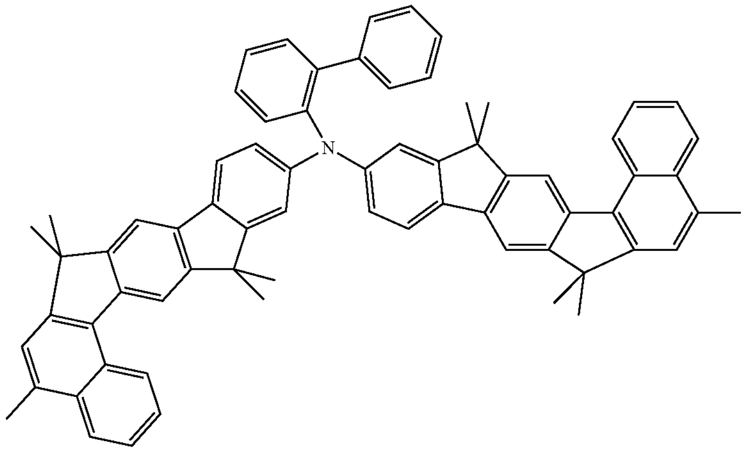
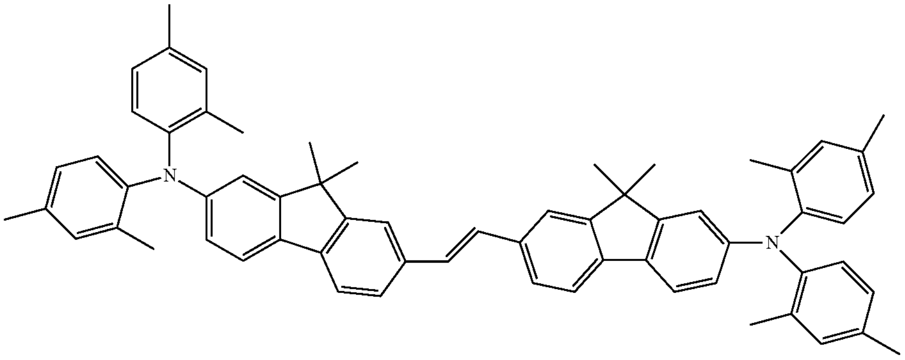
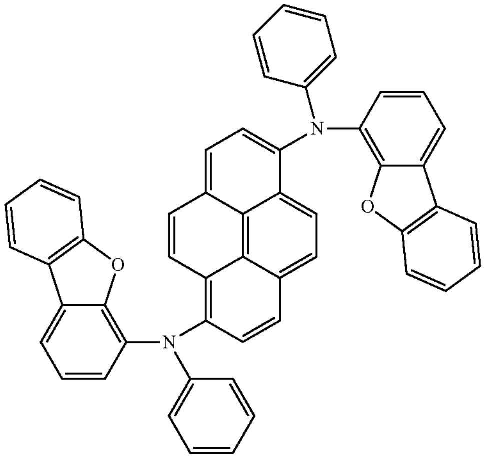 [SMILES: c1ccc(N(c2ccc3ccc4c(N(c5ccccc5)c5cccc6c5oc5ccccc56)ccc5ccc2c3c54)c2cccc3c2oc2ccccc23)cc1]

-continued
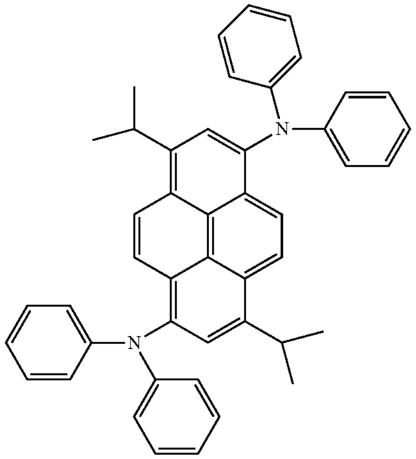 [SMILES: CC(C)c1cc(N(c2ccccc2)c2ccccc2)c2ccc3c(C(C)C)cc(N(c4ccccc4)c4ccccc4)c4ccc1c2c34]
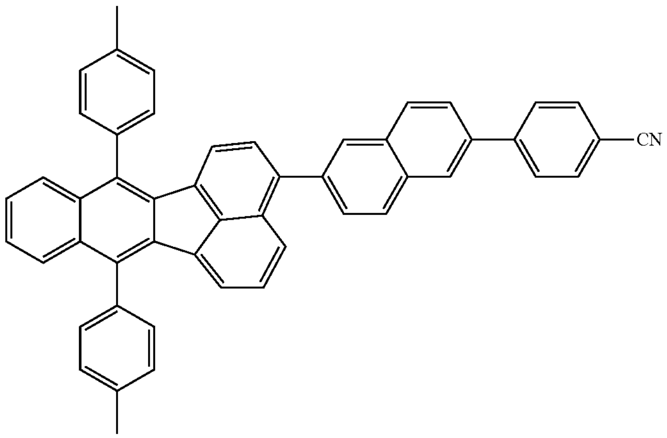 [SMILES: Cc1ccc(-c2c3c(c(-c4ccc(C)cc4)c4ccccc24)-c2ccc(-c4ccc5cc(-c6ccc(C#N)cc6)ccc5c4)c4cccc-3c24)cc1]
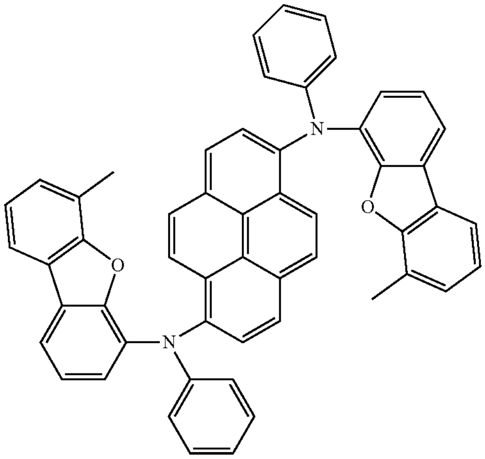 [SMILES: Cc1cccc2c1oc1c(N(c3ccccc3)c3ccc4ccc5c(N(c6ccccc6)c6cccc7c6oc6c(C)cccc67)ccc6ccc3c4c65)cccc12]

-continued

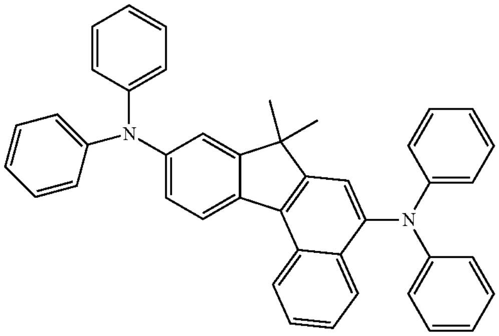 [SMILES: CC1(C)c2cc(N(c3ccccc3)c3ccccc3)ccc2-c2c1cc(N(c1ccccc1)c1ccccc1)c1ccccc21]

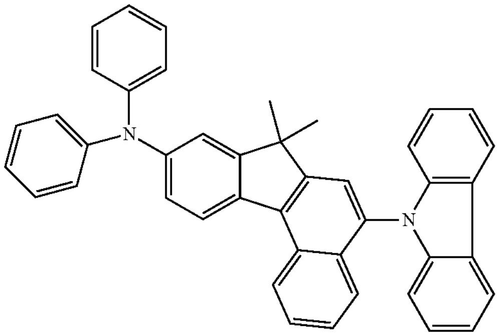 [SMILES: CC1(C)c2cc(N(c3ccccc3)c3ccccc3)ccc2-c2c1cc(-n1c3ccccc3c3ccccc31)c1ccccc21]

Preferred matrix materials for use in combination with fluorescent emitting compounds are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiroDPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Particularly preferred matrix materials for use in combination with the compounds of the formula (1) in the emitting layer are depicted in the following table.

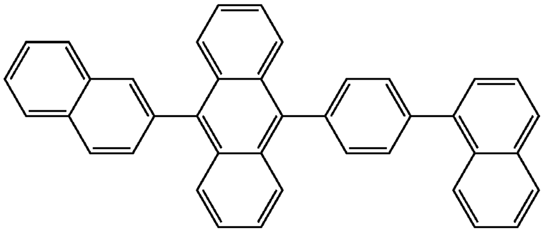 [SMILES: c1ccc2cc(-c3c4ccccc4c(-c4ccc(-c5cccc6ccccc56)cc4)c4ccccc34)ccc2c1]

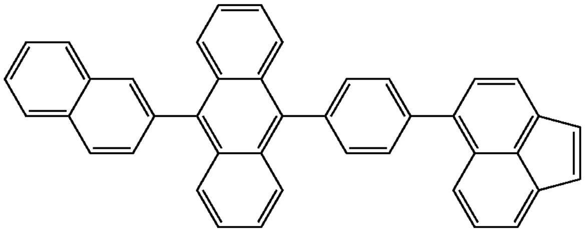 [SMILES: C1=Cc2ccc(-c3ccc(-c4c5ccccc5c(-c5ccc6ccccc6c5)c5ccccc45)cc3)c3cccc1c23]

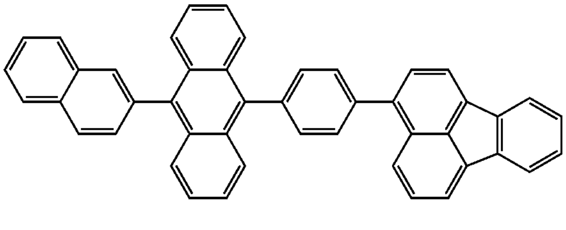 [SMILES: c1ccc2c(c1)-c1cccc3c(-c4ccc(-c5c6ccccc6c(-c6ccc7ccccc7c6)c6ccccc56)cc4)ccc-2c13]

-continued
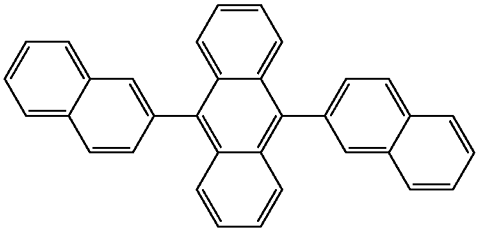 [SMILES: c1ccc2cc(-c3c4ccccc4c(-c4ccc5ccccc5c4)c4ccccc34)ccc2c1]
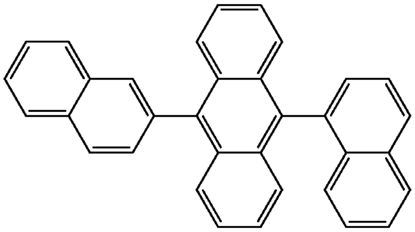 [SMILES: c1ccc2cc(-c3c4ccccc4c(-c4cccc5ccccc45)c4ccccc34)ccc2c1]
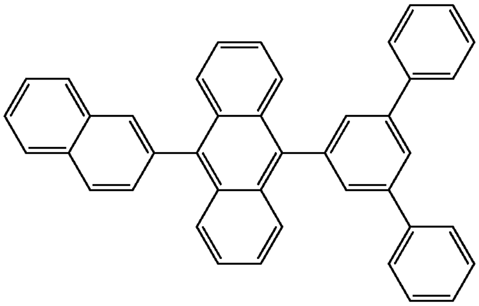 [SMILES: c1ccc(-c2cc(-c3ccccc3)cc(-c3c4ccccc4c(-c4ccc5ccccc5c4)c4ccccc34)c2)cc1]
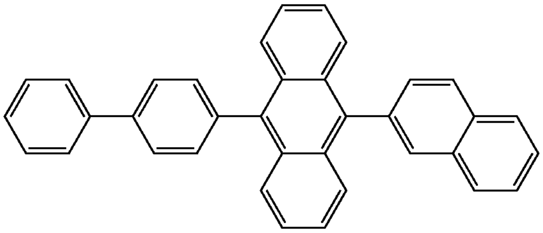 [SMILES: c1ccc(-c2ccc(-c3c4ccccc4c(-c4ccc5ccccc5c4)c4ccccc34)cc2)cc1]
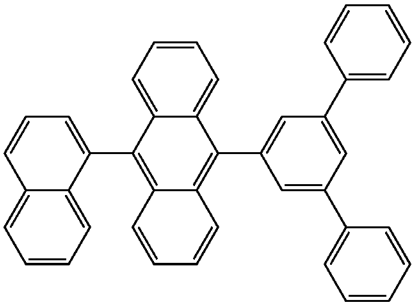 [SMILES: c1ccc(-c2cc(-c3ccccc3)cc(-c3c4ccccc4c(-c4cccc5ccccc45)c4ccccc34)c2)cc1]
-continued
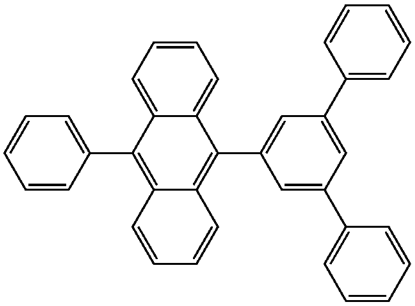 [SMILES: c1ccc(-c2cc(-c3ccccc3)cc(-c3c4ccccc4c(-c4ccccc4)c4ccccc34)c2)cc1]
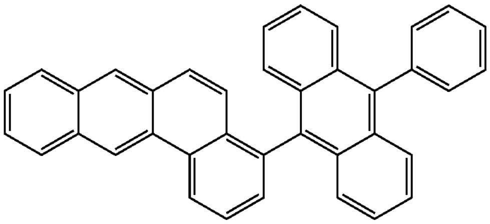 [SMILES: c1ccc(-c2c3ccccc3c(-c3cccc4c3ccc3cc5ccccc5cc34)c3ccccc23)cc1]
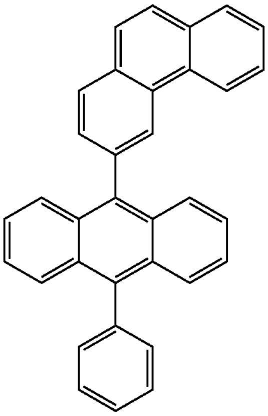 [SMILES: c1ccc(-c2c3ccccc3c(-c3ccc4ccc5ccccc5c4c3)c3ccccc23)cc1]
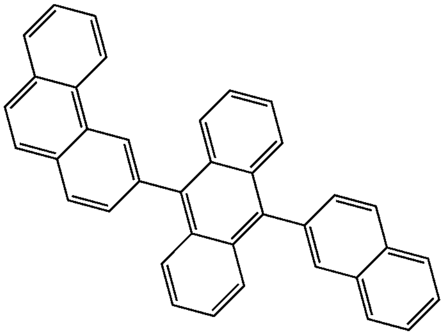 [SMILES: c1ccc2cc(-c3c4ccccc4c(-c4ccc5ccc6ccccc6c5c4)c4ccccc34)ccc2c1]
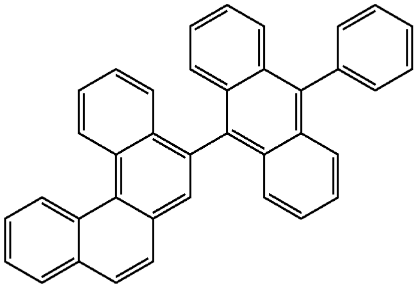 [SMILES: c1ccc(-c2c3ccccc3c(-c3cc4ccc5ccccc5c4c4ccccc34)c3ccccc23)cc1]

-continued
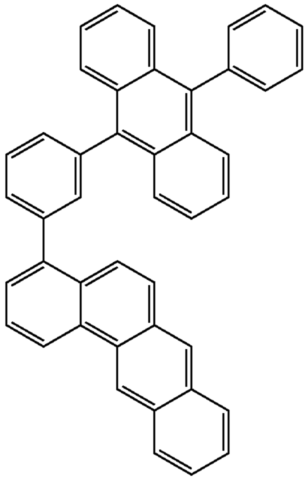 [SMILES: c1ccc(-c2c3ccccc3c(-c3cccc(-c4cccc5c4ccc4cc6ccccc6cc45)c3)c3ccccc23)cc1]
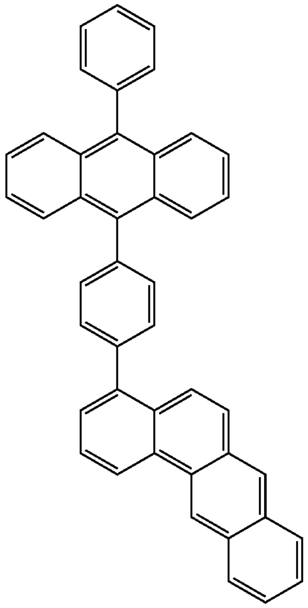 [SMILES: c1ccc(-c2c3ccccc3c(-c3ccc(-c4cccc5c4ccc4cc6ccccc6cc45)cc3)c3ccccc23)cc1]
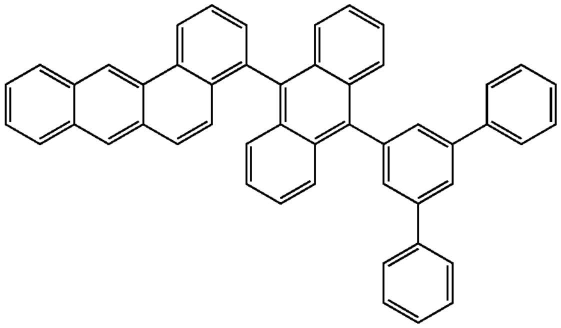 [SMILES: c1ccc(-c2cc(-c3ccccc3)cc(-c3c4ccccc4c(-c4cccc5c4ccc4cc6ccccc6cc45)c4ccccc34)c2)cc1]
-continued
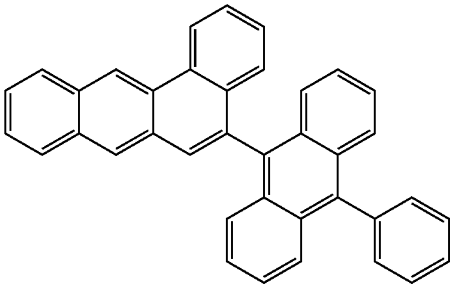 [SMILES: c1ccc(-c2c3ccccc3c(-c3cc4cc5ccccc5cc4c4ccccc34)c3ccccc23)cc1]
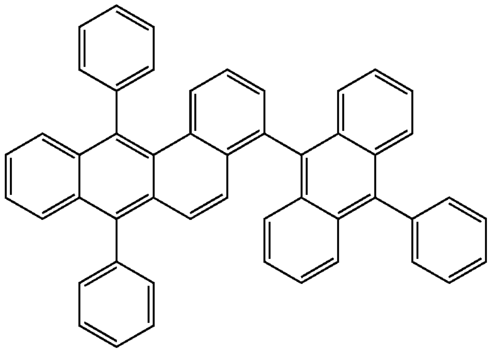 [SMILES: c1ccc(-c2c3ccccc3c(-c3cccc4c3ccc3c(-c5ccccc5)c5ccccc5c(-c5ccccc5)c34)c3ccccc23)cc1]
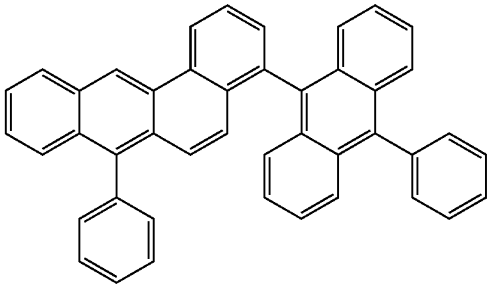 [SMILES: c1ccc(-c2c3ccccc3c(-c3cccc4c3ccc3c(-c5ccccc5)c5ccccc5cc34)c3ccccc23)cc1]
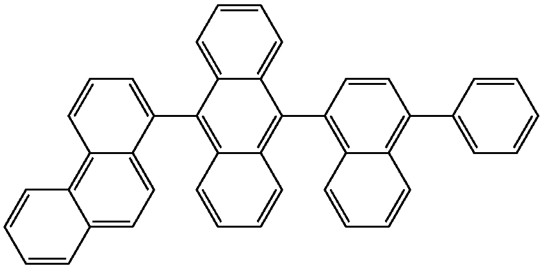 [SMILES: c1ccc(-c2ccc(-c3c4ccccc4c(-c4cccc5c4ccc4ccccc45)c4ccccc34)c3ccccc23)cc1]
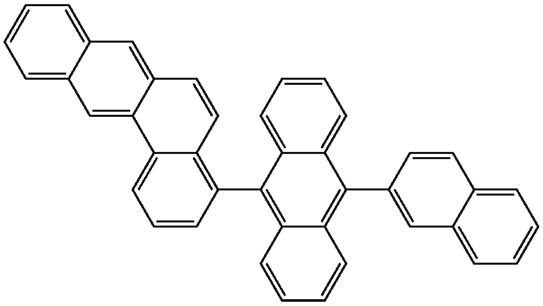 [SMILES: c1ccc2cc(-c3c4ccccc4c(-c4cccc5c4ccc4cc6ccccc6cc45)c4ccccc34)ccc2c1]

-continued
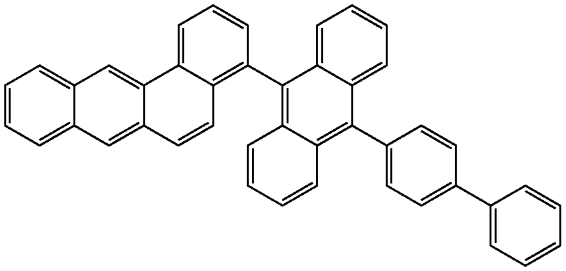 [SMILES: c1ccc(-c2ccc(-c3c4ccccc4c(-c4cccc5c4ccc4cc6ccccc6cc45)c4ccccc34)cc2)cc1]
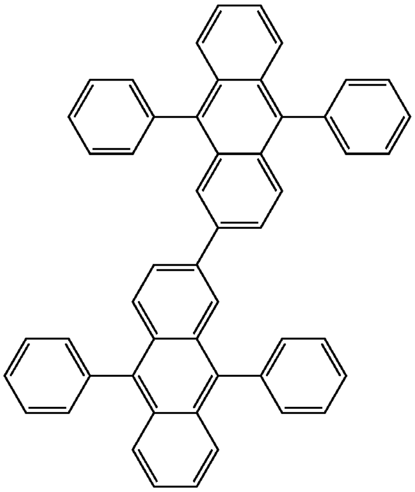 [SMILES: c1ccc(-c2c3ccccc3c(-c3ccccc3)c3cc(-c4ccc5c(-c6ccccc6)c6ccccc6c(-c6ccccc6)c5c4)ccc23)cc1]
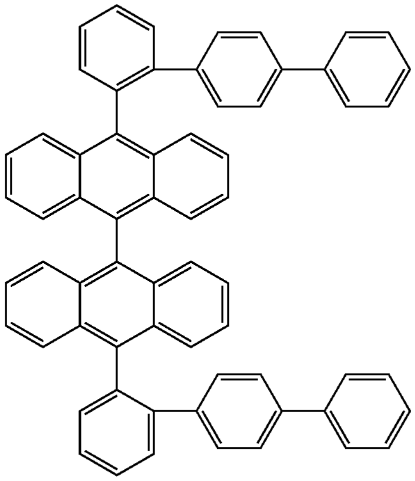 [SMILES: c1ccc(-c2ccc(-c3ccccc3-c3c4ccccc4c(-c4c5ccccc5c(-c5ccccc5-c5ccc(-c6ccccc6)cc5)c5ccccc45)c4ccccc34)cc2)cc1]
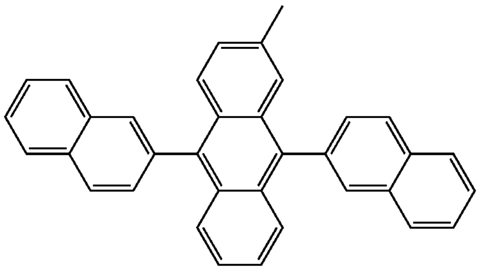 [SMILES: Cc1ccc2c(-c3ccc4ccccc4c3)c3ccccc3c(-c3ccc4ccccc4c3)c2c1]
-continued
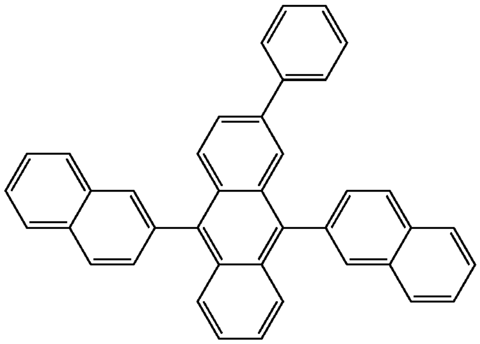 [SMILES: c1ccc(-c2ccc3c(-c4ccc5ccccc5c4)c4ccccc4c(-c4ccc5ccccc5c4)c3c2)cc1]
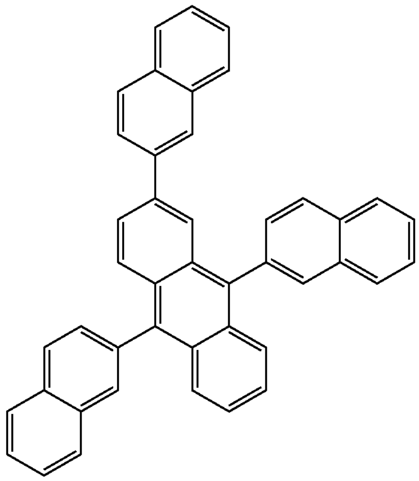 [SMILES: c1ccc2cc(-c3ccc4c(-c5ccc6ccccc6c5)c5ccccc5c(-c5ccc6ccccc6c5)c4c3)ccc2c1]
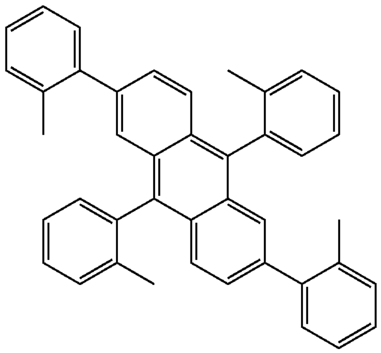 [SMILES: Cc1ccccc1-c1ccc2c(-c3ccccc3C)c3cc(-c4ccccc4C)ccc3c(-c3ccccc3C)c2c1]
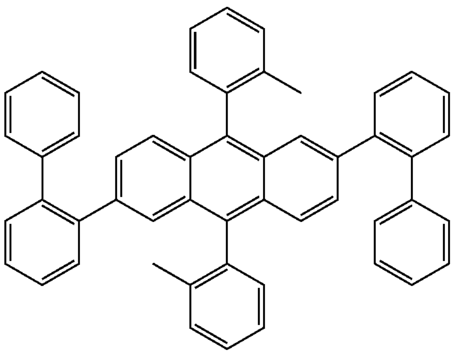 [SMILES: Cc1ccccc1-c1c2ccc(-c3ccccc3-c3ccccc3)cc2c(-c2ccccc2C)c2ccc(-c3ccccc3-c3ccccc3)cc12]

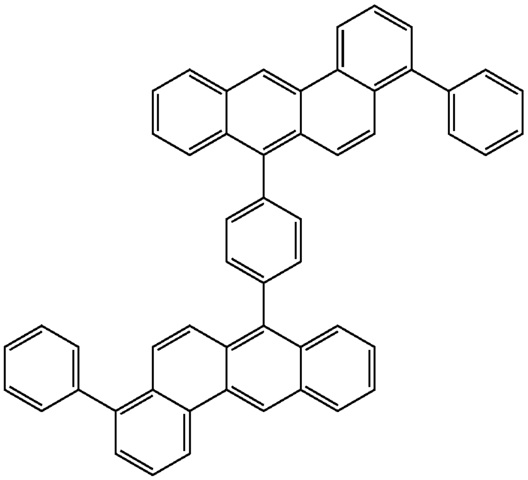 [SMILES: c1ccc(-c2cccc3c2ccc2c(-c4ccc(-c5c6ccccc6cc6c5ccc5c(-c7ccccc7)cccc56)cc4)c4ccccc4cc23)cc1]
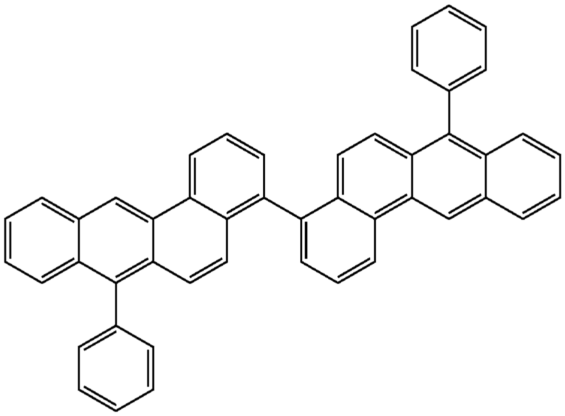 [SMILES: c1ccc(-c2c3ccccc3cc3c2ccc2c(-c4cccc5c4ccc4c(-c6ccccc6)c6ccccc6cc45)cccc23)cc1]
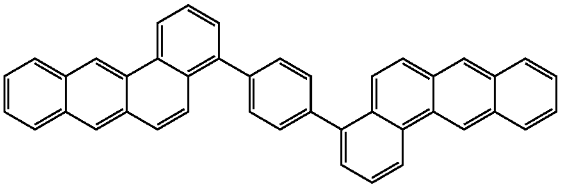 [SMILES: c1ccc2cc3c(ccc4c(-c5ccc(-c6cccc7c6ccc6cc8ccccc8cc67)cc5)cccc43)cc2c1]
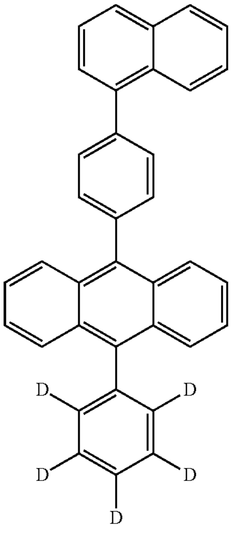 [SMILES: [2H]c1c([2H])c([2H])c(-c2c3ccccc3c(-c3ccc(-c4cccc5ccccc45)cc3)c3ccccc23)c([2H])c1[2H]]
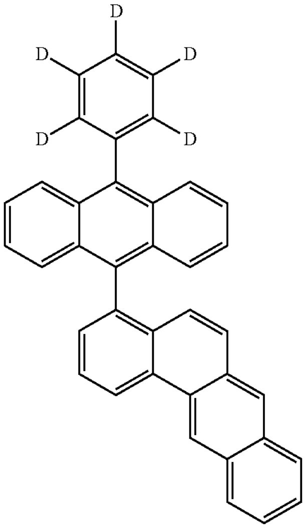 [SMILES: [2H]c1c([2H])c([2H])c(-c2c3ccccc3c(-c3cccc4c3ccc3cc5ccccc5cc34)c3ccccc23)c([2H])c1[2H]]
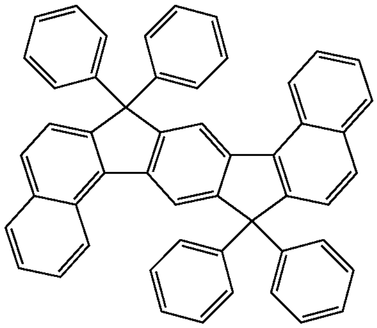 [SMILES: c1ccc(C2(c3ccccc3)c3cc4c(cc3-c3c2ccc2ccccc32)C(c2ccccc2)(c2ccccc2)c2ccc3ccccc3c2-4)cc1]
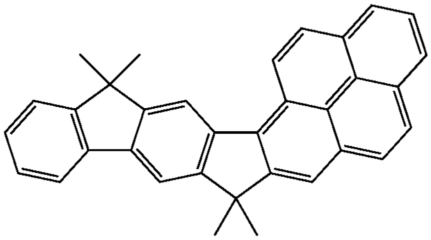 [SMILES: CC1(C)c2ccccc2-c2cc3c(cc21)-c1c(cc2ccc4cccc5ccc1c2c45)C3(C)C]
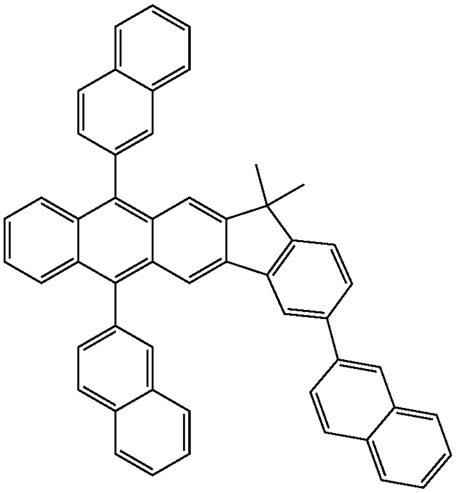 [SMILES: CC1(C)c2ccc(-c3ccc4ccccc4c3)cc2-c2cc3c(-c4ccc5ccccc5c4)c4ccccc4c(-c4ccc5ccccc5c4)c3cc21]

-continued
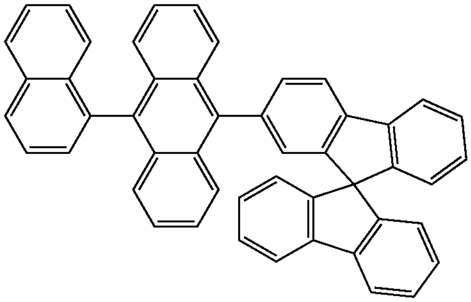 [SMILES: c1ccc2c(c1)-c1ccccc1C21c2ccccc2-c2ccc(-c3c4ccccc4c(-c4cccc5ccccc45)c4ccccc34)cc21]
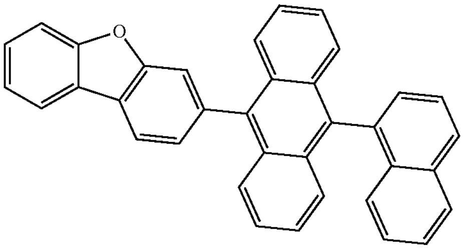 [SMILES: c1ccc2c(-c3c4ccccc4c(-c4ccc5c(c4)oc4ccccc45)c4ccccc34)cccc2c1]
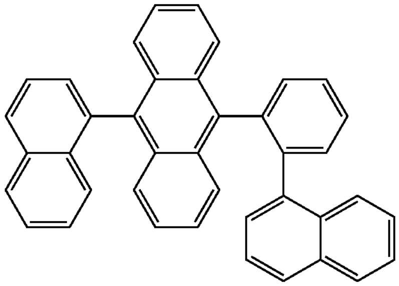 [SMILES: c1ccc(-c2c3ccccc3c(-c3cccc4ccccc34)c3ccccc23)c(-c2cccc3ccccc23)c1]
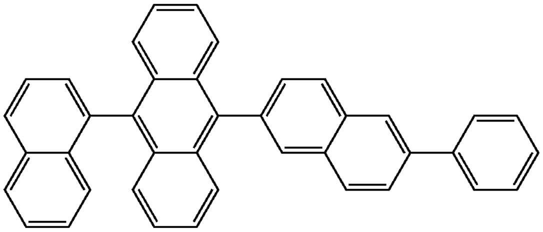 [SMILES: c1ccc(-c2ccc3cc(-c4c5ccccc5c(-c5cccc6ccccc56)c5ccccc45)ccc3c2)cc1]
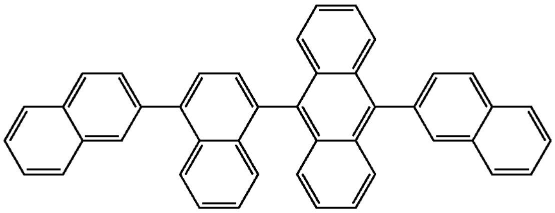 [SMILES: c1ccc2cc(-c3ccc(-c4c5ccccc5c(-c5ccc6ccccc6c5)c5ccccc45)c4ccccc34)ccc2c1]
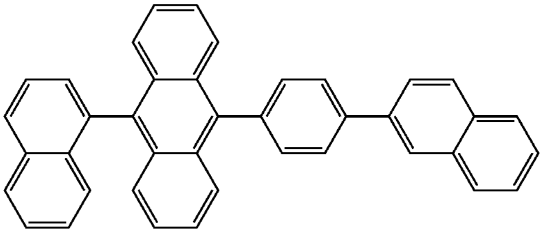 [SMILES: c1ccc2cc(-c3ccc(-c4c5ccccc5c(-c5cccc6ccccc56)c5ccccc45)cc3)ccc2c1]
-continued
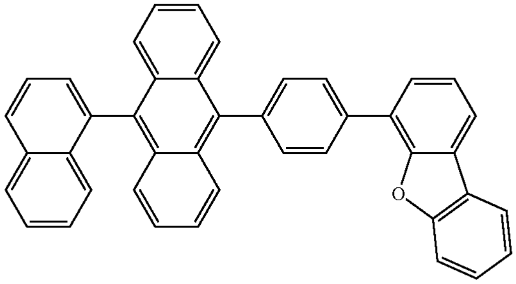 [SMILES: c1ccc2c(-c3c4ccccc4c(-c4ccc(-c5cccc6c5oc5ccccc56)cc4)c4ccccc34)cccc2c1]
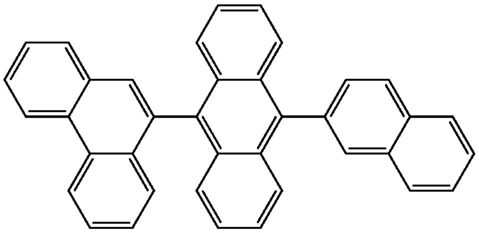 [SMILES: c1ccc2cc(-c3c4ccccc4c(-c4cc5ccccc5c5ccccc45)c4ccccc34)ccc2c1]
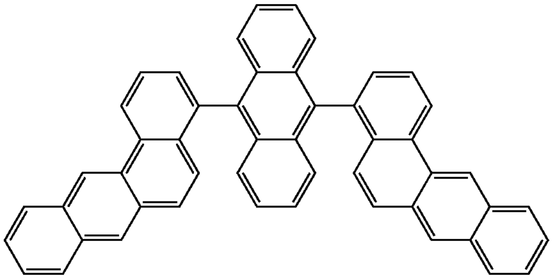 [SMILES: c1ccc2cc3c(ccc4c(-c5c6ccccc6c(-c6cccc7c6ccc6cc8ccccc8cc67)c6ccccc56)cccc43)cc2c1]
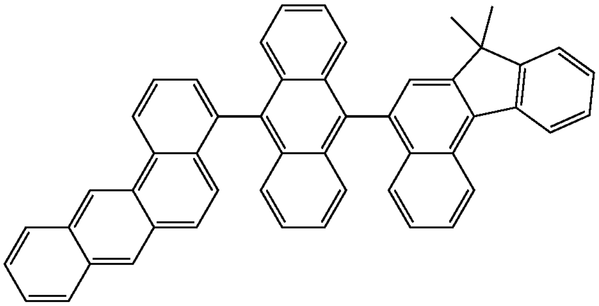 [SMILES: CC1(C)c2ccccc2-c2c1cc(-c1c3ccccc3c(-c3cccc4c3ccc3cc5ccccc5cc34)c3ccccc13)c1ccccc21]
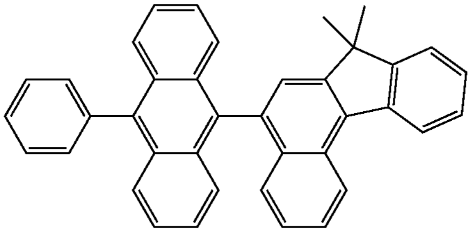 [SMILES: CC1(C)c2ccccc2-c2c1cc(-c1c3ccccc3c(-c3ccccc3)c3ccccc13)c1ccccc21]
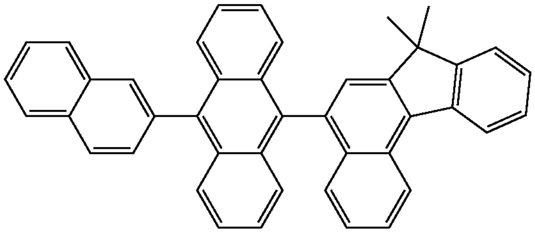 [SMILES: CC1(C)c2ccccc2-c2c1cc(-c1c3ccccc3c(-c3ccc4ccccc4c3)c3ccccc13)c1ccccc21]

-continued
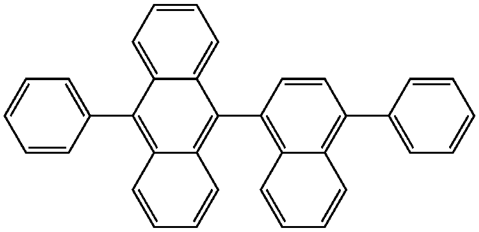 [SMILES: c1ccc(-c2ccc(-c3c4ccccc4c(-c4ccccc4)c4ccccc34)c3ccccc23)cc1]
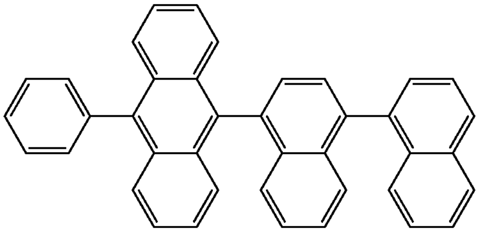 [SMILES: c1ccc(-c2c3ccccc3c(-c3ccc(-c4cccc5ccccc45)c4ccccc34)c3ccccc23)cc1]
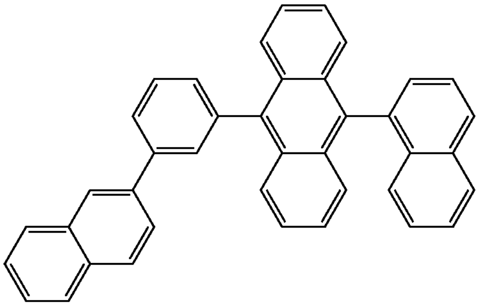 [SMILES: c1cc(-c2ccc3ccccc3c2)cc(-c2c3ccccc3c(-c3cccc4ccccc34)c3ccccc23)c1]
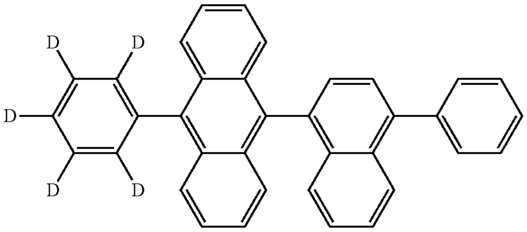 [SMILES: [2H]c1c([2H])c([2H])c(-c2c3ccccc3c(-c3ccc(-c4ccccc4)c4ccccc34)c3ccccc23)c([2H])c1[2H]]
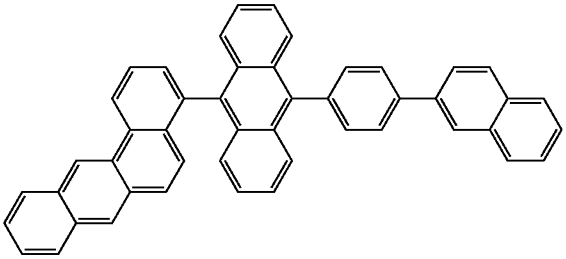 [SMILES: c1ccc2cc(-c3ccc(-c4c5ccccc5c(-c5cccc6c5ccc5cc7ccccc7cc56)c5ccccc45)cc3)ccc2c1]
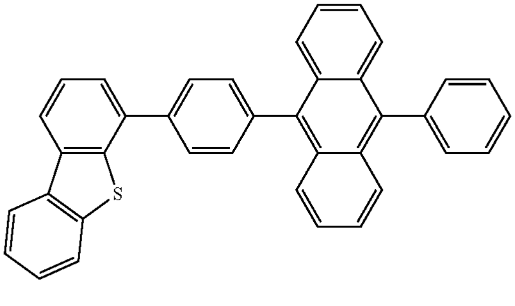 [SMILES: c1ccc(-c2c3ccccc3c(-c3ccc(-c4cccc5c4sc4ccccc45)cc3)c3ccccc23)cc1]
-continued
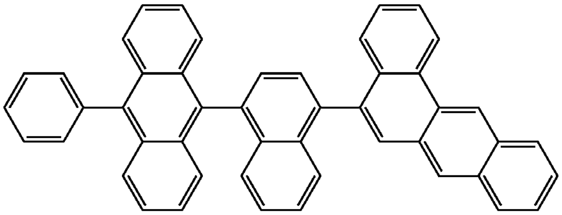 [SMILES: c1ccc(-c2c3ccccc3c(-c3ccc(-c4cc5cc6ccccc6cc5c5ccccc45)c4ccccc34)c3ccccc23)cc1]
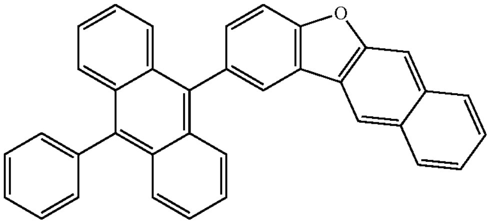 [SMILES: c1ccc(-c2c3ccccc3c(-c3ccc4oc5cc6ccccc6cc5c4c3)c3ccccc23)cc1]
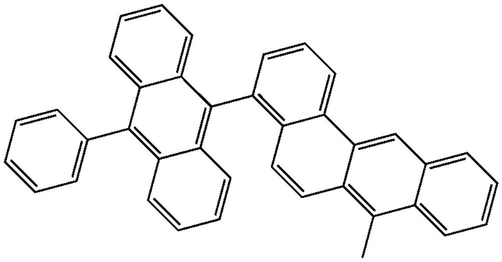 [SMILES: Cc1c2ccccc2cc2c1ccc1c(-c3c4ccccc4c(-c4ccccc4)c4ccccc34)cccc12]
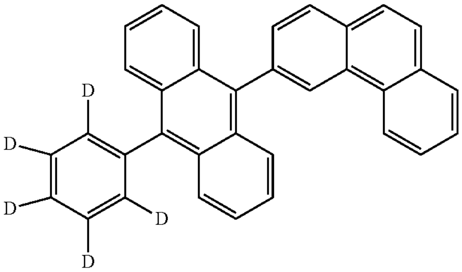 [SMILES: [2H]c1c([2H])c([2H])c(-c2c3ccccc3c(-c3ccc4ccc5ccccc5c4c3)c3ccccc23)c([2H])c1[2H]]
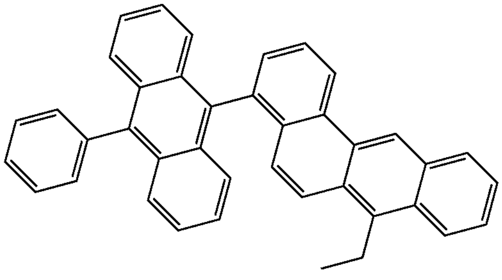 [SMILES: CCc1c2ccccc2cc2c1ccc1c(-c3c4ccccc4c(-c4ccccc4)c4ccccc34)cccc12]

-continued

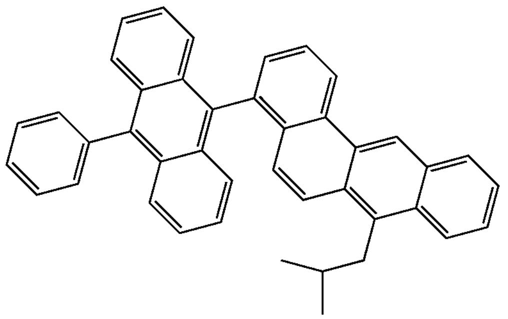 [SMILES: CC(C)Cc1c2ccccc2cc2c1ccc1c(-c3c4ccccc4c(-c4ccccc4)c4ccccc34)cccc12]

Suitable charge-transport materials, as can be used in the hole-injection or hole-transport layer or electron-blocking layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

Examples of preferred hole-transport materials which can be used besides the compounds of the formula (1) in a hole-transport, hole-injection or electron-blocking layer in the electroluminescent device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or WO 2013/120577), fluorenamines (for example in accordance with the as yet unpublished applications EP 12005369.9, EP 12005370.7 and EP 12005371.5), spirodibenzopyranamines (for example in accordance with WO 2013/083216) and dihydroacridine derivatives (for example in accordance with WO 2012/150001).

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (1) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds according to the invention can be employed in displays, as light sources in lighting applications and as light sources in medical and/or cosmetic applications (for example light therapy).

WORKING EXAMPLES
A) Synthesis Examples
Synthesis Scheme:
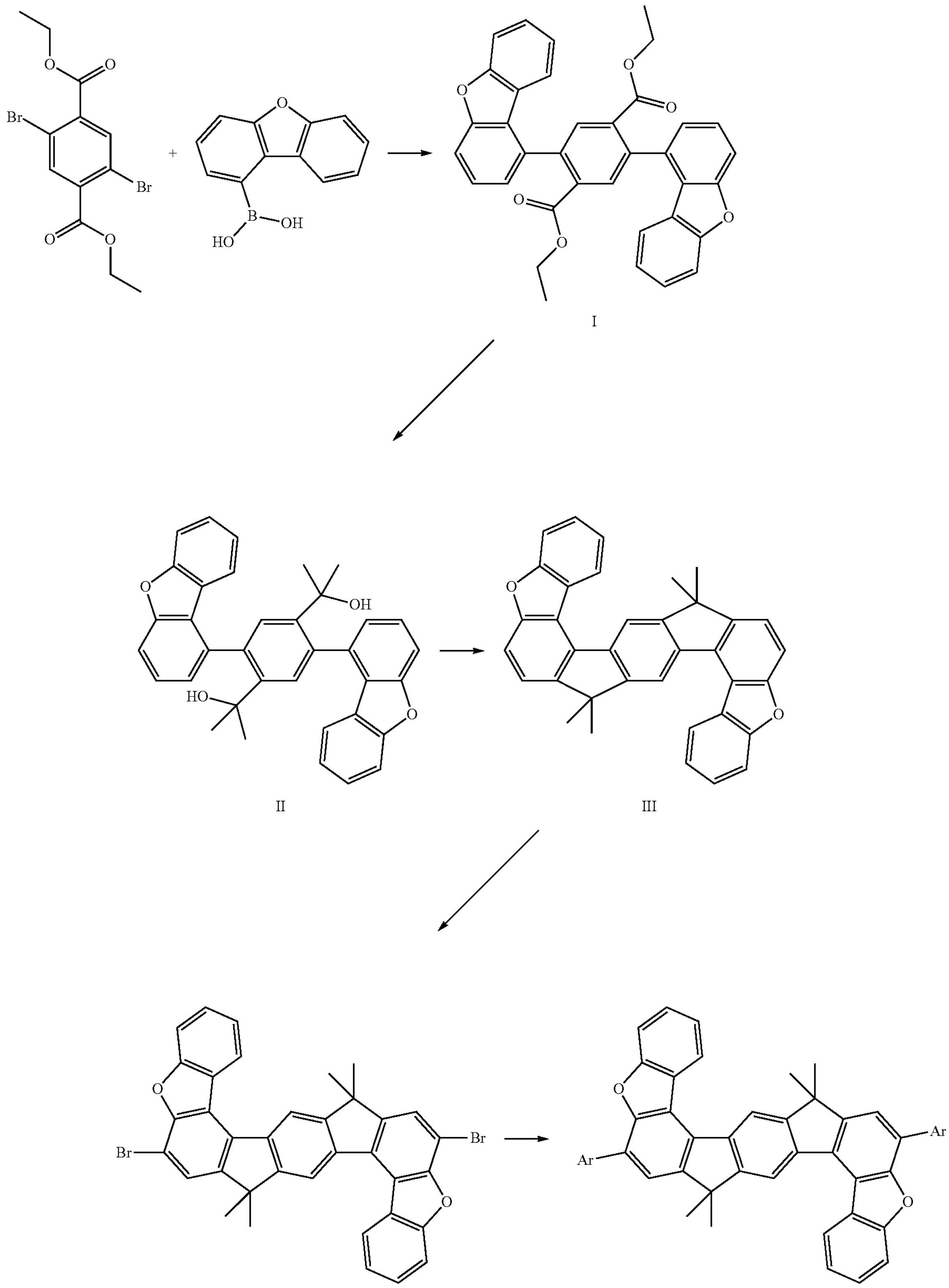
I
II
III
IV
V Compound Ia

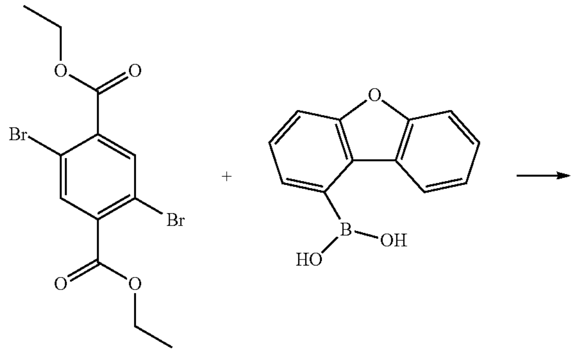

-continued

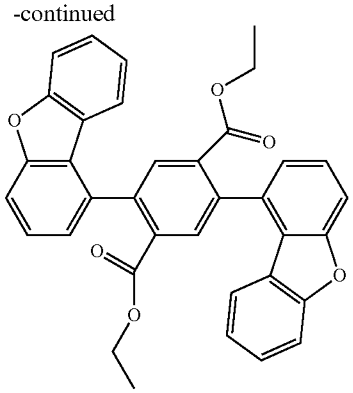

2,5-Dibromo-terephthalic acid diethyl ester (20 g, 53 mmol), dibenzofuran-1-boronic acid (29 g, 137 mmol) and tripotassiumphosphate monohydrate (48.5 g, 160 mmol) were added to water/toluene/dioxane (1:1:1, 0.5 L). The solution was saturated with argon. Palladium(II)-acetate (118 mg, 0.5 mmol) and tri-o-tolyl-phosphine (480 mg, 1.6 mmol) were added and the reaction mixture was refluxed for 16 hours. After cooling down to room temperature, toluene (500 mL) was added and the organic phase was washed with water (3×500 mL) and then concentrated under reduced pressure. The residue was purified by recrystallization from toluene/ethanol. Yield: 22.2 g (40 mol; 76%).

In an analogous manner, the following compounds can be obtained:

| | Starting Material | Starting Material | Product | Yield |
|---|---|---|---|---|
| Ib | 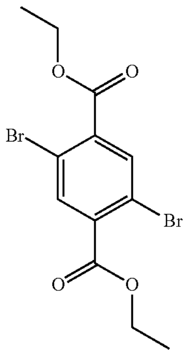 [SMILES: CCOC(=O)c1cc(Br)c(C(=O)OCC)cc1Br] CAS 18013-97-3 | 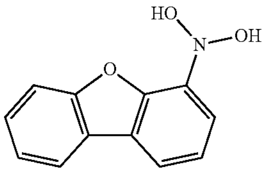 [SMILES: ON(O)c1cccc2c1oc1ccccc12] CAS 100124-06-9 | 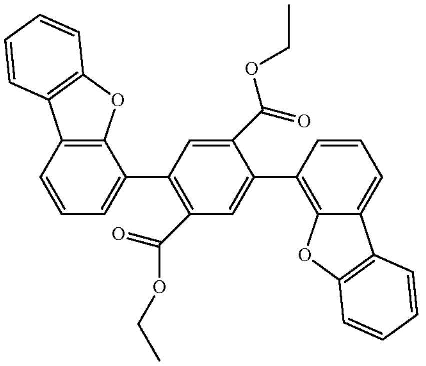 [SMILES: CCOC(=O)c1cc(-c2cccc3c2oc2ccccc23)c(C(=O)OCC)cc1-c1cccc2c1oc1ccccc12] | 75% |
| Ic | Ic-A (see below) | 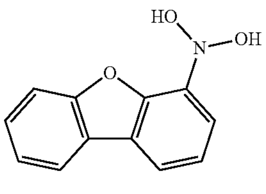 [SMILES: ON(O)c1cccc2c1oc1ccccc12] CAS 100124-06-9 | 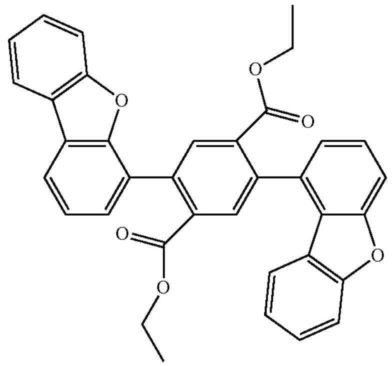 [SMILES: CCOC(=O)c1cc(-c2cccc3oc4ccccc4c23)c(C(=O)OCC)cc1-c1cccc2c1oc1ccccc12] | 69% |

Compound Ic-A

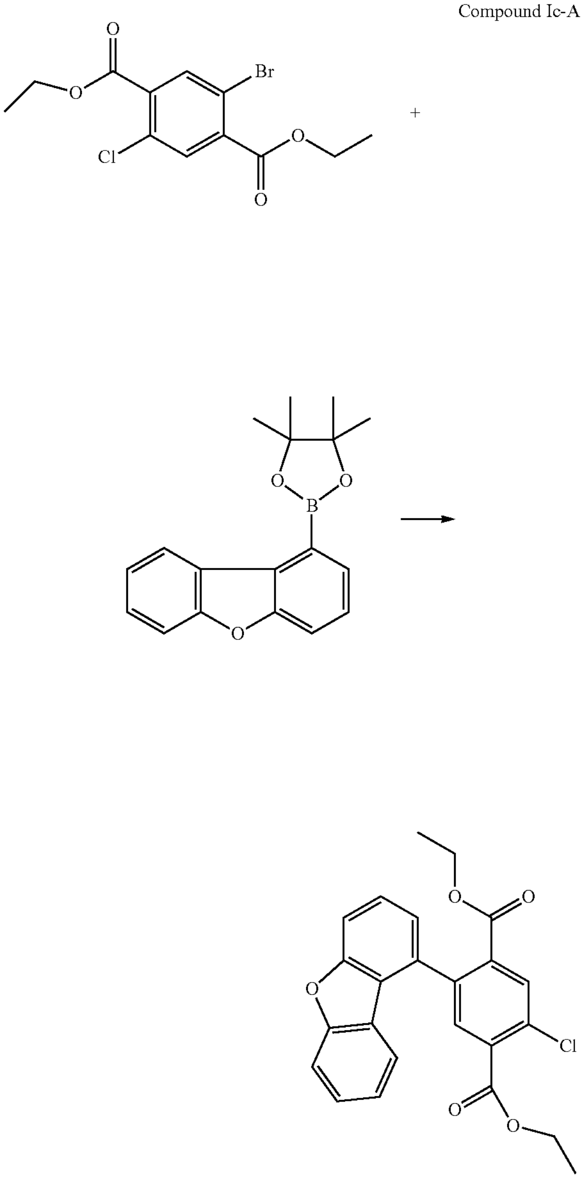

Compound IIa

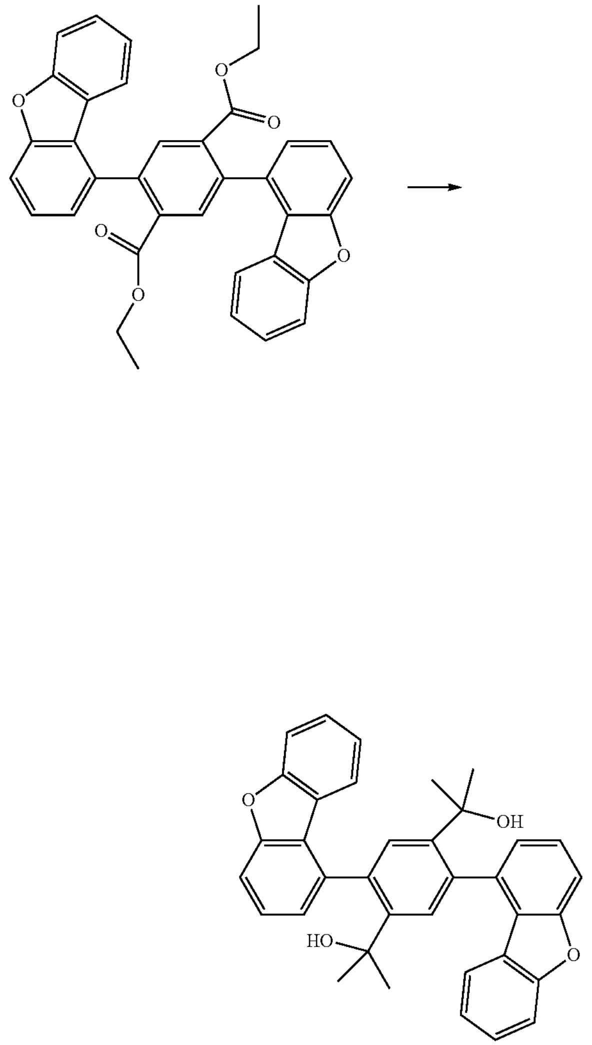

2-Bromo-5-chloro-terephthalic acid diethyl ester (60.5 g, 0.24 mol, CAS:340148-60-9), dibenzofuran-1-pinacolato-boronic ester (78.5 g, 0.27 mol) and tripotassiumphosphate monohydrate (223.4 g, 0.97 mol) were added to water/toluene/dioxane (1:1:1, 1 L). The solution was saturated with argon. Palladium(II)-acetate (547 mg, 2.4 mmol) and tri-o-tolyl-phosphine (2.2 g, 7.3 mmol) were added and the reaction mixture was refluxed for 16 hours. After cooling down to room temperature, toluene (500 mL) was added and the organic phase was washed with water (3×500 mL) and then concentrated under reduced pressure. The residue was purified by recrystallization from toluene/ethanol. Yield: 65.5 g (0.19 mol; 72%).

21 g (38 mmol) of the Ia diluted in 0.5 L THF were added to 37.5 g (40 mmol) cerium(III) chloride and 200 ml THF and the mixture was stirred for 30 minutes and cooled to 0° C. 101 ml (304 mol) methylmagnesiumchloride (3 M in THF) was added dropwise to the reaction mixture at 0° C. The reaction mixture was allowed to warm to room temperature. After 16 hours, 800 ml of an aqueous saturated solution of ammonium chloride were added at 0° C. Ethyl acetate (2×300 mL) was added, the combined organic phases were washed with water (2×300 mL) and concentrated under reduced pressure. The residue was purified by stirring in ethanol. Yield: 18.6 g (35.3 mmol, 93%).

In an analogous manner, the following compounds can be obtained:
| Starting Material | | Product | Yield |
| --- | --- | --- | --- |
| IIb | 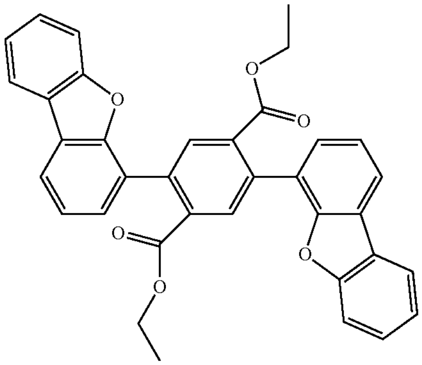 [SMILES: CCOC(=O)c1cc(-c2cccc3c2oc2ccccc23)c(C(=O)OCC)cc1-c1cccc2c1oc1ccccc12] | 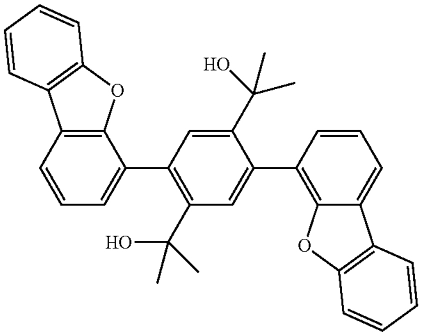 [SMILES: CC(C)(O)c1cc(-c2cccc3c2oc2ccccc23)c(C(C)(C)O)cc1-c1cccc2c1oc1ccccc12] | 98% |
| IIc | 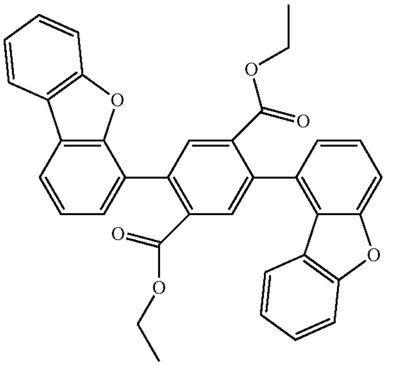 [SMILES: CCOC(=O)c1cc(-c2cccc3oc4ccccc4c23)c(C(=O)OCC)cc1-c1cccc2c1oc1ccccc12] | 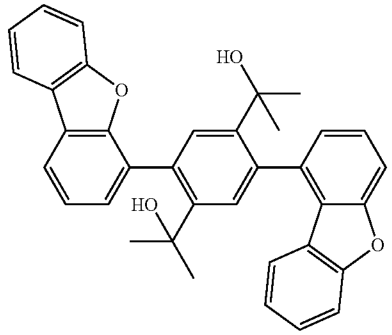 [SMILES: CC(C)(O)c1cc(-c2cccc3oc4ccccc4c23)c(C(C)(C)O)cc1-c1cccc2c1oc1ccccc12] | 97% |
Compound IIIa
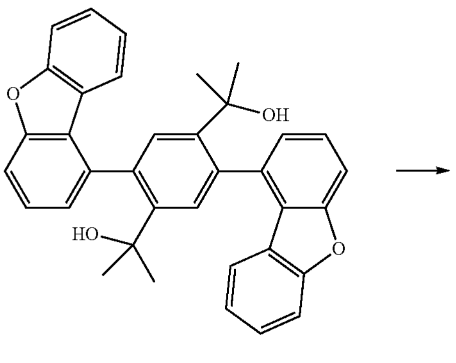
-continued
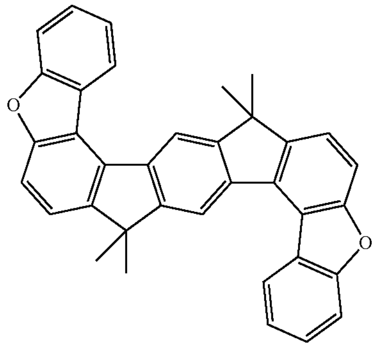

18.4 g (34 mmol) of IIa were solved in 750 mL toluene and 5 g amberlyst 15 were added. The reaction mixture was refluxed for 16 hours using a DeanStark apparatus. After cooling down to room temperature, amberlyst was removed by filtration and the organic phase was concentrated under reduced pressure. The residue was purified by several recrystallizations from ethanol and heptane/toluene.

Yield: 12.2 g (25 mmol; 73%).

In an analogous manner, the following compounds can be obtained:

| | Starting Material | Product | Yield |
|---|---|---|---|
| IIIb | 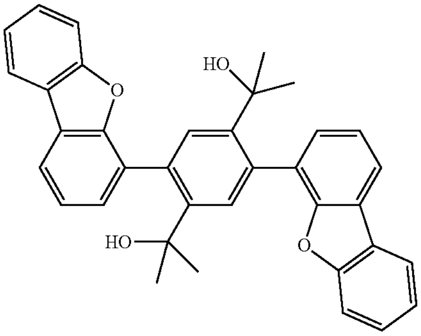 [SMILES: CC(C)(O)c1cc(-c2cccc3c2oc2ccccc23)c(C(C)(C)O)cc1-c1cccc2c1oc1ccccc12] | 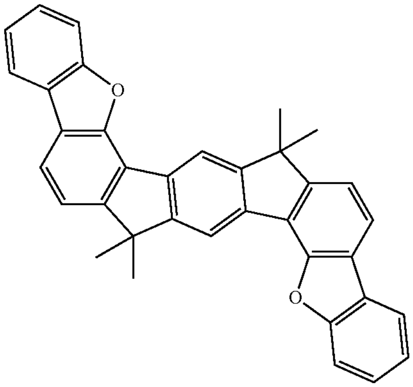 [SMILES: CC1(C)c2cc3c(cc2-c2c1ccc1c2oc2ccccc21)C(C)(C)c1ccc2c(oc4ccccc42)c1-3] | 77% |
| IIIc | 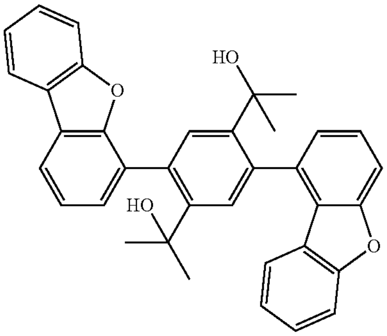 [SMILES: CC(C)(O)c1cc(-c2cccc3oc4ccccc4c23)c(C(C)(C)O)cc1-c1cccc2c1oc1ccccc12] | 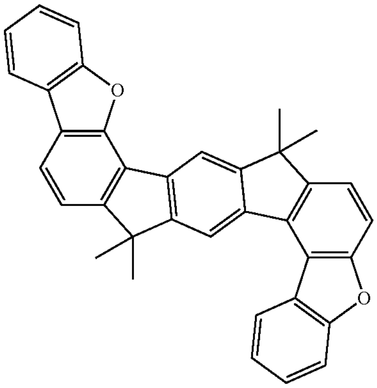 [SMILES: CC1(C)c2cc3c(cc2-c2c1ccc1c2oc2ccccc21)C(C)(C)c1ccc2oc4ccccc4c2c1-3] | 78% |

Compound IV

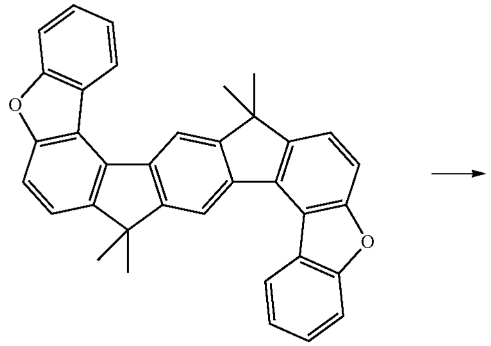

-continued

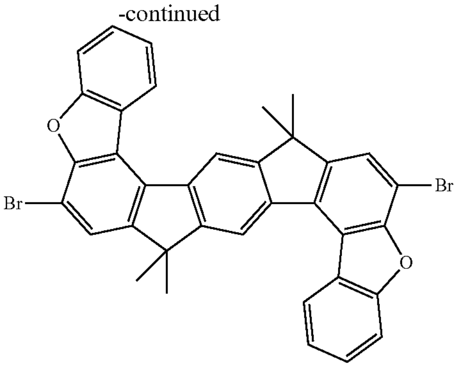

IIIa (12.5 g, 25 mmol) was suspended in 0.5 L chloroform. Bromine (9 g, 56 mmol) in 350 ml chloroform was added dropwise. The reaction mixture was stirred at room temperature. After 16 hours, 20 ml of an aqueous saturated solution of ammonium chloride were added and the mixture was stirred for 15 minutes. Water (1 L) was added, the organic phase was washed with water (3×500 mL) and the combined organic phases were concentrated under reduced pressure. The residue was purified by several recrystallizations from chloroform and toluene. Yield: 12.0 g (19 mmol; 73%).

In analogous manner, the following compounds can be obtained:

| | Starting Material | Product | Yield |
|---|---|---|---|
| IVb | 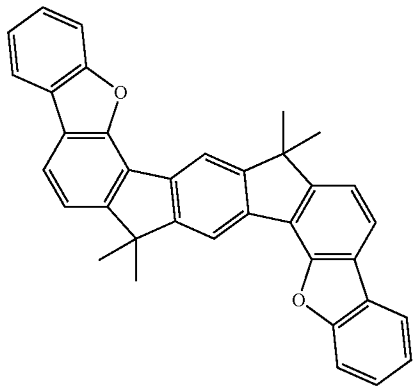 [SMILES: CC1(C)c2cc3c(cc2-c2c1ccc1c2oc2ccccc21)C(C)(C)c1ccc2c(oc4ccccc42)c1-3] | 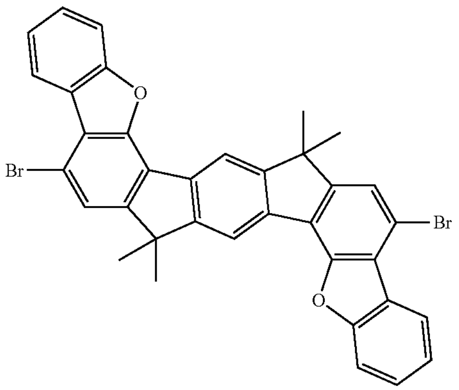 [SMILES: CC1(C)c2cc3c(cc2-c2c1cc(Br)c1c2oc2ccccc21)C(C)(C)c1cc(Br)c2c(oc4ccccc42)c1-3] | 69% |
| IVc | 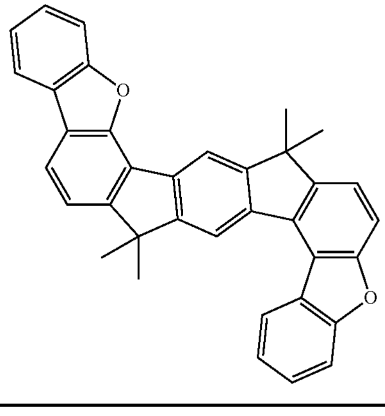 | 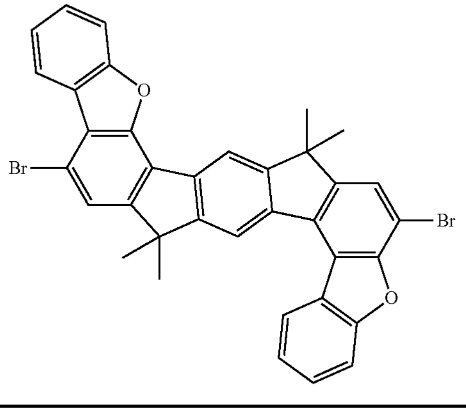 | 78% |

Compound Va

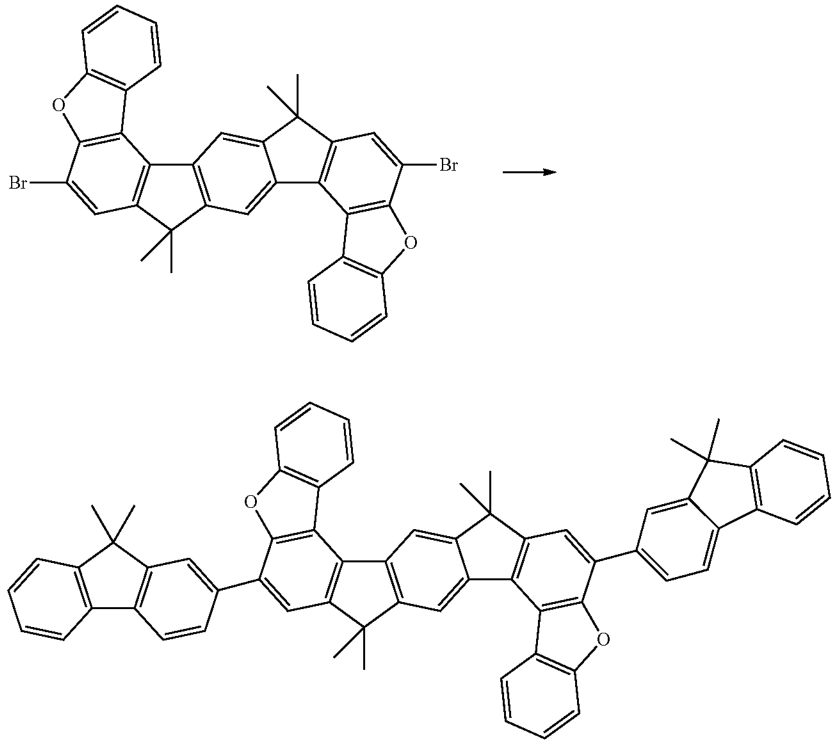

IVa (12.1 g, 19 mmol), 9,9-dimethyl-9H-fluorene-2-boronic acid (13.7 g, 58 mmol) and tripotassiumphosphate monohydrate (25.7 g, 0.11 mol) were mixed in 300 mL toluene/dioxane/water (2:1:1). Palladium(II)-acetate (0.31 g, 0.45 mmol) and tri-tert-butylphosphonium tetrafluoroborate (0.26 g, 1.4 mmol) were added and the reaction mixture was refluxed for 16 hours. After cooling down to room temperature, 200 mL water was added and the organic phase was washed with water (3×200 mL). The combined organic phases were concentrated under reduced pressure. The residue was purified by several recrystallizations from toluene and finally by sublimation.

Yield: 8.7 g (0.010 mol; 53%)

In an analogous manner, the following compounds can be obtained:

| | Starting Material A | Starting Material B | Product | Yield |
|---|---|---|---|---|
| IVb | 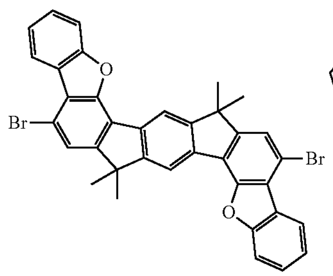 | 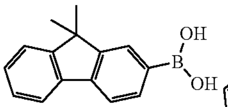 CAS 333432-28-3 | 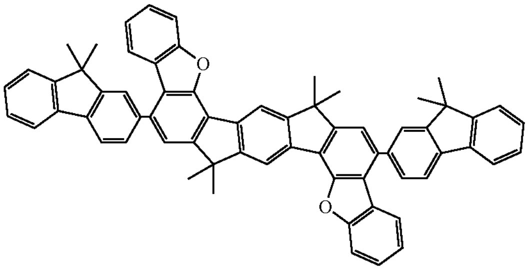 [SMILES: CC1(C)c2ccccc2-c2ccc(-c3cc4c(c5oc6ccccc6c35)-c3cc5c(cc3C4(C)C)-c3c(cc(-c4ccc6c(c4)C(C)(C)c4ccccc4-6)c4c3oc3ccccc34)C5(C)C)cc21] | 58% |
| IVc | 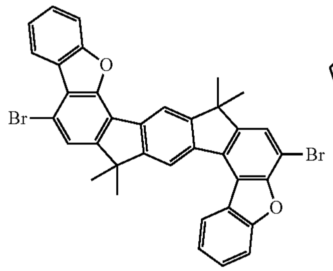 | 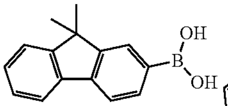 CAS 333432-28-3 | 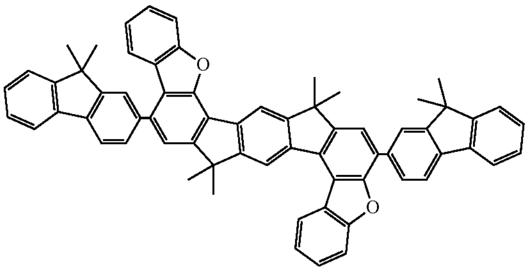 [SMILES: CC1(C)c2ccccc2-c2ccc(-c3cc4c(c5c3oc3ccccc35)-c3cc5c(cc3C4(C)C)-c3c(cc(-c4ccc6c(c4)C(C)(C)c4ccccc4-6)c4c3oc3ccccc34)C5(C)C)cc21] | 61% |

-continued
| | Starting Material A | Starting Material B | Product | Yield |
|---|---|---|---|---|
| IVd | 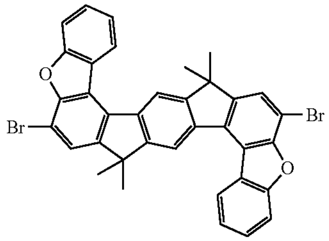 [SMILES: CC1(C)c2cc3c(cc2-c2c1cc(Br)c1oc4ccccc4c21)C(C)(C)c1cc(Br)c2oc4ccccc4c2c1-3] | 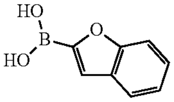 [SMILES: OB(O)c1cc2ccccc2o1] CAS 98437-24-2 | 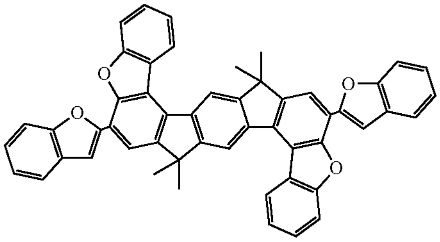 [SMILES: CC1(C)c2cc3c(cc2-c2c1cc(-c1cc4ccccc4o1)c1oc4ccccc4c21)C(C)(C)c1cc(-c2cc4ccccc4o2)c2oc4ccccc4c2c1-3] | 57% |
| IVe | 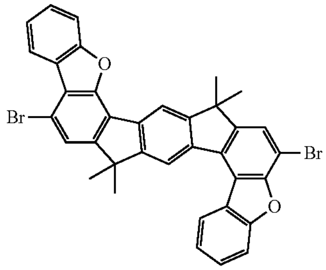 [SMILES: CC1(C)c2cc3c(cc2-c2c1cc(Br)c1c2oc2ccccc21)C(C)(C)c1cc(Br)c2oc4ccccc4c2c1-3] | 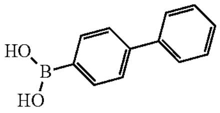 [SMILES: OB(O)c1ccc(-c2ccccc2)cc1] | 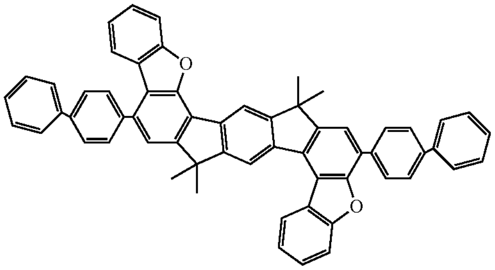 [SMILES: CC1(C)c2cc3c(cc2-c2c1cc(-c1ccc(-c4ccccc4)cc1)c1c2oc2ccccc21)C(C)(C)c1cc(-c2ccc(-c4ccccc4)cc2)c2oc4ccccc4c2c1-3] | 68% |
| IVf | 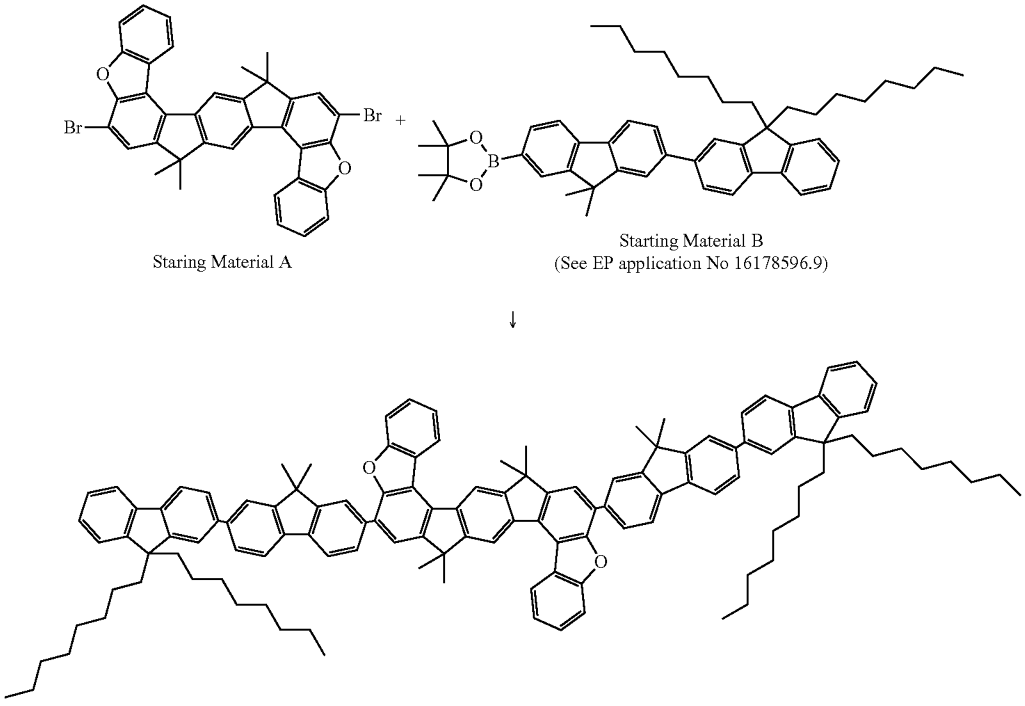  Product | | | 63% |
| IVg | 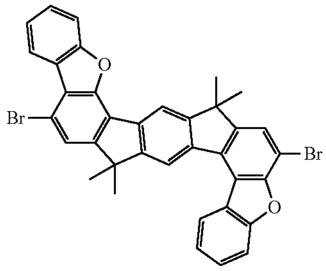 [SMILES: CC1(C)c2cc3c(cc2-c2c1cc(Br)c1c2oc2ccccc21)C(C)(C)c1cc(Br)c2oc4ccccc4c2c1-3] | 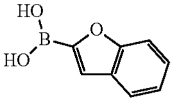 [SMILES: OB(O)c1cc2ccccc2o1] CAS 98437-24-2 | 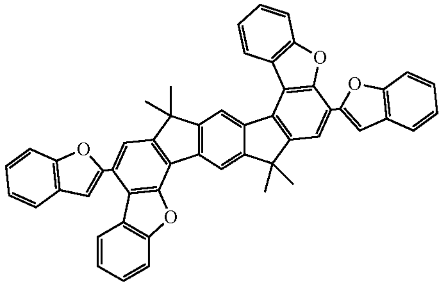 [SMILES: CC1(C)c2cc3c(cc2-c2c1cc(-c1cc4ccccc4o1)c1c2oc2ccccc21)C(C)(C)c1cc(-c2cc4ccccc4o2)c2oc4ccccc4c2c1-3] | 54% |

B) Device Examples

B-1) Device Examples Processed from Vapor: Production of OLEDs

The manufacturing of the OLED devices is performed accordingly to WO 04/05891 with adapted film thicknesses and layer sequences. The following examples V1, V2, E3 and E4 (see Table 1) show data of various OLED devices.

Substrate Pre-Treatment of Examples V1-E4:

Glass plates with structured ITO (50 nm, indium tin oxide) are coated with 20 nm PEDOT:PSS (Poly(3,4-ethylenedioxythiophene) poly(styrenesulfonate, CLEVIOS™ P VP Al 4083 from Heraeus Precious Metals GmbH Germany, spin-coated from a water-based solution) to form the substrates on which the OLED devices are fabricated.

The OLED devices have in principle the following layer structure:

Substrate,
ITO (50 nm),
Buffer (20 nm),
Hole injection layer (HTL1 95%, HIL 5%) (20 nm),
Hole transporting layer (HTL) (see table 1),
Emissive layer (EML) (see table 1),
Electron transporting layer (ETL) (20 nm),
Electron injection layer (EIL) (3 nm),
Cathode.

The cathode is formed by an aluminium layer with a thickness of 100 nm. The detailed stack sequence is shown in Table 1. The materials used for the OLED fabrication are presented in Table 3.

All materials are applied by thermal vapour deposition in a vacuum chamber. The emission layer here always consists of at least one matrix material (host material=H) and an emitting dopant (emitter=D), which is mixed with the matrix material or matrix materials in a certain proportion by volume by co-evaporation. An expression such as H1:D1 (97%:3%) here means that material H1 is present in the layer in a proportion by volume of 97%, whereas D1 is present in the layer in a proportion of 3%. Analogously, the electron-transport layer may also consist of a mixture of two or more materials.

The OLED devices are characterised by standard methods. For this purpose, the electroluminescence spectra, the current efficiency (measured in cd/A) and the external quantum efficiency (EQE, measured in % at 1000 cd/$m^2$) are determined from current/voltage/luminance characteristic lines (IUL characteristic lines) assuming a Lambertian emission profile. The electroluminescence (EL) spectra are recorded at a luminous density of 1000 cd/$m^2$ and the CIE 1931 x an y coordinates are then calculated from the EL spectrum. EQE @ 1000 cd/$m^2$ is defined as the external quantum efficiency at luminous density of 1000 cd/m2. For all experiments, the lifetime LT80 is determined. The lifetime LT80 @ 60 mA/$cm^2$ is defined as the time after which the initial luminous density (cd/m2) at a constant current density of 60 mA/$cm^2$ has dropped by 20%. The device data of various OLED devices is summarized in Table 2.

The examples V1 and V2 represent the comparative example according to the state-of-the-art. The example E3 and E4 shows data of inventive OLED devices.

In the following section, several examples are described in more detail to show the advantages of the inventive OLED devices.

Use of Inventive Compounds as Emitting Material in Fluorescent OLEDs

The inventive compounds are especially suitable as an emitter (dopant) when blended into a fluorescent blue matrix to form the emissive layer of a fluorescent blue OLED device. The representative example is D1 and D2. Comparative compound for the state-of-the-art are represented by VD-1 and VD-2 (structures see table 3).

The use of the inventive compound as an emitter (dopant) in a fluorescent blue OLED device results in significantly improved device data (E3 and E4) compared to state-of-the-art examples (V1 and V2), especially in terms of external quantum efficiency and deeper blue color. This demonstrates the applicability of the inventive compound as emitting material in fluorescent blue OLED devices. The material can be also used also as hole transporting material.

TABLE 1

Stack sequence of OLEDs

| Example | HTL (195 nm) | EML (20 nm) |
|---|---|---|
| V1 | HTL2 | H(97%): VD-1 (3%) |
| V2 | HTL2 | H(97%): VD-2 (3%) |
| E3 | HTL2 | H(97%): D1 (3%) |
| E4 | HTL2 | H(97%): D2 (3%) |

TABLE 2

Device data of OLEDs

| Example | CIE x | CIE y | EQE [%] @ 1000 cd/$m^2$ | LT 80 [h] @ 60 mA/$m^2$ |
|---|---|---|---|---|
| V1 | 0.14 | 0.13 | 6.9 | 95 |
| V2 | 0.14 | 0.14 | 7.2 | 140 |
| E3 | 0.15 | 0.10 | 8.2 | 145 |
| E4 | 0.15 | 0.09 | 7.9 | 135 |

TABLE 3

Chemical structure of OLED materials

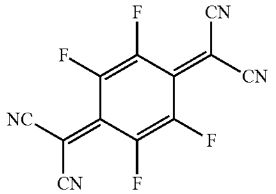 [SMILES: N#CC(C#N)=c1c(F)c(F)c(=C(C#N)C#N)c(F)c1F]

HIL

TABLE 3-continued
| Chemical structure of OLED materials |
| --- |
| 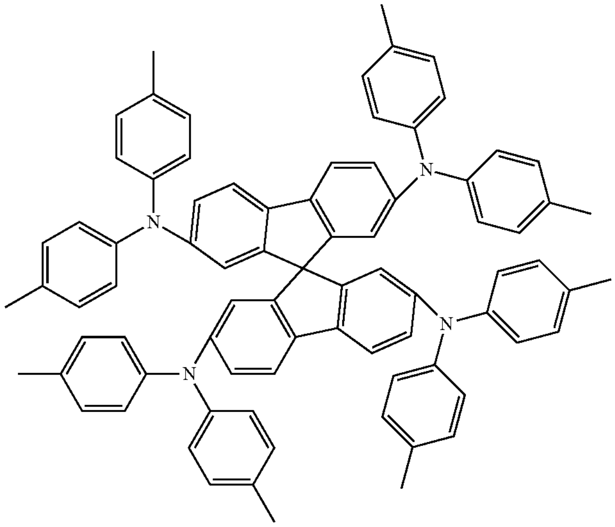 |
| HTL1 |
| 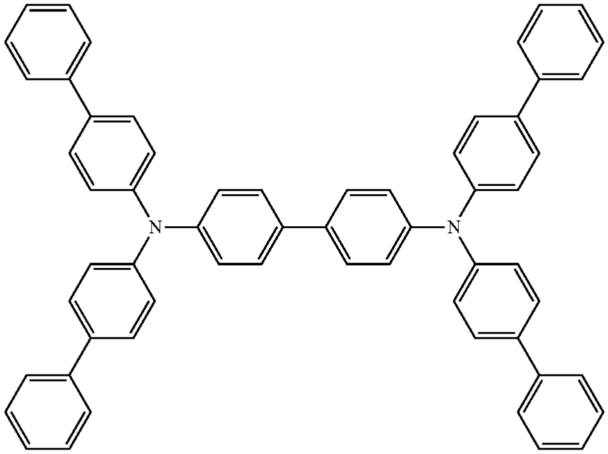 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] |
| HTL2 |
| 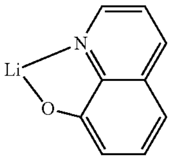 |
| EIL |
| 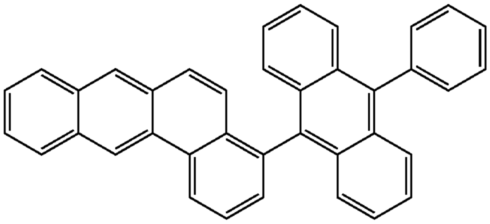 [SMILES: c1ccc(-c2c3ccccc3c(-c3cccc4c3ccc3cc5ccccc5cc34)c3ccccc23)cc1] |
| H |

TABLE 3-continued
| Chemical structure of OLED materials |
| --- |
| 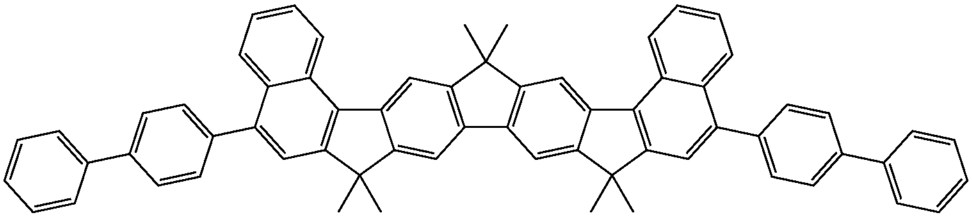 [SMILES: CC1(C)c2cc3c(cc2-c2cc4c(cc21)-c1c(cc(-c2ccc(-c5ccccc5)cc2)c2ccccc12)C4(C)C)C(C)(C)c1cc(-c2ccc(-c4ccccc4)cc2)c2ccccc2c1-3] |
| VD-1 |
| 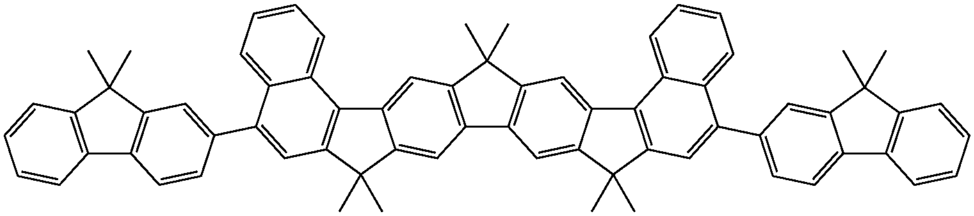 [SMILES: CC1(C)c2ccccc2-c2ccc(-c3cc4c(c5ccccc35)-c3cc5c(cc3C4(C)C)-c3cc4c(cc3C5(C)C)-c3c(cc(-c5ccc6c(c5)C(C)(C)c5ccccc5-6)c5ccccc35)C4(C)C)cc21] |
| VD-2 |
| 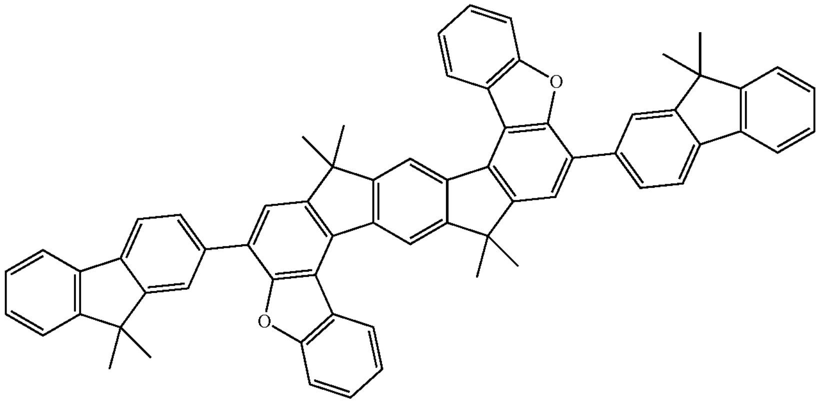 [SMILES: CC1(C)c2ccccc2-c2ccc(-c3cc4c(c5c3oc3ccccc35)-c3cc5c(cc3C4(C)C)-c3c(cc(-c4ccc6c(c4)C(C)(C)c4ccccc4-6)c4oc6ccccc6c34)C5(C)C)cc21] |
| D1 |
| 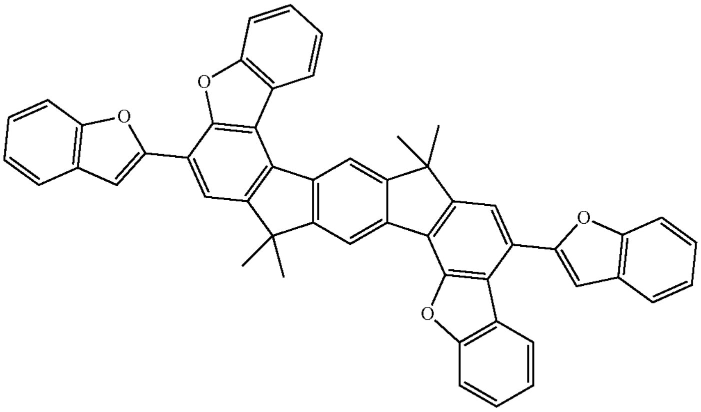 [SMILES: CC1(C)c2cc3c(cc2-c2c1cc(-c1cc4ccccc4o1)c1c2oc2ccccc21)C(C)(C)c1cc(-c2cc4ccccc4o2)c2oc4ccccc4c2c1-3] |
| D2 |

TABLE 3-continued

Chemical structure of OLED materials

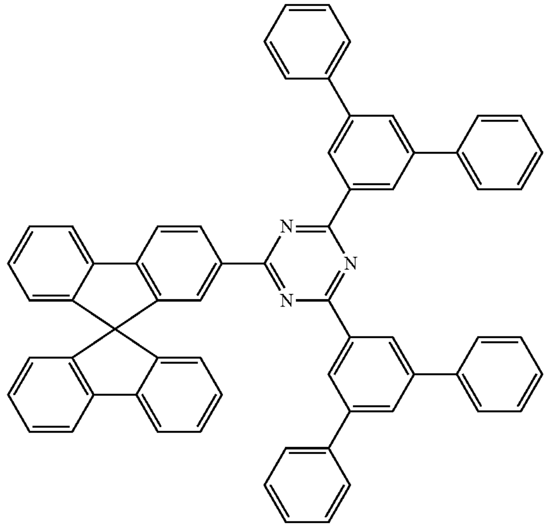 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]

ETL

B-2) Device Examples Processed from Solution: Production of OLEDs

The production of solution-based OLEDs is described in principle in the literature, for example in WO 2004/037887 and WO 2010/097155. In the following examples, the two production methods (application from gas phase and solution processing) were combined, so that processing up to and including the emission layer was carried out from solution and the subsequent layers (hole-blocking layer/electron-transport layer) were applied by vacuum vapour deposition. The general processes described above are for this purpose adapted to the circumstances described here (layer-thickness variation, materials) and combined as follows.

The device structure used is thus as follows:

substrate,

ITO (50 nm),

PEDOT (20 nm), hole-transport layer (HTL) (20 nm), emission layer (92% of host, 8% of dopant) (60 nm), electron-transport layer (ETL2) (20 nm), electron-injection layer (EIL) (3 nm)

cathode (Al) (100 nm).

The substrates used are glass plates coated with structured ITO (indium tin oxide) in a thickness of 50 nm. For better processing, these are coated with the buffer PEDOT:PSS (Poly(3,4-ethylenedioxythiophene) poly(styrenesulfonate, CLEVIOS™ P VP Al 4083 from Heraeus Precious Metals GmbH Germany). The spin coating of the buffer is carried out from water in air. The layer is subsequently dried by heating at 180° C. for 10 minutes. The hole-transport and emission layers are applied to the glass plates coated in this way.

The hole-transport layer is the polymer of the structure shown in Table 5, which was synthesised in accordance with WO 2010/097155. The polymer is dissolved in toluene, so that the solution typically has a solid content of approx. 5 g/l if, as here, the layer thickness of 20 nm which is typical for a device is to be achieved by means of spin coating. The layers are applied by spin coating in an inert-gas atmosphere, in the present case argon, and dried by heating at 180° C. for 60 min.

The emission layer (EML) is always composed of at least one matrix material (host=H) and an emitting dopant (emitter=D). An expression such as H1 (92%): D1 (8%) here means that material H1 is present in the emission layer in a proportion by weight of 92% and dopant D1 is present in the emission layer in a proportion by weight of 8%. The mixture for the emission layer is dissolved in toluene. The typical solid content of such solutions is approx. 18 g/l if, as here, the layer thickness of 60 nm which is typical for a device is to be achieved by means of spin coating. The layers are applied by spin coating in an inert-gas atmosphere, in the present case argon, and dried by heating at 140° C. for 10 minutes. The materials used are shown in Table 5.

The materials for the electron-transport layer, the electron-injection layer and for the cathode are applied by thermal vapour deposition in a vacuum chamber. The electron-transport layer, for example, may consist of more than one material, which are admixed with one another in a certain proportion by volume by co-evaporation. An expression such as ETM:EIL (50%:50%) would mean that materials ETM and EIL are present in the layer in a proportion by volume of 50% each. The materials used in the present case are shown in Table 5.

The OLEDs are characterised by standard methods. For this purpose, the electroluminescence spectra are recorded, the current efficiency (measured in cd/A) and the external quantum efficiency (EQE, measured in percent) as a function of the luminous density assuming Lambert emission characteristics are calculated from current/voltage/luminous density characteristic lines (IUL characteristic lines), and finally the lifetime of the components is determined. The electroluminescence spectra are recorded at a luminous density of 1000 cd/$m^2$, and the CIE 1931 x and y colour coordinates are calculated from this data. The term EQE @ 1000 cd/$m^2$ denotes the external quantum efficiency at an operating luminous density of 1000 cd/m2. The lifetime LD80 @ 10 $mA/cm^2$ is the time which passes until the initial luminance at a driving current density of 10 $mA/cm^2$ has dropped by 20%. The data obtained for the various OLEDs are summarised in Table 4.

Use of Compounds According to the Invention as Fluorescent Emitter Materials in Organic Light Emitting Diodes The compounds according to the invention are particularly suitable as emitter materials in blue-fluorescent OLEDs. Emitters D3 and D4 are shown as compounds according to the invention. The state-of-the-art compound for comparison is represented by V-D3 and V-D4. All emitters are used in combination with either host H1 or H2.

Examples E9 to E12 show in a comparative examination with Comparative Examples V5 to V8 that compounds D3 and D4 according to the invention achieve an improved external quantum efficiency (EQE) and an increased lifetime (LD80) with deep-blue emission as compared to comparative material V-D1 and V-D2.

TABLE 4

Device data of the OLEDs

| | Host | Emitter | EQE @ 1000 $cd/m^2$ | LD80 @ 10mA/ $cm^2$ | CIE | |
|---|---|---|---|---|---|---|
| Example | 92% | 8% | % | [h] | x | y |
| V5 | H1 | V-D1 | 2.9 | 140 | 0.14 | 0.13 |
| V6 | H2 | V-D2 | 3.3 | 160 | 0.15 | 0.13 |
| E7 | H1 | D3 | 3.7 | 190 | 0.14 | 0.16 |
| E8 | H2 | D3 | 3.9 | 200 | 0.14 | 0.17 |
| E9 | H1 | D4 | 4.8 | 240 | 0.14 | 0.18 |
| E10 | H2 | D4 | 4.9 | 250 | 0.14 | 0.18 |

TABLE 5

Structures of the materials used

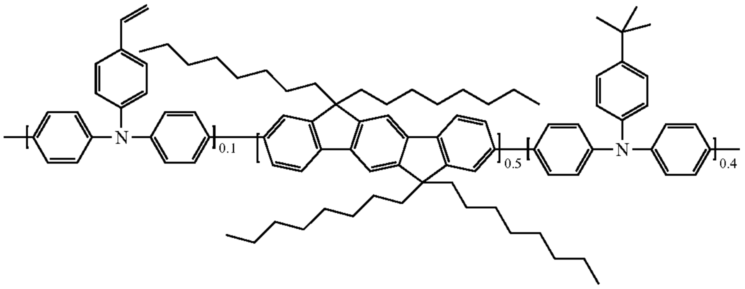

HTL

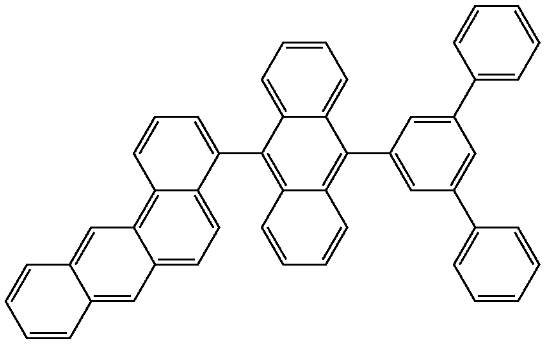 [SMILES: c1ccc(-c2cc(-c3ccccc3)cc(-c3c4ccccc4c(-c4cccc5c4ccc4cc6ccccc6cc45)c4ccccc34)c2)cc1]

H1

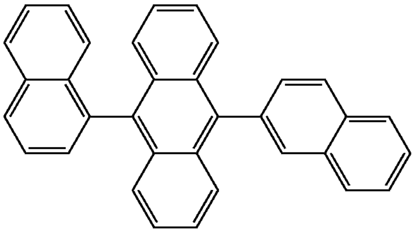 [SMILES: c1ccc2cc(-c3c4ccccc4c(-c4cccc5ccccc45)c4ccccc34)ccc2c1]

H2

TABLE 5-continued
| Structures of the materials used |
| --- |
| 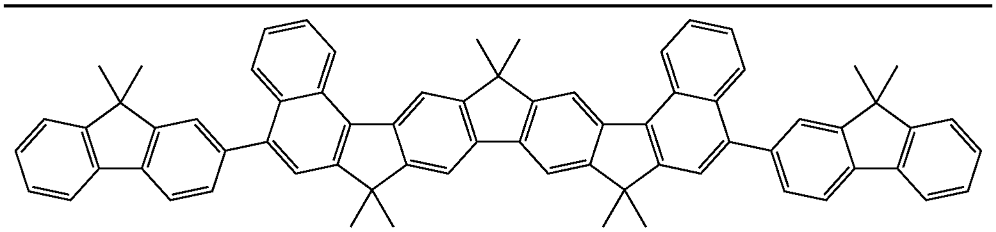 |
| V-D1 |
| 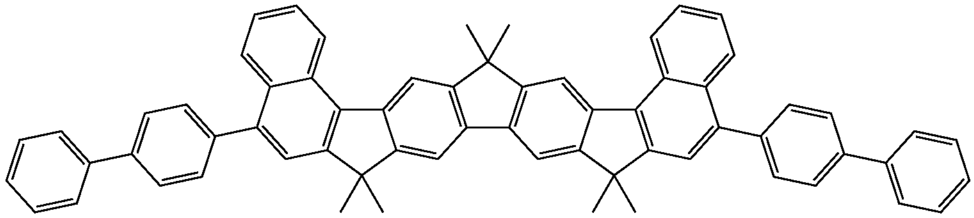 [SMILES: CC1(C)c2cc3c(cc2-c2cc4c(cc21)-c1c(cc(-c2ccc(-c5ccccc5)cc2)c2ccccc12)C4(C)C)C(C)(C)c1cc(-c2ccc(-c4ccccc4)cc2)c2ccccc2c1-3] |
| V-D2 |
| 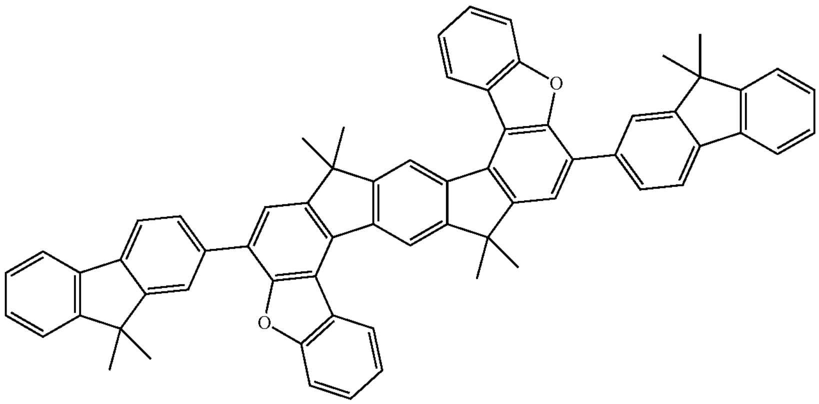 [SMILES: CC1(C)c2ccccc2-c2ccc(-c3cc4c(c5c3oc3ccccc35)-c3cc5c(cc3C4(C)C)-c3c(cc(-c4ccc6c(c4)C(C)(C)c4ccccc4-6)c4oc6ccccc6c34)C5(C)C)cc21] |
| D3 |
| 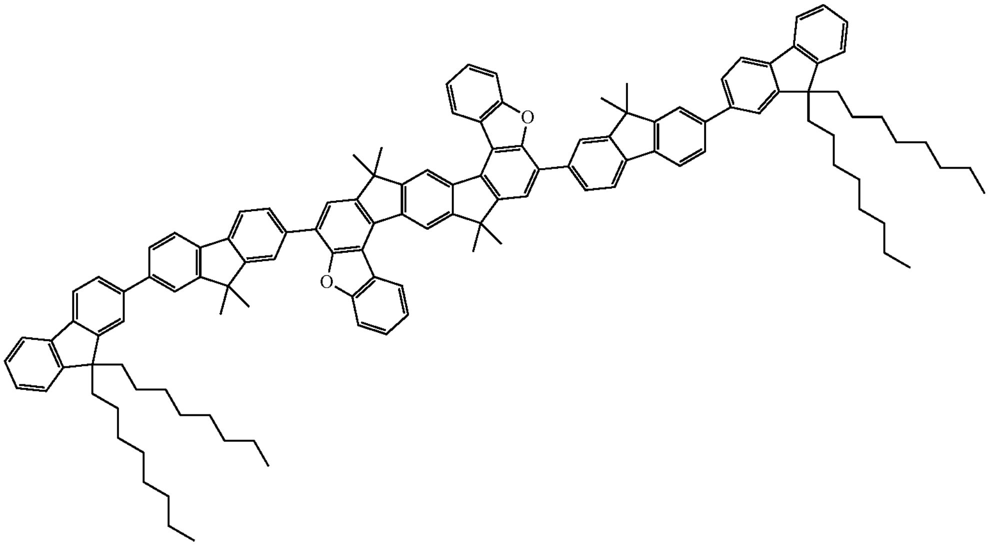 [SMILES: CCCCCCCCC1(CCCCCCCC)c2ccccc2-c2ccc(-c3ccc4c(c3)C(C)(C)c3cc(-c5cc6c(c7c5oc5ccccc57)-c5cc7c(cc5C6(C)C)-c5c(cc(-c6ccc8c(c6)C(C)(C)c6cc(-c9ccc%10c(c9)C(CCCCCCCC)(CCCCCCCC)c9ccccc9-%10)ccc6-8)c6oc8ccccc8c56)C7(C)C)ccc3-4)cc21] |
| D4 |

TABLE 5-continued

Structures of the materials used

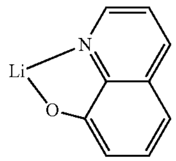

EIL

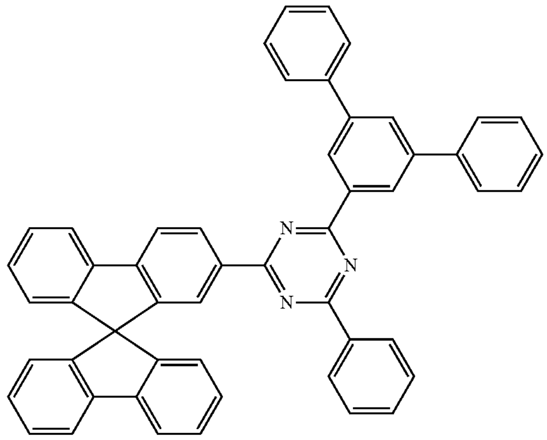 [SMILES: c1ccc(-c2cc(-c3ccccc3)cc(-c3nc(-c4ccccc4)nc(-c4ccc5c(c4)C4(c6ccccc6-c6ccccc64)c4ccccc4-5)n3)c2)cc1]

ETL2

Compounds according to the invention possess decent solubility and thus are well suitable for solution processing. By this technique, electronic devices based on blue fluorescent emitters with excellent performance data can be generated.

Alternatively, or in addition, the compounds according to the invention may serve as host materials inside the emission layer (EML), as hole injection material (HIL), as hole transporting material (HTL), as electron transporting material (ETL) or as electron-injection material (EIL) in an organic light emitting diode.

The invention claimed is:

1. A compound of formula (1-1a)-(1-6a):

(1-1a)

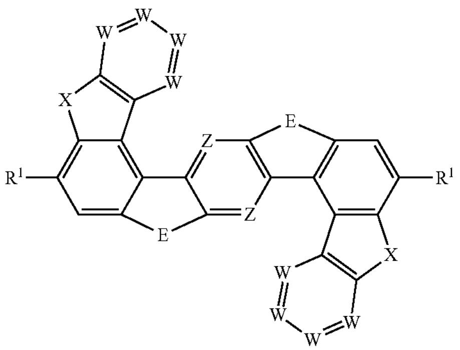

-continued (1-2a)

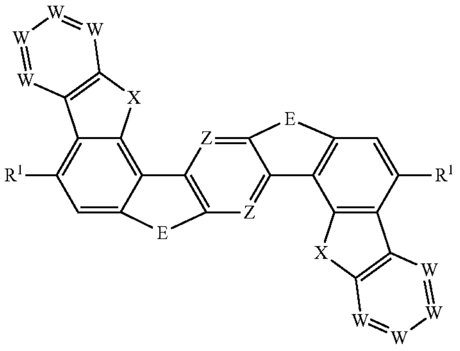

(1-3a)

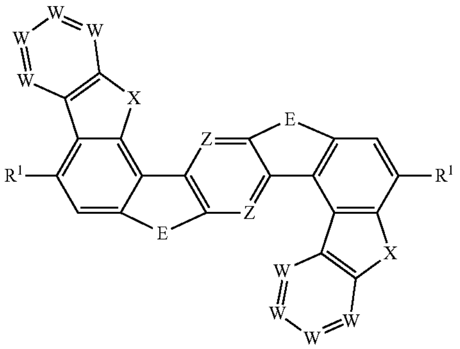

-continued (1-4a)

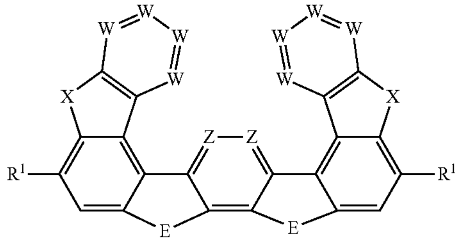

(1-5a)

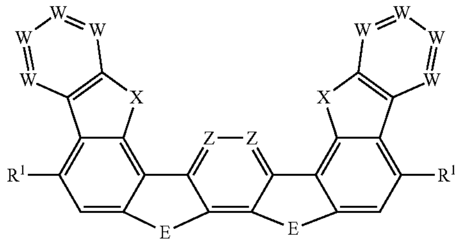

(1-6a)

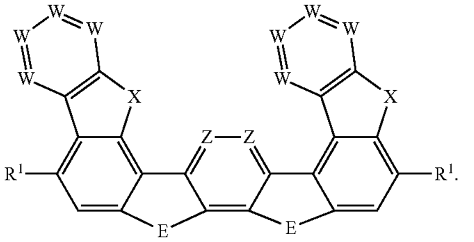

wherein

Z is on each occurrence, identically or differently, CR or N;

E is on each occurrence, identically or differently, selected from the group consisting of —$BR^0$—, —$C(R^0)_2$—, —$C(R^0)_2$—$C(R^0)_2$—, —$C(R^0)_2$—O—, —$C(R^0)_2$—S—, —$R^0C$═$CR^0$—, —$R^0C$═N—, —$Si(R^0)_2$—, —$Si(R^0)_2$—$Si(R^0)_2$—, $Ge(R^0)_2$, —C(═O)—, —C(═$NR^0$)—, —C(═$C(R^0)_2$)—, —O—, —S—, —Se—, —S(═O)—, —$SO_2$—, —$N(R^0)$—, —$P(R^0)$— and —P((═O)$R^0$)—, X is on each occurrence, identically or differently, selected from the group consisting of —O—, —S—, —S(═O)—, —$SO_2$—, —$N(R^0)$—, —$BR^0$—, $Si(R^0)_2$, —$P(R^0)$—, and —P((═O)$R^0$)—;

W is on each occurrence, identically or differently, CR or N;

R and $R^0$ are on each occurrence, identically or differently, H, D, F, Cl, Br, I, CHO, CN, $N(Ar)_2$, C(═O)Ar, P(═O)$(Ar)_2$, S(═O)Ar, S(═O)$_2$Ar, $NO_2$, $Si(R^2)_3$, $B(OR^2)_2$, $OSO_2R^2$, a straight-chain alkyl, alkoxy, or thioalkyl group having 1 to 40 C atoms or a branched or cyclic alkyl, alkoxy, or thioalkyl group having 3 to 40 C atoms, each of which is optionally substituted by one or more radicals $R^2$, wherein one or more non-adjacent $CH_2$ groups are optionally replaced by $R^2C$═$CR^2$, C≡C, $Si(R^2)_2$, $Ge(R^2)_2$, $Sn(R^2)_2$, C═O, C═S, C═Se, P(═O)($R^2$), SO, $SO_2$, O, S, or $CONR^2$ and wherein one or more H atoms are optionally replaced by D, F, Cl, Br, I, CN, or $NO_2$, an aromatic or heteroaromatic ring system having 5 to 60 aromatic ring atoms, which is optionally substituted by one or more radicals $R^2$, or an aryloxy group having 5 to 60 aromatic ring atoms, which is optionally substituted by one or more radicals $R^2$, and wherein two adjacent substituents R and/or two adjacent substituents $R^0$ optionally define a mono- or polycyclic, aliphatic ring system or aromatic ring system, which is optionally substituted by one or more radicals $R^2$;

$R^1$ is on each occurrence, identically or differently, D, F CN, C(═O)Ar, P(═O)$(Ar)_2$, S(═O)Ar, S(═O)$_2$Ar, —$Si(R^2)_3$, $B(OR^2)_2$, $OSO_2R^2$, a straight-chain alkyl, alkoxy, or thioalkyl group having 1 to 40 C atoms or a branched or cyclic alkyl, alkoxy, or thioalkyl group having 3 to 40 C atoms, each of which is optionally substituted by one or more radicals $R^2$, wherein one or more non-adjacent $CH_2$ groups are optionally replaced by $R^2C$═$CR^2$, $Si(R^2)_2$, $Ge(R^2)_2$, $Sn(R^2)_2$, C═O, C═S, C═Se, P(═O)($R^2$), SO, $SO_2$, O, S, or $CONR^2$ and wherein one or more H atoms are optionally replaced by D, F, Cl, Br, I, CN, or $NO_2$, an aromatic or heteroaromatic ring system having 5 to 60 aromatic ring atoms, which is optionally substituted by one or more radicals $R^2$, or an aryloxy group having 5 to 60 aromatic ring atoms, which is optionally substituted by one or more radicals $R^2$, and wherein two adjacent substituents $R^1$ optionally define a mono- or polycyclic, aliphatic ring system or aromatic ring system, which is optionally substituted by one or more radicals $R^2$;

$R^2$ is on each occurrence, identically or differently, H, D, F, Cl, Br, I, CHO, CN, $N(Ar)_2$, C(═O)Ar, P(═O)$(Ar)_2$, S(═O)Ar, S(═O)$_2$Ar, $NO_2$, $Si(R^3)_3$, $B(OR^3)_2$, $OSO_2R^3$, a straight-chain alkyl, alkoxy, or thioalkyl group having 1 to 40 C atoms or a branched or cyclic alkyl, alkoxy, or thioalkyl group having 3 to 40 C atoms, each of which is optionally substituted by one or more radicals $R^3$, wherein one or more non-adjacent $CH_2$ groups are optionally replaced by $R^3C$═$CR^3$, $Si(R^3)_2$, $Ge(R^3)_2$, $Sn(R^3)_2$, C═O, C═S, C═Se, P(═O)($R^3$), SO, $SO_2$, O, S, or $CONR^3$ and wherein one or more H atoms are optionally replaced by D, F, Cl, Br, I, CN, or $NO_2$, an aromatic or heteroaromatic ring system having 5 to 60 aromatic ring atoms, which is optionally substituted by one or more radicals $R^3$, or an aryloxy group having 5 to 60 aromatic ring atoms, which is optionally substituted by one or more radicals $R^3$, and wherein two adjacent substituents $R^2$ optionally define a mono- or polycyclic, aliphatic ring system or aromatic ring system, which is optionally substituted by one or more radicals $R^3$;

$R^3$ is on each occurrence, identically or differently, H, D, F, Cl, Br, I, CN, a straight-chain alkyl, alkoxy, or thioalkyl group having 1 to 20 C atoms or a branched or cyclic alkyl, alkoxy, or thioalkyl group having 3 to 20 C atoms, wherein one or more non-adjacent $CH_2$ groups are optionally replaced by SO, $SO_2$, O, S and wherein one or more H atoms are optionally replaced by D, F, Cl, Br, or I, or an aromatic or heteroaromatic ring system having 5 to 24 C atoms; and Ar is on each occurrence, identically or differently, an aromatic or heteroaromatic ring system having 5 to 60 aromatic ring atoms, which is optionally substituted by one or more radicals $R^3$.

2. The compound of claim 1, wherein X is O or S.

3. The compound of claim 1, wherein E is —$C(R^0)_2$— or —$Si(R^0)_2$—.

4. The compound of claim 1, wherein the compound is selected from the group consisting of compounds of formulae (1-1b) through (1-6c):

(1-1b)
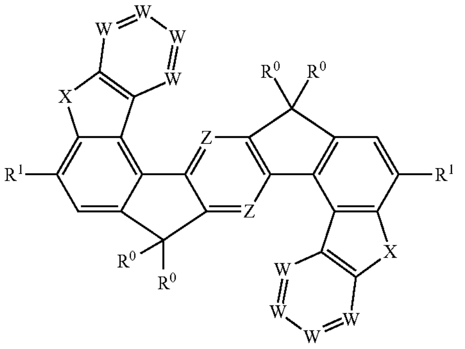
(1-2b)
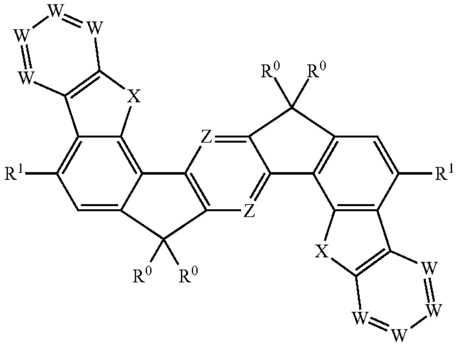
(1-3b)
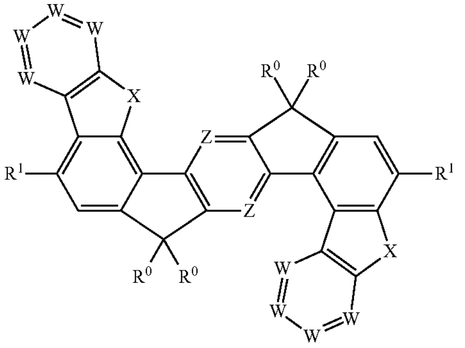
(1-4b)
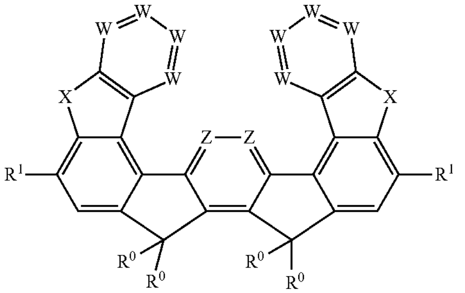
(1-5b)
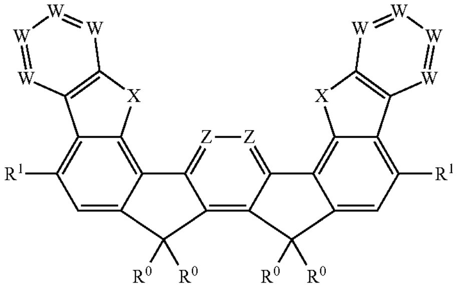
-continued
(1-6b)
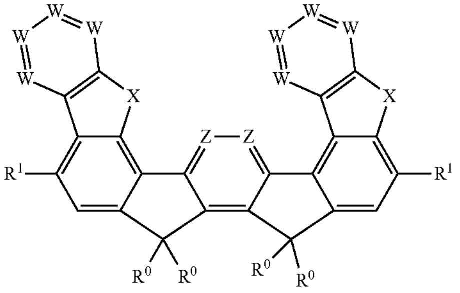
(1-1c)
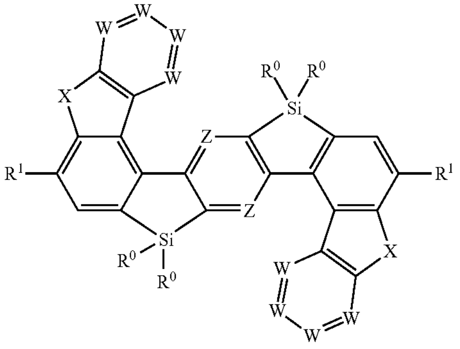
(1-2c)
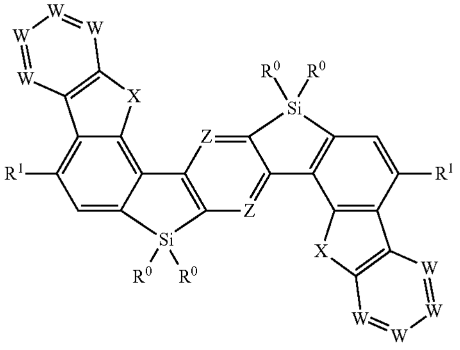
(1-3c)
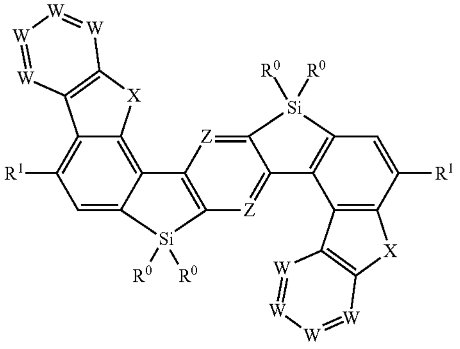
(1-4c)
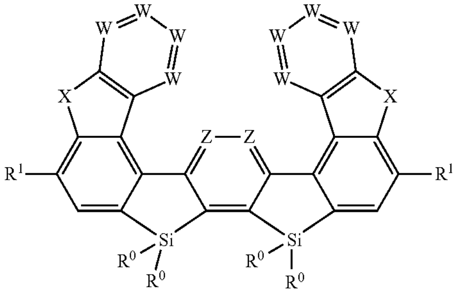

-continued (1-5c)

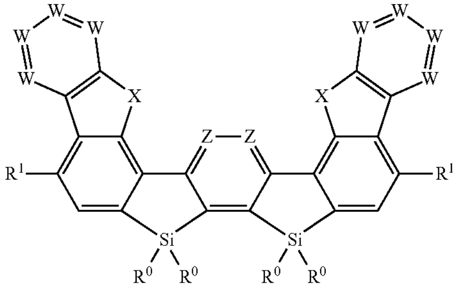

(1-6c)

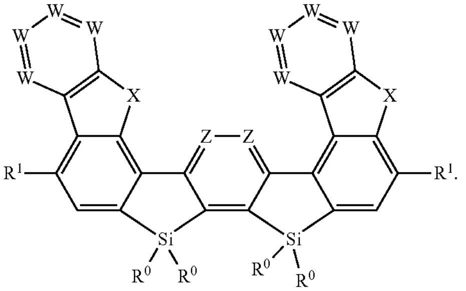

5. The compound of claim 1, wherein when $R^1$ is an aromatic or heteroaromatic ring system, then $R^1$ is selected on each occurrence, identically or differently, from the group consisting of formula ($R^1$-1):

$$---[Ar^3]_n Ar^4 \qquad (R^1\text{-}1)$$

wherein the dashes denotes the bond to the structure of formula (1);

$Ar^3$ and $Ar^4$ are selected on each occurrence, identically or differently, from the group consisting of benzene, naphthalene, anthracene, phenanthrene, biphenyl, terphenyl, fluorene, benzofluorene, spirobifluorene, cis-indenofluorene, trans-indenofluorene, cis-benzindenofluorene, trans-benzindenofluorene, furan, benzofuran, dibenzofuran, thiophene, benzothiophene, dibenzothiophene, pyrrole, indole, carbazole, indolocarbazole, indenocarbazole, pyridine, quinoline, pyrazole, indazole, imidazole, benzimidazole, pyridazine, benzopyridazine, pyrimidine, benzopyrimidine, pyrazine, quinoxaline, 1,3,5-triazine, 1,2,4-triazine, and 1,2,3-triazine, which are optionally substituted by one or more radicals $R^2$; and n is an integer from 0 to 20.

6. The compound of claim 5, wherein $Ar^3$ and $Ar^4$ are on each occurrence, identically or differently, selected from the group consisting of benzene, naphthalene, anthracene, phenanthrene, biphenyl, terphenyl, fluorene, benzofluorene, spirobifluorene, cis-indenofluorene, trans-indenofluorene, cis-benzindenofluorene, trans-benzindenofluorene, furan, benzofuran, dibenzofuran, thiophene, benzothiophene, dibenzothiophene, pyrrole, indole, carbazole, indolocarbazole, and indenocarbazole, which in each case is optionally substituted by one or more radicals $R^2$.

7. The compound of claim 1, wherein $R^0$ is on each occurrence, identically or differently, H, D, F, CN, a straight-chain alkyl group having 1 to 10 C atoms or a branched or cyclic alkyl group having 3 to 10 C atoms, each of which is optionally substituted by one or more radicals $R^2$, wherein one or more H atoms are optionally replaced by F, or an aryl or heteroaryl group having 5 to 25 aromatic ring atoms, which is optionally substituted by one or more radicals $R^2$, and wherein two adjacent substituents $R^0$ optionally define a mono- or polycyclic, aliphatic ring system or aromatic ring system, which is optionally substituted by one or more radicals $R^2$.

8. The compound of claim 1, wherein $R^0$ is on each occurrence, identically or differently, for H, D, F, CN, a straight-chain alkyl group having 1 to 10 C atoms or a branched or cyclic alkyl group having 3 to 10 C atoms, each of which was optionally substituted by one or more radicals $R^2$, and wherein one or more H atoms is optionally replaced by F.

9. An oligomer, polymer, or dendrimer comprising one or more compounds of claim 1, wherein the bond(s) to the polymer, oligomer, or dendrimer are located at any desired position in formula (1) substituted by R or $R^1$.

10. A formulation comprising at least one compound of claim 1 and at least one solvent.

11. A formulation comprising at least one oligomer, polymer, or dendrimer of claim 9 and at least one solvent.

12. An electronic device comprising at least one compound of claim 1, wherein the electronic device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes, and organic plasmon emitting devices.

13. An electronic device comprising at least one oligomer, polymer, or dendrimer of claim 9, wherein the electronic device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes, and organic plasmon emitting devices.

14. The electronic device of claim 12, wherein the electronic device is an organic electroluminescent device and the at least one compound is employed as a fluorescent emitter or as a matrix material for fluorescent emitters.

15. The electronic device of claim 13, wherein the electronic device is an organic electroluminescent device and the at least one oligomer, polymer, or dendrimer is employed as a fluorescent emitter or as a matrix material for fluorescent emitters.

16. The compound of claim 1, wherein the compound is of the formula (1-1a).

17. The compound of claim 1, wherein the compound is of the formula (1-2a).

18. The compound of claim 1, wherein the compound is of the formula (1-3a).

19. The compound of claim 1, wherein the compound is of the formula (1-4a).

20. The compound of claim 1, wherein the compound is of the formula (1-5a).

* * * * *